(12) United States Patent
Chiosis et al.

(10) Patent No.: US 9,328,114 B2
(45) Date of Patent: *May 3, 2016

(54) HSP90 INHIBITORS

(75) Inventors: Gabriela Chiosis, New York, NY (US); Tony Taldone, New York, NY (US); Weilin Sun, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 515 days.

This patent is subject to a terminal disclaimer.

(21) Appl. No.: 13/500,809

(22) PCT Filed: Oct. 7, 2010

(86) PCT No.: PCT/US2010/051872
§ 371 (c)(1),
(2), (4) Date: Apr. 6, 2012

(87) PCT Pub. No.: WO2011/044394
PCT Pub. Date: Apr. 14, 2011

(65) Prior Publication Data
US 2012/0208806 A1  Aug. 16, 2012

Related U.S. Application Data

(60) Provisional application No. 61/249,349, filed on Oct. 7, 2009.

(51) Int. Cl.
| C07D 473/34 | (2006.01) |
| A61K 31/52 | (2006.01) |
| A61P 35/00 | (2006.01) |
| A61P 25/28 | (2006.01) |
| A61P 25/16 | (2006.01) |

(52) U.S. Cl.
CPC .................................. *C07D 473/34* (2013.01)

(58) Field of Classification Search
CPC .............................. C07D 473/34; A61K 31/52
USPC ........................................ 544/277; 514/263.4
See application file for complete search history.

(56) References Cited

U.S. PATENT DOCUMENTS

| 7,834,181 B2 | 11/2010 | Chiosis et al. |
| 8,703,942 B2 | 4/2014 | Chiosis et al. |
| 2005/0004026 A1 | 1/2005 | Kasibhatla et al. |
| 2005/0049263 A1 | 3/2005 | Kasibhatla et al. |
| 2005/0107343 A1 | 5/2005 | Kasibhatla et al. |
| 2005/0113339 A1 | 5/2005 | Kasibhatla et al. |
| 2005/0113340 A1 | 5/2005 | Kasibhatla et al. |
| 2005/0119292 A1 | 6/2005 | Gravestock et al. |
| 2005/0256183 A1 | 11/2005 | Kasibhatla et al. |
| 2007/0299258 A1 | 12/2007 | Bajji et al. |
| 2008/0096903 A1 | 4/2008 | Chen et al. |
| 2008/0234297 A1 | 9/2008 | Qian et al. |
| 2008/0234314 A1 | 9/2008 | Cai et al. |
| 2008/0253965 A1 | 10/2008 | Chiosis et al. |
| 2009/0298857 A1 | 12/2009 | Chiosis et al. |
| 2010/0292255 A1 | 11/2010 | Bajji et al. |
| 2011/0104054 A1 | 5/2011 | Chiosis et al. |
| 2011/0312980 A1 | 12/2011 | Chiosis |
| 2014/0045867 A1 | 2/2014 | Taldone et al. |
| 2014/0227183 A1 | 8/2014 | Chiosis et al. |

FOREIGN PATENT DOCUMENTS

| CN | 101490052 A | 7/2009 |
| WO | 98/51702 | 11/1998 |
| WO | 00/61578 | 10/2000 |
| WO | 02/36075 A2 | 5/2002 |
| WO | 03/037860 A2 | 5/2003 |
| WO | WO-03037860 A2 | 5/2003 |
| WO | 2006/084030 A2 | 8/2006 |
| WO | 2007/134298 A2 | 11/2007 |
| WO | WO-2007134298 A2 | 11/2007 |
| WO | WO-2007/143630 A2 | 12/2007 |
| WO | 2008/005937 A2 | 1/2008 |
| WO | WO-2008005937 A2 | 1/2008 |
| WO | WO-2008/049105 A2 | 4/2008 |
| WO | 2008/115719 A1 | 9/2008 |
| WO | WO-2008115719 A1 | 9/2008 |
| WO | 2009/007399 A1 | 1/2009 |
| WO | 2009/042646 A1 | 4/2009 |
| WO | 2009/065035 A1 | 5/2009 |
| WO | WO-2009065035 A1 | 5/2009 |

OTHER PUBLICATIONS

He, H. et al. "Identification of Potent Water Soluble Purine-Scaffold Inhibitors of the Heat Shock Protein 90", J. Med. Chem. 2006, pp. 381-390, vol. 49.
Extended European Search Report for EP 10 82 2718.2, 2 pages (Jun. 21, 2012).
International Search Report for PCT/US2010/051872, 8 pages (Jan. 14, 2011).
Written Opinion for PCT/US2010/051872, 11 pages (Jan. 14, 2011).

*Primary Examiner* — Susanna Moore
(74) *Attorney, Agent, or Firm* — Choate, Hall & Stewart LLP; John P. Rearick; Gang Wang

(57) ABSTRACT

The present application provides compounds useful in the inhibition of Hsp90, and hence in the treatment of disease.

50 Claims, 3 Drawing Sheets

HSP90 INHIBITORS

STATEMENT OF RELATED CASES

This application is related to U.S. patent application Ser. No. 12/307,063 filed Dec. 30, 2008, and U.S. patent application Ser. No. 11/814,506, filed Jul. 23, 2007 which are incorporated herein by reference in their entirety for all purposes.

BACKGROUND OF THE INVENTION

This application relates to compounds that inhibit heat shock protein 90 (Hsp90).

The Hsp90 family of proteins has four recognized members in mammalian cells: Hsp90 α and β, Grp94 and Trap-1. Hsp90 α and β exist in the cytosol and the nucleus in association with a number of other proteins. Hsp90 in its various forms is the most abundant cellular chaperone, and has been shown in experimental systems to be required for ATP-dependent refolding of denatured or "unfolded" proteins. It has therefore been proposed to function as part of the cellular defense against stress. When cells are exposed to heat or other environmental stresses, the aggregation of unfolded proteins is prevented by pathways that catalyze their refolding or degradation. This process depends on the association of the unfolded protein in an ordered fashion with multiple chaperones (Hsp 60, 90 and 70 and p23), forming a "refoldosome" and ultimately the ATP-dependent release of the chaperones from the refolded protein.

Hsp90 may also play a role in maintaining the stability and function of mutated proteins. It seems to be required for expression of mutated p53 and v-src to a much greater extent than for their wild-type counterparts. It has been suggested that this occurs as a result of Hsp90-mediated suppression of the phenotypes of mutations that lead to protein unfolding.

Hsp90 is also necessary to the conformational maturation of several key proteins involved in the growth response of the cell to extracellular factors. These include the steroid receptors as well as certain transmembrane kinases (i.e., Raf serine kinase, v-src and Her2). The mechanism whereby Hsp90 affects these proteins is not fully understood, but appears to be similar to its role in protein refolding. In the case of the progesterone receptor, it has been shown that binding and release of Hsp90 from the receptor occurs in a cyclic fashion in concert with release of other chaperones and immunophilins and is required for high affinity binding of the steroid to the receptor. Thus, Hsp90 could function as a physiologic regulator of signaling pathways, even in the absence of stress.

Hsp90 has been shown to be overexpressed in multiple tumor types and as a function of oncogenic transformation. Whether it plays a necessary role in maintaining transformation is unknown, but it could have at least three functions in this regard. Cancer cells grow in an environment of hypoxia, low pH and low nutrient concentration. They also rapidly adapt to or are selected to become resistant to radiation and cytotoxic chemotherapeutic agents. Thus, the general role of Hsp90 in maintaining the stability of proteins under stress may be necessary for cell viability under these conditions. Secondly, cancer cells harbor mutated oncogenic proteins. Some of these are gain-of-function mutations which are necessary for the transformed phenotype. Hsp90 may be required for maintaining the folded, functionally-active conformation of these proteins. Thirdly, activation of signaling pathways mediated by steroid receptors, Raf and other Hsp90 targets is necessary for the growth and survival of many tumors which thus probably also require functional Hsp90.

Hsp90 has been recognized as a viable target for therapeutic agents. Hsp90 family members possess a unique pocket in their N-terminal region that is specific to and conserved among all Hsp90s from bacteria to mammals, but which is not present in other molecular chaperones. The endogenous ligand for this pocket is not known, but it binds ATP and ADP with low affinity and has weak ATPase activity. The ansamycin antibiotics geldanamycin (GM) and herbimycin (HA) have been shown to bind to this conserved pocket, and this binding affinity has been shown for all members of the Hsp90 family. International Patent Publication No. WO98/51702 discloses the use of ansamycin antibiotics coupled to a targeting moiety to provide targeted delivery of the ansamycin leading to the degradation of proteins in and death of the targeted cells. International Patent Publication No. WO00/61578 relates to bifunctional molecules having two moieties which interact with the chaperone protein Hsp90, including in particular homo- and heterodimers of ansamycin antibiotics. These bifunctional molecules act to promote degradation and/or inhibition of HER-family tyrosine kinases and are effective for treatment of cancers which overexpress Her-kinases.

Exemplary small molecule therapeutics that bind to the same binding pocket of Hsp90 as ATP and the ansamycin antibiotics are disclosed in PCT Publication Nos. WO02/36075, WO2006/084030, WO09/042646 and WO09/065035, and US Patent Publications 2005/0113339, 2005/0004026, 2005/0049263, 2005/0256183, 2005/0119292, 2005/0113340, 2005/0107343, 2008/0096903, 2008/0234297, 2008/0234314 and 2008/0253965, all of which are incorporated herein by reference.

Many of these compounds are based on a scaffold of the type disclosed by Chiosis et al in PCT Publication No. WO02/36075, with variations in substituents. In some cases, the compositions can be described by one of the following two general formulas:

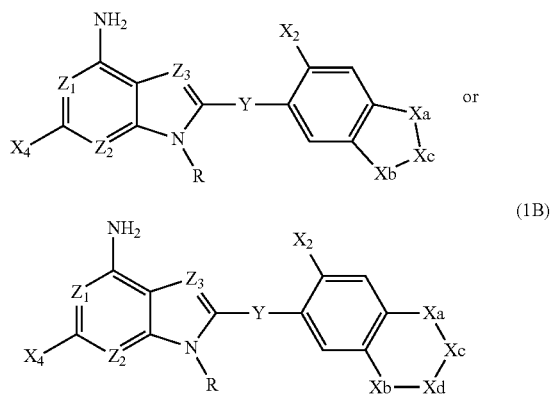

wherein Z1, Z2, Z3 are selected from C and N in which numerous options are disclosed for each variable substituent, resulting in an astronomical number of combinations and permutations. In other cases, the compositions can be described by a structural formula in which Xa, Xb, Xc and Xd are not connected to one another but are simply substituents on the benzene ring. These structures have the general formula:

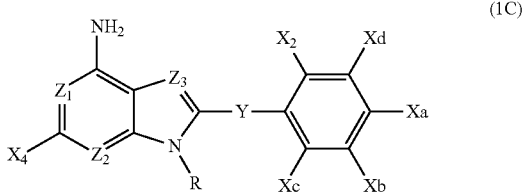

(1C)

wherein Z1, Z2, Z3 are selected from C and N. While these compounds are generally active as inhibitors of Hsp90, the level of activity is extremely variable with measured values for $EC_{50}$ and $IC_{50}$ being reported in both micromolar and nanomolar ranges.

SUMMARY OF THE INVENTION

The present application provides compounds useful in the inhibition of Hsp90, and hence in the treatment of disease.

DETAILED DESCRIPTION OF THE INVENTION

Figure 1:
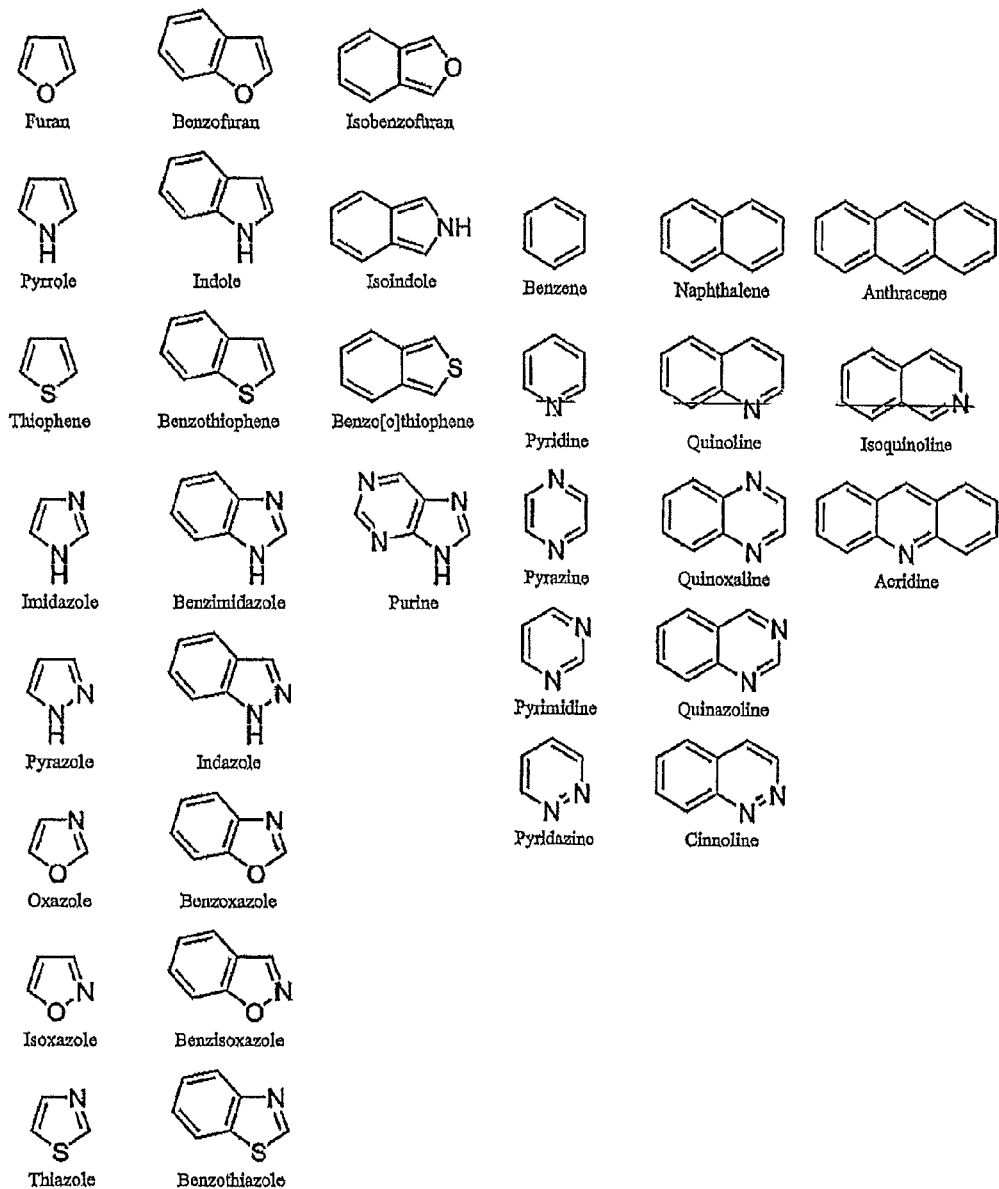
FIG. 1 shows examples of unsubstituted aryl groups, including some heterocyclic aryl groups.

The present invention provides compounds within the scope of Formula 1A, 1B or 1C with particular combinations of substituents that are effective to inhibit Hsp90. Inhibitors of Hsp90 are recognized as effective in treatments of cancer, and also can be used in the treatment of neurodegenerative diseases as described in PCT Patent Publication WO2008/005397. WO 2007/143630 discloses the use of Hsp90 inhibitors in treatment of neurofibromatosis. Thus, the compounds of the invention can be used in therapeutic methods in the same manner as used other known Hsp90 inhibitors, by administering a therapeutically effective amount of a compound of the invention to an individual, including a human, in need of treatment for cancer, neurodegenerative disease or other condition for which Hsp90 inhibition is relevant.

As used in this application, the term "treatment" refers to delaying the onset of symptoms, reducing the severity or delaying the symptomatic progression of cancer, neurodegenerative disease or other condition in the individual. A cure of the disease is not required to fall within the scope of treatment. Further, it will be appreciated that the specific results of these treatment goals will vary from individual to individual, and that some individuals may obtain greater or lesser benefits than the statistical average for a representative population. Thus, treatment refers to administration of composition to an individual in need, with the expectation that they will obtain a therapeutic benefit.

The term "administering" refers to the act of introducing into the individual the therapeutic compound. In general, any route of administration can be used. Thus, administration by oral, intrathecal, intravenous, intramuscular or parenteral injection is appropriate depending on the nature of the condition to be treated. Administration may also be done to the brain by inhalation because there is a compartment at the upper side of the nose that connects with the brain without having the BBB capillaries. Compounds that cross the blood brain barrier are preferred for this mode of administration, although this characteristic is not strictly required.

The term "therapeutically effective amount" encompasses both the amount of the compound administered and the schedule of administration that on a statistical basis obtains the result of preventing, reducing the severity or delaying the progression of the disease in the individual. As will be appreciated, preferred amounts will vary from compound to compound in order to balance toxicity/tolerance with therapeutic efficacy and the mode of administration. Determination of maximum tolerated dose and of the treatment regime in terms of number and frequency of dosing is a routine part of early clinical evaluation of a compound.

In all of the compounds of the present invention, the compound may be as depicted, or as a pharmaceutically acceptable salt or ester thereof.

In naming options for $X_2$, $X_4$ and R, the name refers to the type of group that is directly attached to the central structure, which group may include additional functionality. Thus, "alkyl" group refers to a linear, cyclic or branched saturated hydrocarbon, for example a hydrocarbon having from 1 to 10 carbon atoms, in which the atom directly attached to the central structure is a carbon atom. Such an alkyl group may include substituents other than hydrogen, for example an oxygen-containing group including without limitation hydroxyl and alkoxy; a halogen group; a nitrogen-containing group including without limitation amino, amido and alkylamino; an aryl group; a sulfur-containing group including without limitation thioalkyl; and/or a non-aromatic cyclic group including heterocycles and carbocycles. Carbon atoms in these substituents may increase the total number of carbon atoms in the alkyl group to above 10 without departing from the invention. All references to alkyl groups in the specification and claims hereof encompass both substituted and unsubstituted alkyl groups unless the context is clearly to the contrary.

"Alkenyl" group refers to a linear, cyclic or branched hydrocarbon, for example a hydrocarbon having from 1 to 10 carbon atoms, and at least one double bond, in which the atom directly attached to the central structure is a carbon atom. The alkenyl group may include any of the substituents mentioned above for an alkyl group. All references to alkenyl groups in the specification and claims hereof encompass both substituted and unsubstituted alkenyl groups unless the context is clearly to the contrary.

"Alkynyl" group refers to a linear, cyclic or branched hydrocarbon, for example a hydrocarbon having from 1 to 10 carbon atoms, and at least one triple bond, in which the atom directly attached to the central structure is a carbon atom. The alkynyl group may include any of the substituents mentioned above for an alkyl group. All references to alkynyl groups in the specification and claims hereof encompass both substituted and unsubstituted alkynyl groups unless the context is clearly to the contrary.

"Aryl" group refers to any group derived from a simple aromatic ring. Aryl group includes heteroaryl. (See FIG. 1) Aryl groups may be substituted or unsubstituted. When $X_2$, $X_4$ and R is identified as an aryl group, an atom of the aryl ring is bound directly to an atom of the central structure. An aryloxy substituent is an aryl group connected to the central structure through an oxygen atom. The aryl group may include any of the substituents mentioned above for an alkyl group, and in addition an aryl group may include an alkyl, alkenyl or alkynyl group. All references to aryl groups in the specification and claims hereof encompass both substituted and unsubstituted aryl groups unless the context is clearly to the contrary.

"Amino" group refers to any group which consists of a nitrogen attached by single bonds to carbon or hydrogen atoms. In certain instances, the nitrogen of the amino group is directly bound to the central structure. In other instances, an amino group may be a substituent on or within a group, with the nitrogen of the amino group being attached to the central structure through one or more intervening atoms. Examples of amino groups include $NH_2$, alkylamino, alkenylamino groups and N-containing non-aromatic heterocyclic moiety (i.e., cyclic amines). Amino groups may be substituted or unsubstituted. All references to amino groups in the specification and claims hereof encompass substituted and unsubstituted amino groups unless the context is clearly to the contrary.

"Halogen" group refers to fluorine, chlorine, bromine or iodine.

Figure 2:
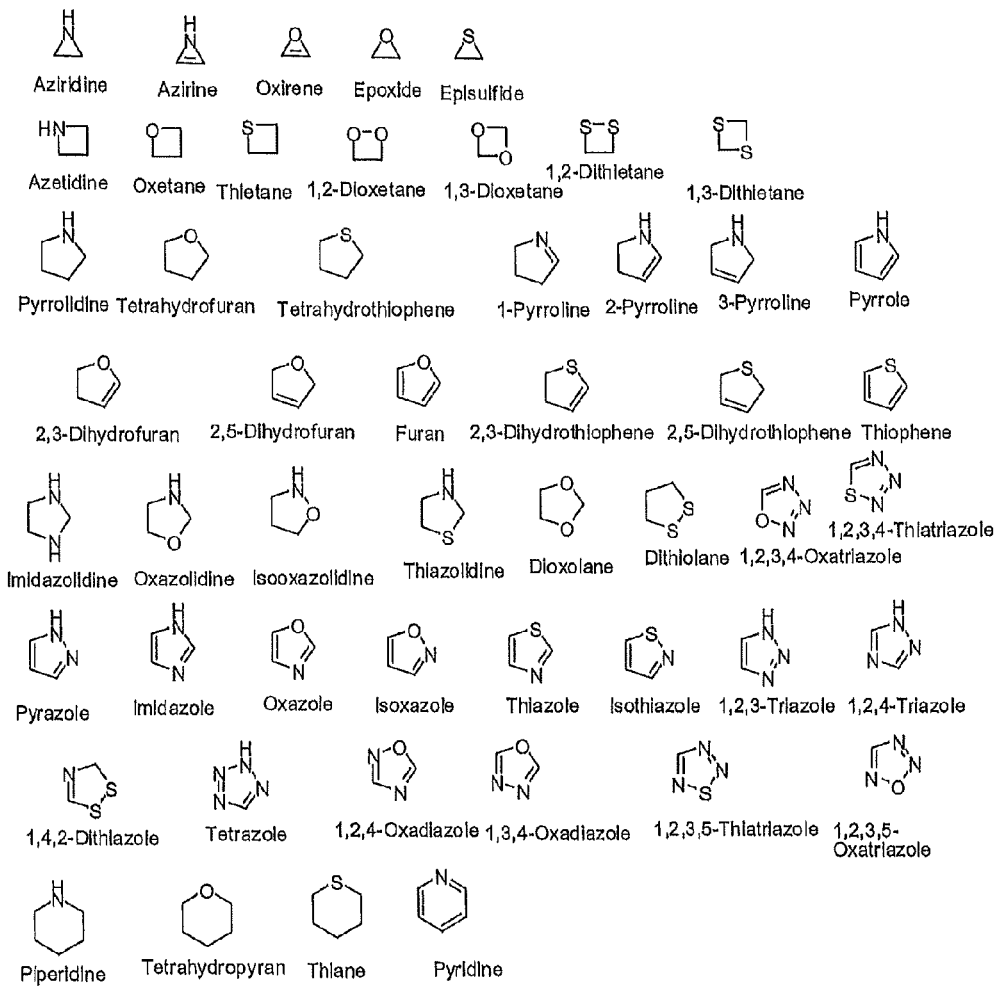
FIG. 2 shows examples of unsubstituted heterocyclic groups.

"Heterocyclic" group refers to a moiety containing at least one atom of carbon, and at least one atom of an element other than carbon, such as sulfur, oxygen or nitrogen within a ring structure. These heterocyclic groups may be either aromatic rings or saturated and unsaturated non-aromatic rings. Some examples are given in FIG. 2. Heterocylic groups may be substituted or unsubstituted. All references to heterocyclic groups in the specification and claims encompass substituted and unsubstituted heterocyclic groups unless the context is clearly to the contrary.

In the compounds of the invention, all of the atoms have sufficient hydrogen or non-hydrogen substituents to satisfy valence, or the compound includes a pharmaceutically acceptable counterion, for example in the case of a quaternary amine.

In the structures set forth below examples are provided in which all of Z1, Z2 and Z3 are nitrogen. These examples are intended as exemplary, and are not intended to exclude options in which one or more of Z1, Z2 and Z3 is carbon. In particular, corresponding compositions in which Z2 or Z3 is carbon are considered to be within the scope of this disclosure.

A. Structures of Formula 1A in which Xa or Xb is O

In accordance with a first embodiment of the invention, the compounds have general formula 1A, in which one of Xa or Xb is O, and Xc and the other of Xa and Xb is $CH_2$. Thus, the compounds of this embodiment may be represented by the general formula

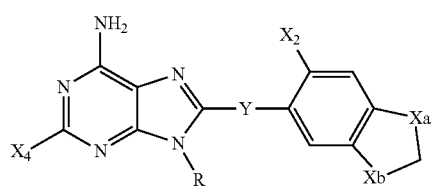

(2)

wherein:
one of Xa and Xb is O and the other is —$CH_2$—;
Y is —$CH_2$— or —S—,
$X_4$ is hydrogen or halogen; and
$X_2$ and R are in combinations as discussed below.

A-I. In some embodiments of the invention, $X_2$ is halogen. In these embodiments, R is suitably a primary aminoalkyl, a secondary or tertiary alkyl-amino-alkyl, an aryl-alkyl, or a nonaromatic heterocycle-alkyl, with the proviso that R is not a piperidino moiety. Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

Specific examples of compounds in accordance with this embodiment of the invention are listed in Tables 1A and 1B (Compounds 1A-1 to 1A-4, 1A-6, 1A-11, 1A-18 to 1A-28, 1A-30, 1A-31, 1A-49, 1B-1 to 1B-5, 1B-18, 1B-23 to 1B-25, 1B-29 to 1B-32, 1B-34, 1B-35, 1B-37, 1B-49, 1B-52 1B-56 and 1B-57).

As shown, in preferred embodiments of formula (2), $X_4$ is H, chlorine or fluorine.

In a particular preferred embodiment of formula (2), Y is S, $X_4$ is H, $X_2$ is I.

In a particular preferred embodiment of formula (2), Y is $CH_2$, $X_4$ is Cl, $X_2$ is I.

In a particular preferred embodiment of formula (2), Y is $CH_2$, $X_4$ is F, $X_2$ is I.

In a particular preferred embodiment of formula (2), Y is S, $X_4$ is F, $X_2$ is I.

Tests were run on compounds in accordance with the first embodiment of the invention, and the $EC_{50}$ for Hsp90 binding in JNPL3 brain cell lysate and SKBr3 cell lysate was assessed. The results are summarized in Table 2A. While all of the compounds had desirable low $EC_{50}$ values, both compounds tested in which Xb is O were superior to the related compound in which Xa is O. In addition, compound 1B-1 was superior to an otherwise identical compound in which both Xa and Xb are O (PU-HZ150 disclosed in U.S. Ser. No. 12/307,063) which has an $EC_{50}$ of 12-14.4 nM and compound 1B-2 was superior to an otherwise identical molecule in which both Xa and Xb are O (PU-H71 disclosed in U.S. Ser. No. 11/814,506) which has an $EC_{50}$ of 30.8-54 nM in the same experimental system.

Animal Studies. Four- to 6-week-old nu/nu athymic female mice were obtained from Taconic Farms. Experiments were carried out under an Institutional Animal Care and Use Committee approved protocol, and institutional guidelines for the proper and humane use of animals in research were followed. Before administration, a solution of 1B-1-HCl was formulated in PBS (pH 7.4). All mice received Augmentin (amoxicillin/clavulanate potassium; SmithKline Beecham) in their drinking water while on therapy. Mice were killed by $CO_2$ euthanasia.

Figure 3:
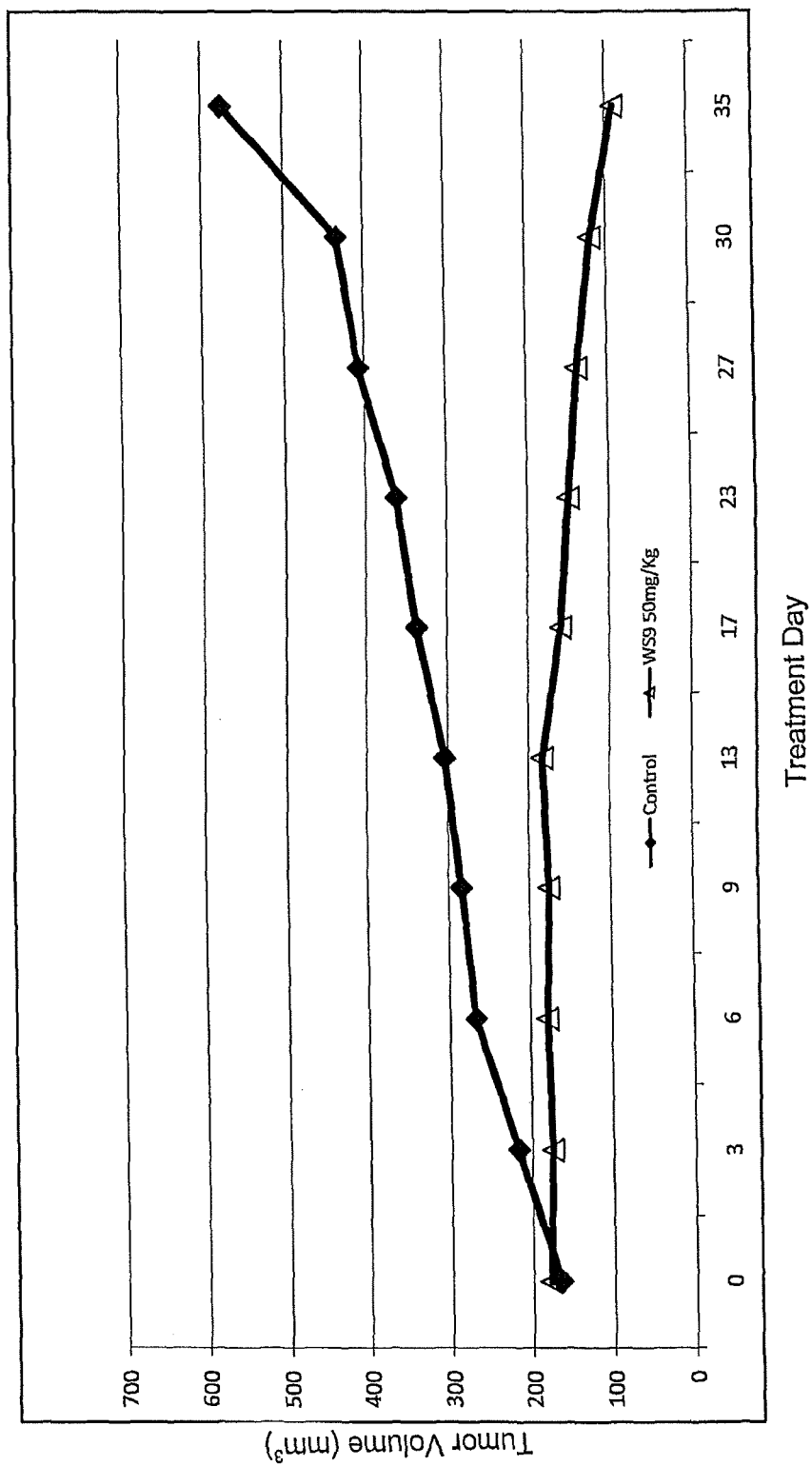
FIG. 3 shows average tumor volume in mice treated with compound 1B-1-HCl or with vehicle.

Mice bearing MDA-MB-468 tumors (n=5) reaching a volume of 100-150 $mm^3$ were treated i.p. (i.p.) using 1B-1-HCl at 50 mg/kg 3×week or vehicle. Tumor volume was determined by measurement with Vernier calipers, and tumor volume was calculated as the product of its length×$width^2$×0.4. Tumor volume was expressed on indicated days as the median tumor volume ±SD indicated for groups of mice. The average tumor volumes are summarized in FIG. 3. As shown, in the 35 days of the experiment the average tumor volume in the control mice increased by about a factor of 3×, while the tumor size in the mice treated with 1B-1-HCl decreased.

Table 2B shows measured values for $EC_{50}$ in JNPL3 brain cell lysates for compounds 1B-3, 1B-4 and 1B-25 in accordance with this embodiment of the invention which incorporates a fluorine as $X_4$ and in which Y is —$CH_2$—. Desirably low values of $EC_{50}$ were observed.

In addition, Table 2B shows measured values for $EC_{50}$ in JNPL3 brain cell lysates for compound 1B-24 in accordance with this embodiment of the invention which incorporates a hydrogen as $X_4$ and in which Y is S. Desirably low values of $EC_{50}$ were observed.

A-II. In some embodiments of the invention, $X_2$ is an aryl group. In these embodiments, R may be any of the groups disclosed as a substituent at the 9-position nitrogen in this application, or in the various patents and patent applications cited herein. Table 8 provides a summary of the R groups from these patents and applications.

In some embodiments within this group, R includes a heteroatom, such as nitrogen, oxygen or sulfur.

In some embodiments, the heteroatom is nitrogen. In some of these embodiments, R is a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of formula (2) within this group, R has the formula:

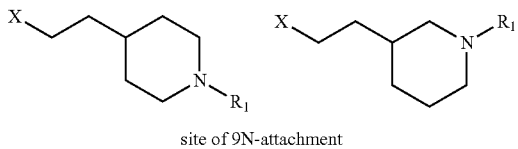

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention within this group, R has the formula

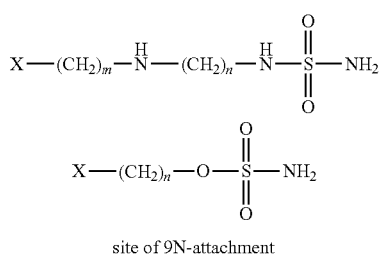

site of 9N-attachment where m=2-3 and n=1-6.

In embodiments within this group, R has the formula

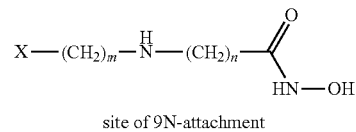

site of 9N-attachment where m=2-3 and n=1-6.

In specific embodiments, $X_2$ is an aromatic heterocycle.

In specific embodiments, $X_2$ is a furan, thiophene, pyrazole, imidazole, pyrrole, oxazole or thiazole.

In specific embodiments, $X_2$ is a furan, thiophene, pyrazole, imidazole, oxazole or thiazole.

In particular embodiments of formula (2), Y is S, $X_4$ is H, $X_2$ is 2-, 3-furan or 5-methyl-2-furanyl.

In particular embodiments of formula (2), Y is $CH_2$, $X_4$ is Cl, $X_2$ is 2-, 3-furan or 5-methyl-2-furanyl.

In particular embodiments of formula (2), Y is $CH_2$, $X_4$ is F, $X_2$ is 2-, 3-furan or 5-methyl-2-furanyl.

In particular embodiments of formula (2), Y is S, $X_4$ is F, $X_2$ is 2-, 3-furan or 5-methyl-2-furanyl.

In particular embodiments of formula (2), Y is S, $X_4$ is H, $X_2$ is 2- or 3-thiophene.

In particular embodiments of formula (2), Y is $CH_2$, $X_4$ is Cl, $X_2$ is 2- or 3-thiophene.

In particular embodiments of formula (2), Y is $CH_2$, $X_4$ is F, $X_2$ is 2- or 3-thiophene.

In particular embodiments of formula (2), Y is S, $X_4$ is F, $X_2$ is 2- or 3-thiophene.

In particular embodiments of formula (2), Y is S, $X_4$ is H, $X_2$ is 2- or 3-pyrazole.

In particular embodiments of formula (2), Y is $CH_2$, $X_4$ is Cl, $X_2$ is 2- or 3-pyrazole.

In particular embodiments of formula (2), Y is $CH_2$, $X_4$ is F, $X_2$ is 2- or 3-pyrazole.

In particular embodiments of formula (2), Y is S, $X_4$ is F, $X_2$ is 2- or 3-pyrazole.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is F, $X_2$ 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-oxazolyl or 5-methyl-2-oxazolyl.

In these particular embodiments, R may be any one of the types of groups described above.

Specific examples of compounds in accordance with this embodiment of the invention are listed in Tables 1A and 1B (Compounds 1A-5, 1A-7, 1A-12, 1A-13, 1A-15 to 1A-17, 1A-36, 1A-37, 1A-42, 1A-45 to 1A-48, 1A-50 to 1A-52, 1B-6, 1B-8, 1B-12, 1B-14, 1B-15, 1B-17, 1B-26, 1B-27, 1B-33, 1B-42 to 1B-44, 1B-46, 1B-50, 1B-51, 1B-53 to 1B-55). As shown, in preferred embodiments of formula (2) in which $X_2$ is an aryl group, $X_4$ is H, chlorine or fluorine.

Table 2C shows measured values for $EC_{50}$ in JNPL3 brain cell lysates for compounds 1B-26 and 1B-27 in accordance with this embodiment of the invention which incorporates a hydrogen as $X_4$ and in which Y is S. Desirably low values of $EC_{50}$ were observed.

A-III. In some embodiments of the invention, $X_2$ is an alkynyl group. In these embodiments, R may be any of the groups disclosed as a substituent at the 9-position nitrogen in this application, or in the various patents and patent applications cited herein. See Table 8.

In some embodiments within this group, R includes a heteroatom, such as nitrogen, oxygen or sulfur.

In some embodiments, the heteroatom is nitrogen. In some of these embodiments, R is a primary amino-alkyl, a secondary or tertiary-alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino) ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of formula (2) within this group, R has the formula:

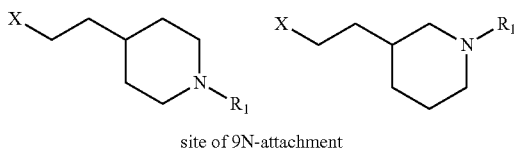

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention within this group, R has the formula

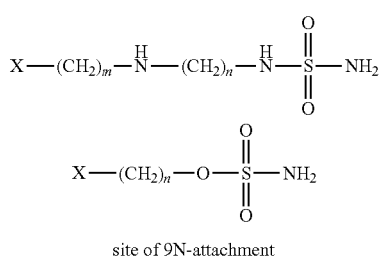

site of 9N-attachment where m=2-3 and n=1-6.

In embodiments within this group, R has the formula

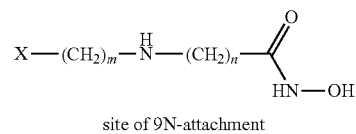

site of 9N-attachment where m=2-3 and n=1-6.

In specific embodiments, $X_2$ is acetylene.

In particular embodiments of formula (2), Y is S, $X_4$ is H, $X_2$ is acetylene.

In particular embodiments of formula (2), Y is $CH_2$, $X_4$ is Cl, $X_2$ is acetylene.

In particular embodiments of formula (2), Y is $CH_2$, $X_4$ is F, $X_2$ is acetylene.

In particular embodiments of formula (2), Y is S, $X_4$ is F, $X_2$ is acetylene.

In these particular embodiments, R may be any one of the types of groups described above.

Specific examples of compounds in accordance with this embodiment of the invention are listed in Tables 1A and 1B (Compounds 1A-8, 1A-14, 1A-29, 1A-32 to 1A-35, 1B-10, 1B-13, 1B-16, 1B-19, 1B-28, 1B-36, 1B-38 to 1B-41, 1B-45 1B-47 and 1B-58). As shown, in preferred embodiments of formula (2) in which $X_2$ is an alkynyl group, $X_4$ is H, chlorine or fluorine.

Table 2D shows a measured value for $EC_{50}$ in JNPL3 brain cell lysates for compound 1B-28 in accordance with this embodiment of the invention which incorporates a hydrogen as $X_4$ and in which Y is S. A desirably low value of $EC_{50}$ was observed.

A-IV. In some embodiments of the invention, $X_2$ is a cyano group. In these embodiments, R is suitably a primary amino-alkyl, a secondary or tertiary alkyl-amino-alkyl, an aryl-alkyl, or a nonaromatic heterocycle-alkyl, and with the proviso that R is not a piperidino moiety. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino) ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In a particular preferred embodiment of formula (2), Y is S, $X_4$ is H, $X_2$ is CN.

In a particular preferred embodiment of formula (2), Y is $CH_2$, $X_4$ is Cl, $X_2$ is CN.

In a particular preferred embodiment of formula (2), Y is $CH_2$, $X_4$ is F, $X_2$ is CN.

In a particular preferred embodiment of formula (2), Y is S, $X_4$ is F, $X_2$ is CN.

Specific examples of compounds in accordance with this embodiment of the invention are listed in Table 1A and 1B (Compounds 1A-9, 1B-11 and 1B-20).

A-V. In some embodiments of the invention, $X_2$ is an amino group. In these embodiments, R may be any of the groups disclosed as a substituent at the 9-position nitrogen in this application, or in the various patents and patent applications cited herein. See Table 8.

In some embodiments within this group, R includes a heteroatom, such as nitrogen, oxygen or sulfur.

In some embodiments, the heteroatom is nitrogen. In some of these embodiments, R is a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of formula (2) within this group, R has the formula:

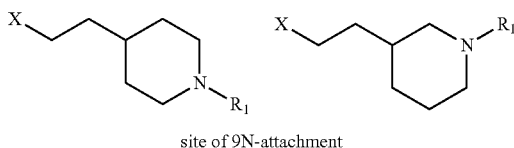

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention within this group, R has the formula

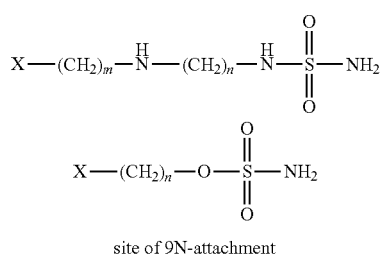

site of 9N-attachment where m=2-3 and n=1-6.

In embodiments within this group, R has the formula

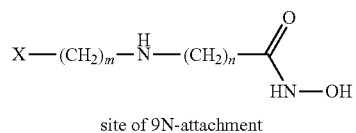

site of 9N-attachment where m=2-3 and n=1-6.

In a particular preferred embodiment of formula (2), Y is S, $X_4$ is H, $X_2$ is dimethylamino In a particular preferred embodiment of formula (2), Y is $CH_2$, $X_4$ is Cl, $X_2$ is dimethylamino In a particular preferred embodiment of formula (2), Y is $CH_2$, $X_4$ is F, $X_2$ is dimethylamino.

In a particular preferred embodiment of formula (2), Y is S, $X_4$ is F, $X_2$ is dimethylamino.

In a particular preferred embodiment of formula (2), Y is S, $X_4$ is H, $X_2$ is aziridino.

In a particular preferred embodiment of formula (2), Y is $CH_2$, $X_4$ is Cl, $X_2$ is aziridino.

In a particular preferred embodiment of formula (2), Y is $CH_2$, $X_4$ is F, $X_2$ is aziridino.

In a particular preferred embodiment of formula (2), Y is S, $X_4$ is F, $X_2$ is aziridino.

Specific examples of compounds in accordance with this embodiment of the invention are listed in Tables 1A and 1B (Compounds 1A-10, 1A-38 to 1A-41, 1A-43, 1A-44, 1B-7, 1B-21 and 1B-48).

A-VI. In some embodiments of the invention, $X_2$ is a cycloalkyl or a cycloalkenyl. In these embodiments, R may be any of the groups disclosed as a substituent at the 9-position nitrogen in this application, or in the various patents and patent applications cited herein. See Table 8.

In some embodiments within this group, R includes a heteroatom, such as nitrogen, oxygen or sulfur.

In some embodiments, the heteroatom is nitrogen. In some of these embodiments, R is a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of formula (2) within this group, R has the formula:

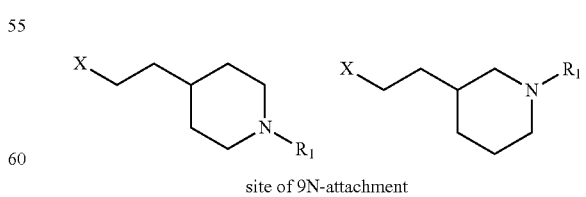

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention within this group, R has the formula

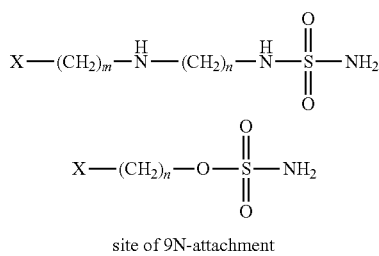

site of 9N-attachment where m=2-3 and n=1-6.

In embodiments within this group, R has the formula

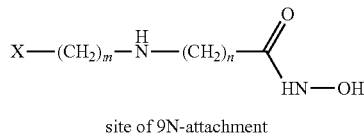

site of 9N-attachment where m=2-3 and n=1-6.

In specific embodiments, $X_2$ is a cycloalkyl with one ring.

In specific embodiments, $X_2$ is a cyclopropane, a cyclobutane or a cyclopentane.

In particular embodiments of formula (2), Y is S, $X_4$ is H, $X_2$ is cyclopentyl.

In particular embodiments of formula (2), Y is $CH_2$, $X_4$ is F, $X_2$ is cyclopentyl.

In particular embodiments of formula (2), Y is $CH_2$, $X_4$ is Cl, $X_2$ is cyclopentyl.

In particular embodiments of formula (2), Y is S, $X_4$ is F, $X_2$ is cyclopentyl.

In these particular embodiments, R may be any one of the types of groups described above.

Specific examples of compounds in accordance with this embodiment of the invention are listed in Table 1B (Compounds 1B-9, and 1B-22) although the embodiment is not limited to the option in which Xb is O, and includes compounds in which Xa is O.

B. Structures of Formula 1A in which Xa or Xb is S

In accordance with a second embodiment of the invention, the compounds have general formula 1A, in which one of Xa or Xb is S, and Xc and the other of Xa and Xb is $CH_2$. Thus, the compounds of this embodiment may be represented by the general formula

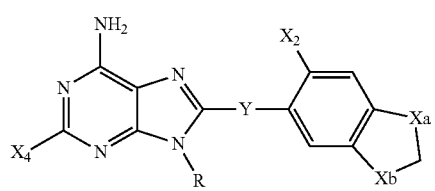

(2)

wherein:
one of Xa and Xb is S and the other is —$CH_2$—;
Y is —$CH_2$— or —S—,
$X_4$ is hydrogen or halogen; and
$X_2$ and R are as discussed below.

In these embodiments, R may be any of the groups disclosed as a substituent at the 9-position nitrogen in this application, or in the various patents and patent applications cited herein. See Table 8.

In some embodiments within this group, R includes a heteroatom, such as nitrogen, oxygen or sulfur.

In some embodiments, the heteroatom is nitrogen. In some of these embodiments, R is a primary amino-alkyl, a secondary or tertiary alkyl-amino-alkyl, an aryl-alkyl, or a nonaromatic heterocycle-alkyl. In some of these embodiments, R is a primary, secondary or tertiary alkyl-amino-alkyl, alkyl-aryl, or an alkyl-nonaromatic heterocycle. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino) ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine) propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of formula (2) within this group, R has the formula:

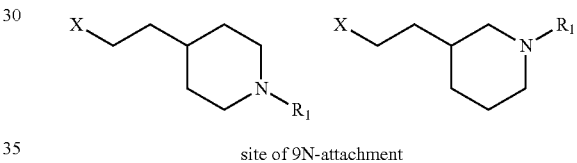

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention within this group, R has the formula

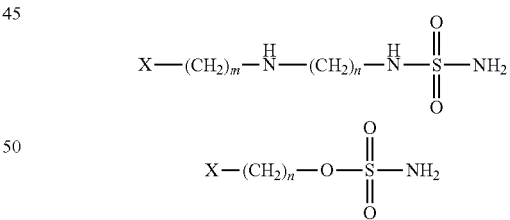

site of 9N-attachment where m=2-3 and n=1-6.

In embodiments within this group, R has the formula

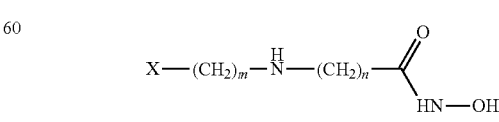

site of 9N-attachment where m=2-3 and n=1-6.

In embodiments of formula (2) in which Xa or Xb is S, $X_2$ may be any group shown to be attached to the same position as $X_2$ in any of the compounds disclosed herein or in the various patents and patent applications cited above. Specifically, $X_2$ may be alkyl, alkenyl, alkynyl, aryl, cycloalkyl, cycloalkenyl, saturated or unsaturated heterocycle, aryl, halogen, aryloxy, alkoxy, halogenated alkoxy, alkenyloxy, hydroxyalkyl, amino, alkylamino, dialkylamino, acylamino, carbamyl, amido, dialkylamido, alkylamido, alkylsulfonamido, sulfonamido, trihalocarbon, -thioalkyl, $SO_2$-alkyl, —COO-alkyl, —COalkyl, OH, $NO_2$, CN or alkyl-CN, or part of a ring formed by R;

In particular embodiments of the invention, $X_2$ is halogen, and R is an (alkylamino)alkyl or (dialkylamino)alkyl.

In particular embodiments, $X_2$ is halogen and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl, or 3-(hydroxyethyl, isopropyl amino)propyl.

In some embodiments of the invention, $X_2$ is an aryl group.

In particular embodiments, $X_2$ is aryl and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl, or 3-(hydroxyethyl, isopropyl amino)propyl.

In some embodiments of the invention, $X_2$ is a heteroaryl group.

In some embodiments, $X_2$ is a heteroaryl group and R is 2-(methyl, t-butyl-amino) ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl, or 3-(hydroxyethyl, isopropyl amino)propyl.

In particular embodiments, $X_2$ is 2- or 3-furan and R is 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl, or 3-(hydroxyethyl, isopropyl amino)propyl.

In particular embodiments, $X_2$ is 2- or 3-thiophene and R is 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl, or 3-(hydroxyethyl, isopropyl amino)propyl.

In particular embodiments, $X_2$ is 3-pyrazolyl and R is 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl, or 3-(hydroxyethyl, isopropyl amino)propyl.

In some embodiments of the invention, $X_2$ is an alkynyl group.

In some embodiments of the invention, $X_2$ is an alkynyl group, and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl, or 3-(hydroxyethyl, isopropyl amino)propyl.

In particular embodiments of the invention, $X_2$ is acetylene, and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino) ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl, or 3-(hydroxyethyl, isopropyl amino)propyl.

In some embodiments of the invention, $X_2$ is CN.

In particular embodiments of the invention, $X_2$ is CN, and R is 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl, or 3-(hydroxyethyl, isopropyl amino)propyl.

In some embodiments of the invention, $X_2$ is an amine.

In some embodiments of the invention, $X_2$ is an amine, and R is 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl, or 3-(hydroxyethyl, isopropyl amino)propyl.

In particular embodiments of the invention, $X_2$ is dimethyl amine, azetidino or aziridino, and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl, or 3-(hydroxyethyl, isopropyl amino)propyl.

Specific examples of compounds in accordance with this embodiment of the invention are listed in Tables 1C and 1D.

C. Structures of Formula 1A in which Xa, Xb and Xc are All Carbon

In accordance with a third embodiment of the invention, the compounds have general formula 1A; in which Xa, Xb and Xc are all carbon, connected by two single or one single bond and one double bond, and wherein Y is —$CH_2$— or —S—;
$X_4$ is hydrogen or halogen; and
$X_2$ and R are in combinations as discussed below.

C-I. In some embodiments of the invention in which Xa, Xb and Xc are all carbon, $X_2$ is halogen.

In some embodiments within this group, R includes a heteroatom, such as nitrogen, oxygen or sulfur with the proviso that R does not include a piperidino moiety.

In some embodiments, R is suitably an optionally substituted primary alkyl-amino, an optionally substituted secondary or tertiary alkyl-amino-alkyl, alkyl-aryl, or an alkyl-nonaromatic heterocycle, with the proviso that R is not a piperidino moiety.

In some embodiments, the heteroatom is nitrogen. In some of these embodiments, R is a primary, secondary or tertiary alkyl-amino-alkyl, alkyl-aryl, or an alkyl-nonaromatic heterocycle, with the proviso that R does not include a piperidino moiety. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of the invention within this group, R has the formula

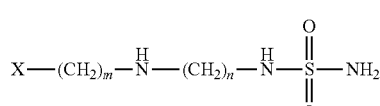

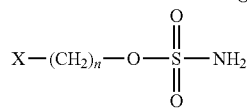

site of 9N-attachment where m=2-3 and n=1-6.

In embodiments within this group, R has the formula

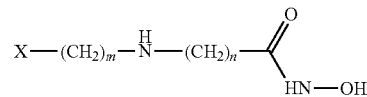

site of 9N-attachment where m=2-3 and n=1-6.

Specific examples of compounds in accordance with this embodiment of the invention are listed in Tables 1E (Compounds 1E-1 to 1E-4, 1E-6, 1E-18, 1E-21, 1E-23 to 1E-26, 1E-35, 1E-38, 1E-39, 1E-42 to 1E-48, 1E-68 to 1E-76). As shown, in preferred embodiments of formula (2), $X_4$ is H, chlorine or fluorine.

In a particular preferred embodiment of formula (2), Y is S, $X_4$ is H, $X_2$ is I.

In a particular preferred embodiment of formula (2), Y is $CH_2$, $X_4$ is Cl, $X_2$ is I.

In a particular preferred embodiment of formula (2), Y is $CH_2$, $X_4$ is F, $X_2$ is I.

In a particular preferred embodiment of formula (2), Y is S, $X_4$ is F, $X_2$ is I.

Table 2E shows measured values for $EC_{50}$ in JNPL3 brain and SKBr3 cell lysates for compounds 1E-2, 1E21 and 1E-23 in accordance with this embodiment of the invention which incorporates a hydrogen as $X_4$ and in which Y is S. Desirably low values of $EC_{50}$ were observed.

C-II. In some embodiments of the invention, $X_2$ is an aryl group. In these embodiments, R may be any of the groups disclosed as a substituent at the 9-position nitrogen in this application, or in the various patents and patent applications cited herein. See Table 8.

In some embodiments within this group, R includes a heteroatom, such as nitrogen, oxygen or sulfur.

In some embodiments, the heteroatom is nitrogen. In some of these embodiments, R is a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of formula (2) within this group, R has the formula:

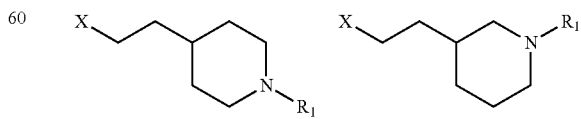

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention within this group, R has the formula

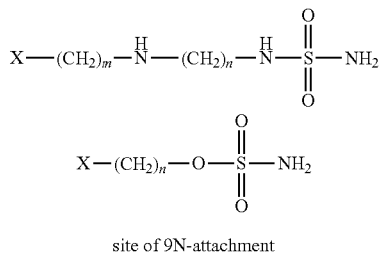

site of 9N-attachment where m=2-3 and n=1-6.

In embodiments within this group, R has the formula

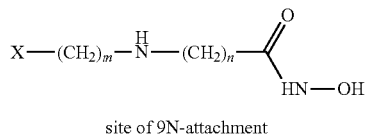

site of 9N-attachment where m=2-3 and n=1-6.

In specific embodiments, $X_2$ is an aromatic heterocycle.

In specific embodiments, $X_2$ is a furan, thiophene, pyrazole, imidazole, pyrrole, oxazole and thiazole.

In specific embodiments of the $X_2$ is a furan, thiophene, pyrazole, oxazole and thiazole or imidazole.

In specific embodiments, $X_2$ is an aromatic heterocycle.

In specific embodiments, $X_2$ is a furan, thiophene, pyrazole, imidazole, pyrrole, oxazole or thiazole.

In specific embodiments, $X_2$ is a furan, thiophene, pyrazole, imidazole, oxazole or thiazole.

In particular embodiments of formula (2), Y is S, $X_4$ is H, $X_2$ is 2-, 3-furan or 5-methyl-2-furanyl.

In particular embodiments of formula (2), Y is $CH_2$, $X_4$ is Cl, $X_2$ is 2-, 3-furan or 5-methyl-2-furanyl.

In particular embodiments of formula (2), Y is $CH_2$, $X_4$ is F, $X_2$ is 2-, 3-furan or 5-methyl-2-furanyl.

In particular embodiments of formula (2), Y is S, $X_4$ is F, $X_2$ is 2-, 3-furan or 5-methyl-2-furanyl.

In particular embodiments of formula (2), Y is S, $X_4$ is H, $X_2$ is 2- or 3-thiophene.

In particular embodiments of formula (2), Y is $CH_2$, $X_4$ is Cl, $X_2$ is 2- or 3-thiophene.

In particular embodiments of formula (2), Y is $CH_2$, $X_4$ is F, $X_2$ is 2- or 3-thiophene.

In particular embodiments of formula (2), Y is S, $X_4$ is F, $X_2$ is 2- or 3-thiophene.

In particular embodiments of formula (2), Y is S, $X_4$ is H, $X_2$ is 2- or 3-pyrazole.

In particular embodiments of formula (2), Y is $CH_2$, $X_4$ is Cl, $X_2$ is 2- or 3-pyrazole.

In particular embodiments of formula (2), Y is $CH_2$, $X_4$ is F, $X_2$ is 2- or 3-pyrazole.

In particular embodiments of formula (2), Y is S, $X_4$ is F, $X_2$ is 2- or 3-pyrazole.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is F, $X_2$ 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-thiazolyl, 2-oxazolyl or 5-methyl-2-oxazolyl.

In these particular embodiments, R may be any one of the types of groups described above.

Specific examples of compounds in accordance with this embodiment of the invention are listed in Tables 1E (Compounds 1E-5, 1E-7, 1E-11 to 1E-13, 1E-15 to 1E-17, 1E-27, 1E-29 to 1E-33, 1E-36, 1E-37, 1E-41, 1E-59 to 1E-76, 1E-84 and 1E-85). As shown, in preferred embodiments of formula (2) in which $X_2$ is an aryl group, $X_4$ is H, chlorine or fluorine.

C-III. In some embodiments of the invention, $X_2$ is an alkynyl group. In these embodiments, R may be as described above in Section CII.

In specific embodiments, $X_2$ is acetylene.

In particular embodiments of formula (2), Y is S, $X_4$ is H, $X_2$ is acetylene.

In particular embodiments of formula (2), Y is $CH_2$, $X_4$ is Cl, $X_2$ is acetylene.

In particular embodiments of formula (2), Y is $CH_2$, $X_4$ is F, $X_2$ is acetylene.

In particular embodiments of formula (2), Y is S, $X_4$ is F, $X_2$ is acetylene.

In these particular embodiments, R may be any one of the types of groups described above.

Specific examples of compounds in accordance with this embodiment of the invention are listed in Tables 1E (Compounds 1E-8, 1E-14, 1E-19. 1E-20, 1E-22, 1E-40, 1E-49 to 1E-58 and 1E-77 to 1E-82). As shown, in preferred embodiments of formula (2) in which $X_2$ is an alkynyl group, $X_4$ is H, chlorine or fluorine.

Table 2F shows a measured value for $EC_{50}$ in JNPL3 brain cell lysates for compound 1E-22 in accordance with this embodiment of the invention which incorporates a hydrogen as $X_4$ and in which Y is S. A desirably low value of $EC_{50}$ was observed.

C-IV. In some embodiments of the invention, $X_2$ is a cyano group. In these embodiments, R may be as described above in Section C-II, with the proviso that R does not include a piperidino moiety.

In a particular preferred embodiment of formula (2), Y is S, $X_4$ is H, $X_2$ is CN.

In a particular preferred embodiment of formula (2), Y is $CH_2$, $X_4$ is Cl, $X_2$ is CN.

In a particular preferred embodiment of formula (2), Y is $CH_2$, $X_4$ is F, $X_2$ is CN.

In a particular preferred embodiment of formula (2), Y is S, $X_4$ is F, $X_2$ is CN.

In these particular embodiments, R may be any one of the types of groups described above.

A specific example of a compound in accordance with this embodiment of the invention is listed in Table 1E (Compound 1E-9).

C-V. In some embodiments of the invention, $X_2$ is an amino group. In these particular embodiments, R may be any one of the types of groups described in Section C-II.

In a particular preferred embodiment of formula (2), Y is S, $X_4$ is H, $X_2$ is azetidino.

In a particular preferred embodiment of formula (2), Y is $CH_2$, $X_4$ is Cl, $X_2$ is azetidino.

In a particular preferred embodiment of formula (2), Y is $CH_2$, $X_4$ is F, $X_2$ is azetidino.

In a particular preferred embodiment of formula (2), Y is S, $X_4$ is F, $X_2$ is azetidino.

Specific examples of compounds in accordance with this embodiment of the invention are listed in Table 1E (Compound 1E-10, 1E-28 and 1E-34).

C-VI. In some embodiments of the invention, $X_2$ is a cycloalkyl or a cycloalkenyl. In these particular embodiments, R may be any one of the types of groups described in Section C-II.

In specific embodiments, $X_2$ is a cycloalkyl with one ring.

In specific embodiments, $X_2$ is a cyclopropane, cyclobutane or cyclopentane.

In particular embodiments of formula (2), Y is S, $X_4$ is H, $X_2$ is cyclopentyl.

In particular embodiments of formula (2), Y is $CH_2$, $X_4$ is Cl, $X_2$ is cyclopentyl.

In particular embodiments of formula (2), Y is $CH_2$, $X_4$ is F, $X_2$ is cyclopentyl.

In particular embodiments of formula (2), Y is S, $X_4$ is F, $X_2$ is cyclopentyl.

In these particular embodiments, R may be any one of the types of groups described above.

D. Structures of Formula 1A in which Xa or Xb is N

In accordance with a fourth embodiment of the invention, the compounds have general formula 1A, in which one of Xa or Xb is N, and Xc and the other of Xa and Xb are $CH_2$. The N may be unsubstituted (i.e. NH) or substituted, for example with methyl, ethyl, acetyl. Thus, the compounds of this embodiment may be represented by the general formula

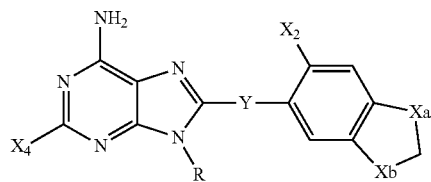

(2)

wherein:
one of Xa and Xb is N bonded to H or a substituent, and the other is —$CH_2$—;
Y is —$CH_2$— or —S—,
$X_4$ is hydrogen or halogen; and
$X_2$ and R are as discussed below.

In these embodiments, R may be any of the groups disclosed as a substituent at the 9-position nitrogen herein or in the various patents and applications cited above. See Table 8. In some embodiments, R includes a nitrogen heteroatom. In further embodiments, R is any of the options discussed above in Section B.

$X_2$ may be any group shown to be attached to the same position in any of the compounds disclosed in the various patents and patent applications cited above, or as described above in Section B.

In particular embodiments of the invention, $X_2$ is halogen, and R is an amino alkyl, an alkylaminoalkyl, dialkylaminoalkyl, or trialkylammonioalkyl group, in which each alkyl portion may be linear, cyclic or branched, or an alkyl heterocycle, where the alkyl may be bound to a nitrogen in the heterocyclic group. Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, and 3-(1H-imidazoyl)propyl.

In some embodiments of the invention, $X_2$ is an aryl group.

In particular embodiments, $X_2$ is aryl and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl or 3-(hydroxyethyl, isopropyl amino)propyl.

In some embodiments of the invention, $X_2$ is a heteroaryl group.

In some embodiments, $X_2$ is a heteroaryl group and R is 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl or 3-(hydroxyethyl, isopropyl amino)propyl.

In particular embodiments, $X_2$ is 2- or 3-furan and R is 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl or 3-(hydroxyethyl, isopropyl amino)propyl.

In particular embodiments, $X_2$ is 2- or 3-thiophene and R is 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)- propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl or 3-(hydroxyethyl, isopropyl amino)propyl.

In particular embodiments, $X_2$ is 3-pyrazolyl and R is 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(N-morpholino)propyl, or 3-(hydroxyethyl, isopropyl amino)propyl.

In some embodiments of the invention, $X_2$ is an alkynyl group.

In some embodiments of the invention, $X_2$ is an alkynyl group, and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl or 3-(hydroxyethyl, isopropyl amino)propyl.

In particular embodiments of the invention, $X_2$ is acetylene, and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino) ethyl, 2-(hydroxyethyl, isopropyl amino)ethyl, 3-(cyclopentylamino)propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl or 3-(hydroxyethyl, isopropyl amino)propyl.

In some embodiments of the invention, $X_2$ is CN.

In particular embodiments of the invention, $X_2$ is CN, and R is 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl or 3-(hydroxyethyl, isopropyl amino)propyl.

In some embodiments of the invention, $X_2$ is an amine.

In some embodiments of the invention, $X_2$ is an amine, and R is 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl or 3-(hydroxyethyl, isopropyl amino)propyl.

In particular embodiments of the invention, $X_2$ is dimethyl amine or aziridino, and R is 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino) ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(N-morpholino)propyl or 3-(hydroxyethyl, isopropyl amino)propyl.

Specific examples of compounds in accordance with this embodiment of the invention are listed in Tables 1F and 1G.

E. Structures of Formula 1A in which Xa or Xb is Carbonyl or Thiocarbonyl

In accordance with a fifth embodiment of the invention, the compounds have general formula 1A, in which one of Xa or Xb is carbonyl (C=O) or thiocarbonyl (C=S), and Xc and the other of Xa and Xb is $CH_2$. Thus, the compounds of this embodiment may be represented by the general formula

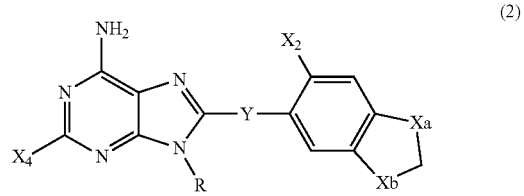

(2)

wherein:

one of Xa and Xb is C=O or C=S, and the other is —$CH_2$—;

Y is —$CH_2$— or —S—, $X_4$ is hydrogen or halogen; and $X_2$ and R are as discussed below.

In these embodiments, R may be any of the groups disclosed as a substituent at the 9-position nitrogen in this application, or in the various patents and patent applications cited herein (See Table 8), with the proviso that when $X_2$ is halogen or CN, R does not include a piperidino moiety.

In some embodiments within this group, R includes a heteroatom, such as nitrogen, oxygen or sulfur. In some embodiments, the heteroatom is nitrogen. In these embodiments, R is suitably a primary amino-alkyl, a secondary or tertiary alkyl-amino-alkyl, an aryl-aryl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino) propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of formula (2) within this group when $X_2$ is thiocarbonyl, R may have the formula:

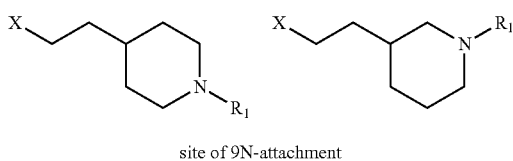

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention within this group, R has the formula

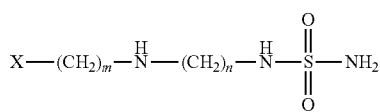

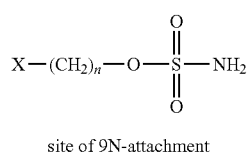

site of 9N-attachment where m=2-3 and n=1-6.

In embodiments within this group, R has the formula

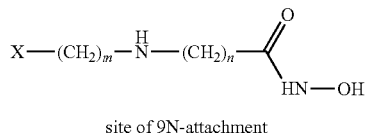

site of 9N-attachment where m=2-3 and n=1-6.

$X_2$ may be any substituent shown to be attached at the same position in any of the compounds disclosed in the various patents and patent applications cited above, or as described above in Section B.

In particular embodiments of the invention, $X_2$ is halogen, and R is suitably a primary amino-alkyl, a secondary or tertiary alkyl-amino-alkyl, an aryl-alkyl, or a nonaromatic heterocycle-alkyl Specific R groups include without limitation 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In some embodiments of the invention, $X_2$ is an aryl group.

In particular embodiments, $X_2$ is aryl and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino) propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In some embodiments of the invention, $X_2$ is a heteroaryl group.

In some embodiments, $X_2$ is a heteroaryl group and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine) propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In particular embodiments, $X_2$ is 2- or 3-furan and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In particular embodiments, $X_2$ is 2- or 3-thiophene and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In particular embodiments, $X_2$ is 3-pyrazolyl and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In some embodiments of the invention, $X_2$ is an alkynyl group.

In some embodiments of the invention, $X_2$ is an alkynyl group, and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, and 3-(1H-imidazoyl)propyl.

In particular embodiments of the invention, $X_2$ is acetylene, and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, and 3-(1H-imidazoyl)propyl.

In some embodiments of the invention, $X_2$ is CN.

In particular embodiments of the invention, $X_2$ is CN, and R is suitably a primary amino-alkyl, a secondary or tertiary alkyl-amino-alkyl, an aryl-alkyl, or a nonaromatic heterocycle-alkyl, with the proviso that R does not include a piperidino moiety. Specific R groups include without limitation 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, and 3-(1H-imidazoyl)propyl.

In some embodiments of the invention, $X_2$ is an amine.

In some embodiments of the invention, $X_2$ is an amine, and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino) ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, and 3-(1H-imidazoyl)propyl.

In particular embodiments of the invention, $X_2$ is dimethyl amine or aziridino, and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, and 3-(1H-imidazoyl)propyl.

Specific examples of compounds in accordance with this embodiment of the invention are listed in Tables 1H and 1I.

F. Structures of Formula 1A in which Xa, Xb and Xc Include at Least One Non-Carbon Atom and -Xa-Xc-Xb- Includes a Double Bond In accordance with a sixth embodiment of the invention, the compounds have general formula 1A, with Xa, Xc, Xb and the bonds between them selected from a combination in the following table:

| Xa | Bond | Xc | bond | Xb |
|---|---|---|---|---|
| C | double | C | single | O |
| C | double | C | single | N |
| C | double | C | single | S |
| O | single | C | double | C |
| N | single | C | double | C |
| S | single | C | double | C |
| N | double | C | single | O |
| N | double | C | single | S |
| N | single | C | double | N |
| O | single | C | double | N |
| S | single | C | double | N |
| N | double | N | single | O |
| N | double | N | single | S |
| N | double | N | single | C |
| O | single | N | double | N |
| N | single | N | double | N |
| S | single | N | double | N |
| C | single | N | double | N |

Y is —CH$_2$— or —S—,
X$_4$ is hydrogen or halogen; and
X$_2$ and R are as discussed below.

In these embodiments, R may be any of the groups disclosed as a substituent at the 9-position nitrogen herein or in the various patents and applications cited above. In some embodiments, R includes a nitrogen heteroatom. In further embodiments, R is any of the options discussed above in Section B.

X$_2$ may be any group shown to be attached at the same position in any of the compounds disclosed in the various patents and patent applications cited above, or as described above in B.

In particular embodiments of the invention, X$_2$ is halogen, and R is an aminoalkyl (alkylamino)alkyl or (dialkylamino) alkyl.

In particular embodiments, X$_2$ is halogen and R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino) propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino) propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In some embodiments of the invention, X$_2$ is an aryl group.

In particular embodiments, X$_2$ is aryl and R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In some embodiments of the invention, X$_2$ is a heteroaryl group.

In some embodiments, X$_2$ is a heteroaryl group and R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In particular embodiments, X$_2$ is 2- or 3-furan and R is suitably an amino alkyl, a secondary or tertiary alkyl-amino-alkyl, a trialkylammonioalkyl group, an aryl-alkyl, or a nonaromatic heterocycle-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In particular embodiments, X$_2$ is 2- or 3-thiophene and R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In some embodiments of the invention, $X_2$ is an alkynyl group, and R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino) ethyl, 2-(methyl, isopropyl amino)ethyl, 3-(neopentyl amino) propyl, 2-(isobutyl-amino)ethyl, 2-(ethyl, isopropyl amino) ethyl, 3-(isopropyl amino)propyl, 3-(t-butyl-amino)propyl, 2-(isopropyl amino)ethyl, 2-(hydroxyethyl, isopropyl amino) ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine) propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In particular embodiments of the invention, $X_2$ is acetylene, and R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino) ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine) propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In some embodiments of the invention, $X_2$ is CN.

In particular embodiments of the invention, $X_2$ is CN, and R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In some embodiments of the invention, $X_2$ is an amine.

In some embodiments of the invention, $X_2$ is an amine, and R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In particular embodiments of the invention, $X_2$ is dimethyl amine or aziridino, and R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino) propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino) propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

Specific examples of compounds in accordance with this embodiment of the invention are listed in Tables 3A-3F.

G. Structures of Formula 1A in which Xa and Xb are Both O

In accordance with a seventh embodiment of the invention, the compounds have general formula 1A, in which Xa and Xb are O and Xc is $CH_2$. Thus, the compounds of this embodiment may be represented by the general formula

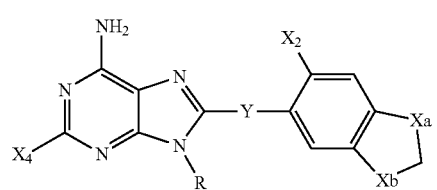

(2)

wherein:

in which Xa and Xb are O,

Y is —$CH_2$— or —S—, $X_4$ is hydrogen or halogen; and $X_2$ and R are in combinations as discussed below.

G-I. In some embodiments of the invention, $X_2$ is an aryl group. In these embodiments, R may be any of the groups disclosed as a substituent at the 9-position nitrogen in this application, or in the various patents and patent applications cited herein. See Table 8.

In some embodiments within this group, R includes a heteroatom, such as nitrogen, oxygen or sulfur.

In some embodiments, the heteroatom is nitrogen. In some of these embodiments, R is suitably a primary amino-alkyl, a secondary or tertiary alkyl-amino-alkyl, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl, and 3-(1H-imidazoyl)propyl.

In embodiments of formula (2) within this group, R has the formula:

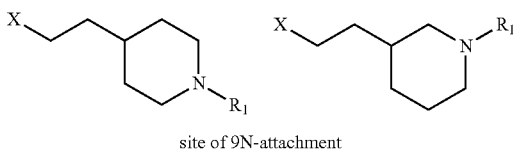

site of 9N-attachment where R1 is selected from COH, COMe, COEt, COnPr, COiPr, SO$_2$Me, CH$_2$OX where X can be H or oxygen, nitrogen, sulphur or halogen containing alkyl of linear, branched or cyclic nature.

In embodiments of the invention within this group, R has the formula

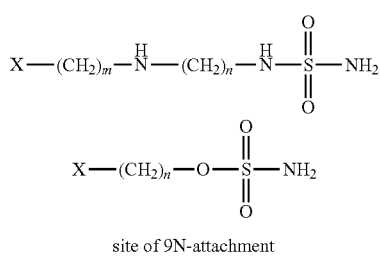

site of 9N-attachment where m=2-3 and n=1-6.

In embodiments within this group, R has the formula

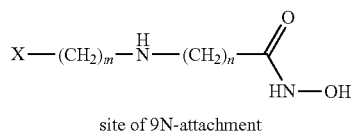

site of 9N-attachment where m=2-3 and n=1-6.

In specific embodiments, $X_2$ is a heterocycle.

In specific embodiments, $X_2$ is phenyl, furan, thiophene, pyrazole, imidazole, thiazole, oxazole or pyrrole.

In specific embodiments of the $X_2$ is phenyl, furan, methylfuran, thiophene, pyrazole, thiazole, oxazole or imidazole.

In particular embodiments of formula (2), Y is S, $X_4$ is H, $X_2$ is 2-, 3-furan or 5-methyl-2-furanyl.

In particular embodiments of formula (2), Y is CH$_2$, $X_4$ is Cl, $X_2$ is 2-, 3-furan or 5-methyl-2-furanyl.

In particular embodiments of formula (2), Y is CH$_2$, $X_4$ is F, $X_2$ is 2-, 3-furan or 5-methyl-2-furanyl.

In particular embodiments of formula (2), Y is S, $X_4$ is F, $X_2$ is 2-, 3-furan or 5-methyl-2-furanyl.

In particular embodiments of formula (2), Y is S, $X_4$ is H, $X_2$ is 2- or 3-thiophene.

In particular embodiments of formula (2), Y is CH$_2$, $X_4$ is Cl, $X_2$ is 2- or 3-thiophene.

In particular embodiments of formula (2), Y is CH$_2$, $X_4$ is F, $X_2$ is 2- or 3-thiophene.

In particular embodiments of formula (2), Y is S, $X_4$ is F, $X_2$ is 2- or 3-thiophene.

In particular embodiments of formula (2), Y is S, $X_4$ is H, $X_2$ is 2- or 3-pyrazole.

In particular embodiments of formula (2), Y is CH$_2$, $X_4$ is Cl, $X_2$ is 2- or 3-pyrazole.

In particular embodiments of formula (2), Y is CH$_2$, $X_4$ is F, $X_2$ is 2- or 3-pyrazole.

In particular embodiments of formula (2), Y is S, $X_4$ is F, $X_2$ is 2- or 3-pyrazole.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is CH$_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is CH$_2$, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is H, $X_2$ is optionally substituted phenyl.

In particular embodiments of formula (2), Y is CH$_2$, $X_4$ is Cl, $X_2$ is optionally substituted phenyl.

In particular embodiments of formula (2), Y is CH$_2$, $X_4$ is F, $X_2$ is optionally substituted phenyl.

In particular embodiments of formula (2), Y is S, $X_4$ is F, $X_2$ is optionally substituted phenyl.

In particular embodiments of formula (2), Y is S, $X_4$ is H, $X_2$ is optionally substituted pyridine.

In particular embodiments of formula (2), Y is CH$_2$, $X_4$ is Cl, $X_2$ is optionally substituted pyridine.

In particular embodiments of formula (2), Y is CH$_2$, $X_4$ is F, $X_2$ is optionally substituted pyridine.

In particular embodiments of formula (2), Y is S, $X_4$ is F, $X_2$ is optionally substituted pyridine.

In particular embodiments of formula (2), Y is S, $X_4$ is H, $X_2$ is optionally substituted isooxazole.

In particular embodiments of formula (2), Y is CH$_2$, $X_4$ is Cl, $X_2$ is optionally substituted isooxazole.

In particular embodiments of formula (2), Y is CH$_2$, $X_4$ is F, $X_2$ is optionally substituted isooxazole.

In particular embodiments of formula (2), Y is S, $X_4$ is F, $X_2$ is optionally substituted isooxazole.

In particular embodiments of formula (2), Y is S, $X_4$ is H, $X_2$ is optionally substituted imidazole.

In particular embodiments of formula (2), Y is $CH_2$, $X_4$ is Cl, $X_2$ is optionally substituted imidazole.

In particular embodiments of formula (2), Y is $CH_2$, $X_4$ is F, $X_2$ is optionally substituted imidazole.

In particular embodiments of formula (2), Y is S, $X_4$ is F, $X_2$ is optionally substituted imidazole.

In these particular embodiments, R may be any one of the types of groups described above.

Specific examples of compounds in accordance with this embodiment of the invention are listed in Tables 4A, 4C, 4D, 4F, 4G and 4H. As shown, in preferred embodiments of formula (2) in which $X_2$ is an aryl group, $X_4$ is H, chlorine or fluorine.

Table 2G shows measured values for $EC_{50}$ in JNPL3 brain cell lysates and in SKBr3 cell lysate for compounds 4A-1 to 4A-8, 4C1 to 4C-11, 4C14, 4C-16, 4C-38 to 4C-41, 4D-1 to 4D-3, 4D-16, 4D-17, 4F-1, 4G-1 to 4G-7, 4G-9, 4H-1 to 4H-7 in accordance with this embodiment of the invention which incorporates a hydrogen as $X_4$ and in which Y is S or a fluorine as $X_4$ and in which Y is —$CH_2$—. Desirably low values of $EC_{50}$ were observed for several examples.

G-II. In some embodiments of the invention, $X_2$ is an alkynyl group. In these embodiments, R may be any of the groups disclosed as a substituent at the 9-position nitrogen in this application, or in the various patents and patent applications cited herein. See Table 8.

In some embodiments, when $X_2$ is alkynyl, R includes a nitrogen heteroatom.

In a further embodiment, when $X_2$ is alkenyl, R is suitably an amino alkyl, a secondary or tertiary alkyl-amino-alkyl, a trialkylammonioalkyl group, an aryl-alkyl, or a nonaromatic heterocycle-alkyl.

Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In embodiments of formula (2) when $X_2$ is alkynyl, R has the formula:

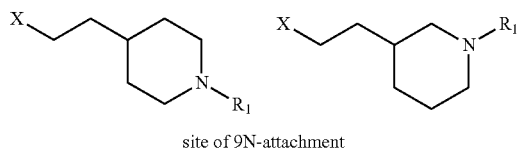

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention when $X_2$ is alkynyl, R has the formula

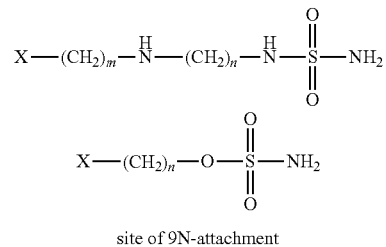

site of 9N-attachment where m=2-3 and n=1-6.

In embodiments when $X_2$ is alkynyl, R has the formula

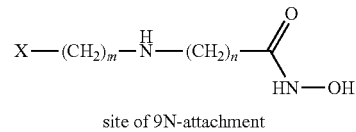

site of 9N-attachment where m=2-3 and n=1-6.

In specific embodiments, $X_2$ is acetylene.

In particular embodiments of formula (2), Y is S, $X_4$ is H, $X_2$ is acetylene.

In particular embodiments of formula (2), Y is $CH_2$, $X_4$ is Cl, $X_2$ is acetylene.

In particular embodiments of formula (2), Y is $CH_2$, $X_4$ is F, $X_2$ is acetylene.

In particular embodiments of formula (2), Y is S, $X_4$ is F, $X_2$ is acetylene.

In these particular embodiments, R may be any one of the types of groups described above.

Specific examples of compounds in accordance with this embodiment of the invention are listed in Tables 4B. As shown, in preferred embodiments of formula (2) in which $X_2$ is an alkynyl group, $X_4$ is H, chlorine or fluorine.

Table 2H shows measured values for $EC_{50}$ in JNPL3 brain cell lysates and in SKBr3 cell lysate for compounds 4B-1 to 4B-4, 4B13 and 4B-14 in accordance with this embodiment of the invention which incorporates a hydrogen as $X_4$ and in which Y is S, or a fluorine as $X_4$ and in which Y is —$CH_2$—. Desirably low values of $EC_{50}$ were observed.

G-III. In some embodiments of the invention, $X_2$ is a cyano or cyanoalkyl group. In these embodiments, R is suitably an amino alkyl, a secondary or tertiary alkyl-amino-alkyl, a trialkylammonioalkyl group, an aryl-alkyl, or a nonaromatic heterocycle-alkyl Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In a particular preferred embodiment of formula (2), Y is S, $X_4$ is H, $X_2$ is CN.

In a particular preferred embodiment of formula (2), Y is $CH_2$, $X_4$ is Cl, $X_2$ is CN.

In a particular preferred embodiment of formula (2), Y is $CH_2$, $X_4$ is F, $X_2$ is CN.

In a particular preferred embodiment of formula (2), Y is S, $X_4$ is F, $X_2$ is CN.

In other embodiments in which $X_2$ is cyano or cyanoalkyl group, R is

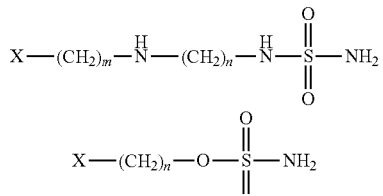

site of 9N-attachment where m=2-3 and n=1-6, or

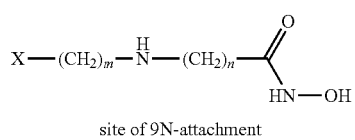

site of 9N-attachment where m=2-3 and n=1-6.

A specific example of a compound in accordance with this embodiment of the invention is listed in Table 4E.

Table 2I shows measured values for $EC_{50}$ in JNPL3 brain cell lysates and in SKBr3 cell lysate for compounds (4E-1 to 4E-4) in accordance with this embodiment of the invention which incorporates a hydrogen as $X_4$ and in which Y is S or a fluorine as $X_4$ and in which Y is —$CH_2$—. Desirably low values of $EC_{50}$ were observed for several examples.

G-IV. In some embodiments of the invention, $X_2$ is a cycloalkyl (saturated carbocyclic) or cycloalkenyl. In these embodiments, R may be any of the groups disclosed as a substituent at the 9-position nitrogen in this application, or in the various patents and patent applications cited herein. (See Table 8)

In some embodiments within this group, R includes a nitrogen heteroatom.

In a further embodiment within this group, R is suitably an amino alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl; 2-(methyl, isobutyl amino)ethyl, 3-(N-morpholino)propyl and 3-(1H-imidazoyl)propyl.

In embodiments of formula (2) within this group, R has the formula:

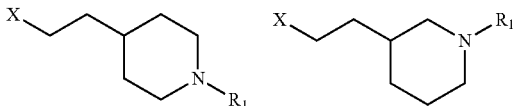

site of 9N-attachment where $R_1$ is selected from COH, COMe, COEt, COnPr, COiPr, $SO_2$Me, $CH_2$OX where X can be H or oxygen, nitrogen, sulphur or halogen containing alkyl of linear, branched or cyclic nature.

In embodiments of the invention within this group, R has the formula

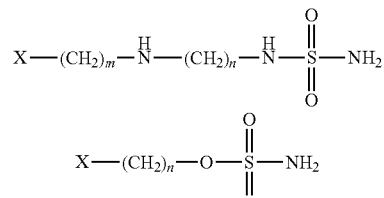

site of 9N-attachment where m=2-3 and n=1-6.

In embodiments when $X_2$ is aryl, R has the formula

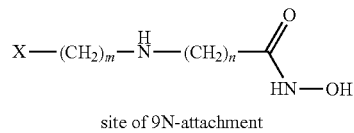

site of 9N-attachment where m=2-3 and n=1-6.

In specific embodiments, $X_2$ is a cycloalkyl with one ring.

In specific embodiments, $X_2$ is a cyclopropane, cyclobutane or cyclopentane.

In particular embodiments of formula (2), Y is S, $X_4$ is H, $X_2$ is cyclopentyl.

In particular embodiments of formula (2), Y is $CH_2$, $X_4$ is F, $X_2$ is cyclopentyl.

In particular embodiments of formula (2), Y is S, $X_4$ is F, $X_2$ is cyclopentyl.

In particular embodiments of formula (2), Y is $CH_2$, $X_4$ is Cl, $X_2$ is cyclopentyl.

In these particular embodiments, R may be any one of the types of groups described above.

Specific examples of compounds of this type are shown in Table 4I.

Table 2J shows measured values for $EC_{50}$ in JNPL3 brain cell lysates and in SKBr3 cell lysate for compound 4I-12 in accordance with this embodiment of the invention which incorporates a hydrogen as $X_4$ and in which Y is S. Desirably low values of $EC_{50}$ were observed for several examples.

Table 2G shows results for $EC_{50}$ measured in SKBr3 breast cancer cells and JNPL3 brain cell lysates for compounds listed in Table 4A. As shown, compounds of this type are generally more active with respect to brain cancer cells. As shown, the greatest activity was observed for compound 4A-1, in which there is no substituent on the $X_2$ phenyl group, and the least activity is seen for compounds 4A-3 and 4A-4 in which electron withdrawing $CF_3$ substituents are at the meta positions.

An embodiment of the invention therefore has the structure (2) shown above, in which Y is S, $X_4$ is hydrogen, $X_2$ is phenyl, optionally substituted at the para position, and R includes a nitrogen heteroatom, and therefore is an alkylamino, an (alkylamino)alkyl or (dialkylamino)alkyl. Preferred R groups of this type are as listed above.

Examples of compounds within this seventh embodiment of the invention, in which $X_2$ is alkynyl are shown in Table 4B. Table 2H shows results for $EC_{50}$ for Hsp90 binding in JNPL3 brain cell lysates. As shown, all of the compounds tested were active, however, those with an acetylene substituent, such as 4B-1, 4B-4, 4B-13 and 4B-14, were most active.

Examples of compounds within this seventh embodiment of the invention, in which $X_2$ is an aryl group containing an oxygen atom are shown in Table 4C. Specific suitable substituent groups are 2-furanyl, 3-furanyl and 5-methyl-2-furanyl.

Table 2G shows results for $EC_{50}$ for Hsp90 binding in SKBr3 breast cancer cells and JNPL3 brain cell lysates for some of the compounds shown in Table 4C. All of the compounds show good activity in both experimental systems. In Table 4C, compound 4-C11 has $X_2$=isoxazole, whereas 4C-11, 4C-38 and 4C-39 have $X_2$=oxazolyl, including both a nitrogen and an oxygen. Compounds with $X_2$=2-oxazolyl (4C-38 and 4C-39) were more active than those with $X_2$=isoxazolyl (4C-11).

Examples of compounds within this seventh embodiment of the invention, in which $X_2$ is an aryl group containing a sulfur atom in the aryl ring are shown in Table 4D. Table 2G shows results for $EC_{50}$ for Hsp90 binding in SKBr3 breast cancer cells and JNPL3 brain cell lysates for some of the compounds shown in Table 4D. All of the compounds show good activity in both experimental systems. In Table 4D, compounds 4D-16 and 4D-17 have $X_2$=2-thiazolyl, including both a nitrogen and an oxygen.

Examples of compounds within this seventh embodiment of the invention, in which $X_2$ is —CN or cyanoalkyl are shown in Table 4E. Table 2I shows results for $EC_{50}$ for Hsp90 binding in JNPL3 brain cell lysates for the two —CN compounds shown in Table 4E. Both of the compounds show good activity in both experimental systems.

An example of a compound within this seventh embodiment of the invention, in which $X_2$ is a 6-membered aryl ring containing a nitrogen atom in the aryl ring, with the proviso that there is not also an oxygen in the ring, is shown in Table 2 (labeled as 4F-1). In Compound 4F-1, $X_2$ is 4-pyridinyl. $X_2$ could also be 2-pyridinyl, 3-pyridinyl, or pyrazinyl, 4-pyrimidinyl, 5-pyrimidinyl, 3-pyridazinyl or 4-pyridazinyl.

$EC_{50}$ for Hsp90 binding in SKBr3 breast cancer cells and JNPL3 brain cells were determined for compound 4F-1 to be 9,620 nM and 4,120 nM, respectively.

Examples of compounds within this seventh embodiment of the invention, in which $X_2$ is a 5-membered aryl rings containing 2 nitrogens in the ring are shown in Table 4G. The specific $X_2$ groups shown are 3-, 4- and 5-pyrazolyl. Other examples of $X_2$ groups in this category are 4- or 5-imidazolyl.

$EC_{50}$ for Hsp90 binding in SKBr3 breast cancer cells and JNPL3 brain cell lysates were determined for some of the compounds listed in Table 4G. The results are summarized in Table 2K. Particularly good results were observed for compounds 4G-3, 4G-6 and 4G-9 in which the substituent is a 3-pyrazolyl.

Examples of compounds within this seventh embodiment of the invention, in which $X_2$ is a pyrrolyl group are shown in Table 4H. The specific $X_2$ groups shown are 2 or 3-pyrrolyl.

$EC_{50}$ for Hsp90 binding in SKBr3 breast cancer cells and JNPL3 brain cell lysates were determined for some of the compounds listed in Table 4H. The results are summarized in Table 2L.

H. Structures of Formula 1B in which Xa and Xb are O

In accordance with an eighth embodiment of the invention, the compounds have general formula 1B, in which both Xa and Xb are O, and Xc and Xd are $CH_2$. Thus, compounds of this embodiment are represented by the formula:

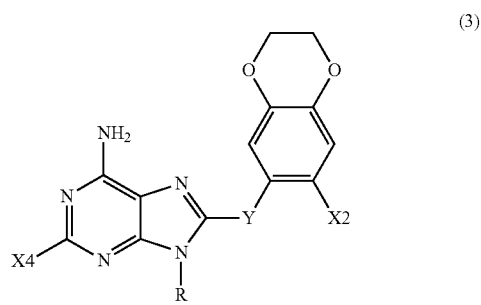

(3)

wherein

Y is —$CH_2$—, —O— or —S—;

$X_4$ is hydrogen or halogen; and $X_2$ and R are as discussed below.

H-I. In some embodiments of compounds in accordance with formula (3), $X_2$ is halogen. In these embodiments, R is suitably an amino-alkyl, a secondary or tertiary alkyl-amino-alkyl, a trialkylammonioalkyl group, an aryl-alkyl, or a non-aromatic heterocycle-alkyl, with the proviso that R does not include a piperidino moiety.

Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In specific embodiments of the invention, $X_2$ is I.

In particular embodiments of the invention $X_2$ is I, Y is S and $X_4$ is H.

Specific examples of compounds within this group are shown in Table 5A.

Examples of compounds within this group, in which $X_2$ is a halogen, are shown in Table 5A (5A-1 to 5A-19). Table 2M shows $EC_{50}$ values for binding of Hsp90 in JNPL3 brain cells for some of the compounds of Table 5A. All show values of less than 100 nM.

H-II. In some embodiments of compounds in accordance with formula (3), $X_2$ is aryl. In these embodiments, R may be any of the groups disclosed as a substituent at the 9-position nitrogen in this application, or in the various patents and patent applications cited herein. See Table 8.

In some embodiments, when $X_2$ is aryl, R includes a nitrogen heteroatom. In these embodiments, R is suitably an amino-alkyl, a secondary or tertiary alkyl-amino-alkyl, a trialkylammonioalkyl group, an aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino) ethyl, 2-(ethyl, isopropyl amino)ethyl, 3-(isopropyl amino) propyl, 3-(t-butyl-amino)propyl, 2-(isopropyl amino)ethyl, 2-(hydroxyethyl, isopropyl amino)ethyl, 3-(cyclopentylamino)propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In embodiments of formula (2) when $X_2$ is aryl, R has the formula:

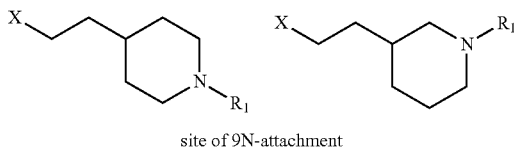

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention when $X_2$ is aryl, R has the formula

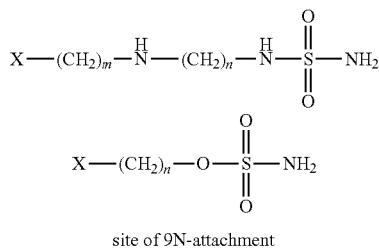

site of 9N-attachment where m=2-3 and n=1-6.

In embodiments when $X_2$ is aryl, R has the formula

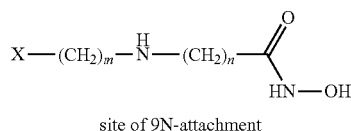

site of 9N-attachment where m=2-3 and n=1-6.

In specific embodiments, $X_2$ is an aromatic heterocycle.

In specific embodiments, $X_2$ is a furan, thiophene, pyrazole, imidazole, pyrrole, oxazole or thiazole.

In specific embodiments, $X_2$ is a furan, thiophene, pyrazole, imidazole, oxazole or thiazole.

In particular embodiments of formula (2), Y is S, $X_4$ is H, $X_2$ is 2-, 3-furan or 5-methyl-2-furanyl.

In particular embodiments of formula (2), Y is $CH_2$, $X_4$ is Cl, $X_2$ is 2-, 3-furan or 5-methyl-2-furanyl.

In particular embodiments of formula (2), Y is $CH_2$, $X_4$ is F, $X_2$ is 2-, 3-furan or 5-methyl-2-furanyl.

In particular embodiments of formula (2), Y is S, $X_4$ is F, $X_2$ is 2-, 3-furan or 5-methyl-2-furanyl.

In particular embodiments of formula (2), Y is S, $X_4$ is H, $X_2$ is 2- or 3-thiophene.

In particular embodiments of formula (2), Y is $CH_2$, $X_4$ is Cl, $X_2$ is 2- or 3-thiophene.

In particular embodiments of formula (2), Y is $CH_2$, $X_4$ is F, $X_2$ is 2- or 3-thiophene.

In particular embodiments of formula (2), Y is S, $X_4$ is F, $X_2$ is 2- or 3-thiophene.

In particular embodiments of formula (2), Y is S, $X_4$ is H, $X_2$ is 2- or 3-pyrazole.

In particular embodiments of formula (2), Y is $CH_2$, $X_4$ is Cl, $X_2$ is 2- or 3-pyrazole.

In particular embodiments of formula (2), Y is $CH_2$, $X_4$ is F, $X_2$ is 2- or 3-pyrazole.

In particular embodiments of formula (2), Y is S, $X_4$ is F, $X_2$ is 2- or 3-pyrazole.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-thiazolyl, 2-oxazolyl or 5-methyl-2-oxazolyl.

In these particular embodiments, R may be any one of the types of groups described above.

Examples of compounds in which $X_2$ is an aryl group containing an oxygen atom in the aryl ring, are shown in Table 5B.

Table 2N shows measured values for $EC_{50}$ in JNPL3 brain cell lysates for compounds 5B-1, 5B-7, 5B-33 and 5B-34 in accordance with this embodiment of the invention which incorporates a fluorine as $X_4$ and in which Y is —$CH_2$— or a hydrogen as $X_4$ and in which Y is S. Desirably low values of $EC_{50}$ were observed.

Examples of compounds in which $X_2$ is an aryl group containing a sulfur atom in the aryl ring are shown in Table 5C.

Examples of compounds in which $X_2$ is a 5-membered aryl rings containing 2 nitrogens in the ring are shown in Table 5D.

Table 2O shows measured values for $EC_{50}$ in JNPL3 brain cell lysates for compounds 5D-2 and 5D-4 in accordance with this embodiment of the invention which incorporates a fluorine as $X_4$ and in which Y is —$CH_2$— or a hydrogen as $X_4$ and in which Y is S. Desirably low values of $EC_{50}$ were observed.

An embodiment of the invention has the structure shown in formula (3), in which Y is —$CH_2$— or S, $X_4$ is hydrogen of fluorine, $X_2$ is $X_2$ is a pyrazolyl, particularly a 3-pyrazolyl, or an imidazolyl. Preferred R groups of this type are as listed above.

H-III. In some embodiments of the invention, $X_2$ is an alkynyl group. In these embodiments, R may be as described above in Section H-II.

In specific embodiments, $X_2$ is acetylene.

In particular embodiments of formula (2), Y is S, $X_4$ is H, $X_2$ is acetylene.

In particular embodiments of formula (2), Y is $CH_2$, $X_4$ is Cl, $X_2$ is acetylene.

In particular embodiments of formula (2), Y is $CH_2$, $X_4$ is F, $X_2$ is acetylene.

In particular embodiments of formula (2), Y is S, $X_4$ is F, $X_2$ is acetylene.

In these particular embodiments, R may be any one of the types of groups described above.

Specific examples of compounds in accordance with this embodiment of the invention are listed in Tables 5E. As shown, in preferred embodiments of formula (2) in which $X_2$ is an alkynyl group, $X_4$ is H, chlorine or fluorine.

H-IV. In some embodiments of the invention, $X_2$ is a cyano group. In these embodiments, R is suitably an amino alkyl, a secondary or tertiary alkyl-amino-alkyl, a trialkylammonio-alkyl group, an aryl-alkyl, or a nonaromatic heterocycle-alkyl, with the proviso that R does not contain a piperidino moiety. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino) propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In a particular preferred embodiment of formula (2), Y is S, $X_4$ is H, $X_2$ is CN.

In a particular preferred embodiment of formula (2), Y is $CH_2$, $X_4$ is Cl, $X_2$ is CN.

In a particular preferred embodiment of formula (2), Y is $CH_2$, $X_4$ is F, $X_2$ is CN.

In a particular preferred embodiment of formula (2), Y is S, $X_4$ is F, $X_2$ is CN.

In other embodiments in which $X_2$ is cyano or cyanoalkyl group, R is

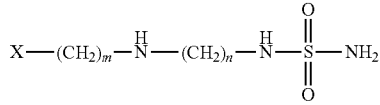

-continued

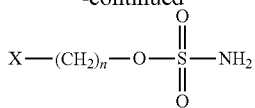

site of 9N-attachment where m=2-3 and n=1-6, or

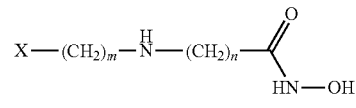

site of 9N-attachment where m=2-3 and n=1-6.

Specific examples of compounds in accordance with this embodiment of the invention are listed in Table 5F.

H-V. In some embodiments of the invention, $X_2$ is an amino group. In these particular embodiments, R may be any of the R groups described in Section H-II.

In a particular preferred embodiment of formula (2), Y is S, $X_4$ is H, $X_2$ is azetidino.

In a particular preferred embodiment of formula (2), Y is $CH_2$, $X_4$ is Cl, $X_2$ is azetidino.

In a particular preferred embodiment of formula (2), Y is $CH_2$, $X_4$ is F, $X_2$ is azetidino.

In a particular preferred embodiment of formula (2), Y is S, $X_4$ is F, $X_2$ is azetidino.

A specific examples of a compounds in accordance with this embodiment of the invention is listed in Table 5G H-VI. In some embodiments of the invention, $X_2$ is a cycloalkyl or cycloalkenyl. In these particular embodiments, R may be any of the R groups described in Section H-II.

In specific embodiments, $X_2$ is a cycloalkyl with one ring.

In specific embodiments, $X_2$ is a cyclopropane, cyclobutane or cyclopentane.

In particular embodiments of formula (2), Y is S, $X_4$ is H, $X_2$ is cyclopentyl.

In particular embodiments of formula (2), Y is $CH_2$, $X_4$ is Cl, $X_2$ is cyclopentyl.

In particular embodiments of formula (2), Y is $CH_2$, $X_4$ is F, $X_2$ is cyclopentyl.

In particular embodiments of formula (2), Y is S, $X_4$ is F, $X_2$ is cyclopentyl.

A specific examples of a compounds in accordance with this embodiment of the invention is listed in Table 5H I. Structures of Formula 1B in which Xa and/or Xb is a Heteroatom, But not Both O In accordance with a ninth embodiment of the invention, the compounds have general formula 1B, in which one or both of Xa or Xb is a heteroatom such as O, N or S, with the proviso that both of Xa and Xb are not O (see Section H). Specific examples of compounds within this group are shown in Table 6A.

I-I. In some embodiments of compounds in accordance with formula (3), $X_2$ is halogen. In these embodiments, R is suitably an amino-alkyl, a secondary or tertiary alkyl-amino-alkyl, a trialkylammonioalkyl group, an aryl-alkyl, or a non-aromatic heterocycle-alkyl, with the proviso that R is not a piperidino moiety.

Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)-propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In specific embodiments of the invention, $X_2$ is I.

In particular embodiments of the invention $X_2$ is I, Y is S and $X_4$ is H.

I-II. In some embodiments of compounds in accordance with formula (3), $X_2$ is aryl.

In these embodiments, R may be any of the groups disclosed as a substituent at the 9-position nitrogen herein or in the various patents and applications cited above. See Table 8.

In some embodiments, when $X_2$ is aryl, R includes a nitrogen heteroatom.

In these embodiments, R is suitably an amino alkyl, a secondary or tertiary alkyl-amino-alkyl, a trialkylammonio-alkyl group, aryl-alkyl, or a nonaromatic heterocycle-alkyl. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine) ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In embodiments of formula (2) when $X_2$ is aryl, R has the formula:

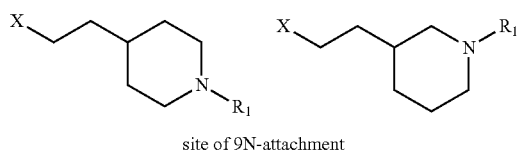

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention when $X_2$ is aryl, R has the formula

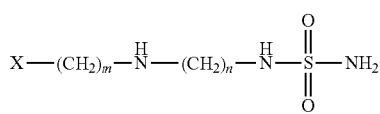

-continued

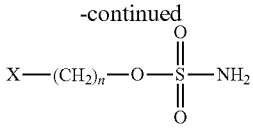

site of 9N-attachment where m=2-3 and n=1-6.

In embodiments when $X_2$ is aryl, R has the formula

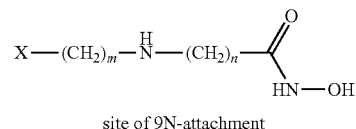

site of 9N-attachment where m=2-3 and n=1-6.

In specific embodiments, $X_2$ is an aromatic heterocycle.

In specific embodiments, $X_2$ is a furan, thiophene, pyrazole, imidazole, pyrrole, oxazole or thiazole.

In specific embodiments, $X_2$ is a furan, thiophene, pyrazole, imidazole, oxazole or thiazole.

In particular embodiments of formula (2), Y is S, $X_4$ is H, $X_2$ is 2-, 3-furan or 5-methyl-2-furanyl.

In particular embodiments of formula (2), Y is $CH_2$, $X_4$ is Cl, $X_2$ is 2-, 3-furan or 5-methyl-2-furanyl.

In particular embodiments of formula (2), Y is $CH_2$, $X_4$ is F, $X_2$ is 2-, 3-furan or 5-methyl-2-furanyl.

In particular embodiments of formula (2), Y is S, $X_4$ is F, $X_2$ is 2-, 3-furan or 5-methyl-2-furanyl.

In particular embodiments of formula (2), Y is S, $X_4$ is H, $X_2$ is 2- or 3-thiophene.

In particular embodiments of formula (2), Y is $CH_2$, $X_4$ is Cl, $X_2$ is 2- or 3-thiophene.

In particular embodiments of formula (2), Y is $CH_2$, $X_4$ is F, $X_2$ is 2- or 3-thiophene.

In particular embodiments of formula (2), Y is S, $X_4$ is F, $X_2$ is 2- or 3-thiophene.

In particular embodiments of formula (2), Y is S, $X_4$ is H, $X_2$ is 2- or 3-pyrazole.

In particular embodiments of formula (2), Y is $CH_2$, $X_4$ is Cl, $X_2$ is 2- or 3-pyrazole.

In particular embodiments of formula (2), Y is $CH_2$, $X_4$ is F, $X_2$ is 2- or 3-pyrazole.

In particular embodiments of formula (2), Y is S, $X_4$ is F, $X_2$ is 2- or 3-pyrazole.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is H, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is Cl, $X_2$ is 2-thiazolyl, 5-methyl-2-thiazolyl, 2-oxazolyl or 5-methyl-2-oxazolyl.

In particular embodiments of formula (2), Y is $CH_2$, $X_4$ is F, $X_2$ is 2-thiazolyl, 5-methyl-2-thiazolyl, 2-oxazolyl or 5-methyl-2-oxazolyl.

In particular embodiments of formula (2), Y is S, $X_4$ is F, $X_2$ is 2-thiazolyl, 5-methyl-2-thiazolyl, 2-oxazolyl or 5-methyl-2-oxazolyl.

In these particular embodiments, R may be any one of the types of groups described above.

I-III. In some embodiments of the invention, $X_2$ is an alkynyl group. In these embodiments, R may be as described above in Section I-II.

In specific embodiments, $X_2$ is acetylene.

In particular embodiments of formula (2), Y is S, $X_4$ is H, $X_2$ is acetylene.

In particular embodiments of formula (2), Y is $CH_2$, $X_4$ is Cl, $X_2$ is acetylene.

In particular embodiments of formula (2), Y is $CH_2$, $X_4$ is F, $X_2$ is acetylene.

In particular embodiments of formula (2), Y is S, $X_4$ is F, $X_2$ is acetylene.

In these particular embodiments, R may be any one of the types of groups described above.

I-IV. In some embodiments of the invention, $X_2$ is a cyano group. In these embodiments, R is suitably an amino alkyl, a secondary or tertiary alkyl-amino-alkyl, a trialkylammonio-alkyl group, an aryl-alkyl, or a nonaromatic heterocycle-alkyl, with the proviso that R does not include a piperidino moiety. Specific R groups include without limitation 2-(methyl, t-butyl-amino)ethyl, 2-(methyl, isopropyl amino)ethyl, 3-(neopentyl amino)propyl, 2-(isobutyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino) propyl, 3-(cyclopentyl, methyl amino)propyl, 3-(ethylamino) propyl, 3-(ethyl, methyl amino)propyl, 2-(neopentyl amino) ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In a particular preferred embodiment of formula (2), Y is S, $X_4$ is H, $X_2$ is CN.

In a particular preferred embodiment of formula (2), Y is $CH_2$, $X_4$ is Cl, $X_2$ is CN.

In a particular preferred embodiment of formula (2), Y is $CH_2$, $X_4$ is F, $X_2$ is CN.

In a particular preferred embodiment of formula (2), Y is S, $X_4$ is F, $X_2$ is CN.

In other embodiments in which $X_2$ is cyano or cyanoalkyl group, R is

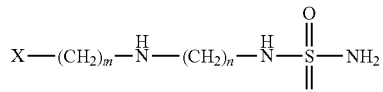

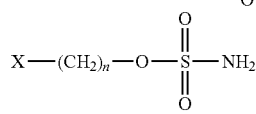

site of 9N-attachment where m=2-3 and n=1-6, or

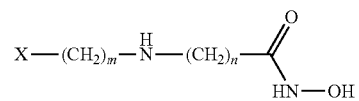

site of 9N-attachment where m=2-3 and n=1-6.

I-V. In some embodiments of the invention, $X_2$ is an amino group. In these particular embodiments, R may be any of the R groups described in Section I-II.

In a particular preferred embodiment of formula (2), Y is S, $X_4$ is H, $X_2$ is aziridino.

In a particular preferred embodiment of formula (2), Y is $CH_2$, $X_4$ is Cl, $X_2$ is aziridino.

In a particular preferred embodiment of formula (2), Y is $CH_2$, $X_4$ is F, $X_2$ is aziridino.

In a particular preferred embodiment of formula (2), Y is S, $X_4$ is F, $X_2$ is aziridino.

J. Structures of Formula 1B in which Xa, Xc, Xd and Xb are All Carbon

In accordance with a tenth embodiment of the invention, the compounds have general formula 1B, in which Xa, Xc, Xd and Xb are all carbon connected by single or double bonds. In these embodiments, R may be any of the groups disclosed as a substituent at the 9-position nitrogen herein or in the various patents and applications cited above. (See Table 8)

In some embodiments, when $X_2$ is aryl, R includes a nitrogen heteroatom.

In these embodiments, R is suitably an aminoalkyl, alkylaminoalkyl, dialkylaminoalkyl, or trialkylammonioalkyl group, in which each alkyl portion may be linear, cyclic or branched, or an alkyl heterocycle, where the alkyl may be bonded to a nitrogen in the heterocyclic group. Specific R groups include without limitation 2-(methyl, t-butyl-amino) ethyl, 2-(methyl, isopropyl amino)ethyl, 3-(neopentyl amino) propyl, 2-(isobutyl-amino)ethyl, 2-(ethyl, isopropyl amino) ethyl, 3-(isopropyl amino)propyl, 3-(t-butyl-amino)propyl, 2-(isopropyl amino)ethyl, 2-(hydroxyethyl, isopropyl amino) ethyl, 3-(cyclopentylamino)propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine) propyl, 2-(methyl, propargyl amine)ethyl, 3-(allyl, methyl amino)propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In embodiments of formula (2) when $X_2$ is aryl, R has the formula:

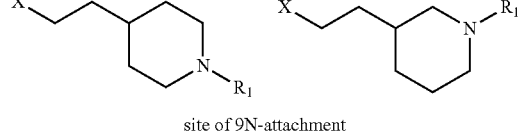

site of 9N-attachment where $R_1$ is selected from COH, COMe, COEt, COnPr, COiPr, $SO_2Me$, $CH_2OX$ where X can be H or oxygen, nitrogen, sulphur or halogen containing alkyl of linear, branched or cyclic nature.

In embodiments of the invention when $X_2$ is aryl, R has the formula $$X-(CH_2)_m-\overset{H}{N}-(CH_2)_n-\overset{H}{N}-\overset{O}{\underset{O}{S}}-NH_2$$

$$X-(CH_2)_n-O-\overset{O}{\underset{O}{S}}-NH_2$$

site of 9N-attachment where m=2-3 and n=1-6.

In embodiments when $X_2$ is aryl, R has the formula $$X-(CH_2)_m-\overset{H}{N}-(CH_2)_n-\overset{O}{\underset{HN-OH}{C}}$$

site of 9N-attachment where m=2-3 and n=1-6.

Specific examples of compounds within this embodiment of the invention are shown in Table 6B.

Table 2P shows measured values for $EC_{50}$ in JNPL3 brain cell lysates for compounds 6B-25 in accordance with this embodiment of the invention which incorporates a hydrogen as $X_4$ and in which. Y is S. Desirably low values of $EC_{50}$ were observed.

K. Structures of Formula 1C

In some embodiments of the present invention having the general formula 1C, the compounds of the invention can be represented by the general formula:

(4)

in which
R1 is alkyl, for example methyl or ethyl,
Y is S or $CH_2$,
$X_4$ is H or halogen,
$X_2$ is saturated or unsaturated non-aromatic carbocycle or heterocycle, aryl, alkylamino, dialkylamino, alkynyl or part of a ring formed by R; and
R is hydrogen, alkyl, alkenyl, or alkynyl, linear, branched or cyclic, optionally including heteroatoms such as N, S or O, optionally connected to the 2'-position to form an 8 to 10 member ring.

In some embodiments, R is suitably an alkylaminoalkyl, dialkylaminoalkyl, or trialkylammonioalkyl group, in which each alkyl portion may be linear, cyclic or branched, or an alkyl heterocycle, where the alkyl may be bonded to a nitrogen in the heterocyclic group. Specific R groups include without limitation 2-(methyl, t-butyl-amino)ethyl, 2-(methyl, isopropyl amino)ethyl, 3-(neopentyl amino)propyl, 2-(isobu- tyl-amino)ethyl, 2-(ethyl, isopropyl amino)ethyl, 3-(isopropyl amino)propyl, 3-(t-butyl-amino)propyl, 2-(isopropyl amino)ethyl, 2-(hydroxyethyl, isopropyl amino)ethyl, 3-(cyclopentylamino)propyl, 3-(cyclopentyl, methyl amino)propyl, 3-(ethylamino)propyl, 3-(ethyl, methyl amino)propyl, 2-(neopentyl amino)ethyl, 3-(methyl, isopropyl amino)propyl, 3-(ethyl, isopropyl amino)propyl, 3-(hydroxyethyl, isopropyl amino)propyl, 3-(methyl, propargyl amine)propyl, 2-(methyl, propargyl amine)ethyl, 3-(allyl, methyl amino) propyl, 3-(propyl, cyclopropylmethyl amino)propane, 3-(hydroxyethyl, cyclohexyl amino)propyl, 2-(cyclopropylmethyl amino)ethyl, 2-(methyl, isobutyl amino)ethyl, 3-(N-morpholino)propyl and 3-(1H-imidazoyl)propyl.

In embodiments of formula (3), R has the formula:

site of 9N-attachment where $R_1$ is selected from COH, COMe, COEt, COnPr, COiPr, $SO_2$Me, $CH_2$OX where X can be H or oxygen, nitrogen, sulphur or halogen containing alkyl of linear, branched or cyclic nature.

In embodiments of formula (3), R has the formula $$X-(CH_2)_m-\overset{H}{N}-(CH_2)_n-\overset{H}{N}-\overset{O}{\underset{O}{S}}-NH_2$$

$$X-(CH_2)_n-O-\overset{O}{\underset{O}{S}}-NH_2$$

site of 9N-attachment where m=2-3 and n=1-6.

In embodiments of formula (3) R has the formula $$X-(CH_2)_m-\overset{H}{N}-(CH_2)_n-\overset{O}{\underset{HN-OH}{C}}$$

site of 9N-attachment where m=2-3 and n=1-6.

In some embodiments, $X_2$ is alkynyl, such as acetylene. Examples of such structures are shown in Table 7A In some embodiments, $X_2$ is cyano or cyanomethyl. Examples of such structures are shown in Table 7B.

In some embodiments, $X_2$ is a heterocycle, including without limitation aziridine, azetidine, oxetane, thietane, tetrahydrofuran, tetrahydropyrrole, tetrahydrothiophane, imidazolidine, oxazolidine, thiazolidine, azirine, oxirine, pyrroline, pyrrole, dihydrofuran, furan, dihydrothiophene, thiophene, pyrazole, imidazole, oxazole, isoxazole, thiazole, isothiazole, 1,2,3-triazole, 1,2,4-triazole, dithiazole, tetrazole, pyridine, pyran, thiine, diazine, thiazine, dioxin, triazine, tetrazine. Examples of such structures are shown in Tables 7C-7F.

Table 2Q shows measured values for $EC_{50}$ in JNPL3 brain and SKBr3 cell lysates for compounds (7A-20, 7C-13, 7D-3 and 7E-6) in accordance with this embodiment of the invention which incorporates a hydrogen as $X_4$ and in which Y is S. Desirably low values of $EC_{50}$ were observed, although $X_2$=OCH$_3$ was observed to be less active than $X_2$=O—CH$_2$—O— in every shown instance: 4C-5 vs 7C-13 (6.5 nM vs 84 nM), 4D-3 vs 7D-3 (18.5 nM vs 240 nM) and 4G-9 vs 7E-6 (5.5 nM vs 32 nM).

L. Structures in which $X_2$ is Alkynyl

In accordance with a further aspect of the present invention, compounds are provided in accordance with any of formulas (1A), (1B) or (1C) in which $X_2$ is alkynyl. In these compounds, Y is CH$_2$, S, O, C=O, C=S, N or any other linking group disclosed in a compound with the same scaffold structure herein or in the patents and patent applications cited above;

$X_4$ is H or halogen or any other group disclosed at this position in a compound with the same scaffold structure herein or in the patents and patent applications cited above;

Xa, Xb, Xc and Xd are any group(s) disclosed at this position herein or in the patents and patent applications cited above; and R is any R group disclosed at this position of the same scaffold structure herein or in the patents and patent applications cited above. (See Table 8)

In some embodiments, Z1, Z2, and Z3 are all nitrogen.

In some embodiments, Z1 and Z3 are nitrogen and Z2 is carbon.

In some embodiments, Z3 is carbon.

M. Structures in which $X_2$ is Furan, Thiophene, Pyrazole, Oxazole or Thiazole

In accordance with a further aspect of the present invention, compounds are provided in accordance with any of formulas (1A), (1B) or (1C) in which $X_2$ is a furan, thiophene, 3-pyrazole, oxazole or thiazole. In these compounds, Y is CH$_2$, S, O, C=O, C=S, N or any other linking group disclosed in a compound with the same scaffold structure herein or in the patents and patent applications cited above;

$X_4$ is H or halogen or any other group disclosed at this position in a compound with the same scaffold structure herein or in the patents and patent applications cited above;

Xa, Xb, Xc and Xd are any group(s) disclosed at this position herein or in the patents and patent applications cited above; and R is any R group disclosed at this position of the same scaffold structure herein or in the patents and patent applications cited above.

In some embodiments, Z1, Z2, and Z3 are all nitrogen.

In some embodiments, Z1 and Z3 are nitrogen and Z2 is carbon.

In some embodiments, Z3 is carbon.

Synthetic Methods

Compounds in accordance with formulas (1A) and (1B) can be made through the application of the following methodologies.

Scheme 1.

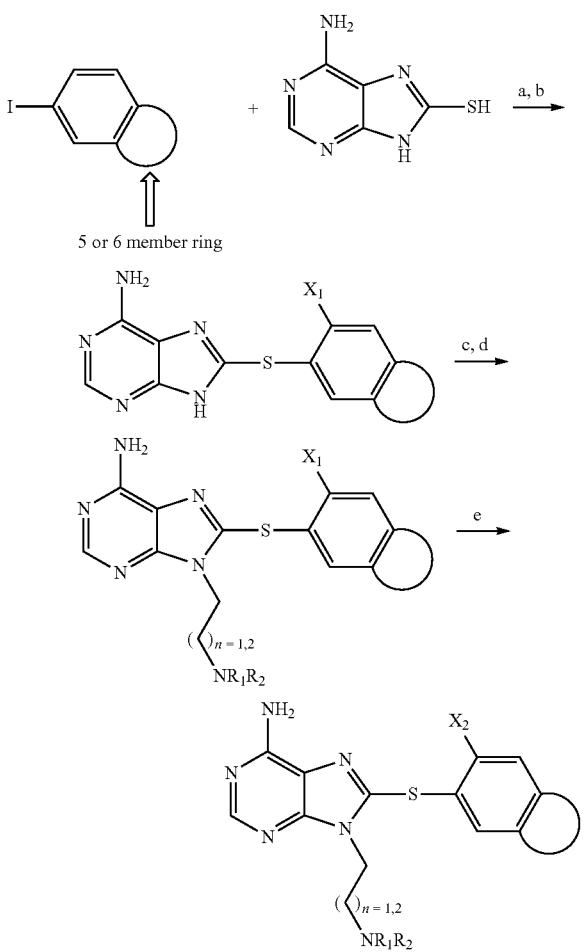

(a) CuI, neocuproine, NaOt-Bu, DMF, 110° C.; (b) NIS, acetonitrile, RT; (c) Cs$_2$CO$_3$, 1,2-dibromoethane or 1,3-dibromopropane; (d) HNR$_1$R$_2$, DMF, rt; (e) X$_2$M, Pd (cat.), DMF, 50-100° C.

Scheme 2.

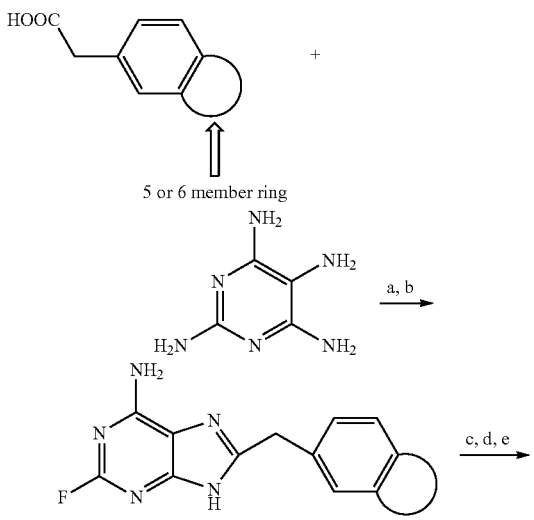

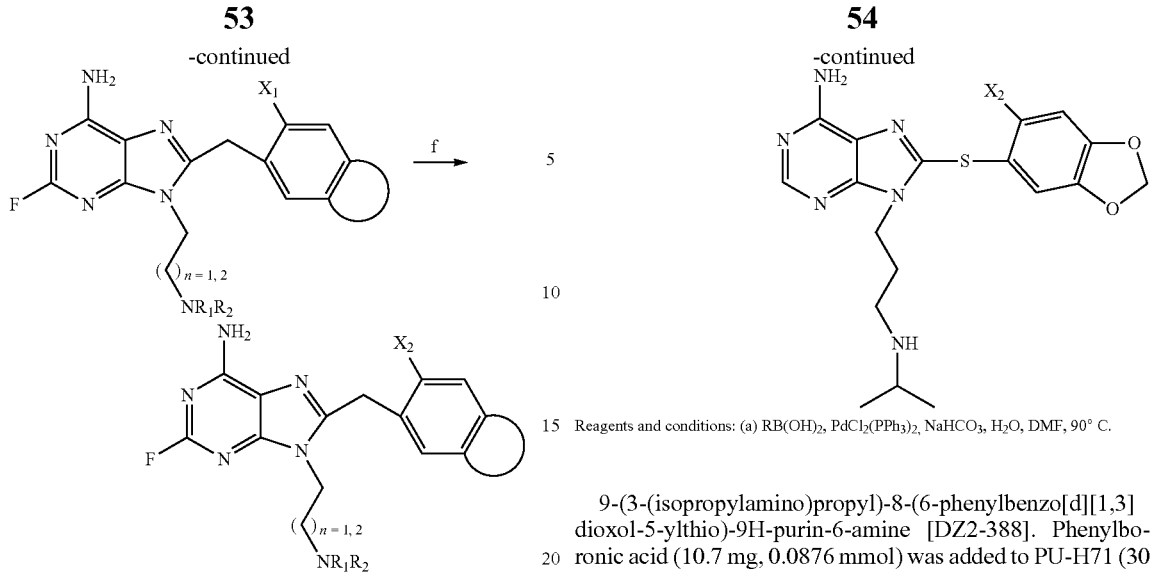

(a) triphenyl phosphite, pyridine, microwave; (b) HF-pyridine, NaNO₂; (c) NIS, acetonitrile, rt; (d) Cs₂CO₃, 1,2-dibromoethane or 1,3-dibromopropane; (e) HNR₁R₂, DMF, rt; (f) X₂M, Pd (cat.), DMF, 50-100° C.

General Methods: $^1$H and $^{13}$C NMR spectra were recorded on a Bruker 500 MHz instrument. Chemical shifts are reported in δ values in ppm downfield from TMS as the internal standard. $^1$H data are reported as follows: chemical shift, multiplicity (s=singlet, d=doublet, t=triplet, q=quartet, br=broad, m=multiplet), coupling constant (Hz), integration. $^{13}$C chemical shifts are reported in δ values in ppm downfield from TMS as the internal standard. High resolution mass spectra were recorded on a Waters LCT Premier system. Low resolution mass spectra were obtained on a Waters Acquity Ultra Performance LC with electrospray ionization and SQ detector. High-performance liquid chromatography analyses were performed on a Waters Autopurification system with PDA, MicroMass ZQ, and ELSD detector, and a reversed phase column (Waters X-Bridge C18, 4.6×150 mm, 5 μm) using a gradient of; method A (a) H₂O+0.1% TFA and (b) CH₃CN+0.1% TFA, 5 to 95% b over 10 minutes at 1.2 mL/min; method B (a) H₂O+0.1% TFA and (b) CH₃CN+0.1% TFA, 20 to 90% b over 16 minutes at 1.0 mL/min. Column chromatography was performed using 230-400 mesh silica gel (EMD).

Specific compounds were synthesized as follows;

Scheme 3. Suzuki coupling of PU-H71.

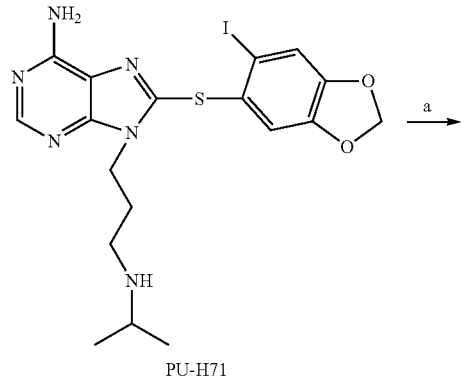

PU-H71

Reagents and conditions: (a) RB(OH)₂, PdCl₂(PPh₃)₂, NaHCO₃, H₂O, DMF, 90° C.

9-(3-(isopropylamino)propyl)-8-(6-phenylbenzo[d][1,3]dioxol-5-ylthio)-9H-purin-6-amine [DZ2-388]. Phenylboronic acid (10.7 mg, 0.0876 mmol) was added to PU-H71 (30 mg, 0.0585 mmol) and NaHCO₃ (14.7 mg, 0.1755 mmol). DMF (0.5 mL) was added and the reaction mixture was evacuated and back filled with nitrogen. This was repeated four times then nitrogen was bubbled through the reaction mixture for 10 minutes. Then H₂O (0.1 mL) and Pd(PPh₃)₂Cl₂ (4 mg, 0.00584 mmol) were added and the reaction mixture was heated under nitrogen at 90° C. for 4 h. Solvent was removed under reduced pressure and the resulting residue was purified by preparatory TLC (CH₂Cl₂:MeOH—NH₃ (7N), 10:1) to give 19.8 mg (73%) of DZ2-388. $^1$H NMR (500 MHz, MeOH-d₄) δ 8.14 (s, 1H), 7.28-7.34 (m, 3H), 7.17-7.21 (m, 2H), 7.12 (s, 1H), 6.90 (s, 1H), 6.09 (s, 2H), 4.03 (t, J=6.4 Hz, 2H), 3.27 (septet, J=6.6 Hz, 1H), 2.72 (t, J=6.6 Hz, 2H), 2.13 (m, 2H), 1.40 (d, J=6.5 Hz, 6H); $^{13}$C NMR (125 MHz, MeOH-d₄) δ 156.0, 153.4, 152.1, 151.1, 150.3, 149.4, 142.3, 141.8, 130.4, 129.1, 128.7, 120.3, 119.8, 115.7, 112.2, 103.8, 52.2, 43.2, 41.1, 27.6, 19.3; HRMS (ESI) m/z [M+H]⁺ calcd. for C₂₄H₂₇N₆O₂S, 463.1916; found. 463.1905; HPLC: method A R$_t$=6.50, method B R$_t$=7.40.

8-(6-(4-tert-butylphenyl)benzo[d][1,3]-dioxol-5-ylthio)-9-(3-(isopropylamino)propyl)-9H-purin-6-amine [DZ2-390]. 4-tert-Butylphenylboronic acid (15.6 mg, 0.0876 mmol) was added to PU-H71 (30 mg, 0.0585 mmol) and NaHCO₃ (14.7 mg, 0.1755 mmol). DMF (0.5 mL) was added and the reaction mixture was evacuated and back filled with nitrogen. This was repeated four times then nitrogen was bubbled through the reaction mixture for 10 minutes. Then H₂O (0.1 mL) and Pd(PPh₃)₂Cl₂ (4 mg, 0.00584 mmol) were added and the reaction mixture was heated under nitrogen at 90° C. for 3 h. Solvent was removed under reduced pressure and the resulting residue was purified by preparatory TLC (hexane:CH₂Cl₂:EtOAc:MeOH—NH₃ (7N), 4:5:2:1) to give 25.0 mg (83%) of DZ2-390. $^1$H NMR (500 MHz, MeOH-d₄) δ 8.11 (s, 1H), 7.27 (d, J=8.4 Hz, 2H), 7.14 (s, 1H), 7.12 (d, J=8.4 Hz, 2H), 6.86 (s, 1H), 6.06 (s, 2H), 3.93 (t, J=6.9 Hz, 2H), 2.92 (septet, J=6.5 Hz, 1H), 2.61 (t, J=7.3 Hz, 2H), 1.86 (m, 2H), 1.28 (s, 9H), 1.12 (d, J=6.5 Hz, 6H); $^{13}$C NMR (125 MHz, MeOH-d₄) δ 155.9, 153.3, 151.9, 151.8, 150.9, 150.2, 149.2, 141.9, 138.8, 130.0, 125.9, 120.4, 120.3, 115.4, 112.3, 103.6, 50.6, 44.0, 41.8, 35.4, 31.8, 29.3, 21.1; HRMS (ESI) m/z [M+H]⁺ calcd. for C₂₈H₃₅N₆O₂S, 519.2542; found. 519.2545; HPLC: method A R$_t$=7.43, method B R$_t$=9.45.

8-(6-(3,5-bis(trifluoromethyl)phenyl)benzo[d][1,3]dioxol-5-ylthio)-9-(3-(isopropylamino)propyl)-9H-purin-6-amine [DZ2-391]. 3,5-Bis(trifluoromethyl)phenylboronic acid (22.6 mg, 0.0877 mmol) was added to PU-H71 (30 mg, 0.0585 mmol) and NaHCO₃ (14.7 mg, 0.1755 mmol). DMF (0.5 mL) was added and the reaction mixture was evacuated and back filled with nitrogen. This was repeated four times then nitrogen was bubbled through the reaction mixture for 10 minutes. Then $H_2O$ (0.1 mL) and $Pd(PPh_3)_2Cl_2$ (4 mg, 0.00584 mmol) were added and the reaction mixture was heated under nitrogen at 90° C. for 3 h. Solvent was removed under reduced pressure and the resulting residue was purified by preparatory TLC (hexane:$CH_2Cl_2$:EtOAc:MeOH—$NH_3$ (7N), 4:5:2:1) to give 24.4 mg (70%) of DZ2-391. $^1$H NMR (500 MHz, $CDCl_3$) δ 8.22 (s, 1H), 7.79 (s, 3H), 7.12 (s, 1H), 6.86 (s, 1H), 6.09 (s, 2H), 5.71 (br s, 2H), 4.07 (t, J=6.6 Hz, 2H), 2.82 (septet, J=6.2 Hz, 1H), 2.49 (t, J=6.5 Hz, 2H), 1.95 (m, 2H), 1.12 (d, J=6.3 Hz, 6H); $^{13}$C NMR (125 MHz, $CDCl_3$) δ 154.1, 152.3, 151.5, 149.6, 148.6, 147.5, 142.1, 137.2, 131.2 (q, J=33 Hz), 129.6, 123.1 (q, J=270 Hz), 121.3, 119.6, 119.4, 114.9, 110.8, 102.4, 49.5, 42.8, 40.6, 28.8, 21.7; HRMS (ESI) m/z [M+H]$^+$ calcd. for $C_{26}H_{25}F_6N_6O_2S$, 599.1664; found. 599.1653; HPLC: method A $R_t$=7.45, method B $R_t$=9.38.

8-(6-(4-(dimethylamino)phenyl)benzo[d][1,3]dioxol-5-ylthio)-9-(3-(isopropylamino)propyl)-9H-purin-6-amine [DZ2-392]. 4-(Dimethylamino)phenylboronic acid (14.5 mg, 0.0877 mmol) was added to PU-H71 (30 mg, 0.0585 mmol) and $NaHCO_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then $H_2O$ (0.1 mL) and $Pd(PPh_3)_2Cl_2$ (4 mg, 0.00584 mmol) were added and the reaction mixture was heated under nitrogen at 90° C. for 3 h. Solvent was removed under reduced pressure and the resulting residue was purified by preparatory TLC (hexane:$CH_2Cl_2$:EtOAc:MeOH—$NH_3$ (7N), 4:5:2:1) to give 25.3 mg (85%) of DZ2-392. $^1$H NMR (500 MHz, $CDCl_3$) δ 8.24 (s, 1H), 7.13 (d, J=8.7 Hz, 2H), 6.93 (s, 1H), 6.83 (s, 1H), 6.67 (d, J=8.7 Hz, 2H), 6.01 (br s, 2H), 5.98 (s, 2H), 4.02 (t, J=6.7 Hz, 2H), 2.97 (s, 6H), 2.78 (septet, J=6.3 Hz, 1H), 2.44 (t, J=6.7 Hz, 2H), 1.87 (m, 2H), 1.10 (d, J=6.3 Hz, 6H); $^{13}$C NMR (125 MHz, $CDCl_3$) δ 154.4, 152.4, 151.5, 149.9, 148.5, 148.0, 147.1, 139.6, 130.0, 127.8, 120.5, 119.7, 112.8, 111.7, 111.0, 101.7, 49.3, 43.1, 40.9, 40.4, 28.9, 21.9; HRMS (ESI) m/z [M+H]$^+$ calcd. for $C_{26}H_{32}N_7O_2S$, 506.2338; found. 506.2330; HPLC: method A $R_t$=5.72, method B $R_t$=5.12.

9-(3-(isopropylamino)propyl)-8-(6-(thiophen-2-yl)benzo[d][1,3]dioxol-5-ylthio)-9H-purin-6-amine [DZ2-395]. 2-Thienylboronic acid (11.2 mg, 0.0877 mmol) was added to PU-H71 (30 mg, 0.0585 mmol) and $NaHCO_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then $H_2O$ (0.1 mL) and $Pd(PPh_3)_2Cl_2$ (4 mg, 0.00584 mmol) were added and the reaction mixture was heated under nitrogen at 90° C. for 5 h. Solvent was removed under reduced pressure and the resulting residue was purified by preparatory TLC ($CH_2Cl_2$:MeOH—$NH_3$ (7N), 12.5:1) to give 12.4 mg (45%) of DZ2-395. $^1$H NMR (500 MHz, $CDCl_3$/MeOH-$d_4$) δ 8.17 (s, 1H), 7.33 (dd, J=1.4, 4.9 Hz, 1H), 7.07 (s, 1H), 7.04 (s, 1H), 7.00-7.02 (m, 2H), 6.09 (s, 2H), 4.12 (t, J=6.6 Hz, 2H), 2.95 (septet, J=6.6 Hz, 1H), 2.62 (t, J=6.8 Hz, 2H), 2.00 (m, 2H), 1.19 (d, J=6.6 Hz, 6H); $^{13}$C NMR (125 MHz, $CDCl_3$/MeOH-$d_4$) δ 154.2, 152.0, 151.1, 149.4, 148.8, 148.4, 140.5, 132.9, 127.8, 126.9, 126.3, 119.2, 119.0, 114.6, 111.8, 102.3, 49.6, 42.5, 40.6, 27.8, 20.7; HRMS (ESI) m/z [M+H]$^+$ calcd. for $C_{22}H_{25}N_6O_2S_2$, 469.1480; found. 469.1461; HPLC: method A $R_t$=6.38, method B $R_t$=7.18.

8-(6-(furan-2-yl)benzo[d][1,3]dioxol-5-ylthio)-9-(3-(isopropylamino)propyl)-9H-purin-6-amine [DZ3-4]. 2-Furanylboronic acid (9.8 mg, 0.0877 mmol) was added to PU-H71 (30 mg, 0.0585 mmol) and $NaHCO_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then $H_2O$ (0.1 mL) and $Pd(PPh_3)_2Cl_2$ (4 mg, 0.00584 mmol) were added and the reaction mixture was heated under nitrogen at 90° C. for 3.5 h. Solvent was removed under reduced pressure and the resulting residue was purified by preparatory TLC ($CH_2Cl_2$:MeOH—$NH_3$ (7N), 12.5:1) to give 19.1 mg (72%) of DZ3-4. $^1$H NMR (500 MHz, $CDCl_3$/MeOH-$d_4$) δ 8.18 (s, 1H), 7.49 (d, J=1.8 Hz, 1H), 7.25 (s, 1H), 6.96 (s, 1H), 6.71 (d, J=3.3 Hz, 1H), 6.47 (dd, J=1.8, 3.2 Hz, 1H), 6.06 (s, 2H), 4.20 (t, J=7.0 Hz, 2H), 2.87 (m, 1H), 2.61 (t, J=6.9 Hz, 2H), 2.00 (m, 2H), 1.14 (d, J=6.3 Hz, 6H); $^{13}$C NMR (125 MHz, $CDCl_3$/MeOH-$d_4$) δ 154.3, 152.2, 151.2, 150.9, 149.5, 148.14, 148.08, 142.4, 129.0, 119.2, 117.5, 114.5, 111.5, 110.0, 109.0, 102.3, 42.8, 41.0, 28.5, 21.2; HRMS (ESI) m/z [M+H]$^+$ calcd. for $C_{22}H_{25}N_6O_3S$, 453.1709; found. 453.1705; HPLC: method A $R_t$=6.23, method B $R_t$=6.82.

9-(3-(isopropylamino)propyl)-8-(6-(4-methoxyphenyl)benzo[d][1,3]dioxol-5-ylthio)-9H-purin-6-amine [DZ3-3]. 4-Methoxyphenylboronic acid (13.3 mg, 0.0877 mmol) was added to PU-H71 (30 mg, 0.0585 mmol) and $NaHCO_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then $H_2O$ (0.1 mL) and $Pd(PPh_3)_2Cl_2$ (4 mg, 0.00584 mmol) were added and the reaction mixture was heated under nitrogen at 90° C. for 4 h. Solvent was removed under reduced pressure and the resulting residue was purified by preparatory TLC ($CH_2Cl_2$:MeOH—$NH_3$ (7N), 12.5:1) to give 20.5 mg (71%) of DZ3-3. $^1$H NMR (500 MHz, $CDCl_3$) δ 8.25 (s, 1H), 7.19 (d, J=8.7 Hz, 2H), 6.95 (s, 1H), 6.86 (d, J=8.7 Hz, 2H), 6.82 (s, 1H), 6.00 (s, 2H), 5.92 (br s, 2H), 4.01 (t, J=6.7 Hz, 2H), 3.82 (s, 3H), 2.75 (septet, J=6.3 Hz, 1H), 2.43 (t, J=6.7 Hz, 2H), 1.85 (m, 2H), 1.07 (d, J=6.3 Hz, 6H); $^{13}$C NMR (125 MHz, $CDCl_3$) δ 159.2, 154.3, 152.5, 151.5, 148.6, 147.8, 147.5, 139.0, 132.5, 130.4, 120.6, 119.8, 113.5, 113.0, 111.0, 101.8, 55.3, 49.1, 43.2, 40.9, 29.2, 22.2; HRMS (ESI) m/z [M+H]$^+$ calcd. for $C_{25}H_{29}N_6O_3S$, 493.2022; found. 493.2010; HPLC: method A $R_t$=6.57, method B $R_t$=7.55.

9-(3-(isopropylamino)propyl)-8-(6-(pyridin-4-yl)benzo[d][1,3]dioxol-5-ylthio)-9H-purin-6-amine [DZ3-5]. 4-Pyridinylboronic acid (10.8 mg, 0.0877 mmol) was added to PU-H71 (30 mg, 0.0585 mmol) and $NaHCO_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then $H_2O$ (0.1 mL) and $Pd(PPh_3)_2Cl_2$ (4 mg, 0.00584 mmol) were added and the reaction mixture was heated under nitrogen at 90° C. for 3.5 h. Solvent was removed under reduced pressure and the resulting residue was purified by preparatory TLC ($CH_2Cl_2$:MeOH—$NH_3$ (7N), 12.5:1) to give 14.8 mg (55%) of DZ3-5. $^1$H NMR (500 MHz, $CDCl_3$/MeOH-$d_4$) δ 8.53 (dd, J=1.6, 4.8 Hz, 2H), 8.19 (s, 1H), 7.25 (dd, J=1.6, 4.5 Hz, 2H), 7.11 (s, 1H), 6.89 (s, 1H), 6.11 (s, 2H), 4.07 (t, J=6.8 Hz, 2H), 2.82 (m, 1H), 2.51 (t, J=6.8 Hz, 2H), 1.91 (m, 2H), 1.13 (d, J=6.3 Hz, 6H); $^{13}$C NMR (125 MHz, $CDCl_3$/MeOH-$d_4$) δ 154.1, 152.0, 151.2, 150.0, 148.90, 148.85, 148.69, 137.9, 124.5, 119.1, 117.7, 115.3, 110.6, 102.5, 49.2, 42.8, 40.7, 28.4, 21.2; HRMS (ESI) m/z [M+H]$^+$ calcd. for $C_{23}H_{26}N_7O_2S$, 464.1869; found. 464.1848; HPLC: method A $R_t$=5.13, method B $R_t$=2.57.

8-(6-(4-bromophenyl)benzo[d][1,3]dioxol-5-ylthio)-9-(3-(isopropylamino)propyl)-9H-purin-6-amine [DZ3-6]. 4-Bromophenylboronic acid (17.6 mg, 0.0877 mmol) was added to PU-H71 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 4:5:2:1) to give 13.9 mg (44%) of DZ3-6. $^1$H NMR (500 MHz, CDCl$_3$) δ 8.23 (s, 1H), 7.44 (d, J=8.2 Hz, 2H), 7.13 (d, J=8.2 Hz, 2H), 7.01 (s, 1H), 6.81 (s, 1H), 6.05 (s, 2H), 5.69 (br s, 2H), 4.08 (t, J=6.0 Hz, 2H), 2.91 (m, 1H), 2.50 (t, J=5.9 Hz, 2H), 1.98 (m, 2H), 1.20 (d, J=6.4 Hz, 6H); $^{13}$C NMR (125 MHz, CDCl$_3$/MeOH-d$_4$) δ 154.2, 152.0, 151.2, 149.8, 149.1, 148.2, 139.8, 139.1, 131.2, 131.0, 122.0, 119.0, 117.9, 115.0, 111.1, 102.4, 50.1, 42.1, 40.2, 27.3, 20.2; HRMS (ESI) m/z [M+H]$^+$ calcd. for C$_{24}$H$_{26}$BrN$_6$O$_2$S, 541.1021/543.1001; found. 541.1016/543.1004; HPLC: method A R$_t$=6.93, method B R$_t$=8.30.

8-(6-(furan-3-yl)benzo[d][1,3]dioxol-5-ylthio)-9-(3-(isopropylamino)propyl)-9H-purin-6-amine [DZ3-27]. 3-Furanylboronic acid (9.8 mg, 0.0877 mmol) was added to PU-H71 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. Solvent was removed under reduced pressure and the resulting residue was purified by preparatory TLC (CH$_2$Cl$_2$:MeOH—NH$_3$ (7N), 20:1) to give 23.9 mg (90%) of DZ3-27. $^1$H NMR (500 MHz, CDCl$_3$/MeOH-d$_4$) δ 8.17 (s, 1H), 7.51 (s, 1H), 7.44 (s, 1H), 7.07 (s, 1H), 6.97 (s, 1H), 6.49 (s, 1H), 6.08 (s, 2H), 4.17 (t, J=6.9 Hz, 2H), 2.93 (septet, J=6.4 Hz, 1H), 2.64 (t, J=7.1 Hz, 2H), 2.02 (m, 2H), 1.17 (d, J=6.4 Hz, 6H); $^{13}$C NMR (125 MHz, CDCl$_3$/MeOH-d$_4$) δ 154.1, 151.8, 151.0, 149.7, 149.0, 147.8, 142.6, 140.4, 131.7, 124.2, 118.9, 117.8, 114.8, 111.5, 110.7, 102.1, 49.2, 42.6, 40.6, 28.0, 20.7; HRMS (ESI) m/z [M+H]$^+$ calcd. for C$_{22}$H$_{25}$N$_6$O$_3$S, 453.1709; found. 453.1711; HPLC: method A R$_t$=6.18, method B R$_t$=6.67.

5-(6-(6-amino-9-(3-(isopropylamino)propyl)-9H-purin-8-ylthio)benzo[d][1,3]dioxol-5-yl)furan-2-carbaldehyde [DZ3-33]. 2-Formyl-5-furanylboronic acid (12.3 mg, 0.0877 mmol) was added to PU-H71 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 9.5 mg (34%) of DZ3-33. $^1$H NMR (500 MHz, CDCl$_3$/MeOH-d$_4$) δ 9.57 (s, 1H), 8.18 (s, 1H), 7.36 (d, J=3.8 Hz, 1H), 7.32 (s, 1H), 7.07 (s, 1H), 6.98 (d, J=3.8 Hz, 1H), 6.12 (s, 2H), 4.32 (t, J=6.7 Hz, 2H), 3.31 (septet, J=6.6 Hz, 1H), 2.93 (t, J=6.8 Hz, 2H), 2.30 (m, 2H), 1.42 (d, J=6.6 Hz, 6H); $^{13}$C NMR (125 MHz, CDCl$_3$/MeOH-d$_4$) δ 177.5, 156.8, 154.5, 152.2, 151.9, 151.4, 150.1, 149.7, 148.1, 127.5, 124.3, 119.2, 118.7, 115.7, 112.7, 109.9, 102.9, 51.3, 41.8, 40.4, 26.4, 19.2;

HRMS (ESI) m/z [M+H]$^+$ calcd. for C$_{23}$H$_{25}$N$_6$O$_4$S, 481.1658; found. 481.1657; HPLC: method A R$_t$=5.87, method B R$_t$=5.93.

8-(6-(1H-pyrrol-2-yl)benzo[d][1,3]dioxol-5-ylthio)-9-(3-(isopropylamino)propyl)-9H-purin-6-amine [DZ3-29]. 1-N-Boc-pyrrole-2-boronic acid (18.5 mg, 0.0877 mmol) was added to PU-H71 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. DMF was removed under reduced pressure and to the resulting residue was added CH$_2$Cl$_2$ (1.5 mL) and TFA (0.3 mL). The mixture was stirred for 5 h at rt, then solvent was removed under reduced pressure and the resulting residue was purified by preparatory TLC (hexane:CH$_2$Cl$_2$:EtOAc:MeOH—NH$_3$ (7N), 4:9:2:1) to give 5.8 mg (22%) of DZ3-29. $^1$H NMR (500 MHz, CDCl$_3$/MeOH-d$_4$) δ 8.17 (s, 1H), 7.04 (s, 1H), 7.01 (s, 1H), 6.88 (m, 1H), 6.27 (m, 1H), 6.21 (m, 1H), 6.03 (s, 2H), 4.17 (t, J=6.8 Hz, 2H), 3.29 (septet, J=6.6 Hz, 1H), 2.80 (t, J=6.7 Hz, 2H), 2.15 (m, 2H), 1.41 (d, J=6.6 Hz, 6H); HRMS (ESI) m/z [M+H]$^+$ calcd. for C$_{22}$H$_{26}$N$_7$O$_2$S, 452.1869; found. 452.1872; HPLC: method A R$_t$=6.13, method B R$_t$=6.43.

8-(6-(1H-pyrazol-4-yl)benzo[d][1,3]dioxol-5-ylthio)-9-(3-(isopropylamino)propyl)-9H-purin-6-amine [DZ3-30]. 1-Boc-pyrazole-4-boronic acid pinacol ester (25.8 mg, 0.0877 mmol) was added to PU-H71 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 13.7 mg (53%) of DZ3-30. $^1$H NMR (500 MHz, CDCl$_3$/MeOH-d$_4$) δ 8.17 (s, 1H), 7.58 (s, 2H), 7.10 (s, 1H), 6.95 (s, 1H), 6.06 (s, 2H), 4.08 (t, J=6.9 Hz, 2H), 2.89 (septet, J=6.4 Hz, 1H), 2.57 (t, J=7.2 Hz, 2H), 1.91 (m, 2H), 1.14 (d, J=6.4 Hz, 6H); $^{13}$C NMR (125 MHz, CDCl$_3$/MeOH-d$_4$) δ 154.0, 152.1, 151.2, 149.7, 148.9, 147.5, 133.6, 132.0, 119.8, 119.1, 117.9, 115.3, 110.9, 102.1, 49.2, 42.9, 40.8, 28.3, 21.3; HRMS (ESI) m/z [M+H]$^+$ calcd. for C$_{21}$H$_{25}$N$_8$O$_2$S, 453.1821; found. 453.1819; HPLC: method A R$_t$=5.60, method B R$_t$=4.87.

9-(3-(isopropylamino)propyl)-8-(6-(5-methylfuran-2-yl)benzo[d][1,3]dioxol-5-ylthio)-9H-purin-6-amine [DZ3-35]. 4,4,5,5-Tetramethyl-2-(5-methyl-furan-2-yl)-(1,3,2)dioxaborolane (21.9 mg, 0.1053 mmol) was added to PU-H71 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 4:9:2:1) to give 11.5 mg (42%) of DZ3-35. $^1$H NMR (500 MHz, CDCl$_3$) δ 8.25 (s, 1H), 7.19 (s, 1H), 6.84 (s, 1H), 6.63 (d, J=3.1 Hz, 1H), 6.07 (d, J=2.5 Hz, 1H), 5.98 (s, 2H), 5.93 (br s, 2H), 4.22 (t, J=6.6 Hz, 2H), 2.94 (m, 1H), 2.59 (t, J=6.6 Hz, 2H), 2.34 (s, 3H), 2.05 (m, 2H), 1.20 (d, J=6.3 Hz, 6H); HRMS (ESI) m/z [M+H]+ calcd. for $C_{23}H_{27}N_6O_3S$, 467.1865; found. 467.1869; HPLC: method A $R_t$=6.49, method B $R_t$=7.53.

2-(6-(6-amino-9-(3-(isopropylamino)propyl)-9H-purin-8-ylthio)benzo[d][1,3]dioxol-5-yl)acetonitrile [DZ3-39]. 4-Isoxazoleboronic acid pinacol ester (20.5 mg, 0.1053 mmol) was added to PU-H71 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 10.3 mg (%) of DZ3-39. $^1$H NMR (500 MHz, CDCl$_3$/MeOH-d$_4$) δ 8.17 (s, 1H), 7.14 (s, 1H), 7.12 (s, 1H), 6.10 (s, 2H), 4.35 (t, J=6.9 Hz, 2H), 3.99 (s, 2H), 3.08 (septet, J=6.5 Hz, 1H), 2.82 (t, J=7.0 Hz, 2H), 2.25 (m, 2H), 1.27 (d, J=6.5 Hz, 6H); $^{13}$C NMR (125 MHz, CDCl$_3$/MeOH-d$_4$) δ 154.2, 152.1, 152.0, 151.5, 150.8, 148.6, 147.7, 129.5, 119.2, 117.6, 116.2, 110.3, 102.7, 49.8, 42.5, 40.7, 27.7, 22.9, 20.4; HRMS (ESI) m/z [M+H]+ calcd. for $C_{20}H_{24}N_7O_2S$, 426.1712; found. 426.1712; HPLC: method A $R_t$=5.69, method B $R_t$=4.57.

8-(6-(1H-pyrrol-3-yl)benzo[d][1,3]dioxol-5-ylthio)-9-(3-(isopropylamino)propyl)-9H-purin-6-amine [DZ3-41]. 1-Boc-pyrrole-3-boronic acid pinacol ester (30.9 mg, 0.1053 mmol) was added to PU-H71 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 7.9 mg (30%) of DZ3-41. $^1$H NMR (500 MHz, CDCl$_3$/MeOH-d$_4$) δ 8.16 (s, 1H), 7.02 (s, 1H), 6.99 (s, 1H), 6.86 (m, 1H), 6.76 (m, 1H), 6.21 (m, 1H), 6.02 (s, 2H), 4.07 (t, J=6.9 Hz, 2H), 2.95 (septet, J=6.4 Hz, 1H), 2.59 (t, J=7.1 Hz, 2H), 1.96 (m, 2H), 1.19 (d, J=6.4 Hz, 6H); $^{13}$C NMR (125 MHz, CDCl$_3$/MeOH-d$_4$) δ 154.4, 152.1, 152.0, 151.0, 149.4, 146.7, 135.9, 131.6, 122.1, 119.1, 117.8, 117.5, 114.6, 111.0, 109.2, 101.9, 53.6, 42.6, 40.6, 27.8, 20.6; HRMS (ESI) m/z [M+H]+ calcd. for $C_{22}H_{26}N_7O_2S$, 452.1869; found. 452.1862; HPLC: method A $R_t$=6.02, method B $R_t$=6.27.

9-(3-(isopropylamino)propyl)-8-(6-(1-methyl-1H-pyrazol-5-yl)benzo[d][1,3]dioxol-5-ylthio)-9H-purin-6-amine [DZ3-44]. 1-Methyl-1-H-pyrazole-5-boronic acid pinacol ester (18.2 mg, 0.0877 mmol) was added to PU-H71 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 2 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 20.1 mg (74%) of DZ3-44. $^1$H NMR (500 MHz, CDCl$_3$) δ 8.25 (s, 1H), 7.40 (d, J=1.8 Hz, 1H), 7.05 (s, 1H), 6.80 (s, 1H), 6.08 (s, 2H), 6.06 (d, J=1.8 Hz, 1H), 5.91 (br s, 2H), 4.10 (t, J=6.7 Hz, 2H), 3.67 (s, 3H), 2.85 (septet, J=6.3 Hz, 1H), 2.53 (t, J=6.7 Hz, 2H), 1.97 (m, 2H), 1.13 (d, J=6.3 Hz, 6H); $^{13}$C NMR (125 MHz, CDCl$_3$) δ 154.4, 152.7, 151.7, 149.3, 149.0, 147.0, 140.6, 138.5, 127.7, 123.3, 120.0, 113.8, 111.7, 107.4, 102.5, 49.6, 43.2, 41.1, 37.1, 29.1, 22.0; HRMS (ESI) m/z [M+H]+ calcd. for $C_{22}H_{27}N_8O_2S$, 467.1978; found. 467.1985; HPLC: method A $R_t$=5.74, method B $R_t$=5.20.

8-(6-(1H-pyrazol-3-yl)benzo[d][1,3]dioxol-5-ylthio)-9-(3-(isopropylamino)propyl)-9H-purin-6-amine [DZ3-46]. 1H-pyrazole-3-boronic acid (33 mg, 0.293 mmol) was added to PU-H71 (50 mg, 0.0975 mmol) and NaHCO$_3$ (24.6 mg, 0.293 mmol). DMF (2 mL) was added and the reaction mixture was evacuated and back filled with nitrogen. This was repeated four times then nitrogen was bubbled through the reaction mixture for 10 minutes. Then H$_2$O (0.2 mL) and Pd(PPh$_3$)$_2$Cl$_2$ (7 mg, 0.0098 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 3.7 mg (8%) of DZ3-46. $^1$H NMR (500 MHz, CDCl$_3$/MeOH-d$_4$) δ 8.17 (s, 1H), 7.59 (d, J=2.0 Hz, 1H), 7.10 (s, 1H), 7.07 (s, 1H), 6.38 (d, J=2.0 Hz, 1H), 6.08 (s, 2H), 4.19 (t, J=6.8 Hz, 2H), 3.31 (septet, J=6.6 Hz, 1H), 2.89 (t, J=7.2 Hz, 2H), 2.10 (m, 2H), 1.39 (d, J=6.6 Hz, 6H); $^{13}$C NMR (125 MHz, CDCl$_3$/MeOH-d$_4$) δ 154.5, 152.2, 152.1, 150.7, 149.5, 148.5, 148.3, 119.3, 119.1, 114.6, 114.5, 111.0, 110.9, 106.1, 102.3, 51.1, 41.7, 40.3, 26.0, 18.7; HRMS (ESI) m/z [M+H]+ calcd. for $C_{21}H_{25}N_8O_2S$, 453.1821; found. 453.1826; HPLC: method A $R_t$=5.65, method B $R_t$=4.83.

9-(3-(isopropylamino)propyl)-8-(6-(isoxazol-4-yl)benzo[d][1,3]dioxol-5-ylthio)-9H-purin-6-amine [DZ3-49]. 4-Isoxazoleboronic acid pinacol ester (20.5 mg, 0.1053 mmol) was added to PU-H71 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 60° C. for 4 h. Solvent was removed under reduced pressure and the resulting residue was attempted to be purified by preparatory TLC (hexane:CH$_2$Cl$_2$:EtOAc:MeOH—NH$_3$ (7N), 4:7:2:1) to give 7.4 mg (28%) of an inseparable mixture of DZ3-49 and DZ3-39 in a ratio of approximately 71:29, respectively, as determined by HPLC. $^1$H NMR (500 MHz, CDCl$_3$/MeOH-d$_4$) δ 8.66 (s, 1H), 8.45 (s, 1H), 8.17 (s, 1H), 7.18 (s, 1H), 7.01 (s, 1H), 6.13 (s, 2H), 4.37 (t, J=7.0 Hz, 2H), 3.27 (septet, J=7.1 Hz, 1H), 2.89 (t, J=7.1 Hz, 2H), 2.22 (m, 2H), 1.38 (d, J=6.5 Hz, 6H); MS (ESI) m/z [M+H]+ 454.1; HPLC: method A $R_t$=5.67 (DZ3-39, 29%) and 5.87 (DZ3-49, 71%); method B $R_t$=4.58 (DZ3-39, 34%) and 5.57 (DZ3-49, 66%).

4-(6-(6-amino-9-(3-(isopropylamino)propyl)-9H-purin-8-ylthio)benzo[d][1,3]dioxol-5-yl)benzaldehyde [DZ3-50]. 4-Formylphenylboronic acid (13 mg, 0.0877 mmol) was added to PU-H71 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 4 h. Solvent was removed under reduced pressure and the resulting residue was purified by preparatory TLC (hexane: CH$_2$Cl$_2$:EtOAc:MeOH—NH$_3$ (7N), 2:2:1:0.5) to give 18.8 mg (66%) of DZ3-50. $^1$H NMR (500 MHz, MeOH-d$_4$) δ 10.01 (s, 1H), 8.15 (s, 1H), 7.85 (d, J=8.1 Hz, 2H), 7.47 (d, J=8.1 Hz, 2H), 7.14 (s, 1H), 6.93 (s, 1H), 6.13 (s, 2H), 4.05 (t, J=6.8 Hz, 2H), 2.99 (septet, J=6.4 Hz, 1H), 2.62 (t, J=6.9 Hz, 2H), 1.99 (m, 2H), 1.24 (d, J=6.4 Hz, 6H); $^{13}$C NMR (125 MHz, MeOH-d$_4$) δ 192.3, 154.1, 151.9, 151.0, 149.8, 148.8, 148.5, 146.4, 139.5, 135.3, 130.0, 129.4, 119.0, 117.7, 115.0, 110.8, 102.4, 49.9, 42.2, 40.3, 27.4, 20.2; HRMS (ESI) m/z [M+H]$^+$ calcd. for $C_{25}H_{27}N_6O_3S$, 491.1865; found. 491.1877; HPLC: method A R$_t$=6.23, method B R$_t$=6.83.

tert-Butyl 6-(3-(6-amino-8-(6-(3,5-bis(trifluoromethyl)phenyl)benzo[d][1,3]dioxol-5-ylthio)-9H-purin-9-yl)propylamino)hexylcarbamate [TT-V-43A]. Bis(trifluoromethyl)phenylboronic acid (22.7 mg, 0.0878 mmol) was added to PU-H71-C6-linker (39.2 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 3 h. Solvent was removed under reduced pressure and the resulting residue was purified by preparatory TLC (hexane:CH$_2$Cl$_2$:MeOH—NH$_3$ (7N), 10:1) to give 27.7 mg (63%) of TT-V-43A. $^1$H NMR (500 MHz, CDCl$_3$) δ 8.17 (s, 1H), 7.78 (s, 3H), 7.14 (s, 1H), 6.89 (s, 1H), 6.12 (s, 2H), 5.80 (br s, 2H), 4.68 (br s, 1H), 4.16 (t, J=6.3 Hz, 2H), 3.10 (m, 2H), 2.81 (t, J=7.7 Hz, 2H), 2.67 (t, J=6.2 Hz, 2H), 2.21 (m, 2H), 1.81 (m, 2H), 1.30-1.53 (m, 15H); HRMS (ESI) m/z [M+H]$^+$ calcd. for $C_{34}H_{40}F_6N_7O_4S$, 756.2767; found. 756.2753; HPLC: method A R$_t$=8.17, method B R$_t$=11.00.

$N^1$-(3-(6-amino-8-(6-(3,5-bis(trifluoromethyl)phenyl)benzo[d][1,3]dioxol-5-ylthio)-9H-purin-9-yl)propyl)hexane-1,6-diamine [TT-V-47B]. TT-V-43A (26 mg, 0.0344 mmol) was dissolved in CH$_2$Cl$_2$ (1.2 mL) and TFA (0.3 mL) was added and stirred at rt for 45 min. Then solvent was removed under reduced pressure and residue dried under high vacuum for 2 h to give TT-V-47B. Purified by preparatory TLC (hexane:CH$_2$Cl$_2$:MeOH—NH$_3$ (7N), 7:1) to give mg (%) of TT-V-47B. $^1$H NMR (500 MHz, CDCl$_3$/MeOH-d$_4$) δ 8.04 (s, 1H), 7.67 (s, 1H), 7.64 (s, 2H), 7.12 (s, 1H), 6.84 (s, 1H), 6.04 (s, 2H), 3.97 (t, J=6.7 Hz, 2H), 2.85 (t, J=7.0 Hz, 2H), 2.84 (t, J=6.9 Hz, 2H), 2.77 (t, J=7.0 Hz, 2H), 2.06 (m, 2H), 1.71 (m, 2H), 1.63 (m, 2H), 1.28 (m, 4H); HRMS (ESI) m/z [M+H]$^+$ calcd. for $C_{29}H_{32}F_6N_7O_2S$, 656.2242; found. 656.2242; HPLC: method A R$_t$=6.98, method B R$_t$=8.38.

Scheme 4. Suzuki coupling of PU-DZ13.

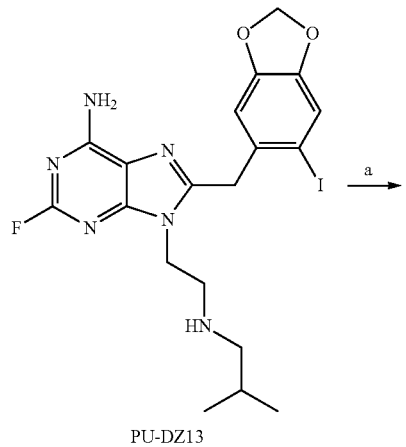

PU-DZ13

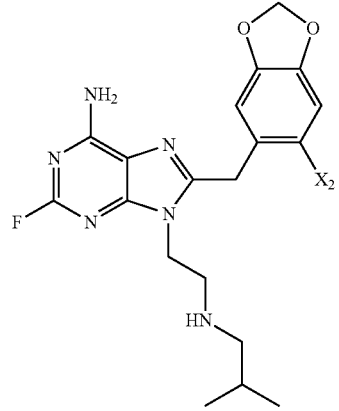

Reagents and conditions: (a) RB(OH)$_2$, PdCl$_2$(PPh$_3$)$_2$, NaHCO$_3$, H$_2$O, DMF, 90° C.

2-fluoro-8-((6-(furan-2-yl)benzo[d][1,3]dioxol-5-yl)methyl)-9-(2-(isobutylamino)ethyl)-9H-purin-6-amine [DZ3-25]. 2-Furanylboronic acid (9.8 mg, 0.0877 mmol) was added to PU-DZ13 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. Solvent was removed under reduced pressure and the resulting residue was purified by preparatory TLC (CH$_2$Cl$_2$:MeOH—NH$_3$ (7N), 20:1) to give 19.1 mg (72%) of DZ3-25. $^1$H NMR (500 MHz, CDCl$_3$/MeOH-d$_4$) δ 7.46 (d, J=1.4 Hz, 1H), 7.08 (s, 1H), 6.64 (s, 1H), 6.46 (dd, J=1.4, 3.2 Hz, 1H), 6.34 (d, J=3.2 Hz, 1H), 6.00 (s, 2H), 4.34 (s, 2H), 4.08 (t, J=6.3 Hz, 2H), 2.85 (t, J=6.3 Hz, 2H), 2.38 (d, J=6.8 Hz, 2H), 1.70 (m, 1H), 0.88 (d, J=6.7 Hz, 6H); $^{13}$C NMR (125 MHz, CDCl$_3$/MeOH-d$_4$) δ 158.9 (d, J=208.5 Hz), 156.2 (d, J=20.2 Hz), 152.6, 152.3 (d, J=18.3 Hz), 151.9, 147.9, 147.1, 142.1, 126.1, 124.3, 115.8, 111.3, 110.0, 108.7, 108.2, 101.6, 57.0, 48.1, 42.3, 32.0, 27.7, 20.2; HRMS (ESI) m/z [M+H]$^+$ calcd. for $C_{23}H_{26}FN_6O_3$, 453.2050; found. 453.2041; HPLC: method A R$_t$=7.10, method B R$_t$=8.52.

2-fluoro-8-((6-(furan-3-yl)benzo[d][1,3]dioxol-5-yl)methyl)-9-(2-(isobutylamino)ethyl)-9H-purin-6-amine [DZ3-26]. 3-Furanylboronic acid (9.8 mg, 0.0877 mmol) was added to PU-DZ13 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. Solvent was removed under reduced pressure and the resulting residue was purified by preparatory TLC (CH$_2$Cl$_2$:MeOH—NH$_3$ (7N), 20:1) to give 23.4 mg (88%) of DZ3-26. $^1$H NMR (500 MHz, CDCl$_3$) δ 7.49 (m, 1H), 7.46 (m, 1H), 6.82 (s, 1H), 6.63 (s, 1H), 6.46 (m, 1H), 5.96 (s, 2H), 5.70 (br s, 2H), 4.22 (s, 2H), 3.91 (t, J=6.1 Hz, 2H), 2.75 (t, J=6.1 Hz, 2H), 2.29 (d, J=6.5 Hz, 2H), 1.70 (m, 1H), 0.83 (d, J=6.7 Hz, 6H); $^{13}$C NMR (125 MHz, CDCl$_3$) δ 158.9 (d, J=208.5 Hz), 156.2 (d, J=20.3 Hz), 152.7 (d, J=18.2 Hz), 152.2, 147.5, 146.9, 143.1, 140.1, 127.0, 125.7, 124.7, 116.6, 111.8, 110.2, 109.4, 101.4, 57.5, 48.5, 43.0, 31.9, 28.1, 20.4; HRMS (ESI) m/z [M+H]$^+$ calcd. for $C_{23}H_{26}FN_6O_3$, 453.2050; found. 453.2044; HPLC: method A R$_t$=7.10, method B R$_t$=8.50.

8-((6-(1H-pyrrol-2-yl)benzo[d][1,3]dioxol-5-yl)methyl)-2-fluoro-9-(2-(isobutylamino)ethyl)-9H-purin-6-amine [DZ3-31]. 1-N-Boc-pyrrole-2-boronic acid (18.5 mg, 0.0877 mmol) was added to PU-DZ13 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. DMF was removed under reduced pressure and to the resulting residue was added CH$_2$Cl$_2$ (1.5 mL) and TFA (0.3 mL). The mixture was stirred for 5 h at rt, then solvent was removed under reduced pressure and the resulting residue was purified by preparatory TLC (hexane:CH$_2$Cl$_2$:EtOAc:MeOH—NH$_3$ (7N), 4:15:2:1) to give 5.2 mg (20%) of DZ3-31. $^1$H NMR (500 MHz, CDCl$_3$/MeOH-d$_4$) δ 6.91 (s, 1H), 6.84 (dd, J=1.4, 2.5 Hz, 1H), 6.65 (s, 1H), 6.22 (m, 1H), 6.08 (dd, J=1.4, 3.3 Hz, 1H), 5.97 (s, 2H), 4.26 (s, 2H), 4.06 (t, Hz, 2H), 2.80 (t, J=6.7 Hz, 2H), 2.55 (d, J=7.0 Hz, 2H), 1.88 (m, 1H), 0.96 (d, J=6.7 Hz, 6H); $^{13}$C NMR (125 MHz, CDCl$_3$/MeOH-d$_4$) δ 158.8 (d, J=208.1 Hz), 156.4 (d, J=20.0 Hz), 152.9, 152.3 (d, J=21.2 Hz), 147.4, 129.8, 127.9, 126.7, 118.5, 110.5, 109.3, 108.7, 108.6, 101.5, 56.6, 47.4, 41.1, 31.6, 27.1, 20.2; HRMS (ESI) m/z [M+H]$^+$ calcd. for C$_{23}$H$_{27}$FN$_7$O$_2$, 452.2210; found. 452.2212; HPLC: method A R$_t$=7.02, method B R$_t$=8.30.

5-(6-((6-amino-2-fluoro-9-(2-(isobutylamino)ethyl)-9H-purin-8-yl)methyl)benzo[d][1,3]dioxol-5-yl)furan-2-carbaldehyde [DZ3-34]. 2-Formyl-5-furanylboronic acid (12.3 mg, 0.0877 mmol) was added to PU-DZ13 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (4 mg, 0.00584 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 2.0 mg (7%) of DZ3-34. $^1$H NMR (500 MHz, CDCl$_3$/MeOH-d$_4$) δ 9.47 (s, 1H), 7.27 (d, J=3.7 Hz, 1H), 7.20 (s, 1H), 6.77 (s, 1H), 6.63 (d, J=3.7 Hz, 1H), 6.06 (s, 2H), 4.45 (s, 2H), 4.32 (t, J=6.3 Hz, 2H), 2.83 (t, J=6.3 Hz, 2H), 2.54 (d, J=6.8 Hz, 2H), 1.83 (m, 1H), 0.93 (d, J=6.7 Hz, 6H); HRMS (ESI) m/z [M+H]$^+$ calcd. for C$_{24}$H$_{26}$FN$_6$O$_4$, 481.2000; found. 481.1984; HPLC: method A R$_t$=6.61, method B R$_t$=7.62.

8-((6-(1H-pyrazol-4-yl)benzo[d][1,3]dioxol-5-yl)methyl)-2-fluoro-9-(2-(isobutylamino)ethyl)-9H-purin-6-amine [DZ3-32]. 1-Boc-pyrazole-4-boronic acid pinacol ester (25.8 mg, 0.0877 mmol) was added to PU-DZ13 (30 mg, 0.0585 mmol) and NaHCO$_3$ (14.7 mg, 0.1755 mmol). DMF (1.5 mL) was added and the reaction mixture was evacuated and back filled with nitrogen. This was repeated four times then nitrogen was bubbled through the reaction mixture for 10 minutes. Then H$_2$O (0.15 mL) and Pd(PPh$_3$)$_2$Cl$_2$ (4 mg, 0.00584 mmol) were added and the reaction mixture was heated under nitrogen at 90° C. for 5 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 10.6 mg (40%) of DZ3-32. $^1$H NMR (500 MHz, CDCl$_3$/MeOH-d$_4$) δ 7.50 (s, 2H), 6.83 (s, 1H), 6.69 (s, 1H), 5.98 (s, 2H), 4.18 (s, 2H), 4.01 (t, J=6.6 Hz, 2H), 2.78 (t, J=6.6 Hz, 2H), 2.40 (d, J=7.0 Hz, 2H), 1.71 (m, 1H), 0.88 (d, J=6.7 Hz, 6H); $^{13}$C NMR (125 MHz, CDCl$_3$/MeOH-d$_4$) δ 158.6 (d, J=208.3 Hz), 156.3 (d, J=19.6 Hz), 152.3, 152.1 (d, J=21.2 Hz), 147.3, 147.1, 126.4, 126.2, 120.1, 115.8, 110.7, 109.9, 101.4, 56.3, 47.3, 40.8, 31.9, 27.0, 20.0; HRMS (ESI) m/z [M+H]$^+$ calcd. for C$_{22}$H$_{26}$FN$_8$O$_2$, 453.2163; found. 453.2162; HPLC: method A R$_t$=6.23, method B R$_t$=6.55.

2-fluoro-9-(2-(isobutylamino)ethyl)-8-((6-(5-methylfuran-2-yl)benzo[d][1,3]dioxol-5-yl)methyl)-9H-purin-6-amine [DZ3-36]. 4,4,5,5-Tetramethyl-2-(5-methyl-furan-2-yl)-(1,3,2)dioxaborolane (21.9 mg, 0.1053 mmol) was added to PU-DZ13 (30 mg, 0.0585 mmol) and NaHCO$_3$ (14.7 mg, 0.1755 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 4:15:2:1) to give 15.6 mg (57%) of DZ3-36. $^1$H NMR (500 MHz, CDCl$_3$) δ 7.04 (s, 1H), 6.53 (s, 1H), 6.26 (d, J=3.1 Hz, 1H), 6.21 (br s, 2H), 6.05 (d, J=3.1 Hz, 1H), 5.94 (s, 2H), 4.37 (s, 2H), 3.98 (t, J=6.3 Hz, 2H), 2.80 (t, J=6.2 Hz, 2H), 2.34 (s, 3H), 2.31 (d, J=6.8 Hz, 2H), 1.64 (m, 1H), 0.83 (d, J=6.7 Hz, 6H); HRMS (ESI) m/z [M+H]$^+$ calcd. for C$_{24}$H$_{28}$FN$_6$O$_3$, 467.2207; found. 467.2200; HPLC: method A R$_t$=7.29, method B R$_t$=9.13.

8-((6-(1H-pyrrol-3-yl)benzo[d][1,3]dioxol-5-yl)methyl)-2-fluoro-9-(2-(isobutylamino)ethyl)-9H-purin-6-amine [DZ3-38]. 1-Boc-pyrrole-3-boronic acid pinacol ester (30.9 mg, 0.1053 mmol) was added to PU-DZ13 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.2 mL) and Pd(PPh$_3$)$_2$Cl$_2$ (8 mg, 0.0117 mmol) were added and the reaction mixture was heated under nitrogen at 90° C. for 4 h, then at 120° C. for 6.5 h. Solvent was removed under reduced pressure and the resulting residue was purified by preparatory TLC (hexane:CH$_2$Cl$_2$:EtOAc:MeOH—NH$_3$ (7N), 4:7:2:1) to give 20.9 mg (79%) of DZ3-38. $^1$H NMR (500 MHz, CDCl$_3$) δ 8.72 (br s, 1H), 6.85 (s, 1H), 6.83 (m, 1H), 6.76 (m, 1H), 6.62 (s, 1H), 6.34 (br s, 2H), 6.23 (m, 1H), 5.91 (s, 2H), 4.29 (s, 2H), 3.84 (t, J=6.3 Hz, 2H), 2.67 (t, J=6.3 Hz, 2H), 2.28 (d, J=6.8 Hz, 2H), 1.60 (m, 1H), 0.82 (d, J=6.6 Hz, 6H); $^{13}$C NMR (125 MHz, CDCl$_3$) δ 158.8 (d, J=208.0 Hz), 156.4 (d, J=19.8 Hz), 153.0, 152.9 (d, J=21.3 Hz), 146.82, 146.76, 130.0, 126.5, 123.3, 118.4, 116.9, 116.6, 110.6, 109.8, 109.3, 101.3, 57.6, 48.7, 43.0, 32.0, 28.3, 20.7; HRMS (ESI) m/z [M+H]$^+$ calcd. for C$_{23}$H$_{27}$FN$_7$O$_2$, 452.2210; found. 452.2204; HPLC: method A R$_t$=6.77, method B R$_t$=7.93.

2-(6-((6-amino-2-fluoro-9-(2-(isobutylamino)ethyl)-9H-purin-8-yl)methyl)benzo[d][1,3]dioxol-5-yl)acetonitrile [DZ3-40]. 4-Isoxazoleboronic acid pinacol ester (20.5 mg, 0.1053 mmol) was added to PU-DZ13 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 4 h. Solvent was removed under reduced pressure and the resulting residue was purified by preparatory TLC (hexane:CH$_2$Cl$_2$:EtOAc:MeOH—NH$_3$ (7N), 4:7:2:1) to give 8.3 mg (%) of DZ3-40. $^1$H NMR (500 MHz, CDCl$_3$/MeOH-d$_4$) δ 6.94 (s, 1H), 6.70 (s, 1H), 6.00 (s, 2H), 4.39 (t, J=6.7 Hz, 2H), 4.31 (s, 2H), 3.84 (s, 2H), 3.18 (t, J=6.6 Hz, 2H), 2.65 (d, J=7.1 Hz, 2H), 1.94 (m, 1H), 0.99 (d, J=6.7 Hz, 6H); $^{13}$C NMR (125 MHz, CDCl$_3$/MeOH-d$_4$) δ 158.7 (d, J=210.4 Hz), 156.6 (d, J=20.1 Hz), 152.1 (d, J=18.2 Hz), 150.5, 148.1, 147.7, 126.7, 122.4, 117.9, 116.1, 110.6, 109.9, 101.8, 56.5, 47.4, 41.2, 31.3, 27.1, 21.5, 20.0; HRMS (ESI) m/z [M+H]$^+$ calcd. for C$_{21}$H$_{25}$FN$_7$O$_2$, 426.2054; found. 426.2048; HPLC: method A R$_t$=6.48, method B R$_t$=7.10.

8-((6-(1H-pyrazol-3-yl)benzo[d][1,3]dioxol-5-yl)methyl)-2-fluoro-9-(2-(isobutylamino)ethyl)-9H-purin-6-amine [DZ3-43]. 1H-pyrazole-3-boronic acid (11.8 mg, 0.1053 mmol) was added to PU-DZ13 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 4.5 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 3.5 mg (13%) of DZ3-43. $^1$H NMR (500 MHz, CDCl$_3$/MeOH-d$_4$) δ 7.63 (d, J=2.15 Hz, 1H), 6.95 (s, 1H), 6.82 (s, 1H), 6.34 (d, J=2.15 Hz, 1H), 6.01 (s, 2H), 4.35 (t, J=6.8 Hz, 2H), 4.29 (s, 2H), 2.98 (t, J=6.9 Hz, 2H), 2.64 (d, J=7.0 Hz, 2H), 1.96 (m, 1H), 0.99 (d, J=6.7 Hz, 6H); $^{13}$C NMR (125 MHz, CDCl$_3$/MeOH-d$_4$) δ 158.8 (d, J=208.7 Hz), 156.6 (d, J=19.3 Hz), 152.4, 152.2 (d, J=18.7 Hz), 148.3, 147.3, 127.1, 115.94, 115.93, 110.3, 110.1, 105.6, 101.8, 56.3, 47.4, 40.5, 31.5, 27.0, 20.2; HRMS (ESI) m/z [M+H]$^+$ calcd. for C$_{22}$H$_{26}$FN$_8$O$_2$, 453.2163; found. 453.2149; HPLC: method A R$_t$=6.37, method B R$_t$=6.93.

2-fluoro-9-(2-(isobutylamino)ethyl)-8-((6-(1-methyl-1H-pyrazol-5-yl)benzo[d][1,3]dioxol-5-yl)methyl)-9H-purin-6-amine [DZ3-45]. 1-Methyl-1-H-pyrazole-5-boronic acid pinacol ester (18.2 mg, 0.0877 mmol) was added to PU-DZ13 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 2 h. Solvent was removed under reduced pressure and the resulting residue was purified by preparatory TLC (hexane:CH$_2$Cl$_2$:EtOAc:MeOH—NH$_3$ (7N), 4:7:2:1) to give 26.5 mg (97%) of DZ3-45. $^1$H NMR (500 MHz, CDCl$_3$) δ 7.49 (d, J=1.5 Hz, 1H), 6.76 (s, 1H), 6.74 (s, 1H), 6.28 (br s, 2H), 6.17 (d, J=1.5 Hz, 1H), 6.01 (s, 2H), 3.99 (s, 2H), 3.90 (t, J=6.3 Hz, 2H), 3.66 (s, 3H), 2.76 (t, J=6.3 Hz, 2H), 2.31 (d, J=6.8 Hz, 2H), 1.72 (m, 1H), 0.84 (d, J=6.7 Hz, 6H); $^{13}$C NMR (125 MHz, CDCl$_3$) δ 159.0 (d, J=208.7 Hz), 156.4 (d, J=20.0 Hz), 152.8 (d, J=18.5 Hz), 151.5, 149.0, 147.1, 141.3, 138.8, 129.4, 123.4, 116.6, 110.7, 109.9, 106.9, 101.9, 57.8, 48.7, 43.1, 36.9, 31.8, 28.3, 20.6; HRMS (ESI) m/z [M+H]$^+$ calcd. for C$_{23}$H$_{28}$FN$_8$O$_2$, 467.2319; found. 467.2323; HPLC: method A R$_t$=6.37, method B R$_t$=6.90.

2-fluoro-9-(2-(isobutylamino)ethyl)-8-((6-(thiophen-2-yl)benzo[d][1,3]dioxol-5-yl)methyl)-9H-purin-6-amine [DZ3-48]. 2-Thienylboronic acid (11.2 mg, 0.0877 mmol) was added to PU-DZ13 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 90° C. for 2 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 18.3 mg (67%) of DZ3-48. $^1$H NMR (500 MHz, CDCl$_3$/MeOH-d$_4$) δ 7.31 (d, J=5.0 Hz, 1H), 7.03 (dd, J=3.1, 5.0 Hz, 1H), 6.92 (s, 1H), 6.87 (d, J=3.0 Hz, 1H), 6.74 (s, 1H), 6.01 (s, 2H), 4.19 (s, 2H), 3.99 (t, J=6.5 Hz, 2H), 2.78 (t, J=6.5 Hz, 2H), 2.37 (d, J=6.9 Hz, 2H), 1.70 (m, 1H), 0.88 (d, J=6.7 Hz, 6H); $^{13}$C NMR (125 MHz, CDCl$_3$/MeOH-d$_4$) δ 158.7 (d, J=209.4 Hz), 156.4 (d, J=19.6 Hz), 152.21 (d, J=18.4 Hz), 152.20, 148.1, 147.0, 141.5, 127.7, 127.3, 127.0, 126.0, 125.8, 115.9, 111.3, 110.0, 101.6, 57.1, 48.1, 42.2, 32.0, 27.8, 20.3; HRMS (ESI) m/z [M+H]$^+$ calcd. for C$_{23}$H$_{26}$FN$_6$O$_2$S, 469.1822; found. 469.1830; HPLC: method A R$_t$=7.21, method B R$_t$=8.93.

2-fluoro-9-(2-(isobutylamino)ethyl)-8-((6-(isoxazol-4-yl)benzo[d][1,3]dioxol-5-yl)methyl)-9H-purin-6-amine [DZ3-51]. 4-Isoxazoleboronic acid pinacol ester (20.5 mg, 0.1053 mmol) was added to PU-DZ13 (30 mg, 0.0585 mmol) and NaHCO$_3$ (14.7 mg, 0.1755 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0117 mmol) were added and the reaction mixture was heated under nitrogen at 60° C. for 4 h. Solvent was removed under reduced pressure and the resulting residue was purified by preparatory TLC (hexane:CH$_2$Cl$_2$:EtOAc:MeOH—NH$_3$ (7N), 2:2:1:0.5) to give 7.8 mg (29%) of an inseparable mixture of DZ3-51 and DZ3-40 in a ratio of approximately 44:56, respectively, as determined by HPLC. MS (ESI) m/z [M+H]$^+$ 454.4; HPLC: method A R$_t$=6.46 (DZ3-40, 56%) and 6.65 (DZ3-51, 44%); method B R$_t$=7.08 (DZ3-40, 65%) and 7.52 (DZ3-51, 35%).

Scheme 5. Suzuki coupling of PU-HZ151.

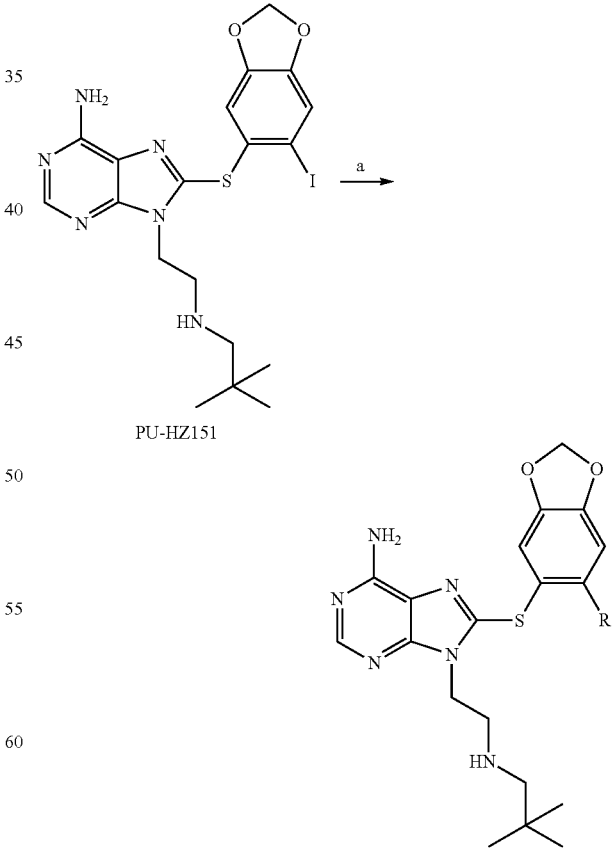

Reagents and conditions: (a) RB(OH)$_2$, PdCl$_2$(PPh$_3$)$_2$, NaHCO$_3$, H$_2$O, DMF, 90° C.

8-(6-(furan-2-yl)benzo[d][1,3]dioxol-5-ylthio)-9-(2-(neopentylamino)ethyl)-9H-purin-6-amine [TT5-53A]. 2-Furanylboronic acid (42.4 mg, 0.379 mmol) was added to PU-HZ151 (66.4 mg, 0.126 mmol) and NaHCO$_3$ (63.6 mg, 0.756 mmol). DMF (2 mL) was added and the reaction mixture was evacuated and back filled with nitrogen. This was repeated four times then nitrogen was bubbled through the reaction mixture for 10 minutes. Then H$_2$O (0.4 mL) and Pd(PPh$_3$)$_2$Cl$_2$ (17.6 mg, 0.025 mmol) were added and the reaction mixture was heated under nitrogen at 90° C. for 3.5 h. Solvent was removed under reduced pressure and the resulting residue was purified by preparatory TLC (CH$_2$Cl$_2$:MeOH—NH$_3$ (7N), 20:1) to give 25.2 mg (43%) of TT5-53A. $^1$H NMR (500 MHz, CDCl$_3$) δ 8.30 (s, 1H), 7.49 (d, J=1.3 Hz, 1H), 7.17 (s, 1H), 6.84 (s, 1H), 6.75 (d, J=3.3 Hz, 1H), 6.48 (dd, J=1.8, 3.3 Hz, 1H), 5.97 (s, 2H), 5.89 (br s, 2H), 4.18 (t, J=6.5 Hz, 2H), 2.86 (t, J=6.5 Hz, 2H), 2.25 (s, 2H), 0.83 (s, 9H); $^{13}$C NMR (125 MHz, CDCl$_3$) δ 154.6, 153.0, 151.7, 151.1, 148.4, 147.9, 146.8, 142.2, 127.2, 120.8, 120.0, 112.8, 111.5, 110.0, 108.7, 101.9, 61.9, 49.6, 43.9, 31.5, 27.6; HRMS (ESI) m/z [M+H]$^+$ calcd. for C$_{23}$H$_{27}$N$_6$O$_3$S, 467.1865; found. 467.1870; HPLC: method A R$_t$=6.78, method B R$_t$=7.83.

8-(6-(5-methylfuran-2-yl)benzo[d][1,3]dioxol-5-ylthio)-9-(2-(neopentylamino)ethyl)-9H-purin-6-amine [DZ3-56]. 4,4,5,5-Tetramethyl-2-(5-methyl-furan-2-yl)-(1,3,2)dioxaborolane (17.7 mg, 0.0853 mmol) was added to PU-HZ151 (30 mg, 0.0569 mmol) and NaHCO$_3$ (14.3 mg, 0.1707 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0113 mmol) were added and the reaction mixture was heated under nitrogen at 90° C. for 4.5 h. Solvent was removed under reduced pressure and the resulting residue was purified by preparatory TLC (CH$_2$Cl$_2$:MeOH—NH$_3$ (7N), 15:1) to give 9.3 mg (34%) of DZ3-56. $^1$H NMR (500 MHz, CDCl$_3$/MeOH-d$_4$) δ 8.19 (s, 1H), 7.24 (s, 1H), 6.89 (s, 1H), 6.62 (d, J=3.2 Hz, 1H), 6.05 (d, J=3.2 Hz, 1H), 6.03 (s, 2H), 4.36 (t, J=6.0 Hz, 2H), 3.04 (t, J=6.0 Hz, 2H), 2.47 (s, 2H), 2.33 (s, 3H), 0.95 (s, 9H); $^{13}$C NMR (125 MHz, CDCl$_3$/MeOH-d$_4$) δ 154.5, 152.4, 152.3, 151.2, 149.4, 149.2, 148.5, 147.7, 129.1, 119.4, 117.4, 114.3, 111.2, 108.6, 107.8, 102.2, 61.4, 49.3, 43.2, 31.4, 27.7, 13.7; HRMS (ESI) m/z [M+H]$^+$ calcd. for C$_{24}$H$_{29}$N$_6$O$_3$S, 481.2022; found. 481.2002; HPLC: method A R$_t$=6.89, method B R$_t$=7.58.

9-(2-(neopentylamino)ethyl)-8-(6-(thiophen-2-yl)benzo[d][1,3]dioxol-5-ylthio)-9H-purin-6-amine [DZ3-58]. 2-Thiopheneboronic acid (10.9 mg, 0.0853 mmol) was added to PU-HZ151 (30 mg, 0.0569 mmol) and NaHCO$_3$ (14.3 mg, 0.1707 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0113 mmol) were added and the reaction mixture was heated under nitrogen at 90° C. for 4 h. Solvent was removed under reduced pressure and the resulting residue was purified by preparatory TLC (CH$_2$Cl$_2$:MeOH—NH$_3$ (7N), 20:1) to give 16.0 mg (58%) of DZ3-58. $^1$H NMR (500 MHz, CDCl$_3$/MeOH-d$_4$) δ 8.18 (s, 1H), 7.32 (dd, J=1.6, 4.7 Hz, 1H), 6.98-7.03 (m, 4H), 6.07 (s, 2H), 4.29 (t, J=5.4 Hz, 2H), 3.03 (t, J=5.4 Hz, 2H), 2.48 (s, 2H), 0.97 (s, 9H); $^{13}$C NMR (125 MHz, CDCl$_3$/MeOH-d$_4$) δ 154.3, 152.0, 150.8, 149.2, 148.9, 148.3, 140.5, 132.5, 127.8, 127.0, 126.3, 120.1, 119.2, 114.4, 111.8, 102.2, 61.1, 49.0, 42.9, 31.2, 27.6; HRMS (ESI) m/z [M+H]$^+$ calcd. for C$_{23}$H$_{27}$N$_6$O$_2$S$_2$, 483.1637; found. 483.1621; HPLC: method A R$_t$=7.14, method B R$_t$=7.73.

8-(6-(1H-pyrrol-3-yl)benzo[d][1,3]dioxol-5-ylthio)-9-(2-(neopentylamino)ethyl)-9H-purin-6-amine [DZ3-59]. 1-Boc-pyrrole-3-boronic acid pinacol ester (25 mg, 0.0853 mmol) was added to PU-HZ151 (30 mg, 0.0569 mmol) and NaHCO$_3$ (14.3 mg, 0.1707 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0113 mmol) were added and the reaction mixture was heated under nitrogen at 90° C. for 4 h. Solvent was removed under reduced pressure and the resulting residue was purified by preparatory TLC (CH$_2$Cl$_2$:MeOH—NH$_3$ (7N), 20:1) to give 10.1 mg (38%) of DZ3-59. $^1$H NMR (500 MHz, CDCl$_3$/MeOH-d$_4$) δ 8.15 (s, 1H), 7.03 (s, 1H), 6.95 (s, 1H), 6.85 (m, 1H), 6.76 (m, 1H), 6.20 (dd, J=1.7, 2.4 Hz, 1H), 6.01 (s, 2H), 4.24 (t, J=5.7 Hz, 2H), 2.98 (t, J=5.7 Hz, 2H), 2.50 (s, 2H), 0.98 (s, 9H); $^{13}$C NMR (125 MHz, CDCl$_3$/MeOH-d$_4$) δ 154.3, 152.1, 149.6, 149.3, 146.8, 135.7, 122.3, 119.3, 118.6, 117.9, 117.4, 114.5, 111.1, 109.4, 101.9, 61.0, 49.3, 42.7, 31.2, 27.7; HRMS (ESI) m/z [M+H]$^+$ calcd. for C$_{23}$H$_{28}$N$_7$O$_2$S, 466.2025; found. 466.2016; HPLC: method A R$_t$=6.86, method B R$_t$=7.20.

8-(6-(furan-3-yl)benzo[d][1,3]dioxol-5-ylthio)-9-(2-(neopentylamino)ethyl)-9H-purin-6-amine [DZ3-60]. 3-Furanylboronic acid (9.5 mg, 0.0853 mmol) was added to PU-HZ151 (30 mg, 0.0569 mmol) and NaHCO$_3$ (14.3 mg, 0.1707 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0113 mmol) were added and the reaction mixture was heated under nitrogen at 90° C. for 4 h. Solvent was removed under reduced pressure and the resulting residue was purified by preparatory TLC (CH$_2$Cl$_2$:MeOH—NH$_3$ (7N), 20:1) to give 13.8 mg (52%) of DZ3-60. $^1$H NMR (500 MHz, CDCl$_3$/MeOH-d$_4$) δ 8.17 (s, 1H), 7.50 (s, 1H), 7.43 (d, J=1.5 Hz, 1H), 7.02 (s, 1H), 6.94 (s, 1H), 6.49 (d, J=1.5 Hz, 1H), 6.06 (s, 2H), 4.29 (t, J=5.9 Hz, 2H), 3.02 (t, J=5.8 Hz, 2H), 2.46 (s, 2H), 0.94 (s, 9H); $^{13}$C NMR (125 MHz, CDCl$_3$/MeOH-d$_4$) δ 154.3, 152.0, 151.1, 149.6, 149.3, 147.9, 142.8, 140.6, 131.5, 124.3, 119.3, 118.8, 114.7, 111.7, 110.9, 102.2, 61.4, 49.1, 43.0, 31.3, 27.6; HRMS (ESI) m/z [M+H]$^+$ calcd. for C$_{23}$H$_{27}$N$_6$O$_3$S, 467.1865; found. 467.1845; HPLC: method A R$_t$=6.65, method B R$_t$=7.09.

8-(6-(1H-pyrazol-3-yl)benzo[d][1,3]dioxol-5-ylthio)-9-(2-(neopentylamino)ethyl)-9H-purin-6-amine [DZ3-61]. 1H-Pyrazole-3-boronic acid (19 mg, 0.1707 mmol) was added to PU-HZ151 (30 mg, 0.0569 mmol) and NaHCO$_3$ (14.3 mg, 0.1707 mmol). DMF (1.2 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (8 mg, 0.0113 mmol) were added and the reaction mixture was heated under nitrogen at 90° C. for 4 h. Solvent was removed under reduced pressure and the resulting residue was purified by preparatory TLC (CH$_2$Cl$_2$:MeOH—NH$_3$ (7N), 15:1) to give 6.5 mg (25%) of DZ3-61. $^1$H NMR (500 MHz, CDCl$_3$/MeOH-d$_4$) δ 8.18 (s, 1H), 7.58 (d, J=2.0 Hz, 1H), 7.05 (s, 2H), 6.40 (d, J=2.0 Hz, 1H), 6.06 (s, 2H), 4.36 (t, J=6.0 Hz, 2H), 3.01 (t, J=6.0 Hz, 2H), 2.51 (s, 2H), 0.97 (s, 9H); $^{13}$C NMR (125 MHz, CDCl$_3$/MeOH-d$_4$) δ 154.6, 152.3, 150.8, 149.4, 148.6, 148.5, 120.1, 119.2, 114.5, 110.9, 106.0, 102.3, 61.2, 49.1, 42.5, 31.1, 27.5; HRMS (ESI)

m/z [M+H]⁺ calcd. for C₂₂H₂₇N₈O₂S, 467.1978; found. 467.1972; HPLC: method A R_t=6.50, method B R_t=6.61.

1H), 7.24 (d, J=7.6 Hz, 1H), 7.07 (d, J=7.3 Hz, 1H), 6.97 (s, 1H), 4.62 (t, J=8.7 Hz, 2H), 3.25 (t, J=8.7 Hz, 2H); MS (ESI)

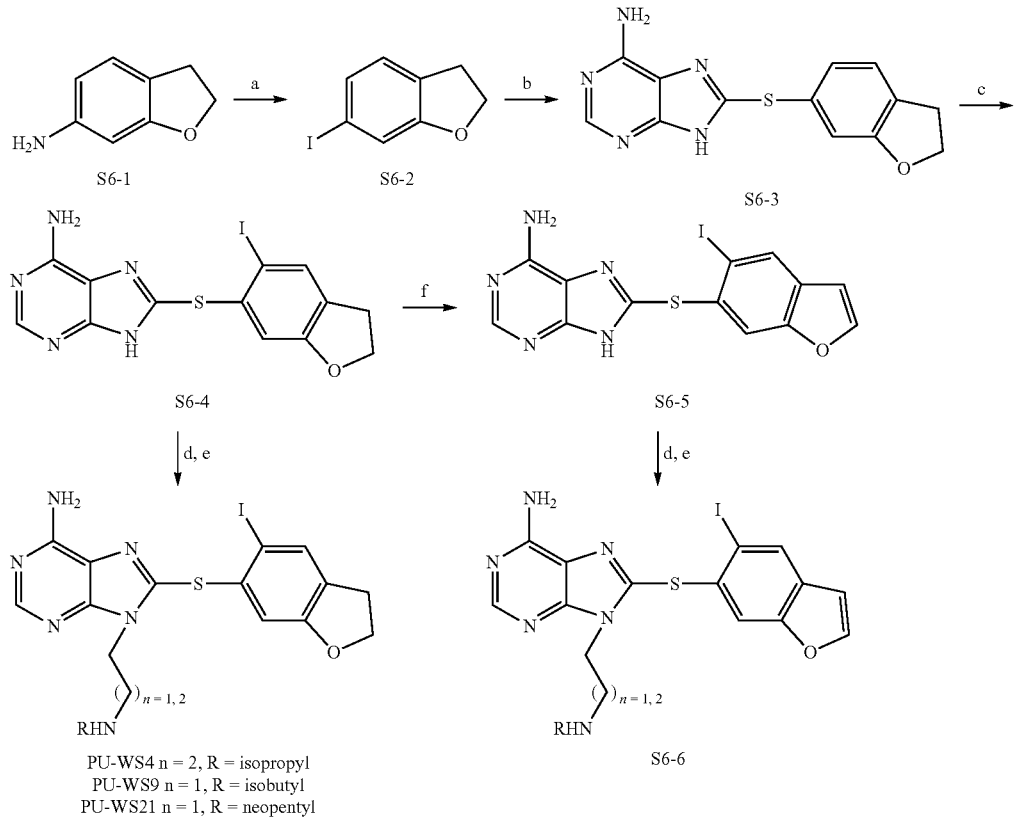

Scheme 6. Synthesis of PU-WS4, PU-WS9 and PU-WS21.

PU-WS4 n = 2, R = isopropyl
PU-WS9 n = 1, R = isobutyl
PU-WS21 n = 1, R = neopentyl Reagents and conditions: (a) NaNO₂, KI, AcOH/TFA, 0° C.; (b) 8-mercaptoadenine, Cs₂CO₃, PdCl₂(dppf), DMF, 80° C., 48 h; (c) NIS, TFA, CH₃CN, rt, 2 h; (d) 1,3-dibromopropane or 1,2-dibromoethane, Cs₂CO₃, DMF, rt; (e) isopropylamine or isobutylamine or neopentylamine, DMF, rt; (f) DDQ, dioxane, 100° C.

6-iodo-2,3-dihydrobenzofuran (S6-2). A solution of 2,3-dihydrobenzofuran-6-amine (S6-1; 0.74 g, 5.5 mmol) in acetic acid (25 mL) and TFA (2 mL) was cooled in an ice bath for 5 minutes. NaNO₂ (0.454 g, 6.6 mmol) was added in 3 portions followed by KI (2.73 g, 16.4 mmol). The resulting mixture was stirred at 0° C. for 15 minutes and quenched with H₂O (20 mL). The mixture was extracted with EtOAc (3×150 mL) and the organic layer was washed with NaS₂O₃, brine, dried over MgSO₄ and filtered. The filtrate was condensed under reduced pressure and the residue was purified by flash chromatography (hexane:EtOAc, 90:10 to 40:60) to yield S6-2 (0.82 g, 61%) as a pale-yellow solid. ¹H NMR (500 MHz, CDCl₃) δ 7.14 (d, J=7.6 Hz, 1H), 7.11 (s, 1H), 6.89 (d, J=7.6 Hz, 1H), 4.54 (t, J=8.7 Hz, 2H), 3.14 (t, J=8.7 Hz, 2H); ¹³C NMR (125 MHz, CDCl₃) δ 161.1, 129.4, 127.1, 126.4, 118.7, 91.7, 71.6, 29.4.

8-(2,3-dihydrobenzofuran-6-ylthio)-9H-purin-6-amine (S6-3). To a solution of S6-2 (50 mg, 0.2 mmol) in DMF (2 mL) was added 8-mercaptoadenine (34 mg, 0.2 mmol), Cs₂CO₃ (99.4 mg, 0.3 mmol) and PdCl₂(dppf) (33 mg, 0.02 mmol). The mixture was degassed for 5 minutes with argon and stirred at 80° C. under argon protection for 48 h. The resulting mixture was concentrated under reduced pressure and the residue was purified by flash chromatography (CH₂Cl₂:MeOH, 100:0 to 90:10) to yield S6-3 (25 mg, 44%) as a yellow solid. ¹H NMR (500 MHz, CD₃OD) δ 8.14 (s, 1H), m/z 285.8 [M+H]⁺; HRMS (ESI) m/z [M+H]⁺ calcd. for C₁₃H₁₂N₅OS, 286.0763; found. 286.0768.

8-(5-iodo-2,3-dihydrobenzofuran-6-ylthio)-9H-purin-6-amine (S6-4) To a solution of S6-3 (40 mg, 0.14 mmol) in 6 mL of acetonitrile was added TFA (40 μL) and NIS (63 mg, 0.28 mmol). The resulting mixture was stirred at rt for 2 h. The reaction mixture was concentrated under reduced pressure and the residue was purified by flash chromatography (CH₂Cl₂:MeOH, 100:0 to 90:10) to afford S6-4 (48 mg, 53%) as a yellow gum. ¹H NMR (500 MHz, CDCl₃) δ 8.26 (s, 1H), 7.79 (s, 1H), 7.12 (s, 1H), 4.65 (t, J=8.8 Hz, 2H), 3.28 (t, J=8.7 Hz, 2H); MS (ESI) m/z 412.0 (M+H)⁺.

8-(5-iodo-2,3-dihydro-benzofuran-6-ylsulfanyl)-9-(3-isopropylamino-propyl)-9H-purin-6-ylamine (PU-WS4). A mixture of S6-4 (54 mg, 0.13 mmol), Cs₂CO₃ (127 mg, 0.39 mmol) and 1,3-dibromopropane (202 mg, 0.65 mmol) in anhydrous DMF (2 mL) was stirred at rt for 2 h. Solvent was removed under reduced pressure and the residue purified by chromatography (CH₂Cl₂:MeOH:AcOH). The resulting solid was dissolved in DMF (2 mL) and isopropylamine (0.347 g, 0.5 mL, 5.9 mmol) was added and the solution stirred overnight at rt. The reaction afforded PU-WS4 (13 mg, 20%; over two-steps) as a yellow solid after purification. ¹H NMR (500 MHz, CDCl₃/CD₃OD) δ 8.26 (s, 1H), 7.77 (s, 1H), 7.07 (s, 1H), 4.65 (t, J=8.7 Hz, 2H), 4.47 (t, J=6.9 Hz, 2H), 3.20-3.33 (m, 3H), 3.01 (t, J=7.5 Hz, 2H), 2.33 (m, 2H), 1.34 (d, J=6.5 Hz, 6H); MS (ESI) m/z 511.2 [M+H]⁺; HRMS (ESI) m/z [M+H]⁺ calcd. for C$_{19}$H$_{24}$N$_6$OS, 511.0777; found. 511.0779.

8-(5-iodo-2,3-dihydro-benzofuran-6-ylsulfanyl)-9-(2-isobutylamino-ethyl)-9H-purin-6-ylamine (PU-WS9). A mixture of S6-4 (30 mg, 0.073 mmol), Cs$_2$CO$_3$ (71 mg, 0.22 mmol) and 1,2-dibromoethane (69 mg, 0.365 mmol) in anhydrous DMF (1 mL) was stirred at rt for 2 h. Solvent was removed under reduced pressure and the residue purified by chromatography (CH$_2$Cl$_2$:MeOH:AcOH). The resulting solid was dissolved in DMF (2 mL) and isobutylamine (0.241 g, 0.33 mL, 3.3 mmol) was added and the solution stirred overnight at rt. The reaction afforded PU-WS9 (15 mg, 40%; over two-steps) as a pale yellow solid. $^1$H NMR (500 MHz, CDCl$_3$) δ 8.26 (s, 1H), 7.63 (s, 1H), 6.56 (s, 1H), 6.27 (br s, 2H), 4.57 (t, J=8.5 Hz, 2H), 4.50 (t, J=5.5 Hz, 2H), 3.20 (t, J=8.5 Hz, 2H), 3.12 (t, J=5.5 Hz, 2H), 2.59 (d, J=7 Hz, 2H), 1.99 (m, 1H), 0.97 (d, J=7 Hz, 6H); HRMS (ESI) m/z [M+H]⁺ calcd. for C$_{19}$H$_{24}$N$_6$OS, 511.0777; found. 511.0790.

8-((5-iodo-2,3-dihydrobenzofuran-6-yl)thio)-9-(2-(neopentylamino)ethyl)-9H-purin-6-amine (PU-WS21). Following the procedure to make PU-WS9, compound PU-WS21 was obtained as a white solid. $^1$HNMR (500 MHz, CDCl$_3$, δ): 7.56 (s, 1H), 6.60 (s, 1H), 4.47 (t, J=8.7 Hz, 2H), 4.37 (m, 2H), 3.06-3.11 (m, 4H), 2.45 (s, 2H), 0.83 (s, 9H); HRMS (m/z): [M+H]⁺ calcd for C$_{20}$H$_{26}$IN$_6$OS 525.0933; found. 525.0927.

Scheme 7. Synthesis of PU-WS10.

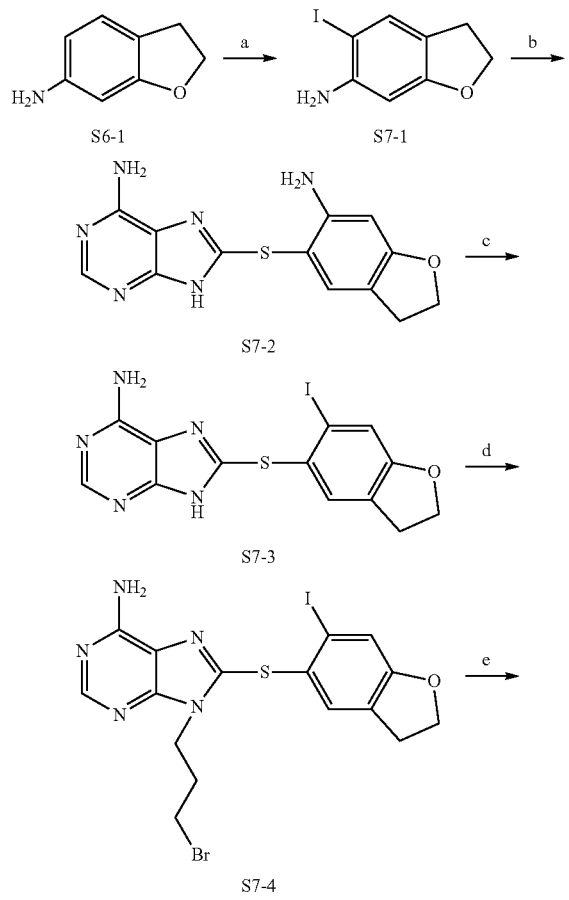

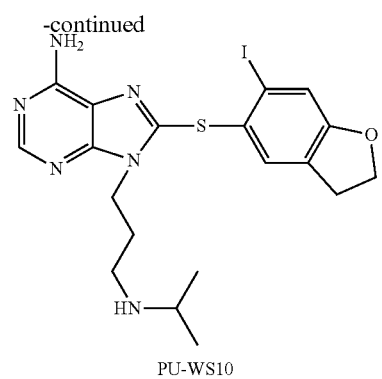

Reagents and conditions: (a) NIS, CH$_3$CN, 0° C., 20 min.; (b) 8-mercaptoadenine, neocuproine, CuI, NaOt-Bu, DMF, 110° C.; (c) NaNO$_2$, KI, AcOH/TFA, 0° C.; (d) 1,3-dibromopropane, Cs$_2$CO$_3$, DMF, rt; (e) isopropylamine, DMF, rt.

5-iodo-2,3-dihydrobenzofuran-6-amine (S7-1). To a solution of 2,3-dihydrobenzofuran-6-amine (S6-1; 95 mg, 0.7 mmol) in acetonitrile (3 mL) cooled in an ice-bath was added NIS (158 mg, 0.7 mmol). After stirring at 0° C. for 20 min, the mixture was condensed and purified by flash chromatography (hexane:EtOAc, 90:10 to 20:80) to yield S7-1 (180 mg, 98%) as a yellow solid. $^1$H NMR (500 MHz, CDCl$_3$) δ 7.38 (s, 1H), 6.26 (s, 1H), 4.53 (t, J=8.5 Hz, 2H), 3.09 (t, J=8.4 Hz, 2H); MS (ESI) m/z 261.9 [M+H]⁺.

8-(6-amino-2,3-dihydrobenzofuran-5-ylthio)-9H-purin-6-amine (S7-2). The mixture of S7-1 (80 mg, 0.31 mmol), 8-mercaptoadenine (52 mg, 0.3 mmol), neocuproine (7 mg, 0.03 mmol), CuI (7 mg, 0.03 mmol) and sodium t-butoxide (100 mg, 1.04 mmol) was suspended in 10 mL of DMF and stirred at 110° C. overnight. The mixture was concentrated under reduced pressure and the residue purified by flash chromatography (hexane:EtOAc, 90:10 to 20:80) to yield S7-2 (50 mg, 56%) as a pale yellow solid. $^1$H NMR (500 MHz, CDCl$_3$) δ 8.15 (s, 1H), 7.33 (s, 1H), 6.35 (s, 1H), 4.57 (t, J=8.5 Hz, 2H), 3.14 (t, J=8.4 Hz, 2H); MS (ESI) m/z 301.0 [M+H]⁺.

8-(6-iodo-2,3-dihydrobenzofuran-5-ylthio)-9H-purin-6-amine (S7-3). To a solution of S7-2 (25 mg, 0.08 mmol) in acetic acid/TFA (5 mL/1 mL) cooled in ice-bath was added NaNO$_2$ (7 mg, 0.1 mmol) and KI (27 mg, 0.16 mmol). The mixture was stirred at 0° C. for 10 minutes and condensed under reduced pressure. The residue was purified by flash chromatography (CH$_2$Cl$_2$:MeOH, 100:0 to 90:10) to yield S7-3 (13 mg, 41%) as a yellow solid. $^1$H NMR (500 MHz, CD$_3$OD) δ 8.13 (s, 1H), 7.57 (s, 1H), 7.44 (s, 1H), 4.66 (t, J=8.5 Hz, 2H), 3.22 (t, J=8.6 Hz, 2H); MS (ESI) m/z 411.9 [M+H]⁺.

9-(3-bromopropyl)-8-(6-iodo-2,3-dihydrobenzofuran-5-ylthio)-9H-purin-6-amine (S7-4). To a solution of S7-3 (13 mg, 0.03 mmol) in DMF (2 mL) was added 1,3-dibromopropane (16 μL, 0.16 mmol) and Cs$_2$CO$_3$ (20 mg, 0.06 mmol) and the resulting mixture was stirred at rt for 40 minutes. The mixture was condensed under reduced pressure and the residue was purified by flash chromatography to yield S7-4 (6.2 mg, 34%). $^1$H NMR (500 MHz, CDCl$_3$) δ 8.31 (s, 1H), 7.37 (s, 2H), 6.00 (br s, 2H), 4.62 (t, J=8.7 Hz, 2H), 4.36 (t, J=6.7 Hz, 2H), 3.42 (t, J=6.2 Hz, 2H), 3.18 (t, J=8.9 Hz, 2H), 2.39 (m, 2H); MS (ESI) m/z 531.9/533.9 [M+H]⁺.

8-(6-iodo-2,3-dihydro-benzofuran-5-ylsulfanyl)-9-(3-isobutylamino-ethyl)-9H-purin-6-ylamine (PU-WS10). A solution of S7-4 (6.2 mg, 0.012 mmol) and isopropylamine (0.2 mL) in DMF (1 mL) was stirred for 12 h. Solvent was removed under reduced pressure and the residue purified by preparative thin layer chromatography (CHCl$_3$:MeOH—

NH₃ (7N), 20:1) to afford PU-WS10 (4.0 mg, 60%) as a pale yellow solid. ¹H NMR (400 MHz, CDCl₃) δ 8.27 (s, 1H), 7.69 (s, 1H), 7.27 (s, 1H), 5.93 (br s, 2H), 4.66 (t, J=8.8 Hz, 2H), 4.29 (t, J=7 Hz, 2H), 3.33 (t, J=8.7 Hz, 2H), 2.74 (septet, J=6.2 Hz, 1H), 2.58 (t, J=6.8 Hz, 2H), 1.98 (m, 2H), 1.05 (d, J=6.5 Hz, 6H); ¹³C NMR (100 MHz, CDCl₃) δ 162.0, 154.4, 152.7, 151.9, 147.8, 141.7, 130.2, 128.6, 121.1, 120.0, 74.1, 71.7, 48.9, 44.0, 41.6, 30.9, 30.2; MS (ESI) m/z 511.1 [M+H]⁺.

Scheme 8. Synthesis of PU-WS3, PU-WS5, PU-WS6, PU-WS7, and PU-WS8, PU-WS16, PU-WS19 and PU-WS20.

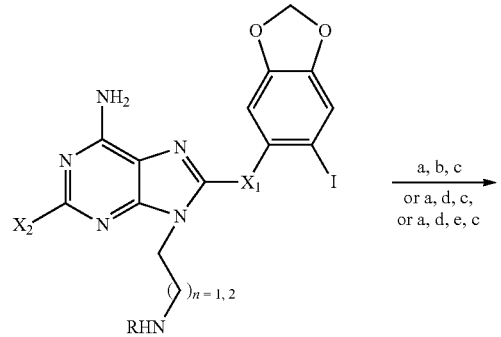

| | | | | |
|---|---|---|---|---|
| PU-DZ8 | X₁ = CH₂, X₂ = F, n = 2, R = isopropyl | | | |
| PU-H71 | X₁ = S, X₂ = H, n = 2, R = isopropyl | | | |
| PU-HZ150 | X₁ = S, X₂ = H, n = 1, R = isobutyl | | | |
| PU-HZ151 | X₁ = S, X₂ = H, n = 1, R = neopentyl | | | |
| PU-DZ13 | X₁ = CH₂, X₂ = F, n = 1, R = isobutyl | | | |

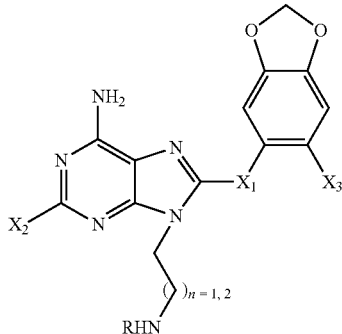

| | |
|---|---|
| PU-WS3 | X₁ = CH₂, X₂ = F, X₃ = CN, n = 2, R = isopropyl |
| PU-WS5 | X₁ = S, X₂ = H, X₃ = CN, n = 2, R = isopropyl |
| PU-WS6 | X₁ = S, X₂ = H, X₃ = CCt-Bu, n = 2, R = isopropyl |
| PU-WS7 | X₁ = S, X₂ = H, X₃ = CCPh, n = 2, R = isopropyl |
| PU-WS8 | X₁ = S, X₂ = H, X₃ = CCH, n = 2, R = isopropyl |
| PU-WS16 | X₁ = S, X₂ = H, X₃ = CCH, n = 1, R = isobutyl |
| PU-WS19 | X₁ = S, X₂ = H, X₃ = CCH, n = 1, R = neopentyl |
| PU-WS20 | X₁ = CH₂, X₂ = F, X₃ = CCH, n = 1, R = isobutyl |

Reagents and conditions: (a) Boc₂O, Et₃N, THF, rt, 12 h; (b) PdCl₂(dppf), Zn(CN)₂, Zn, DMF, 130° C.; (c) 10% TFA—CH₂Cl₂, rt, 2-5 h; (d) CuI, PdCl₂(PPh₃)₂, t-butylacetylene or phenylacetylene or trimethylsilanylacetylene, Et₃N, DMF, 90° C., 24 h; (e) KOH, MeOH, rt, 2 h.

6-[6-amino-2-fluoro-9-(3-isopropylamino-propyl)-9H-purin-8-ylmethyl]-benzo[1,3]dioxole-5-carbonitrile (PU-WS3). A solution of PU-DZ8 (118 mg, 0.231 mmol), (Boc)₂O (55 mg, 0.254 mmol) and triethylamine (16 mg, 0.231 mmol) in THF (2 mL) was stirred at room temperature for 12 h. Following solvent removal, the residue was purified by preparative thin layer chromatography (CHCl₃:MeOH—NH₃ (7N), 20:1) to afford Boc-protected PU-DZ8 (120 mg, 85%; MS (ESI) m/z 613.05 [M+H]⁺). To a solution of Boc-protected PU-DZ8 (26 mg, 0.04 mmol) in DMF (3 mL) was added PdCl₂(dppf) (17 mg, 0.02 mmol), Zn(CN)₂ (10 mg, 0.08 mmol) and Zn (3 mg, 0.04 mL) and the resulting mixture was stirred at 130° C. overnight. The reaction mixture was condensed under reduced pressure and the residue was purified by flash chromatography (CHCl₃:MeOH—NH₃ (7N), 20:1) to yield Boc-protected PU-WS3 as a white solid. To a solution of this in 2 mL of CH₂Cl₂ was added 0.2 mL of TFA and the mixture was stirred at room temperature for 5 h. The reaction mixture was condensed under reduced pressure and the residue purified by flash chromatography (CHCl₃:MeOH—NH₃ (7N), 20:1) to yield PU-WS3 as a white solid in quantitative yield (12 mg, 59% for three steps). ¹H NMR (500 MHz, CD₃OD) δ 7.13 (s, 1H), 6.96 (s, 1H), 6.03 (s, 2H), 4.31 (s, 2H), 4.25 (t, J=7 Hz, 2H), 3.26 (m, 1H), 3.01 (t, J=7.5 Hz, 2H), 2.14 (m, 2H), 1.23 (d, J=6.5 Hz, 6H); ¹³C NMR (125 MHz, CD₃OD) δ 160.4 (d, J=208 Hz), 158.5 (d, J=19 Hz), 153.8, 153.5 (d, J=19 Hz), 151.7, 149.1, 137.2, 119.1, 117.4, 112.6, 112.4, 106.3, 104.4, 52.3, 43.4, 40.8, 33.2, 27.7, 19.3; MS (ESI) m/z 412.3 [M+H]⁺.

6-[6-amino-9-(3-isopropylamino-propyl)-9H-purin-8-ylsulfanyl]benzo[1,3]dioxole-5-carbonitrile (PU-WS5). The procedure for the preparation of PU-WS3 was followed starting from PU-H71. The reaction afforded PU-WS5 (6.5 mg, 32% for three steps) as a white solid. ¹H NMR (500 MHz, CDCl₃/CD₃OD) δ 8.21 (s, 1H), 7.22 (s, 1H), 7.19 (s, 1H), 6.19 (s, 2H), 4.40 (t, J=7 Hz, 2H), 3.09 (septet, J=6.5 Hz, 1H), 2.83 (t, J=7.5 Hz, 2H), 2.26 (m, 2H), 1.25 (d, J=6.5 Hz, 6H); MS (ESI) m/z 412.2 [M+H]⁺; HRMS (ESI) m/z [M+H]⁺ calcd. for C₁₉H₂₂N₇O₂S, 412.1556; found. 412.1560.

8-[6-(3,3-dimethyl-but-1-ynyl)-benzo[1,3]dioxol-5-ylsulfanyl]9-(3-isopropylamino-propyl)-9H-purin-6-ylamine (PU-WS6). A solution of PU-H71 (70 mg, 0.137 mmol), (Boc)₂O (35 mg, 0.161 mmol) and triethylamine (13 mg, 0.137 mmol) in THF (2 mL) was stirred at room temperature for 12 h. Following solvent removal, the residue was purified by preparative thin layer chromatography (CHCl₃:MeOH—NH₃ (7N), 20:1) to afford Boc-protected PU-H71 (74 mg, 88%; MS (ESI) m/z 612.89 [M+H]⁺). To a solution of Boc-protected PU-H71 (0.24 g, 0.39 mmol) in DMF (2 mL) was added CuI (4 mg, 0.1 mmol), PdCl₂(PPh₃)₂ (14 mg, 0.02 mmol), t-butylacetylene (72 µL, 0.59 mmol) and triethylamine (137 µL) and the mixture was stirred at 90° C. for 24 h. The reaction mixture was condensed under reduced pressure and purified by chromatography to afford a solid. To a solution of the solid in 15 mL of CH₂Cl₂ was added TFA (1.5 mL) and stirred at RT for 2 hrs. The mixture was condensed and purified by flash chromatography to afford PU-WS6 (97 mg, 52% for three steps) as a white solid. ¹H NMR (500 MHz, CDCl₃/CD₃OD) δ 8.25 (s, 1H), 6.99 (s, 1H), 6.97 (s, 1H), 6.05 (s, 2H), 4.41 (t, J=7 Hz, 2H), 3.29 (m, 1H), 2.98 (t, J=7.5 Hz, 2H), 2.24 (m, 2H), 1.34 (d, J=6.5 Hz, 6H), 1.18 (s, 9H); ¹³C NMR (125 MHz, CDCl₃/CD₃OD) δ 50.5, 41.3, 40.2, 30.3, 27.8, 25.9, 18.5; MS (ESI) m/z 467.3 [M+H]⁺; HRMS (ESI) m/z [M+H]⁺ calcd. for C₂₄H₃₁N₆O₂S, 467.2229; found. 467.2233.

9-(3-isopropylamino-propyl)-8-(6-phenylethynyl-benzo[1,3]dioxool-5-ylsulfanyl)-9H-purin-6-ylamine (PU-WS7). The procedure for the preparation of PU-WS6 was followed with phenylacetylene (65 µL, 0.59 mmol) to afford PU-WS7 (46 mg, 34% in three steps) as a white solid. ¹H NMR (500 MHz, CDCl₃/CD₃OD) δ 8.2 (s, 1H), 7.30-7.40 (m, 5H), 7.08 (s, 1H), 6.96 (s, 1H), 6.06 (s, 2H), 4.27 (m, 2H), 2.69 (m, 1H), 2.51 (m, 2H), 1.97 (m, 2H), 1.01 (d, J=6.5 Hz, 6H); ¹³C NMR (125 MHz, CDCl₃/CD₃OD) δ 154.3, 152.3, 151.1, 148.8, 147.3, 131.3, 128.7, 128.3, 124.4, 122.4, 120.4, 119.3, 112.9, 112.4, 102.3, 94.2, 86.6, 50.5, 43.1, 41.3, 29.2, 21.7; MS (ESI) m/z 487.2 [M+H]$^+$; HRMS (ESI) m/z [M+H]$^+$ calcd. for $C_{26}H_{27}N_6O_2S$, 487.1903; found. 487.1913.

8-(6-ethynyl-benzo[1,3]dioxol-5-ylsulfanyl)-9-(3-isopropylamino-propyl)-9H-purin-6-ylamine (PU-WS8). The procedure for the preparation of PU-WS6 was followed with trimethylsilanylacetylene (82 μL, 0.59 mmol), and following coupling a white solid was obtained and used without further purification. To this was added MeOH (10 mL) and KOH (90 mg) and was stirred at rt for 2 hrs. The reaction mixture was concentrated under reduced pressure and to the resulting residue was added 2 mL of 10% TFA-CH$_2$Cl$_2$ and was stirred at rt for 2 hrs. The mixture was concentrated under reduced pressure and the residue chromatographed to afford PU-WS8 (5.2 mg, 26% for four steps) as a pale yellow solid. $^1$H NMR (500 MHz, CDCl$_3$) δ 8.32 (s, 1H), 6.99 (s, 1H), 6.84 (s, 1H), 6.00 (s, 2H), 5.61 (br s, 2H), 4.31 (t, J=7 Hz, 2H), 3.31 (s, 1H), 2.71 (m, 1H), 2.56 (t, J=7 Hz, 2H), 1.97 (m, 2H), 1.02 (d, J=6.5 Hz, 6H); MS (ESI) m/z 411.2 [M+H]$^+$; HRMS (ESI) m/z [M+H]$^+$ calcd. for $C_{20}H_{23}N_6O_2S$, 411.1603; found. 411.1605.

8-((6-ethynylbenzo[d][1,3]dioxol-5-yl)thio)-9-(2-(isobutylamino)ethyl)-9H-purin-6-amine (PU-WS16). Following the procedure to make PU-WS8, PU-WS16 was obtained as a white solid. $^1$H NMR (500 MHz, CDCl$_3$) δ 8.24 (s, 1H), 6.91 (s, 1H), 6.77 (s, 1H), 6.01 (s, 2H), 5.78 (br s, 2H), 4.33 (t, J=6.1 Hz, 2H), 3.24 (s, 1H), 2.92 (t, J=6.1 Hz, 2H), 2.38 (d, J=6.8 Hz, 2H), 1.63 (m, 1H), 0.77 (d, J=6.6 Hz, 6H); $^{13}$C NMR (125 MHz, CDCl$_3$) δ 155.1, 153.5, 151.9, 149.6, 148.5, 147.0, 128.0, 124.1, 117.0, 114.8, 111.3, 102.6, 82.9, 81.4, 57.9, 49.3, 44.2, 28.8, 28.4, 20.9; HRMS (ESI) m/z [M+H]$^+$ calcd. for $C_{20}H_{22}N_6O_2S$, 411.1603; found. 411.1606.

8-(6-ethynylbenzo[d][1,3]dioxol-5-ylthio)-9-(2-(neopentylamino)ethyl)-9H-purin-6-amine (PU-WS19). Following the procedure to make PU-WS8, PU-WS19 was obtained as a white solid. $^1$H NMR (500 MHz, CDCl$_3$) δ 8.32 (s, 1H), 6.97 (s, 1H), 6.83 (s, 1H), 5.98 (s, 2H), 5.76 (br s, 2H), 4.35 (m, 2H), 3.06 (s, 1H), 2.97 (m, 2H), 2.33 (s, 2H), 0.82 (s, 9H); $^{13}$C NMR (125 MHz, CDCl$_3$) δ 154.5, 152.9, 151.5, 149.1, 147.9, 146.5, 120.1, 117.7, 112.9, 111.9, 102.2, 82.3, 81.0, 61.9, 49.8, 43.9, 31.5, 27.7; HRMS (ESI) m/z [M+H]$^+$ calcd. for $C_{21}H_{25}N_6O_2S$, 425.1760; found. 425.1753.

8-((6-ethynylbenzo[d][1,3]dioxol-5-yl)methyl)-2-fluoro-9-(2-(isobutylamino)ethyl)-9H-purin-6-amine (PU-WS20). Following the procedure to make PU-WS8, PU-WS20 was obtained from PU-DZ13 as a white solid. $^1$H NMR (MeOH-d$_4$, 500 MHz) δ: 6.98 (s, 1H), 6.70 (s, 1H), 6.02 (s, 2H), 4.36 (s, 2H), 4.20 (t, J=6.4 Hz, 2H), 2.92 (t, J=6.4 Hz, 2H), 2.42 (d, J=6.9 Hz, 2H), 2.03 (s, 1H), 1.69 (m, 1H), 0.87 (d, J=6.8 Hz, 6H); $^{13}$C NMR (MeOH-d$_4$, 125 MHz) δ: 159.8, 158.1, 152.6, 151.4, 149.8, 147.2, 134.3, 116.2, 114.2, 112.5, 109.8, 102.3, 80.9, 57.5, 43.0, 32.6, 29.8, 28.2, 20.5.

Scheme 9. Synthesis of PU-HT165, PU-HT175, PU-RK11, PU-RK12.

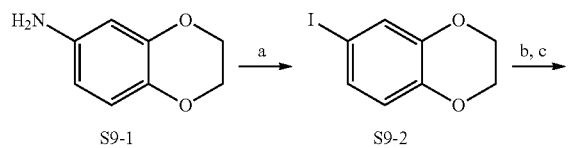

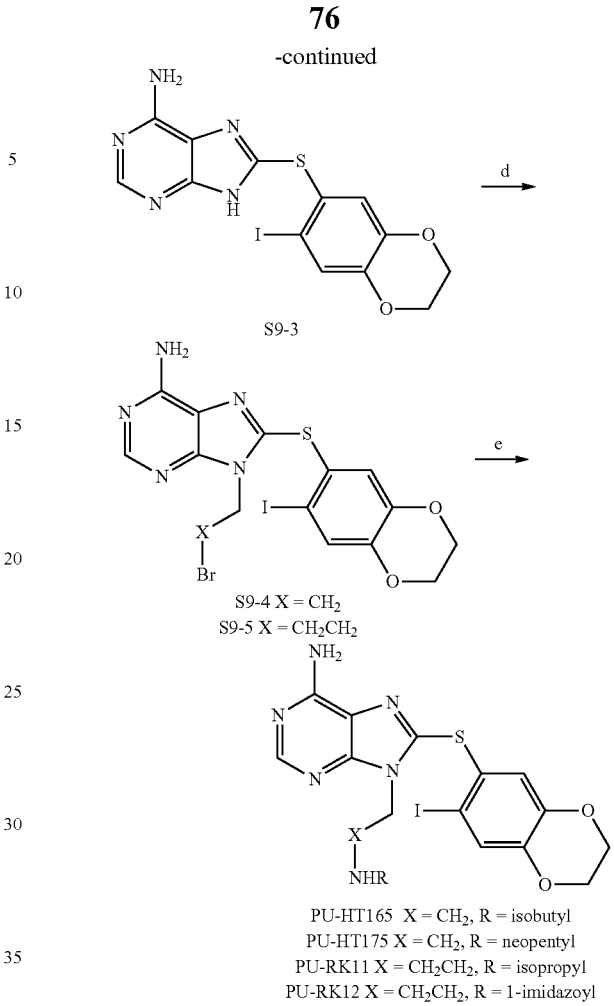

Reagents and conditions: (a) NaNO$_2$, 10% HCl, 0° C.; KI, 0° C. to rt; (b) 8-mercaptoadenine, neocuproine, CuI, NaOt-Bu, DMF, 110° C., 24 h; (c) NIS, TFA, CH$_3$CN, rt; (d) 1,2-dibromoethane or 1,3-dibromopropane, Cs$_2$CO$_3$, DMF, rt; (e) isobutylamine or neopentylamine or isopropylamine or imidazole, DMF, rt.

6-Iodo-2,3-dihydrobenzo[b][1,4]dioxine (S9-2). 2,3-dihydrobenzo[b][1,4]dioxin-6-amine (S9-1; 5 g, 33 mmol) was dissolved in 10% HCl solution and cooled to 0° C. Then, 30 mL of a cold aqueous solution of NaNO$_2$ (4.6 g, 66 mmol) was added over a period of 15 min and the reaction mixture was stirred at 0° C. for an additional 10 min, followed by the addition of urea (1.6 g, 27 mmol). After 15 min, 40 mL of a suspension of KI (16.5 g, 100 mmol) in water/CH$_2$Cl$_2$ (1:1) was added. The reaction mixture was stirred overnight at room temperature then extracted with CH$_2$Cl$_2$, dried over MgSO$_4$. And condensed under reduced pressure and the residue was purified by flash chromatography (hexane:EtOAc, 100:0 to 90:10) to afford S9-2 (7.4 g, 86%) as a colorless oil. $^1$H NMR (500 MHz, CDCl$_3$) δ 7.28 δ (s, 1H), 7.13 (d, J=8.5 Hz, 1H), 6.63 (d, J=8.5 Hz, 1H), 4.27-4.24 (m, 4H).

8-(7-Iodo-2,3-dihydrobenzo[b][1,4]dioxin-6-ylthio)-9H-purin-6-amine (S9-3). To a solution of S9-2 (1.26 g, 4.8 mmol) in DMF (15 mL) was added 8-mercaptoadenine (0.400 g, 2.4 mmol), neocuproine (0.056 g, 0.24 mmol), CuI (0.044 g, 0.24 mmol) and NatOBu (0.460 g, 4.8 mmol). The reaction mixture was stirred at 110° C. for 24 h. Solids were filtered and the filtrate was condensed under reduced pressure. The residue was flash chromatographed (CHCl$_3$:MeOH:AcOH, 60:0.5:0.5 to 30:0.5:0.5) to yield 0.578 g (80%) of intermediate coupling product (MS (ESI) m/z 301.9

[M+H]⁺). To 0.400 g (1.4 mmol) of this and NIS (0.945 g, 4.2 mmol) in acetonitrile (15 mL) was added TFA (540 μL, 0.800 g, 7 mmol) and the mixture was stirred at room temperature overnight. The solvent was removed under reduced pressure and the residue was purified by flash chromatography (CHCl₃:MeOH:AcOH, 60:0.5:0.5 to 30:0.5:0.5) to give S9-3 (0.436 g, 73%). ¹H NMR (DMSO-d₆, 500 MHz) δ 8.37 (s, 1H), 8.03 (br s, 2H), 7.47 (s, 1H), 7.10 (s, 1H), 4.25-4.27 (m, 4H); MS (ESI) m/z 427.9 [M+H]⁺.

9-(2-Bromoethyl)-8-(7-iodo-2,3-dihydrobenzo[b][1,4]dioxin-6-ylthio)-9H-purin-6-amine (S9-4). A mixture of S9-3 (0.213 g, 0.5 mmol), 1,2-dibromoethane (0.500 g, 2.5 mmol) and Cs₂CO₃ (0.184 g, 0.75 mmol) in anhydrous DMF (6 mL) was stirred at room temperature for 3 h. Solids were filtered and the filtrate was condensed under reduced pressure to give a residue that was purified by preparative thin layer chromatography (CHCl₃:MeOH—NH₃ (7N), 20:1) to give S9-4 (0.107 g, 40%). ¹H NMR (CDCl₃, 500 MHz) δ 8.29 (s, 1H), 7.36 (s, 1H), 7.00 (s, 1H), 6.23 (br s, 2H), 4.62 (t, J=7.0 Hz, 2H), 4.16-4.24 (m, 4H), 3.69 (t, J=7.0 Hz, 2H); MS (ESI) m/z 533.9/535.9 [M+H]⁺.

9-(3-Bromopropyl)-8-(7-iodo-2,3-dihydrobenzo[b][1,4]dioxin-6-ylthio)-9H-purin-6-amine (S9-5). A mixture of S9-3 (0.213 g, 0.5 mmol), 1,3-dibromopropane (0.512 g, 2.5 mmol) and Cs₂CO₃ (0.184 g, 0.75 mmol) in anhydrous DMF (6 mL) was stirred at room temperature for 3 h. Solids were filtered and the filtrate was condensed under reduced pressure to give a residue that was purified by preparative thin layer chromatography (CHCl₃:MeOH—NH₃ (7N), 20:1) to give S9-5 (0.104 g, 38%). ¹H NMR (CDCl₃, 500 MHz) δ 8.26 (s, 1H), 7.32 (s, 1H), 6.94 (s, 1H), 5.6 (br s, 2H), 4.27 (t, J=7.0 Hz, 2H), 4.10-4.17 (m, 4H), 3.32 (t, J=7.0 Hz, 2H), 2.26 (m, 2H); MS (ESI) m/z 547.9/549.8 [M+H]⁺.

8-(7-Iodo-2,3-dihydrobenzo[b][1,4]dioxin-6-ylthio)-9-(2-(isobutylamino)ethyl)-5,9-dihydro-4H-purin-6-amine (PU-HT165). S9-4 (0.052 g, 0.097 mmol) and isobutylamine (0.354 g, 4.9 mmol) in DMF (1 ml) was stirred overnight at rt. Solvent was removed under reduced pressure and the resulting residue was purified by chromatography (CH₂Cl₂:MeOH) to give 0.040 g, 78%) of PU-HT165 as a yellow solid. ¹H NMR (500 MHz, CDCl₃) δ 8.24 (s, 1H), 7.37 (s, 1H), 6.94 (s, 1H), 6.24 (br s, 2H), 4.44 (br s, 2H), 4.22-4.24 (m, 4H), 3.08 (m, 2H), 2.52 (d, J=5.7 Hz, 2H), 1.92 (m, 1H), 0.92 (d, J=6.0 Hz, 6H); ¹³C NMR (125 MHz, CDCl₃) δ 155.4, 152.8, 151.4, 147.7, 145.5, 145.2, 128.9, 127.5, 122.0, 120.5, 91.6, 64.9, 64.7, 57.3, 49.0, 43.9, 28.0, 21.0; MS (ESI) m/z 527.1 [M+H]⁺.

8-(7-Iodo-2,3-dihydrobenzo[b][1,4]dioxin-6-ylthio)-9-(2-(neopentylamino)ethyl)-5,9-dihydro-4H-purin-6-amine (PU-HT175). S9-4 (0.052, 0.097 mmol) and neopentylamine (0.426 g, 4.9 mmol) in DMF (1 mL) was stirred overnight at rt. Solvent was removed under reduced pressure and the resulting residue was purified by chromatography (CH₂Cl₂:MeOH) to give 0.038 g (73%) of PU-HT175 as a yellow solid. ¹H NMR (500 MHz, CDCl₃) δ 8.31 (s, 1H), 7.37 (s, 1H), 6.94 (s, 1H), 5.79 (br s, 2H), 4.33 (t, J=6.5 Hz, 2H), 4.20-4.24 (m, 4H), 2.99 (t, J=6.5 Hz, 2H), 2.34 (s, 2H), 0.84 (s, 9H); ¹³C NMR (125 MHz, CDCl₃) δ 154.5, 152.9, 151.7, 147.0, 144.7, 144.6, 128.2, 127.8, 121.2, 120.2, 90.7, 64.3, 64.2, 62.0, 49.8, 44.0, 31.6, 27.7; MS m/z 541.1 [M+H]⁺.

8-(7-Iodo-2,3-dihydrobenzo[b][1,4]dioxin-6-ylthio)-9-(3-(isopropylamino)propyl)-9H-purin-6-amine (PU-RK11). S9-5 (0.045 g, 0.082 mmol) and isopropylamine (0.242 g, 4.1 mmol) in DMF (1 mL) was stirred overnight at rt. Solvent was removed under reduced pressure and the resulting residue was purified by chromatography (CH₂Cl₂:MeOH) to give 0.038 g (88%) of PU-RK11. ¹H NMR (500 MHz, CDCl₃) δ 8.30 (s, 1H), 7.38 (s, 1H), 6.95 (s, 1H), 5.65 (br s, 2H), 4.32 (t, J=6.9 Hz, 2H), 4.22-4.24 (m, 4H), 2.80 (septet, J=6.7 Hz, 1H), 2.61 (t, J=6.7 Hz, 2H), 2.07 (m, 2H), 1.11 (d, J=6.7 Hz, 6H); ¹³C NMR (125 MHz, CDCl₃) δ 154.4, 152.8, 151.7, 146.7, 144.8, 144.6, 128.3, 127.8, 121.3, 120.1, 91.0, 64.3, 64.2, 49.0, 43.6, 41.6, 29.8, 22.5; MS (ESI) m/z 527.1 [M+H]⁺.

9-(3-(1H-imidazol-1-yl)propyl)-8-(7-iodo-2,3-dihydrobenzo[b][1,4]dioxin-6-ylthio)-9H-purin-6-amine (PU-RK12). S9-5 (0.045 g, 0.082 mmol) and imidazole (0.056 g, 0.82 mmol) in DMF (1 mL) was stirred overnight at rt. Solvent was removed under reduced pressure and the resulting residue was purified by chromatography (CH₂Cl₂:MeOH) to give 0.029 g (67%) of PU-RK12. ¹H NMR (500 MHz, CDCl₃) δ 8.34 (s, 1H), 7.62 (s, 1H), 7.39 (s, 1H), 7.09 (s, 1H), 6.98 (s, 1H), 6.94 (s, 1H), 5.70 (br s, 2H), 4.19-4.28 (m, 6H), 4.00 (t, J=7.5 Hz, 2H), 2.25 (m, 2H); ¹³C NMR (125 MHz, CDCl₃) δ 154.5, 153.2, 151.8, 146.3, 145.0, 144.7, 137.1, 129.6, 128.3, 126.9, 121.3, 120.1, 118.7, 90.9, 64.3, 64.2, 44.3, 41.0, 31.8; MS (ESI) m/z 536.1 [M+H]⁺.

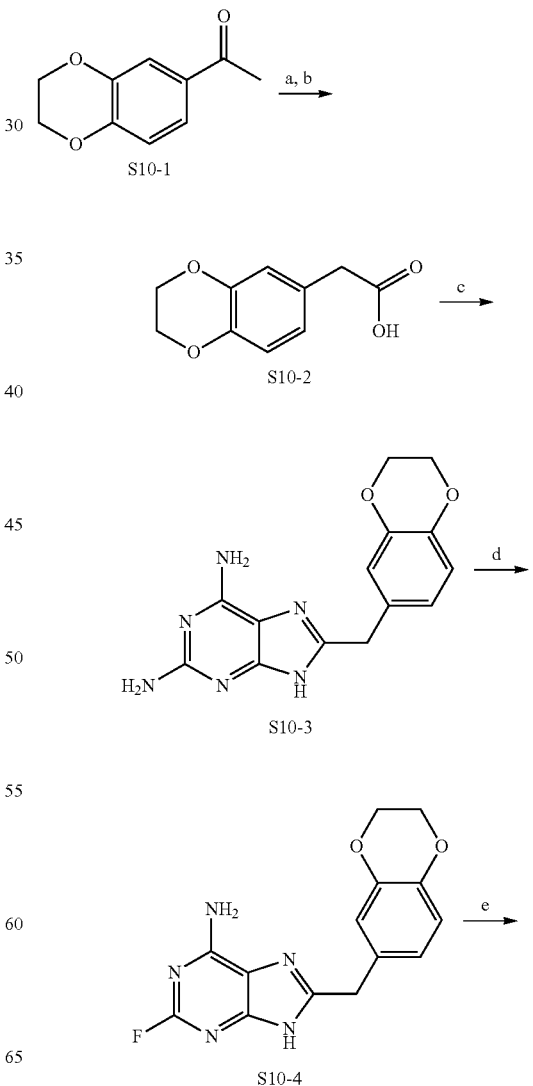

Scheme 10. Synthesis of DZ3-73 and DZ4-84.

-continued

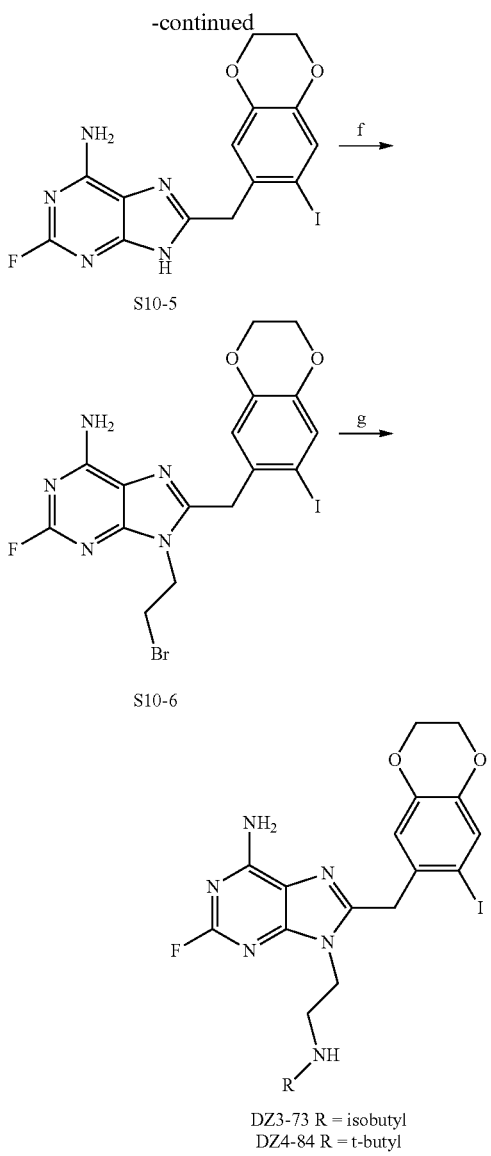

DZ3-73 R = isobutyl
DZ4-84 R = t-butyl

Reagents and conditions: (a) sulfur, morpholine, 140° C., 14 h; (b) 10% KOH (aq.), reflux, 12 h; (c) 2,4,5,6-tetraaminopyrimidine, triphenyl phosphite, pyridine, microwave irradiation at 220° C., 75 min.; (d) HF/pyridine, NaNO$_2$, 0° C. to rt, 1 h; (e) NIS, TFA, CH$_3$CN, rt overnight; (f) Cs$_2$CO$_3$, 1,2-dibromoethane, DMF, rt, 3.5 h; (g) isobutylamine or t-butylamine, DMF, overnight, rt.

2-(2,3-dihydrobenzo[b][1,4]dioxin-6-yl)acetic acid (S10-2). A mixture of 1,4-benzodioxan-6-yl methyl ketone (S10-1; 5.5 g, 30.9 mmol), sulfur (1.98 g, 61.8 mmol) and morpholine (6.73 g, 6.76 mL, 77.3 mmol) was refluxed at 140° C. for 14 h. After cooling to rt, the reaction mixture was diluted with 150 mL of CH$_2$Cl$_2$, transferred to a seperatory funnel and washed with 25 mL of ice-cold brine. The aqueous layer was further extracted with CH$_2$Cl$_2$ (2×75 mL). The organic layers were combined, dried with Na$_2$SO$_4$, and filtered. Activated charcoal was added to the filtrate and after several minutes was filtered and concentrated to give 12.7 g of a brown oil. A mixture of this in 75 mL of 10% KOH (aq.) was refluxed for 12 h. After cooling the reaction mixture was transferred to a seperatory funnel and washed with ether (30 mL), The aqueous layer was acidified with 6N HCl (~25 mL) to pH 2 and extracted with CH$_2$Cl$_2$ (4×100 mL). The organic layers were combined, washed with distilled water (100 ml), dried with Na$_2$SO$_4$ and filtered. This was treated with charcoal, filtered, and solvent removed under reduced pressure and the resulting residue was purified by chromatography (hexane:EtOAc, 90:10 to 70:30) to give 3.90 g (65%) of S10-2. $^1$H NMR (500 MHz, CDCl$_3$) δ 6.80-6.82 (m, 2H), 6.74 (dd, J=2.0, 8.2 Hz, 1H), 4.24 (s, 4H), 3.53 (s, 2H); MS (ESI) m/z 195.1 [M+H]$^+$.

8-((2,3-dihydrobenzo[b][1,4]dioxin-6-yl)methyl)-9H-purine-2,6-diamine (S10-3). A mixture of S10-2 (1.00 g, 5.15 mmol), 2,4,5,6-tetraminopyrimidine (0.868 g, 6.19 mmol), triphenyl phosphite (1.92 g, 1.63 mL, 6.19 mmol) in 15 mL of pyridine was sonicated for several minutes. It was then subjected to microwave irradiation at 220° C. for 75 minutes. The mixture was concentrated and the resulting residue was purified by chromatography (CH$_2$Cl$_2$:MeOH:MeOH—NH$_3$ (7N), 60:0.5:0.5 to 20:0.5:0.5) to give 1.12 g (73%) of S10-3. $^1$H NMR (500 MHz, CDCl$_3$/MeOH-d4) δ 6.75-6.84 (m, 3H), 4.24 (s, 4H), 3.98 (s, 2H); MS (ESI) m/z 299.3 [M+H]$^+$.

8-((2,3-dihydrobenzo[b][1,4]dioxin-6-yl)methyl)-2-fluoro-9H-purin-6-amine (S10-4). To a solution of S10-3 (1.00 g, 3.35 mmol) in HF/pyridine (2.4 mL) at 0° C., NaNO$_2$ (0.3 g, 4.36 mmol) was slowly added. The reaction was brought to room temperature and further stirred for 1 h. Following dilution with CH$_2$Cl$_2$ (20 mL), the excess HF was quenched by stirring for 1 h with CaCO$_3$ (1.19 g). The mixture was dried under reduced pressure and subsequently purified by chromatography (CH$_2$Cl$_2$:MeOH:AcOH, 90:1:0.5) to give 1.15 g (96%) of S10-4. $^1$H NMR (500 MHz, CDCl$_3$/MeOH-d4) δ 6.75-6.84 (m, 3H), 4.24 (s, 4H), 4.04 (s, 2H); MS (ESI) m/z 302.3 [M+H]$^+$.

2-fluoro-8-((7-iodo-2,3-dihydrobenzo[b][1,4]dioxin-6-yl)methyl)-9H-purin-6-amine (S10-5). S10-4 (0.310 g, 1.03 mmol), NIS (0.301 g, 1.34 mmol), CH$_3$CN (20 mL), TFA (2.34 g, 1.56 mL, 20.5 mmol) was stirred at rt overnight. The mixture was dried under reduced pressure and the residue chromatographed (CH$_2$Cl$_2$:MeOH:AcOH, 120:1:0.5 to 90:1:0.5) to give 0.340 g (77%) of a mixture of S10-5 (m/z 428.2 [M+H]$^+$) along with diiodinated compound (m/z 554.1 [M+H]$^+$). LC-MS shows ratio of S10-5 to diiodinated compound to be 83:17. This mixture was not separated but used further in the following step. $^1$H NMR (500 MHz, CDCl$_3$/MeOH-d4) δ 7.37 (s, 1H), 6.82 (s, 1H), 4.25 (s, 4H), 4.18 (s, 2H); MS (ESI) m/z 428.2 [M+H]$^+$.

9-(2-bromoethyl)-2-fluoro-8-((7-iodo-2,3-dihydrobenzo[b][1,4]dioxin-6-yl)methyl)-9H-purin-6-amine (S10-6). S10-5 (0.340 g, 0.796 mmol), Cs$_2$CO$_3$ (0.337 g, 1.035 mmol), 1,2-dibromoethane (0.747 g, 0.343 mL, 3.99 mmol) in DMF (10 mL) was stirred at rt for 3.5 h. The mixture was dried under reduced pressure and the residue chromatographed (CH$_2$Cl$_2$:MeOH:AcOH, 200:1:0.5 to 120:1:0.5) to give 0.360 g (85%) of a mixture of S10-6 (m/z 534.0/536.2 [M+H]$^+$) along with diiodinated compound (m/z 659.5/661.9 [M+H]$^+$). LC-MS shows ratio of titled compound to diiodinated compound to be 80:20. This mixture was not separated but used further in the following step.

2-fluoro-8-((7-iodo-2,3-dihydrobenzo[b][1,4]dioxin-6-yl)methyl)-9-(2-(isobutylamino)ethyl)-9H-purin-6-amine [DZ3-73]. S10-6 (0.360 g, 0.674 mmol) and isobutylamine (2.46 g, 3.38 ml) in DMF (8 mL) was stirred overnight at rt. Solvent was removed under reduced pressure and the resulting residue was chromatographed (CH$_2$Cl$_2$:MeOH:MeOH—NH$_3$ (7N), 120:0.5:0.5 to 60:0.5:0.5) to give 0.220 g of a mixture of DZ3-73 along with the diiodinated compound. This mixture was separated by reverse phase HPLC ((a) H$_2$O+0.1% TFA and (b) CH$_3$CN+0.1% TFA, 10 to 75% b over 22 minutes at 16 mL/min) to give 0.196 g (58%) of DZ3-73. $^1$H NMR (500 MHz, CDCl$_3$) δ 7.35 (s, 1H), 6.57 (s, 1H), 6.37 (br s, 2H), 4.24 (s, 2H), 4.20 (s, 4H), 4.08 (t, J=6.4 Hz, 2H), 2.91 (t, J=6.4 Hz, 2H), 2.37 (d, J=6.3 Hz, 2H), 1.64

(m, 1H), 0.85 (d, J=6.2 Hz, 6H); $^{13}$C NMR (125 MHz, CDCl$_3$) δ 158.8 (d, J=208.1 Hz), 156.4 (d, J=19.5 Hz), 152.8 (d, J=18.8 Hz), 151.2, 144.2, 143.6, 131.5, 127.6, 117.9, 116.7, 88.3, 64.5, 57.8, 48.8, 43.5, 38.6, 28.4, 20.5; HRMS (ESI) m/z [M+H]$^+$ calcd. for C$_{20}$H$_{25}$FIN$_6$O$_2$, 527.1068; found. 527.1066; HPLC: method A R$_t$=6.91, method B R$_t$=8.48.

9-(2-(tert-butylamino)ethyl)-2-fluoro-8-((7-iodo-2,3-dihydrobenzo[b][1,4]dioxin-6-yl)methyl)-9H-purin-6-amine [DZ4-84]. S10-6 (8 mg, 0.0149 mmol) and tert-butylamine (109 mg, 157 μl) in DMF (0.5 mL) was stirred overnight at rt. Solvent was removed under reduced pressure and the resulting residue was purified by preparatory TLC (hexane:CH$_2$Cl$_2$:EtOAc:MeOH—NH$_3$ (7N), 7:2:1:0.5) to give 6 mg (77%) of DZ4-84. $^1$H NMR (500 MHz, CDCl$_3$) δ 7.36 (s, 1H), 6.55 (s, 1H), 5.86 (br s, 2H), 4.29 (s, 2H), 4.17-4.23 (m, 4H), 4.04 (t, J=6.4 Hz, 2H), 2.85 (t, J=6.4 Hz, 2H), 0.99 (s, 9H); MS (ESI) m/z 527.1 [M+H]$^+$.

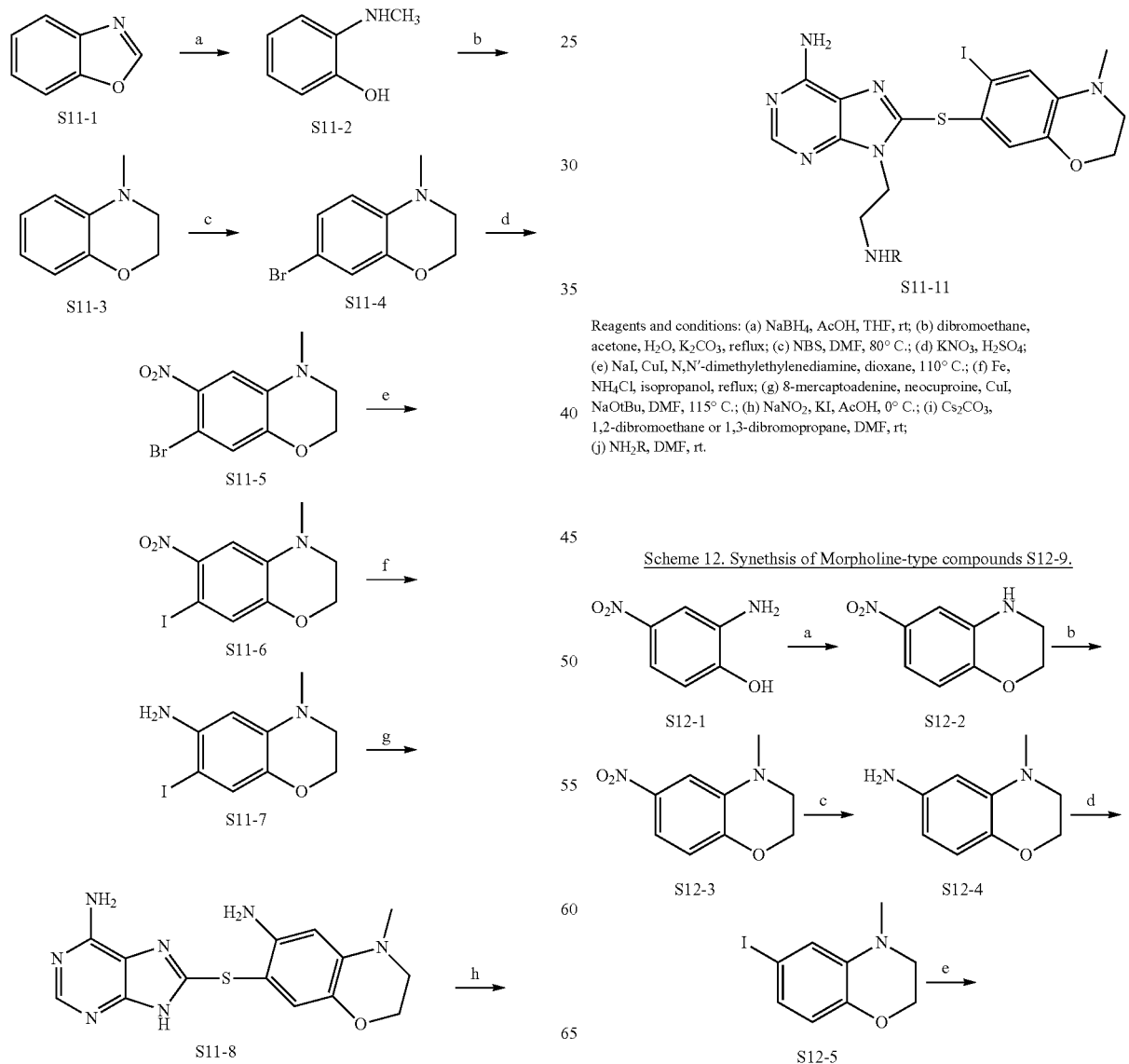

Reagents and conditions: (a) NaBH$_4$, AcOH, THF, rt; (b) dibromoethane, acetone, H$_2$O, K$_2$CO$_3$, reflux; (c) NBS, DMF, 80° C.; (d) KNO$_3$, H$_2$SO$_4$; (e) NaI, CuI, N,N'-dimethylethylenediamine, dioxane, 110° C.; (f) Fe, NH$_4$Cl, isopropanol, reflux; (g) 8-mercaptoadenine, neocuproine, CuI, NaOtBu, DMF, 115° C.; (h) NaNO$_2$, KI, AcOH, 0° C.; (i) Cs$_2$CO$_3$, 1,2-dibromoethane or 1,3-dibromopropane, DMF, rt; (j) NH$_2$R, DMF, rt.

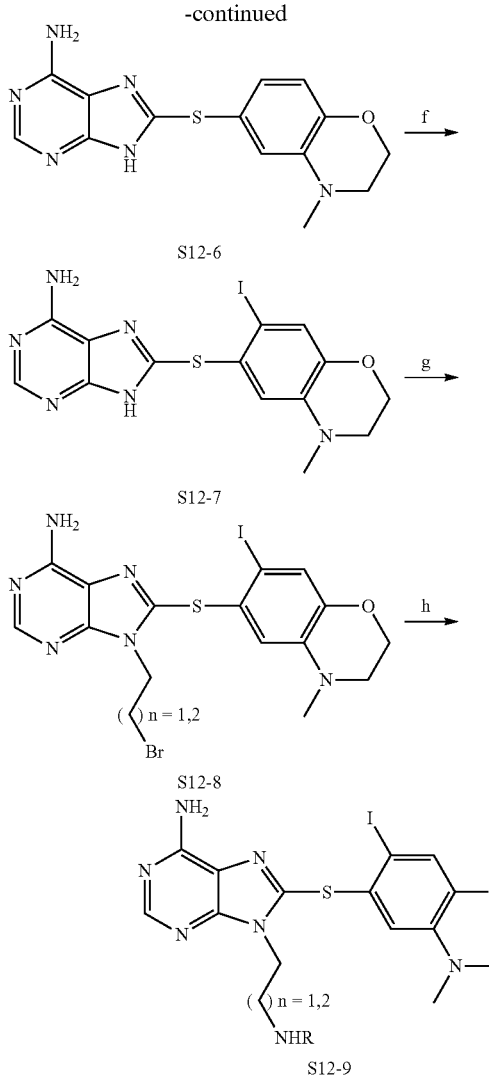

S12-6

S12-7

S12-8

S12-9

Reagents and conditions: (a) 1,2-dibromoethane, K₂CO₃, DMF, 125° C.; (b) MeI, DMF, 0° C. then rt; (c) Pd/C, H₂, MeOH, rt; (d) NaNO₂, AcOH, KI, 0° C.; (e) 8-mercaptoadenine, neocuproine, CuI, NaOtBu, DMF, 115° c.; (f) NIS, CH₃CN, rt; (g) Cs₂CO₃, 1,3-dibromopropane or 1,2-dibromoethane, DMF, rt; (h) NH₂R, DMF, rt.

6-Nitro-3,4-dihydro-2H-benzo[b][1,4]oxazine [S12-2]. To a solution of 2-amino-4-nitrophenol (S12-1; 1.5 g, 9.7 mmol) in 50 mL of DMF was added K₂CO₃ (4.04 g, 29.2 mmol) and 1,2-dibromoethane (1 mL, 11.7 mmol). The resulting mixture was stirred at 125° C. under argon overnight. The resulting mixture was concentrated under vacuum and purified by flash chromatography to give S12-2 (1.2 g, 68%) as a yellow solid. ¹H NMR (CDCl₃, 500 MHz) δ 7.55-7.58 (dd, J=2.7, 8.9 Hz, 1H), 7.48 (d, J=2.6 Hz, 1H), 6.81 (d, J=8.9 Hz, 1H), 4.34 (m, 2H), 4.12 (br s, 1H), 3.47 (m, 2 h); ¹³C NMR (CDCl₃, 125 MHz) δ 149.4, 141.8, 133.8, 115.0, 114.8, 110.2, 65.6, 40.0.

4-Methyl-6-nitro-3,4-dihydro-2H-benzo[b]1,4]oxazine [S12-3]. To a solution of S12-2, (0.66 g, 3.7 mmol) in 30 mL of DMF was added NaH (106 mg, 4.4 mmol) and stirred at 0° C. for 30 min. To the resulting mixture was added MeI (229 µL, 3.7 mmol) and kept stirring at rt for 2 h. The reaction mixture was concentrated in vacuum and purified by flash chromatography to give compound S12-3 (564 mg, 79%) as yellow solid. ¹H NMR (CDCl₃, 500 MHz) δ 7.56 (d, J=8.8 Hz, 1H), 7.45 (s, 1H), 6.76 (d, J=8.8 Hz, 1H), 4.36 (m, 2H), 3.32 (m, 2H), 2.95 (s, 3H); ¹³C NMR (CDCl₃, 125 MHz) δ: 149.7, 142.2, 136.5, 115.4, 114.5, 106.9, 65.3, 47.9, 38.6; MS (ESI) m/z 194.8 (M+H)⁺.

4-Methyl-3,4-dihydro-2H-benzo[b][1,4]oxazin-6-amine [S12-4]. To a solution of S12-3 (560 mg, 2.9 mmol) in 20 mL of methanol was added Pd/C powder (10%, 96 mg). The resulting suspension was stirred at rt under hydrogen overnight. The reaction mixture was filtered, concentrated in vacuum and purified by flash chromatography to give S12-4 (420 mg, 89%) as a yellow solid. ¹H NMR (CDCl₃, 500 MHz) δ 6.56 (d, J=8.3 Hz, 1H), 6.04 (d, J=2.5 Hz, 1H), 5.98 (dd, J=2.5, 8.3 Hz, 1H), 4.19 (t, J=4.4 Hz, 2H), 3.21 (t, J=4.5 Hz, 2H), 2.82 (s, 3H); ¹³C NMR (CDCl₃, 125 MHz) δ 140.8, 137.4, 137.0, 116.2, 104.8, 100.4, 64.6, 49.5, 38.7.

6-Iodo-4-methyl-3,4-dihydro-2H-benzo[b][1,4]oxazine [S12-5]. To solution of S12-4 (2.1 g, 12.8 mmol) in 50 mL of acetic acid cooled in ice bath was added NaNO₂ (1.77 g, 26.9 mmol) slowly in portions. The resulting mixture was stirred at 0° C. for 10 min and was added KI (4.24 g, 38.4 mmol) in portions. The reaction mixture was stirred at 0° C. for 30 min, allowed to warm up to rt and stirred for 2 h. The resulting mixture was quenched with 100 mL of water, extracted with ethyl acetate (3×150 mL). The organic layer was combined, treated with Na₂S₂O₃, washed with brine, dried over MgSO₄ and purified by flash chromatography to give S12-5 (1.86 g, 53%) as a yellow solid. ¹H NMR (CDCl₃, 500 MHz) δ 6.64 (d, J=8.3 Hz, 1H), 6.56 (s, 1H), 6.48 (d, J=8.4 Hz, 1H), 4.25 (m, 2H), 3.24 (m, 2H), 2.85 (s, 3H); ¹³C NMR (CDCl₃, 125 MHz) δ 138.1, 126.6, 120.5, 117.6, 111.9, 83.7, 64.8, 48.7, 36.5.

Scheme 13. Synthesis of DZ4-52-N9.

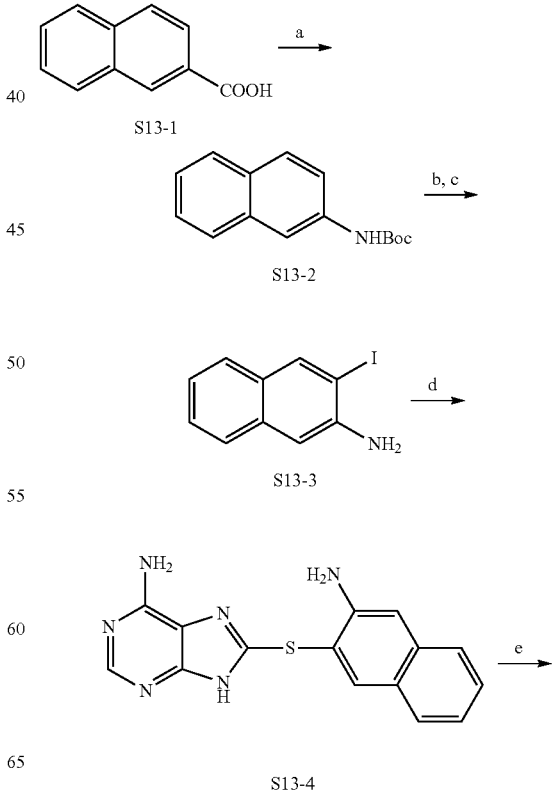

S13-1

S13-2

S13-3

S13-4

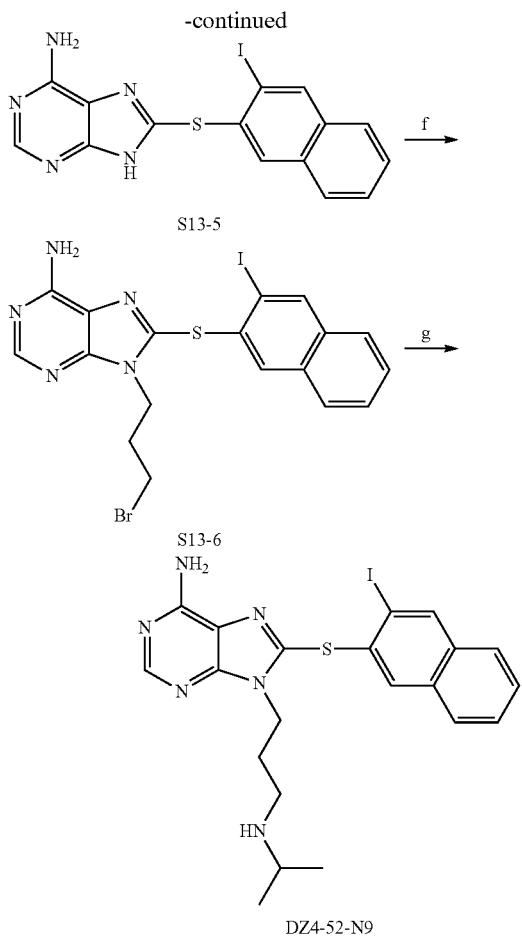

Reagents and conditions: (a) (C₆H₅O)₂P(O)N₃, t-BuOH, Et₃N, toluene, reflux; (b) t-BuLi, THF, -20° C., then ICH₂CH₂I, -78° C. to rt; (c) TFA, CH₂Cl₂, rt; (d) 8-mercaptodenine, neocuproine, CuI, NaOtBu, DMF, 115° C.; (e) KI, NaNO₂, HCl, H₂O, <5° C.; (f) 1,3-dibromopropane, Cs₂CO₃, DMF, rt; (g) isopropylamine, DMF, rt.

tert-Butyl naphthalen-2-ylcarbamate (S13-2). 2-Naphthoic acid (S13-1; 2.5 g, 14.3 mmol) in tert-BuOH (85 mL) and toluene (85 mL) was treated with Et₃N (2.3 mL, 16.4 mmol), 3 Å molecular sieves (16.7 g) and diphenyl phosphorylazide (3.5 mL, 16.4 mmol). The reaction mixture was refluxed for 24 h. After cooling to rt, solid was filtered off through Celite and the solvent was removed under reduced pressure. The residue was dissolved in EtOAc (75 mL) and washed with 1N aqueous HCl (2×50 mL), saturated aqueous NaHCO₃ (2×50 mL), dried over sodium sulfate and concentrated under reduced pressure. Chromatography (10% EtOAc in hexanes) afforded 2.5 g (71%) of S13-2. $^1$H NMR (500 MHz, CDCl₃) δ 7.99 (s, 1H), 7.72-7.78 (m, 3H), 7.44 (t, J=7.8 Hz, 1H), 7.31-7.38 (m, 2H), 6.61 (br s, 1H), 1.55 (s, 9H); MS (ESI) m/z 244.02 [M+H]⁺.

2-Amino-3-iodonaphthalene (S13-3). To a solution of S13-2 (1.0 g, 4.11 mmol) in 20 mL dry THF under argon at −20° C. was added tert-butyl lithium (1.5 M solution in pentane, 6.9 mL, 10.27 mmol) dropwise and was stirred for 2 h at −20° C. After cooling to −78° C., a solution of diiodoethane (2.9 g, 10.27 mmol) in 10 mL dry THF was added dropwise and then allowed to warm to rt for 3 h. A saturated aqueous NH₄Cl solution was added, and the solution was extracted with diethyl ether. The organic layer was washed with 10% sodium thiosulfate solution and dried over MgSO₄. The solvents were evaporated under reduced pressure and the residue was purified by chromatography (3% EtOAc in hexanes) to afford 1.1 g of a 79/21 mixture (NMR) of regioisomeric 3-iodo and 1-iodo Boc-protected 2-aminonaphthalene, respectively. This mixture (1.1 g) was dissolved in dichloromethane (12.5 mL), and trifluoroacetic acid (12.5 mL) was added dropwise at rt. After stirring for 1 h at rt, the solution was neutralized with a concentrated NaOH solution. The organic layer was separated and the aqueous layer was extracted with dichloromethane. The organic layers were combined, dried over MgSO₄, concentrated under reduced pressure and the resulting residue was purified by chromatography (0.5% EtOAc in hexanes) to afford 0.50 g (45%) of S13-3. $^1$H NMR (500 MHz, CDCl₃) δ 8.25 (s, 1H), 7.59 (d, J=8.3 Hz, 1H), 7.56 (d, J=8.3 Hz, 1H), 7.37 (dt, J=1.0, 7.5 Hz, 1H), 7.22 (dt, J=0.8, 7.5 Hz, 1H), 7.09 (s, 1H), 4.23 (br s, 2H); $^{13}$C NMR (125 MHz, CDCl₃) δ 144.3, 139.5, 135.3, 129.9, 127.5, 127.2, 126.3, 123.7, 109.0, 88.7; MS (ESI) m/z 269.96.

8-(3-aminonaphthalen-2-ylthio)-9H-purin-6-amine (S13-4). A mixture of 8-mercaptoadenine (20.7 mg, 0.124 mmol), neocuproine hydrate (3.9 mg, 0.0185 mmol), CuI (3.5 mg, 0.0185 mmol), sodium tert-butoxide (23.7 mg, 0.24 mmol), S13-3 (100 mg, 0.37 mmol) and DMF (2 mL) were heated at 115° C. for 20 h. The solvent was removed under reduced pressure and the residue was purified by preparatory TLC (CH₂Cl₂:MeOH—NH₃ (7N), 10:1) to give 14 mg (37%) of S13-4 as a solid. $^1$H NMR (500 MHz, CDCl₃/MeOH-d₄) δ 8.18 (s, 1H), 8.12 (s, 1H), 7.71 (d, J=8.3 Hz, 1H), 7.62 (d, J=8.1 Hz, 1H), 7.40-7.46 (m, 1H), 7.24-7.30 (m, 1H), 7.20 (s, 1H); MS (ESI) m/z 308.95 [M+H]⁺.

8-(3-iodonaphthalen-2-ylthio)-9H-purin-6-amine (S13-5). To a suspension of S13-4 (14 mg, 0.0454 mmol) in water (150 μL) at 5° C. was added 6 M HCl (140 μL) over 5 min. Then a solution of NaNO₂ (6.3 mg, 0.0908 mmol) in water (70 μL) was added dropwise over 30 min. at below 5° C. The mixture was stirred for an additional 10 min., then urea (1.9 mg, 0.0317 mmol) was added slowly. After 10 minutes, a solution of KI (22.6 mg, 0.136 mmol) in water (70 μL) was added dropwise over 5 min. and the mixture was stirred overnight. The solvent was removed under reduced pressure and the residue was purified by preparatory TLC (CH₂Cl₂:MeOH—NH₃ (7N), 8:1) to give 8 mg (42%) of S13-5 as a solid. $^1$H NMR (500 MHz, CDCl₃/MeOH-d₄) δ 8.51 (s, 1H), 8.17 (s, 2H), 7.75-7.80 (m, 2H), 7.52-7.60 (m, 2H); MS (ESI) m/z 420.01 [M+H]⁺.

9-(3-bromopropyl)-8-(3-iodonaphthalen-2-ylthio)-9H-purin-6-amine (S13-6). S13-5 (8 mg, 0.019 mmol), Cs₂CO₃ (7.4 mg, 0.0228 mmol), 1,3-dibromopropane (19.2 mg, 9.7 μL, 0.095 mmol) in DMF (0.2 mL) was stirred for 30 min. Then additional Cs₂CO₃ (7.4 mg, 0.0228 mmol) and 1,3-dibromopropane (19.2 mg, 9.7 μL, 0.095 mmol) was added and the mixture stirred for 30 min. The mixture was dried under reduced pressure and the residue purified by preparatory TLC (CH₂Cl₂:MeOH:AcOH, 15:1:0.5) to give 4.6 mg (45%) of S13-6. $^1$H NMR (500 MHz, CDCl₃/MeOH-d₄) δ 8.51 (s, 1H), 8.27 (s, 1H), 8.05 (s, 1H), 7.74-7.80 (m, 2H), 7.53-7.60 (m, 2H), 4.42 (t, J=7.1 Hz, 2H), 3.45 (t, J=6.6 Hz, 2H), 2.45 (m, 2H); MS (ESI) m/z 539.84/541.89 [M+H]⁺.

8-(3-iodonaphthalen-2-ylthio)-9-(3-(isopropylamino)propyl)-9H-purin-6-amine [DZ4-52-N9]. S13-6 (4.6 mg, 0.0085 mmol) and isopropylamine (100 μL) in DMF (100 μL) was stirred overnight at rt. Solvent was removed under reduced pressure and the resulting residue was purified by preparatory TLC (CH₂Cl₂:MeOH—NH₃ (7N), 10:1) to give 4.0 mg (91%) of DZ4-52-N9. $^1$H NMR (500 MHz, CDCl₃) δ 8.44 (s, 1H), 8.34 (s, 1H), 7.77 (s, 1H), 7.70-7.74 (m, 1H), 7.64-7.68 (m, 1H), 7.45-7.54 (m, 2H), 4.36 (t, J=6.9 Hz, 2H), 2.74

(septet, J=6.1 Hz, 1H), 2.58 (t, J=6.8 Hz, 2H), 2.06 (m, 2H), 1.05 (d, J=6.3 Hz, 6H); MS (ESI) m/z 518.82 [M+H]+.
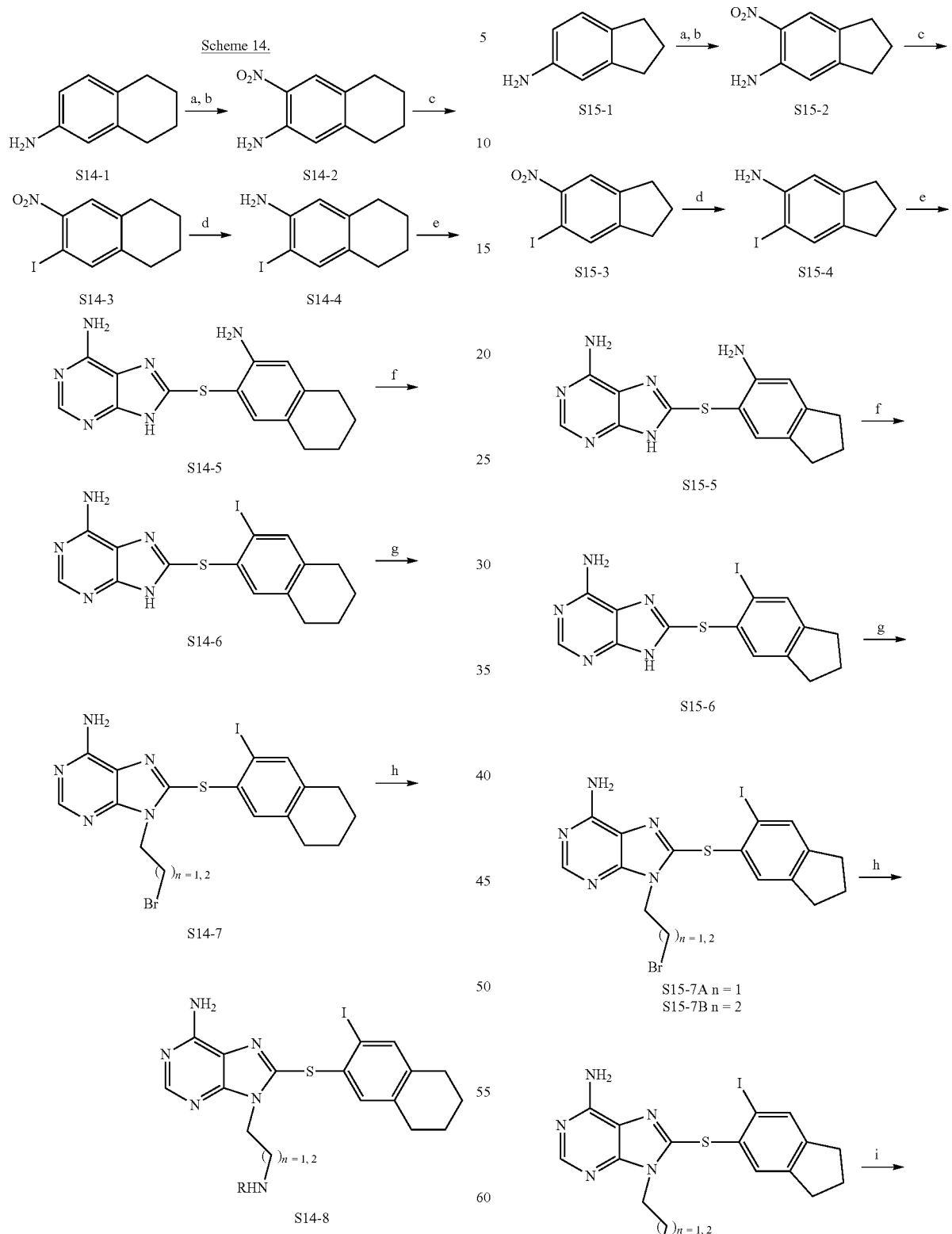
Reagents and conditions: (a) Ac2O, dioxane, 0° C. to rt; (b) KNO3, H2SO4, 0° C. to rt; (c) NaNO2, KI, AcOH, 0° C. to rt; (d) Fe, NH4Cl, isopropanol, reflux; (e) 8-mercaptoadenine, CuI, nBu4NBr, NaOtBu, mv; (f) NaNO2, KI, AcOH, 0° C.; (g) 1,3-dibromopropane or 1,2-dibromoethane, Cs2CO3, DMF, rt; (h) amine, DMF, rt.

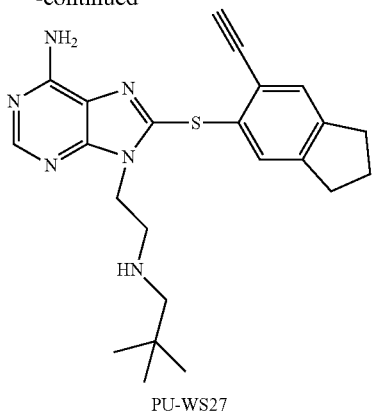

PU-WS27

Reagents and conditions: (a) Ac₂O, dioxane, 0° C. to rt; (b) KNO₃, H₂SO₄, 0° C. to rt; (c) NaNO₂, KI, AcOH, 0° C. to rt; (d) Fe, NH₄Cl, isopropanol, reflux; (e) 8-mercaptoadenine, CuI, nBu₄NBr, NaOt-Bu, mv; (f) NaNO₂, KI, AcOH, 0° C.; (g) 1,3-dibromopropane or 1,2-dibromoethane, Cs₂CO₃, DMF, rt; (h) isopropylamine or isobutylamine or neopentylamine, DMF, rt; (i) CuI, PdCl₂(PPh₃)₂, trimethylsilanylacetylene, Et₃N, DMF, 90° C.

5-amino-6-nitro-indane (S15-2). A solution of 5-aminoindane (S15-1; 10 g, 75 mmol) in 100 mL of dioxane cooled in ice bath was added acetic anhydride (15 mL) dropwise and kept stirring at room temperature for 2 days. The resulting mixture was condensed and dried under vacuum. The residue was dissolved in 100 mL of concentrated H₂SO₄, cooled in ice bath. KNO₃ in 15 mL of concentrated H₂SO₄ was added dropwise. The resulting solution was stirred at 0° C. for 2 h and then at rt for 2 h. The reaction mixture was poured into 150 g of ice and the resulting yellow precipitate was filtered and washed with cold water to give S15-2 (7.1 g, 43%). ¹H NMR (500 MHz, CDCl₃) δ 7.94 (s, 1H), 6.65 (s, 1H), 6.02 (br, 2H), 2.83 (m, 4H), 2.06 (m, 2H); ¹³CNMR (125 MHz, CDCl₃) δ 154.4, 144.2, 134.1, 131.2, 120.8, 113.5, 33.1, 31.4, 25.7.

5-iodo-6-nitro-indane (S15-3). To a solution of S15-2 (0.14 g, 0.78 mmol) in acetic acid cooled in ice bath was added NaNO₂ (65 mg, 0.94 mmol). The reaction mixture was stirred for 2 minutes. KI (0.39 g, 2.45 mmol) was added and the mixture was stirred at rt for 20 minutes. The resulting suspension was quenched with water (15 mL) and extracted with ethyl acetate (2×20 mL). The organic layer was washed with saturated aqueous Na₂S₂O₃ solution, brine and dried over MgSO4 and evaporated to dryness to give a residue that was purified by flash chromatography (ethyl acetate/hexane, gradient 0 to 50%) to give S15-3 (0.12 g, 65%) as a yellow solid. ¹HNMR (500 MHz, CDCl₃) δ 7.83 (s, 1H), 7.71 (s, 1H), 2.95 (m, 4H), 2.11 (m, 2H).

5-amino-6-iodo-indane (S15-4). To a solution of S15-3 (1.65 g, 5.7 mmol) in isopropanol (100 mL) and saturated aqueous NH₄Cl solution (20 mL) was added iron powder (1.1 g). The resulting suspension was refluxed for 1 h. The reaction mixture was filtered and the filtrate was condensed and purified by flash chromatography (ethyl acetate/hexane, gradient 0 to 50%) to give S15-4 (1.36 g, 92%) as a pale yellow solid. ¹H NMR (500 MHz, CDCl₃) δ 7.44 (s, 1H), 6.59 (s, 1H), 3.88 (s, 2H), 2.74 (m, 4H), 1.98 (m, 2H); ¹³CNMR (125 MHz, CDCl₃) δ 146.2, 144.9, 136.5, 134.1, 111.0, 32.8, 31.8, 26.1; MS (ESI): m/z 259.99 [M+H]⁺.

8-((6-amino-2,3-dihydro-1H-inden-5-yl)thio)-9-H-purin-6-amine (S15-5). The mixture of 8-mercaptoadenine (64 mg, 0.38 mmol), S15-4 (100 mg, 0.38 mmol), CuI (14.7 mg, 0.07 mmol), sodium t-butoxide (111 mg, 1.15 mmol) and tetrabutylammonium bromide (24.9 mg, 0.07 mmol) in anhydrous DMF (4 mL) was vortexed and heated at 190° C. under microwave for 1 h. The resulting mixture was condensed and purified by flash chromatography (methylene chloride/methanol, gradient 0 to 10%) to give S15-5 (54 mg, 47%) as a while solid. ¹HNMR (500 MHz, MeOH-d₄/CDCl₃) δ 8.11 (s, 1H), 7.36 (s, 1H), 6.81 (s, 1H), 2.85 (m, 4H), 2.06 (m, 2H); MS (ESI): m/z 299.02 [M+H]⁺.

8-((6-iodo-2,3-dihydro-1H-inden-5-yl)thio)-9-H-purin-6-amine (S15-6). To a solution of S15-5 (54 mg, 0.18 mmol) in acetic acid (5 mL) cooled in ice bath was added NaNO₂ (15 mg, 0.22 mmol) followed by KI (90 mg, 0.54 mmol). The reaction mixture was stirred at 0° C. for 15 min and quenched with water (10 mL). The resulting mixture was extracted with methylene chloride (2×20 mL). The organic layer was washed with saturated aqueous Na₂S₂O₃, brine, dried over MgSO₄ and evaporated to dryness. The residue was purified by flash chromatography (methylene chloride/methanol, gradient 0 to 10%) to give S15-6 (42 mg, 56%) as a white solid. ¹HNMR (500 MHz, CDCl₃) δ 8.12 (s, 1H), 7.84 (s, 1H), 7.39 (s, 1H), 2.91 (m, 4H), 2.11 (m, 2H); MS (ESI) m/z 410.10 [M+H]⁺.

9-(2-bromoethyl)-8-((6-iodo-dihydro-1H-inden-5-yl)thio)-9H-purin-6-amine (S15-7A). To a solution of S15-6 (70 mg, 0.17 mmol) in DMF (3 mL) was added 1,2-dibromoethane (74 uL, 0.86 mmol) and Cs₂CO₃ (111 mg, 0.34 mmol). The resulting mixture was stirred at rt for 2 h. S15-7A (36 mg, 41%) was obtained following preparatory TLC (methylene chloride/methanol, 20/1) as a white solid. ¹HNMR (500 MHz, CDCl₃) δ 8.36 (s, 1H), 7.75 (s, 1H), 7.18 (s, 1H), 4.62 (t, 2H), 3.68 (t, 2H), 2.88 (t, 2H), 2.81 (t, 2H), 2.06 (m, 2H); ¹³CNMR (125 MHz, CDCl₃, δ): 155.9, 153.9, 152.4, 149.8, 148.9, 148.1, 137.6, 132.8, 131.1, 101.7, 46.3, 33.9, 29.7, 26.8; MS (ESI): m/z 516.15, 518.16 [M, M+2]⁺.

8-((6-iodo-2,3-dihydro-1H-inden-5-yl)thio)-9-(2-(neopentylamino)ethyl)-9H-purin-6-amine (PU-WS25). To a solution of S15-7A (31 mg, 0.06 mmol) in DMF (1.5 mL) was added neopentylamine (250 uL). The reaction mixture was stirred at rt overnight and condensed under vacuum. PU-WS25 (28 mg, 89%) was obtained following preparatory TLC (methylene chloride/methanol, 10/1) as a white solid. ¹H NMR (500 MHz, CDCl₃) δ 8.32 (s, 1H), 7.73 (s, 1H), 7.1 (s, 1H), 5.63 (br, 2H), 4.38 (m, 2H), 3.03 (m, 2H), 2.87 (t, J=7.4 Hz, 2H), 2.78 (t, J=7.4 Hz, 2H), 2.37 (s, 2H), 2.04 (m, 2H), 0.93 (s, 9H); ¹³C NMR (125 MHz, CDCl₃, δ): 154.7, 152.9, 151.6, 147.1, 146.7, 146.4, 135.9, 133.5, 127.5, 120.2, 97.7, 61.8, 50.7, 49.7, 43.9, 32.5, 32.2, 31.5, 27.7, 25.5; HRMS (m/z): [M+H]⁺ calcd for C₂₁H₂₈IN₆S, 523.1141; found. 523.1140.

8-((6-iodo-2,3-dihydro-1H-inden-5-yl)thio)-9-(2-(isobutylamino)ethyl)-9H-purin-6-amine (PU-WS26). To a solution of S15-7A (6 mg, 0.01 mmol) in DMF (1 mL) was added isobutylamine (150 uL). The reaction mixture was stirred at rt overnight and condensed under vacuum. PU-WS26 (5.9 mg, 99%) was obtained following preparatory TLC (methylene chloride/methanol, 10/1) as a white solid. ¹HNMR (500 MHz, CDCl₃) δ 8.31 (s, 1H), 7.74 (s, 1H), 7.11 (s, 1H), 5.73 (br, 2H), 4.43 (m, 2H), 3.04 (m, 2H), 2.87 (t, J=7.4 Hz, 2H), 2.78 (t, J=7.4 Hz, 2H), 2.49 (d, J=6.6 Hz, 2H), 2.05 (m, 2H), 1.81 (m, 1H), 0.92 (m, 6H); HRMS (m/z): [M+H]⁺ calcd for C₂₀H₂₆IN₆S 509.0984; found. 509.0990.

9-(3-bromopropyl)-8-((6-iodo-2,3-dihydro-1H-inden-5-yl)thio)-9H-purin-6-amine (S15-7B). To a solution of S15-6 (30 mg, 0.07 mmol) in DMF (3 mL) was added 1,3-dibromopropane (37 μL, 0.86 mmol) and Cs₂CO₃ (46 mg, 0.14 mmol). The resulting mixture was stirred at rt for 2 h. S15-7B (8 mg, 21%) was obtained following preparatory TLC (methylene chloride/methanol, 20/1) as a white solid. $^1$H NMR (500 MHz, CDCl$_3$) δ 8.27 (s, 1H), 7.75 (s, 1H), 7.12 (s, 1H), 6.55 (br s, 2H), 4.33 (m, 2H), 2.88 (m, 2H), 2.79 (t, J=7.4 Hz, 2H), 2.29 (m, 2H), 1.97 (m, 2H); MS (ESI): m/z 530.3, 532.3 [M, M+2]$^+$.

8-((6-iodo-2,3-dihydro-1H-inden-5-yl)thio)-9-(3-(isopropylamino)propyl)-9H-purin-6-amine (PU-WS29). To a solution of S15-7B (8 mg, 0.015 mmol) in DMF (3 mL) was added isopropylamine (100 µL), stirred at rt overnight and condensed under vacuum. PU-WS29 (5.9 mg, 99%) was obtained following preparatory TLC (methylene chloride/methanol, 10/1) as a white solid. $^1$H NMR (500 MHz, CDCl$_3$) δ 8.32 (s, 1H), 7.75 (s, 1H), 7.12 (s, 1H), 5.73 (br s, 2H), 4.29 (t, 2H), 2.87 (t, J=7.4 Hz, 2H), 2.7-2.79 (m, 3H), 2.55 (t, 2H), 2.03-2.09 (m, 4H), 1.05 (d, J=11.2 Hz, 6H); $^{13}$C NMR (125 MHz, CDCl$_3$) δ 154.5, 152.9, 151.7, 147.2, 146.5, 135.9, 133.1, 127.6, 120.2, 97.9, 48.8, 43.7, 41.7, 32.5, 32.2, 30.0, 25.5, 22.7; HRMS (m/z): [M+H]$^+$ calcd for C$_{20}$H$_{26}$IN$_6$S 509.0984; found. 509.1003.

8-((6-ethynyl-2,3-dihydro-1H-inden-5-yl)thio)-9-(2-(neopentylamino)ethyl)-9H-purin-6-amine (PU-WS27). Following the procedure to make PU-WS8, PU-WS27 was obtained from PU-WS25 as a white solid. $^1$H NMR (CDCl$_3$, 500 MHz) δ 8.32 (s, 1H), 7.41 (s, 1H), 7.13 (s, 1H), 5.67 (br s, 2H), 4.42 (m, 2H), 3.48 (s, 1H), 3.02 (m, 2H), 2.77-2.91 (m, 4H), 2.39 (s, 2H), 2.06 (m, 2H), 0.89 (s, 9H); HRMS (ESI) m/z [M+H]$^+$ calcd. for C$_{23}$H$_{28}$N$_6$S, 421.2174; found. 421.2164.

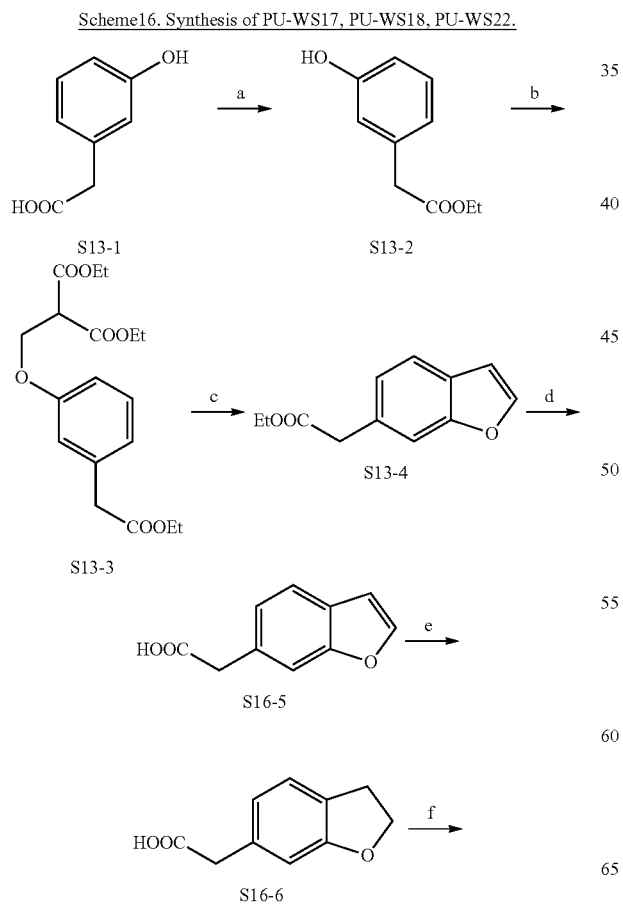

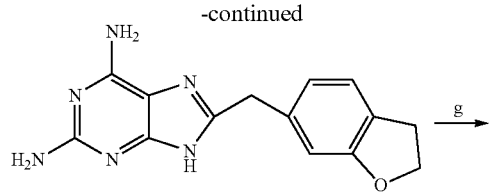

S16-7

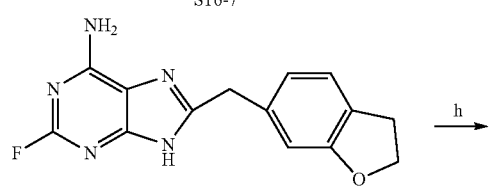

S16-8

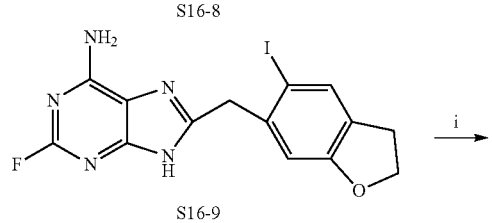

S16-9

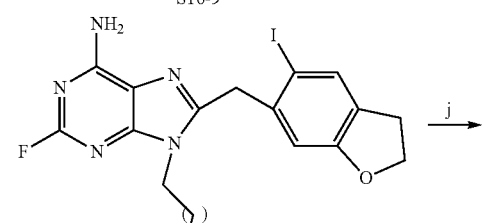

S16-10A n = 2
S16-10B n = 1

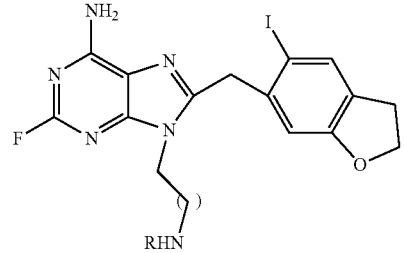

PU-WS18 n = 2, R = isopropyl
PU-WS17 n = 1, R = isobutyl
PU-WS22 n = 1, R = neopentyl Reagents and conditions: (a) EtOH, H$_2$SO$_4$, reflux; (b) 2-bromomethylmalonate, NaH, DMF, 110° C.; (c) PPA, toluene, reflux; (d) NaOH, MeOH, rt, then HCl; (e) Pd/C, H$_2$ (2 atm.), MeOH; (f) 2,4,5,6-tetraaminopyrimidine, triphenyl phosphite, pyridine, microwave, 210° C.; (g) HF/pyridine, NaNO$_2$, 0° C. to rt; (h) NIS, TFA, ACN; (i) 1,3-dibromopropane o 1,2-dibromoethane, Cs$_2$CO$_3$, DMF, rt; (h) isopropylamine or isobutylamine or neopentylamine, DMF, rt.

Ethyl 2-(3-hydroxyphenyl)acetate (S16-2). To a solution of 2-(3-hydroxyphenyl)acetic acid (S16-1; 10 g, 65.8 mmol) in 200 mL of ethanol was added 8 mL of concentrated sulfuric acid. The resulting mixture was refluxed overnight and condensed under vacuum. The residue was dissolved in ethyl acetate and washed with water. The organic layer was combined, washed with brine, dried over MgSO$_4$, evaporated to dryness and purified by flash chromatography to give S16-2 as a colorless oil in quantitative yield. $^1$H NMR (500 MHz, CDCl$_3$) δ 7.35 (br, 1H), 7.12 (m, 1H), 6.69-6.78 (m, 3H), 4.12 (m, 2H), 3.53 (s, 2H), 1.21 (m, 3H).

Diethyl 2-((3-ethoxy-2-oxoethyl)phenox)methyl)malonate (S16-3). To a solution of S16-2 (11.8 g, 65.5 mmol) in 150 mL of DMF cooled in ice bath was added NaH (2.36 g, 98 mmol) and stirred at 0° C. under argon for 20 min. To the resulting mixture was added diethyl 2-bromomethylmalonate (11.8 mL, 78 mmol) dropwise. The reaction mixture was stirred at 110° C. overnight, evaporated to dryness and purified by flash chromatography to give compound S16-3 (15.2 g, 66%) as a colorless oil. $^1$H NMR (500 MHz, CDCl$_3$) δ 7.19 (t, 1H), 6.80-6.86 (m, 3H), 4.81 (m, 1H), 4.12 (m, 2H), 3.97 (m, 2H), 3.74 (m, 2H), 3.63 (m, 2H), 3.55 (s, 2H), 1.19 (m, 9H); $^{13}$C NMR (125 MHz, CDCl$_3$) δ 171.3, 158.8, 135.6, 129.5, 121.8, 115.6, 113.3, 100.5, 68.5, 62.5, 60.7, 41.3, 15.4, 14.1.

Ethyl 2-(benzofuran-6-yl)acetate (S16-4). To a solution of S16-3 (6 g, 17 mmol) in 100 mL of toluene was added 3 g of polyphosphoric acid. The resulting mixture was refluxed overnight, condensed and purified by flash chromatography to give S16-4 (1.42 g, 41%) as colorless oil. $^1$H NMR (500 MHz, CDCl$_3$) δ 7.31-7.42 (m, 3H), 6.95 (m, 1H), 6.51 (s, 1H), 3.94 (m, 2H), 3.51 (s, 2H), 1.02 (m, 3H); $^{13}$C NMR (125 MHz, CDCl$_3$) δ 171.6, 155.2, 145.1, 130.6, 126.4, 124.3, 121.1, 112.2, 106.4, 60.9, 41.5, 14.2.

2-(benzofuran-6-yl)acetic acid (S13-5). To a solution of S16-4 (3 g, 14.7 mmol) in 100 mL methanol was add 25 mL of 1 N NaOH. The resulting mixture was stirred at rt for 2 h, neutralized with concentrated HCl, and adjusted pH to 2. The reaction mixture was condensed, purified by flash chromatography to yield S16-5 as a white solid in quantitative yield. $^1$H NMR (500 MHz, MeOH-d$_4$) δ 7.73 (s, 1H), 7.53 (d, J=7.9 Hz, 1H), 7.43 (s, 1H), 7.15 (d, J=8.0 Hz, 1H), 6.79 (s, 1H), 3.70 (s, 2H); $^{13}$C NMR (125 MHz, MeOH-d$_4$) δ 175.7, 156.6, 146.6, 132.5, 127.7, 125.4, 121.9, 113.0, 107.4, 41.9.

2-(2,3-dihydrobenzofuran-6-yl)acetic acid (S16-6). To a solution of S16-5 (1.8 g, 10 mmol) in 20 mL of methanol was added Pd/C (10%, 120 mg) and stirred at rt under H$_2$ (2 atm) overnight. The reaction mixture was filtered, washed with cold methanol, evaporated to dryness and purified by flash chromatography to give S16-6 (1.6 g, 88%) as a white solid. $^1$H NMR (500 MHz, MeOH-d$_4$) δ 7.12 (d, J=7.6 Hz, 1H), 6.73 (d, J=7.9 Hz, 1H), 6.71 (s, 1H), 4.55 (m, 2H), 3.56 (s, 2H), 3.16 (m, 2H); $^{13}$C NMR (125 MHz, MeOH-d$_4$) δ 177.9, 160.4, 133.3, 126.2, 124.8, 121.5, 110.5, 71.5, 41.1, 29.4.

8-((2,3-dihydrobenzofuran-6-yl)methyl)-9H-purine-2,6-diamine (S16-7). The mixture of 2,4,5,6-tetraminopyrimidine (200 mg, 1.4 mmol), S16-6 (254 mg, 1.4 mmol) and triphenyl phosphite (451 μL, 1.7 mmol) in 2 mL of pyridine was irradiated in the microwave for 15 min at 210° C. After cooling, the reaction mixture was concentrated under vacuum and the residue purified by flash chromatography to give S16-7 (350 mg, 89%) as a yellow solid. $^1$H NMR (500 MHz, MeOH-d$_4$) δ 7.16 (m, 1H), 6.79 (m, 1H), 6.73 (s, 1H), 4.57 (m, 2H), 4.12 (s, 2H), 3.18 (m, 2H); MS: m/z 283.2 (M+H)$^+$.

8-((2,3-dihydrobenzofuran-6-yl)methyl)-2-fluoro-9H-purin-6-amine (S16-8). A plastic tube charged with S16-7 (0.72 g, 2.5 mmol) was cooled in ice bath, added HF/pyridine (73%, 1.76 mL) and stirred to dissolve. To the resulting mixture was added NaNO$_2$ (0.23 g, 3.3 mmol) in portions and kept stirring for 5 min. The reaction mixture was allowed to warm up to rt and stirred for 3 h. CaCO$_3$ (0.68 g) was added to quench excess HF. The resulting suspension was stirred for 1 h, filtered, concentrated in vacuo and purified by flash chromatography to give S16-8 (0.45 g, 62%) as a yellow solid. $^1$H NMR (500 MHz, MeOH-d$_4$) δ: 7.16 (m, 1H), 6.77 (m, 1H), 6.71 (s, 1H), 4.57 (m, 2H), 4.12 (s, 2H), 3.19 (m, 2H); MS: m/z 286.0 (M+H)$^+$.

2-fluoro-8-((5-iodo-2,3-dihydrobenzofuran-6-yl)methyl)-9H-purin-6-amine (S16-9). To a suspension of S16-8 (0.45 g, 1.6 mmol) in 50 mL acetonitrile was added 1 mL of TFA. To the resulting solution was added NIS (1.06 g, 4.7 mmol) and the reaction mixture was stirred at rt for 3 h. It was then evaporated to dryness and purified by flash chromatography to give S16-9 (0.408 g, 63%) as a yellow solid. $^1$H NMR (500 MHz, MeOH-d$_4$) δ 7.67 (s, 1H), 6.76 (s, 1H), 4.59 (m, 2H), 4.28 (s, 2H), 3.21 (m, 2H); MS: m/z 412 (M+H)$^+$.

9-(3-bromopropyl)-2-fluoro-8-((5-iodo-2,3-dihydrobenzofuran-6-yl)methyl)-9H-purin-6-amine (S16-10A). To a solution of S16-9 (50 mg, 0.12 mmol) in 2 mL of DMF was added 1,3-dibromopropane (150 μL) and Cs$_2$CO$_3$ (80 mg, 0.24 mmol). The resulting mixture was stirred at rt for 2 h, evaporated to dryness and purified by preparatory TLC to give S16-10A (23 mg, 36%) as a white solid. $^1$H NMR (500 MHz, MeOH-d$_4$) δ 7.48 (s, 1H), 6.31 (s, 1H), 4.35 (m, 2H), 4.12 (s, 2H), 3.92 (m, 2h), 3.14 (m, 2H), 3.01 (m, 2H), 2.03 (m, 2H); MS: m/z 530, 532 (M, M+2)$^+$.

2-fluoro-8-((5-iodo-2,3-dihydrobenzofuran-6-yl)methyl)-9-(3-(isopropylamino)propyl)-9H-purin-6-amine (PU-WS18). To a solution of S16-10A (15 mg, 0.03 mmol) in 1 mL of DMF was added isopropylamine (0.5 mL), stirred at rt overnight, evaporated to dryness and purified by flash chromatography to give PU-WS18 (13 mg, 90%) as a white solid. $^1$H NMR (500 MHz, MeOH-d$_4$) δ 7.67 (s, 1H), 6.72 (s, 1H), 4.63 (m, 2H), 4.26 (m, 4H), 3.22-3.29 (m, 3H), 2.93 (t, J=7.1 Hz, 2H), 2.27 (t, J=7.0 Hz, 2H), 1.38 (d, J=6.5 Hz, 6H); HRMS (ESI) m/z [M+H]$^+$ calcd. for C$_{20}$H$_{25}$N$_6$OFI, 511.1119; found. 511.1103.

2-fluoro-8-((5-iodo-2,3-dihydrobenzofuran-6-yl)methyl)-9-(2-(isobutylamino)ethyl)-9H-purin-6-amine [PU-WS17]. To a solution of S16-9 (70 mg, 0.17 mmol) in 2 mL of DMF was added 1,2-dibromoethane (150 μL) and Cs$_2$CO$_3$ (110 mg, 0.34 mmol). The resulting mixture was stirred at rt for 2 h, evaporated to dryness and purified by preparatory TLC to give bromide intermediate S16-10B. To a solution of S16-10B (10 mg, 0.19 mmol) in 1 mL of DMF was added isobutylamine (100 uL), stirred at rt overnight, evaporated to dryness and purified by flash chromatography to give PU-WS17 as a white solid. $^1$H NMR (MeOH-d$_4$/CDCl$_3$, 500 MHz) δ: 7.67 (s, 1H), 6.62 (s, 1H), 4.59 (t, J=8.7 Hz, 2H), 4.29 (s, 2H), 4.15 (t, J=6.5 Hz, 2H), 3.22 (t, J=8.7 Hz, 2H), 2.93 (t, J=6.5 Hz, 2H), 2.45 (d, J=6.9 Hz, 2H), 1.69 (m, 1H), 0.88 (d, J=6.8 Hz, 6H); HRMS (ESI) m/z [M+H]$^+$ calcd. for C$_{20}$H$_{25}$FIN$_6$O, 511.1119; found. 511.1113.

2-fluoro-8-((5-iodo-2,3-dihydrobenzofuran-6-yl)methyl)-9-(2-(neopentylamino)ethyl)-9H-purin-6-amine [PU-WS22]. To a solution of S16-9 (70 mg, 0.17 mmol) in 2 mL of DMF was added 1,2-dibromoethane (150 μL) and Cs$_2$CO$_3$ (110 mg, 0.34 mmol). The resulting mixture was stirred at rt for 2 h, evaporated to dryness and purified by preparatory TLC to give bromide intermediate S16-10B. To a solution of S16-10B (65 mg, 0.13 mmol) in 1 mL of DMF was added neopentylamine (50 μL), stirred at rt overnight, evaporated to dryness and purified by flash chromatography to give compound PU-WS22 as a white solid. $^1$H NMR (CDCl$_3$, 500 MHz) δ 7.46 (s, 1H), 6.53 (s, 1H), 5.79 (s, 2H), 5.52 (br, 2H), 4.52 (m, 2H), 4.09 (m, 2H), 3.19 (m, 2H), 2.94-3.02 (m, 2H), 2.34 (s, 2H), 0.91 (s, 9H); HRMS (ESI) m/z [M+H]$^+$ calcd. for C$_{21}$H$_{27}$FIN$_6$O, 525.1275; found. 525.1249.

Scheme 17.

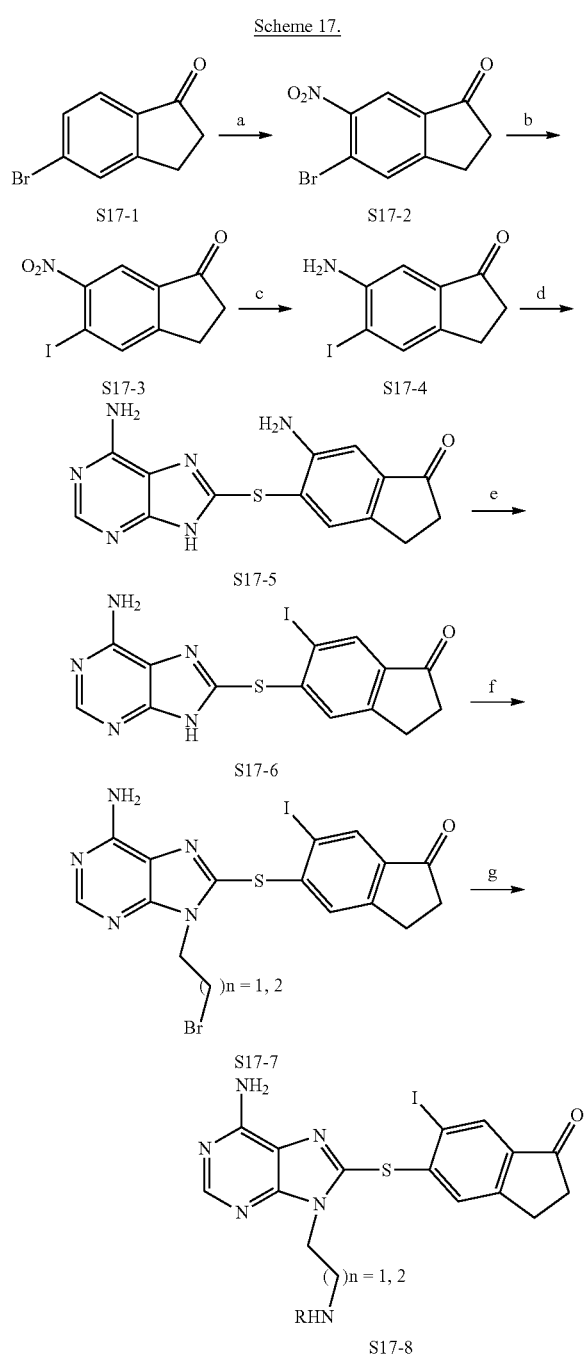

Reagents and condtitions: (a) HNO₃, H₂SO₄; (b) NaI, CuI, N,N'-dimethylethylenediamine, dioxane, 110° C.; (C) Fe, HCl; (d) 8-mercaptoadenine, neocuproine, CuI, NaOtBu, DMF, 115° C.; (e) KI, NaNO₂, HCl, <5° C.; (f) Cs₂CO₃, 1,3-dibromopropane, DMF, rt; (g) isopropylamine, DMF, rt.

Scheme 18.

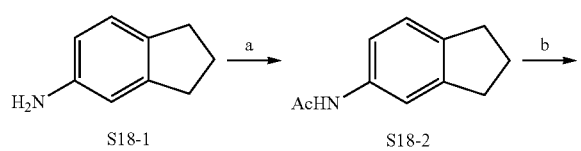

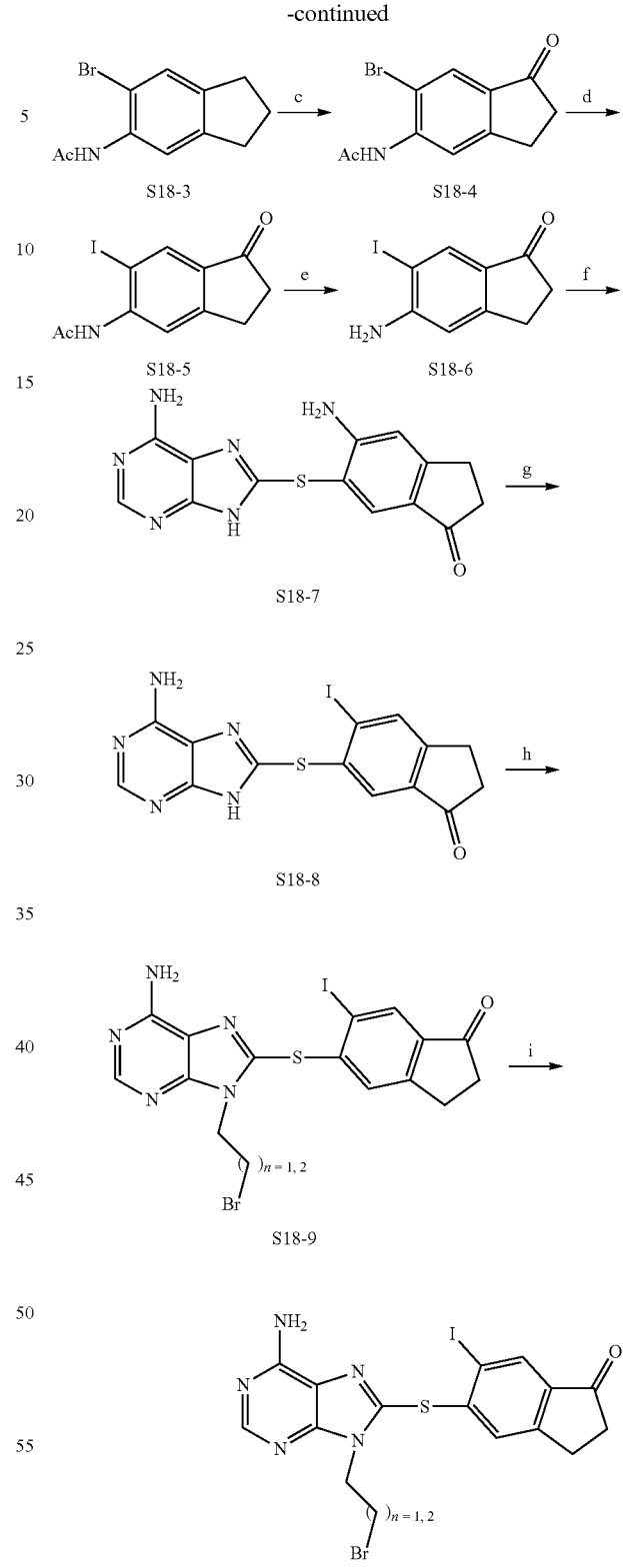

Reagents and condtitions: (a) Ac₂O, CH₂Cl₂, rt; (b) Br₂, AcOH, 10° C.; (c) CrO₃, AcOH/H₂O, 50-55° C.; (d) NaI, CuI, N,N'-dimethylethylenediamine, dioxane, 110° C.; (e) 6M HCl (aq.), reflux; (f) 8-mercaptoadenine, neocuproine, CuI, NaOtBu, DMF, 115° C.; (g) KI, NaNO₂, HCl, <5° C.; (h) Cs₂CO₃, 1,3-dibromopropane, DMF, rt; (i) isopropylamine, DMF, rt.

Scheme 19. Cross-coupling reactions of PU-RK11, PU-HT165 and DZ3-73.

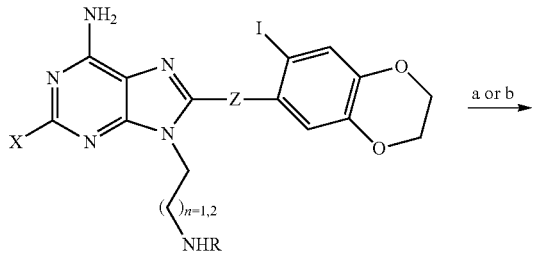

PU-RK11   X = H, Z = S, n = 2, R = isopropyl
PU-HT165  X = H, Z = S, n = 1, R = isobutyl
DZ3-73    X = F, Z = CH$_2$, n = 1, R = isobutyl

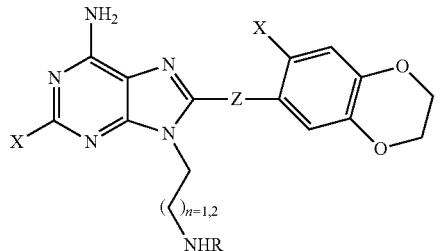

PU-HJP18   X = H, Z = S, n = 2, R = isopropyl, X = 2-furanyl
PU-HJP19   X = H, Z = S, n = 2, R = isopropyl, X = 3-pyrazolyl
PU-HJP23   X = H, Z = S, n = 1, R = isobutyl, X = 2-furanyl
TT-VI-53A  X = F, Z = CH$_2$, n = 1, R = isobutyl, X = 2-furanyl
TT-VI-54A  X = F, Z = CH$_2$, n = 1, R = isobutyl, X = 3-pyrazolyl
PU-HJP20   X = H, Z = S, n = 2, R= isopropyl, X = 2-oxazolyl Reagents or conditions: (a) boronic acid, PdCl$_2$(PPh$_3$)$_2$, NaHCO$_3$, H$_2$O, DMF; (b) XSn(Bu)$_3$, LiCl, Pd(PPh$_3$)$_4$, DMF, 90° C.

8-((7-(furan-2-yl)-2,3-dihydrobenzo[b][1,4]dioxin-6-yl)thio)-9-(3-(isopropylamino)propyl)-9H-purin-6-amine [HJP18]. 2-Furanylboronic acid (8 mg, 0.0712 mmol) was added to PU-RK11 (25 mg, 0.0475 mmol) and NaHCO$_3$ (12 mg, 0.1425 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (6.7 mg, 0.0095 mmol) were added and the reaction mixture was heated under nitrogen at 90° C. for 12 h. Solvent was removed under reduced pressure and the resulting residue was purified by preparatory TLC (CH$_2$Cl$_2$:MeOH—NH$_3$ (7N), 20:1) to give 10.2 mg (45%) of HJP18. $^1$H NMR (500 MHz, CDCl$_3$/MeOH-d$_4$) δ 8.29 (s, 1H), 7.47 (s, 1H), 7.26 (d, J=3.8 Hz, 1H), 6.89 (s, 1H), 6.73 (d, J=3.9 Hz, 1H), 6.46 (m, 1H), 4.25 (m, 4H), 4.16 (t, J=6.2 Hz, 2H), 2.67 (m, 1H), 2.47 (t, J=7.1 Hz, 2H), 1.86 (m, 2H), 1.01 (d, J=6.2 Hz, 6H); $^{13}$C NMR (125 MHz, CDCl$_3$/MeOH-d4) δ 154.4, 152.8, 151.7, 151.0, 146.7, 144.2, 143.7, 142.2, 126.6, 122.1, 119.9, 119.3, 117.6, 111.5, 109.5, 64.4, 64.3, 48.6, 43.8, 41.6, 30.1, 22.8; MS (ESI) m/z 467.14 [M+H]$^+$.

8-((7-(1H-pyrazol-3-yl)-2,3-dihydrobenzo[b][1,4]dioxin-6-yl)thio)-9-(3-(isopropylamino)propyl)-9H-purin-6-amine [HJP19]. 1H-Pyrazole-3-boronic acid (6.4 mg, 0.057 mmol) was added to PU-RK11 (20 mg, 0.038 mmol) and NaHCO$_3$ (9.8 mg, 0.117 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (5.3 mg, 0.0076 mmol) were added and the reaction mixture was heated under nitrogen at 90° C. for 12 h. Solvent was removed under reduced pressure and the resulting residue was purified by preparatory TLC (CH$_2$Cl$_2$:MeOH—NH$_3$ (7N), 15:1) to give 7.6 mg (43%) of HJP19. Additionally, 15.9 mg of unreacted PU-RK11 was recovered for an actual yield of 86%. $^1$H NMR (500 MHz, CDCl$_3$/MeOH-d$_4$) δ 8.18 (s, 1H), 7.53 (d, J=2.4 Hz, 1H), 7.15 (s, 1H), 7.14 (s, 1H), 6.36 (d, J=2.4 Hz, 1H), 4.29 (m, 4H), 4.19 (t, J=6.6 Hz, 2H), 2.75 (septet, J=6.1 Hz, 1H), 2.52 (t, J=6.6 Hz, 2H), 1.93 (m, 2H), 1.06 (d, J=6.1 Hz, 6H); MS (ESI) m/z 468.0 [M+H]$^+$.

8-((7-(furan-2-yl)-2,3-dihydrobenzo[b][1,4]dioxin-6-yl)thio)-9-(2-(isobutylamino)ethyl)-9H-purin-6-amine [HJP23]. 2-Furanylboronic acid (5.4 mg, 0.0486 mmol) was added to PU-HT165 (9 mg, 0.0171 mmol) and NaHCO$_3$ (5.7 mg, 0.0684 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (2.4 mg, 0.0034 mmol) were added and the reaction mixture was heated under nitrogen at 90° C. for 12 h. Solvent was removed under reduced pressure and the resulting residue was purified by preparatory TLC (CH$_2$Cl$_2$:MeOH—NH$_3$ (7N), 20:1) to give 1.8 mg (23%) of HJP23. $^1$H NMR (500 MHz, CDCl$_3$) δ 8.29 (s, 1H), 7.48 (d, J=1.8 Hz, 1H), 7.26 (s, 1H), 6.90 (s, 1H), 6.74 (d, J=3.2 Hz, 1H), 6.47 (m, 1H), 5.63 (br s, 2H), 4.20-4.30 (m, 6H), 2.90 (t, J=6.0 Hz, 2H), 2.38 (d, J=6.8 Hz, 2H), 1.65 (m, 1H), 0.85 (d, J=6.9 Hz, 6H); HRMS (ESI) m/z [M+H]$^+$ calcd. for C$_{23}$H$_{27}$N$_6$O$_3$S, 467.1865; found. 467.1884.

2-fluoro-8-((7-(furan-2-yl)-2,3-dihydrobenzo[b][1,4]dioxin-6-yl)methyl)-9-(2-(isobutylamino)ethyl)-9H-purin-6-amine [TT-VI-53A]. 2-Furanylboronic acid (8 mg, 0.0712 mmol) was added to DZ3-73 (25 mg, 0.0475 mmol) and NaHCO$_3$ (12 mg, 0.1425 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (6.7 mg, 0.0095 mmol) were added and the reaction mixture was heated under nitrogen at 90° C. for 12 h. Solvent was removed under reduced pressure and the resulting residue was purified by preparatory TLC (CH$_2$Cl$_2$:MeOH—NH$_3$ (7N), 20:1) to give 20.9 mg (94%) of TT-VI-53A. $^1$H NMR (500 MHz, CDCl$_3$/MeOH-d$_4$) δ 7.45 (d, J=1.8 Hz, 1H), 7.13 (s, 1H), 6.60 (s, 1H), 6.44 (dd, J=1.8, 3.3 Hz, 1H), 6.35 (d, J=3.3 Hz, 1H), 4.34 (s, 2H), 4.26 (s, 4H), 4.05 (t, J=6.4 Hz, 2H), 2.85 (t, J=6.4 Hz, 2H), 2.35 (d, J=6.9 Hz, 2H), 1.67 (m, 1H), 0.85 (d, J=6.7 Hz, 6H); $^{13}$C NMR (125 MHz, CDCl$_3$/MeOH-d4) δ 158.8 (d, J=209.1 Hz), 156.3 (d, J=19.5 Hz), 152.8, 152.2, 143.9, 142.9, 142.2, 126.0, 124.1, 118.7, 117.7, 117.6, 116.3, 111.6, 108.2, 64.6, 57.5, 48.6, 43.1, 31.8, 28.2, 20.6; HRMS (ESI) m/z [M+H]$^+$ calcd. for C$_{24}$H$_{28}$FN$_6$O$_3$, 467.2207; found. 467.2203; HPLC: method A R$_t$=7.05, method B R$_t$=8.74.

8-((7-(1H-pyrazol-3-yl)-2,3-dihydrobenzo[b][1,4]dioxin-6-yl)methyl)-2-fluoro-9-(2-(isobutylamino)ethyl)-9H-purin-6-amine [TT-VI-54A]. 1H-Pyrazole-3-boronic acid (26 mg, 0.228 mmol) was added to DZ3-73 (30 mg, 0.0570 mmol) and NaHCO$_3$ (29 mg, 0.342 mmol). DMF (1 mL) was added and the reaction mixture was evacuated and back filled with nitrogen. This was repeated four times then nitrogen was bubbled through the reaction mixture for 10 minutes. Then H$_2$O (0.2 mL) and Pd(PPh$_3$)$_2$Cl$_2$ (8 mg, 0.0114 mmol) were added and the reaction mixture was heated under nitrogen at 90° C. for 12 h. Solvent was removed under reduced pressure and the resulting residue was purified by preparatory TLC (CH$_2$Cl$_2$:MeOH—NH$_3$ (7N), 15:1) to give 11.3 mg (42%) of TT-VI-54A. Additionally, 15.9 mg of unreacted DZ3-73 was recovered for an actual yield of 90%. $^1$H NMR (500 MHz, CDCl$_3$/MeOH-d$_4$) δ 7.60 (d, J=2.1 Hz, 1H), 7.02 (s, 1H), 6.82 (s, 1H), 6.33 (d, J=2.1 Hz, 1H), 4.32 (t, J=6.8 Hz, 2H), 4.29 (s, 2H), 4.28 (s, 4H), 2.96 (t, J=6.8 Hz, 2H), 2.59 (d, J=7.0 Hz, 2H), 1.92 (m, 1H), 0.96 (d, J=6.7 Hz, 6H); $^{13}$C NMR (125 MHz, CDCl$_3$/MeOH-d$_4$) δ 158.2 (d, J=210.1 Hz), 156.5 (d, J=19.9 Hz), 152.6, 152.2, 152.1, 144.0, 143.0, 126.5, 119.1, 118.9, 115.94, 115.91, 105.4, 64.65, 64.56, 56.5, 47.7, 41.0, 31.1, 27.2, 20.3; HRMS (ESI) m/z [M+H]$^+$ calcd. for C$_{23}$H$_{28}$FN$_8$O$_2$, 467.2319; found. 467.2323; HPLC: method A R$_t$=6.39, method B R$_t$=7.03.

9-(3-(isopropylamino)propyl)-8-((7-(oxazol-2-yl)-2,3-dihydrobenzo[b][1,4]dioxin-6-yl)thio)-9H-purin-6-amine [HJP20]. 2-(Tributyltin)oxazole (54 mg, 0.1518 mmol) was added to PU-RK11 (20 mg, 0.038 mmol) and LiCl (3.2 mg, 0.076 mmol). DMF (1 mL) was added and the reaction mixture was evacuated and back filled with nitrogen. This was repeated four times then nitrogen was bubbled through the reaction mixture for 10 minutes. Then Pd(PPh$_3$)$_4$ (6.7 mg, 0.0095 mmol) was added and the reaction mixture was heated under nitrogen at 90° C. for 12 h. Solvent was removed under reduced pressure and the resulting residue was purified by preparatory TLC (CH$_2$Cl$_2$:MeOH—NH$_3$ (7N), 20:1) to give 4.7 mg (27%) of HJP20. Additionally, 7 mg of unreacted PU-RK11 was recovered for an actual yield of 45%. $^1$H NMR (500 MHz, CDCl$_3$) δ 8.32 (s, 1H), 7.70 (s, 1H), 7.54 (s, 1H), 7.26 (s, 1H), 6.59 (s, 1H), 5.79 (br s, 2H), 4.20-4.34 (m, 6H), 2.67 (m, J=6.1 Hz, 1H), 2.50 (t, J=6.8 Hz, 2H), 1.93 (m, J=7.1 Hz, 2H), 0.99 (d, J=6.4 Hz, 6H); MS (ESI) m/z 468.15 [M+H]$^+$.

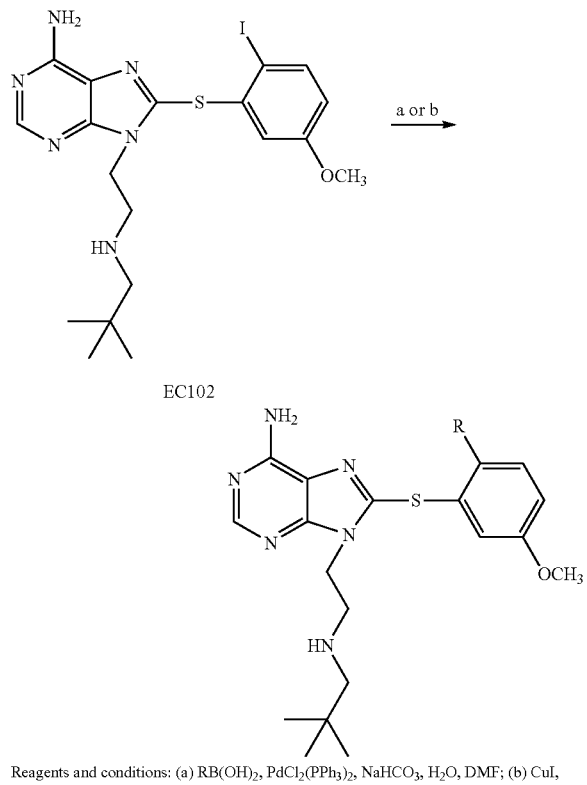

Scheme 20. Cross-coupling reactions of EC102.

Reagents and conditions: (a) RB(OH)$_2$, PdCl$_2$(PPh$_3$)$_2$, NaHCO$_3$, H$_2$O, DMF; (b) CuI, PdCl$_2$(PPh$_3$)$_2$, trimethylsilanylacetylene, Et$_3$N, DMF, 90° C.

8-(2-(furan-2-yl)-5-methoxyphenylthio)-9-(2-(neopentylamino)ethyl)-9H-purin-6-amine [TT-V-138]. 2-Furanylboronic acid (8.2 mg, 0.0732 mmol) was added to EC102 (25 mg, 0.0488 mmol) and NaHCO$_3$ (12.3 mg, 0.1464 mmol). DMF (1 mL) was added and the reaction mixture was evacuated and back filled with nitrogen. This was repeated four times then nitrogen was bubbled through the reaction mixture for 10 minutes. Then H$_2$O (0.1 mL) and Pd(PPh$_3$)$_2$Cl$_2$ (6.8 mg, 0.00976 mmol) were added and the reaction mixture was heated under nitrogen at 90° C. for 5 h. Solvent was removed under reduced pressure and the resulting residue was purified by preparatory TLC (CH$_2$Cl$_2$:MeOH—NH$_3$ (7N), 20:1) to give 20.7 mg (94%) of TT-V-138. $^1$H NMR (500 MHz, CDCl$_3$) δ 8.31 (s, 1H), 7.62 (d, J=8.7 Hz, 1H), 7.50 (d, J=1.8 Hz, 1H), 6.86 (dd, J=2.6, 8.7 Hz, 1H), 6.70-6.73 (m, 2H), 6.49 (dd, J=1.8, 3.3 Hz, 1H), 5.98 (br s, 2H), 4.26 (t, J=6.2 Hz, 2H), 3.70 (s, 3H), 2.89 (t, J=6.2 Hz, 2H), 2.28 (s, 2H), 0.84 (s, 9H); $^{13}$C NMR (125 MHz, CDCl$_3$) δ 159.4, 154.8, 153.2, 151.6, 151.2, 145.4, 142.0, 130.9, 130.2, 124.3, 120.1, 116.5, 113.4, 111.4, 109.1, 61.8, 55.3, 49.6, 43.9, 31.5, 27.6; HRMS (ESI) m/z [M+H]$^+$ calcd. for C$_{23}$H$_{29}$N$_6$O$_2$S, 453.2073; found. 453.2071; HPLC: method A R$_t$=6.76, method B R$_t$=7.29.

8-(5-methoxy-2-(thiophen-2-yl)phenylthio)-9-(2-(neopentylamino)ethyl)-9H-purin-6-amine [TT-V-139]. 2-Thiopheneboronic acid (18.8 mg, 0.147 mmol) was added to EC102 (25 mg, 0.0488 mmol) and NaHCO$_3$ (24.6 mg, 0.293 mmol). DMF (1 mL) was added and the reaction mixture was evacuated and back filled with nitrogen. This was repeated four times then nitrogen was bubbled through the reaction mixture for 10 minutes. Then H$_2$O (0.25 mL) and Pd(PPh$_3$)$_2$Cl$_2$ (10.4 mg, 0.0148 mmol) were added and the reaction mixture was heated under nitrogen at 90° C. for 5 h. Solvent was removed under reduced pressure and the resulting residue was purified by preparatory TLC (CH$_2$Cl$_2$: MeOH—NH$_3$ (7N), 20:1) to give 16.2 mg (71%) of TT-V-139. $^1$H NMR (500 MHz, CDCl$_3$/MeOH-d$_4$) δ 8.19 (s, 1H), 7.45 (d, J=8.5 Hz, 1H), 7.30-7.33 (m, 1H), 6.99-7.04 (m, 3H), 6.97 (dd, J=2.6, 8.5 Hz, 1H), 4.24 (t, J=6.1 Hz, 2H), 3.82 (s, 3H), 2.97 (t, J=6.1 Hz, 2H), 2.41 (s, 2H), 0.91 (s, 9H); $^{13}$C NMR (125 MHz, CDCl$_3$/MeOH-d$_4$) δ 159.9, 154.6, 152.4, 150.9, 147.6, 140.4, 133.2, 130.8, 129.3, 127.6, 127.1, 126.2, 119.5, 118.9, 114.6, 61.4, 55.6, 49.3, 43.3, 31.3, 27.6; HRMS (ESI) m/z [M+H]$^+$ calcd. for C$_{23}$H$_{29}$N$_6$OS$_2$, 469.1844; found. 469.1830; HPLC: method A R$_t$=6.84, method B R$_t$=7.48.

8-(5-methoxy-2-(1H-pyrazol-3-yl)phenylthio)-9-(2-(neopentylamino)ethyl)-9H-purin-6-amine [TT-V-140]. 1H-Pyrazole-3-boronic acid (26.2 mg, 0.234 mmol) was added to EC102 (30 mg, 0.0585 mmol) and NaHCO$_3$ (29.5 mg, 0.351 mmol). DMF (1 mL) was added and the reaction mixture was evacuated and back filled with nitrogen. This was repeated four times then nitrogen was bubbled through the reaction mixture for 10 minutes. Then H$_2$O (0.2 mL) and Pd(PPh$_3$)$_2$Cl$_2$ (8.2 mg, 0.0117 mmol) were added and the reaction mixture was heated under nitrogen at 90° C. for 7 h. Solvent was removed under reduced pressure and the resulting residue was purified by preparatory TLC (CH$_2$Cl$_2$: MeOH—NH$_3$ (7N), 15:1) to give 6.2 mg (23%) of TT-V-140. Additionally, 16.4 mg of unreacted EC102 was recovered for an actual yield of 52%. $^1$H NMR (500 MHz, CDCl$_3$/MeOH-d$_4$) δ 8.19 (s, 1H), 7.58 (d, J=2.1 Hz, 1H), 7.50 (d, J=8.5 Hz, 1H), 7.03 (d, J=2.4 Hz, 1H), 6.99 (dd, J=2.6, 8.6 Hz, 1H), 6.40 (d, J=2.1 Hz, 1H), 4.42 (t, J=6.1 Hz, 2H), 3.81 (s, 3H), 3.02 (t, J=6.1 Hz, 2H), 2.52 (s, 2H), 0.98 (s, 9H); $^{13}$C NMR (125 MHz, CDCl$_3$/MeOH-d$_4$) δ 154.6, 152.3, 150.8, 149.4, 148.6, 148.5, 120.1, 119.2, 114.5, 110.9, 106.0, 102.3, 61.2, 49.1, 42.5, 31.1, 27.5; HRMS (ESI) m/z [M+H]⁺ calcd. for $C_{22}H_{29}N_8OS$, 453.2185; found. 453.2186; HPLC: method A $R_t$=6.61, method B $R_t$=6.82.

8-((2-ethynyl-5-methoxyphenyl)thio)-9-(2-(neopentylamino)ethyl)-9H-purin-6-amine (PU-WS31). Following the procedure to make PU-WS8, PU-WS31 was obtained from EC102 as a white solid. ¹H NMR (CDCl₃, 500 MHz) δ: 8.35 (s, 1H), 7.46 (d, J=8.4 Hz, 1H), 6.75 (m, 2H), 5.65 (br, 2H), 4.35 (t, J=6.3 Hz, 2H), 3.72 (s, 3H), 3.30 (s, 1H), 2.97 (t, J=6.3 Hz, 2H), 2.31 (s, 2H), 0.87 (s, 9H); MS (ESI) m/z 411.3 (M+H)⁺.

Scheme 21. Stille coupling of PU-H71 and PU-DZ13.

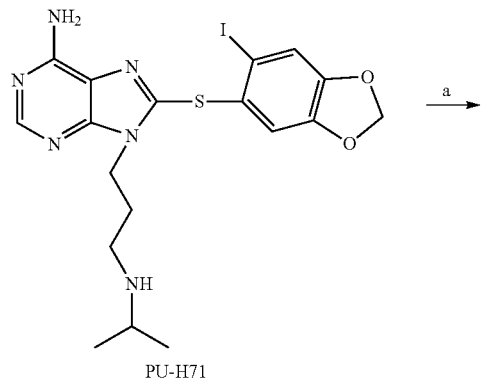

PU-H71

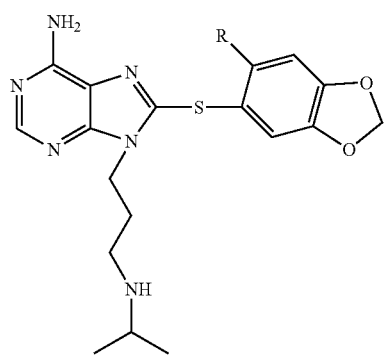

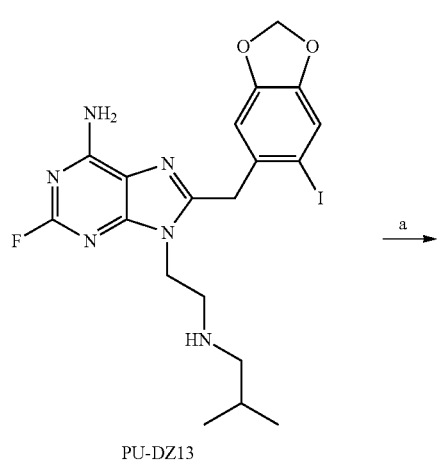

PU-DZ13

-continued

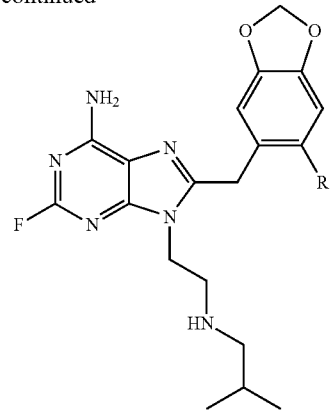

Reagents and conditions: (a) RSn(Bu)₃, LiCl, Pd(PPh₃)₄, DMF, 90° C.

9-(3-(isopropylamino)propyl)-8-(6-(oxazol-2-yl)benzo[d][1,3]dioxol-5-ylthio)-9H-purin-6-amine [DZ4-20]. A mixture of PU-H71 (30 mg, 0.0585 mmol), 2-(tri-n-butylstannyl)oxazole (83.8 mg, 49 µl, 0.234 mmol), LiCl (5 mg, 0.117 mmol) and Pd(PPh₃)₄ (6.7 mg, 0.0058 mmol) in DMF (1 mL) was evacuated and back filled with nitrogen. This was repeated four times then the reaction mixture was heated under nitrogen at 90° C. for 18 h. Solvent was removed under reduced pressure and the resulting residue was purified by preparatory TLC (hexane:CH₂Cl₂:EtOAC:MeOH—NH₃ (7N), 2:2:1:0.5) to give 20.8 mg (78%) of DZ4-20. ¹H NMR (500 MHz, CDCl₃/MeOH-d₄) δ 8.25 (s, 1H), 7.75 (s, 1H), 7.46 (s, 1H), 7.27 (s, 1H), 6.71 (s, 1H), 6.06 (s, 2H), 4.26 (t, J=6.9 Hz, 2H), 2.75 (septet, J=6.3 Hz, 1H), 2.53 (t, J=6.9 Hz, 2H), 1.98 (m, 2H), 1.06 (d, J=6.3 Hz, 6H); HRMS (ESI) m/z [M+H]⁺ calcd. for $C_{21}H_{24}N_7O_3S$, 454.1661; found. 454.1650; HPLC: method A $R_t$=5.77, method B $R_t$=5.28.

9-(3-(isopropylamino)propyl)-8-(6-(thiazol-2-yl)benzo[d][1,3]dioxol-5-ylthio)-9H-purin-6-amine [DZ4-21]. A mixture of PU-H71 (30 mg, 0.0585 mmol), 2-(tri-n-butylstannyl)thiazole (87.6 mg, 72.4 µl, 0.234 mmol), LiCl (5 mg, 0.117 mmol) and Pd(PPh₃)₄ (6.7 mg, 0.0058 mmol) in DMF (1 mL) was evacuated and back filled with nitrogen. This was repeated four times then the reaction mixture was heated under nitrogen at 90° C. for 18 h. Then additional 2-(tri-n-butylstannyl)thiazole (21.9 mg, 18 µl, 0.0585 mmol) was added and the reaction mixture was heated under nitrogen at 90° C. for an additional 18 h. Solvent was removed under reduced pressure and the resulting residue was purified by preparatory TLC (hexane:CH₂Cl₂:EtOAC:MeOH—NH₃ (7N), 2:2:1:0.5) to give 17.6 mg (64%) of DZ4-21. ¹H NMR (500 MHz, CDCl₃/MeOH-d₄) δ 8.20 (s, 1H), 7.87 (d, J=3.3 Hz, 1H), 7.45 (s, 1H), 7.44 (d, J=3.3 Hz, 1H), 6.98 (s, 1H), 6.11 (s, 2H), 4.21 (t, J=6.9 Hz, 2H), 2.78 (septet, J=6.3 Hz, 1H), 2.55 (t, J=6.9 Hz, 2H), 1.98 (m, 2H), 1.09 (d, J=6.3 Hz, 6H); HRMS (ESI) m/z [M+H]⁺ calcd. for $C_{21}H_{24}N_7O_2S_2$, 470.1433; found. 470.1438; HPLC: method A $R_t$=5.86, method B $R_t$=5.66.

2-fluoro-9-(2-(isobutylamino)ethyl)-8-((6-(oxazol-2-yl)benzo[d][1,3]dioxol-5-yl)methyl)-9H-purin-6-amine [DZ4-23]. A mixture of PU-DZ13 (20 mg, 0.039 mmol), 2-(tri-n-butylstannyl)oxazole (55.9 mg, 32.7 µl, 0.156 mmol), LiCl (3.3 mg, 0.078 mmol) and Pd(PPh₃)₄ (4.5 mg, 0.0039 mmol) in DMF (1 mL) was evacuated and back filled with nitrogen. This was repeated four times then the reaction mixture was heated under nitrogen at 90° C. for 18 h. Then additional LiCl (3.3 mg, 0.078 mmol) and Pd(PPh₃)₄ (4.5 mg, 0.0039 mmol) were added and the reaction mixture was heated under nitrogen at 90° C. for an additional 18 h. Solvent was removed under reduced pressure and the resulting residue was purified by preparatory TLC two times (hexane:CH₂Cl₂:EtOAC:

MeOH—NH₃ (7N), 2:2:1:0.5 then CH₂Cl₂:MeOH—NH₃ (7N), 20:1) to give 5.5 mg (31%) of DZ4-23. ¹H NMR (500 MHz, CDCl₃/MeOH-d₄) δ 7.68 (s, 1H), 7.53 (s, 1H), 7.12 (s, 1H), 6.84 (s, 1H), 6.07 (s, 2H), 4.74 (s, 2H), 4.41 (t, J=6.4 Hz, 2H), 3.15 (t, J=6.4 Hz, 2H), 2.59 (d, J=6.9 Hz, 2H), 1.88 (m, 1H), 0.96 (d, J=6.8 Hz, 6H); HRMS (ESI) m/z [M+H]⁺ calcd. for $C_{22}H_{25}FN_7O_3$, 454.2003; found. 454.1995; HPLC: method A $R_t$=6.61, method B $R_t$=7.58.

2-fluoro-9-(2-(isobutylamino)ethyl)-8-((6-(thiazol-2-yl)benzo[d][1,3]dioxol-5-yl)methyl)-9H-purin-6-amine [DZ4-24]. A mixture of PU-DZ13 (20 mg, 0.039 mmol), 2-(tri-n-butylstannyl)thiazole (58.3 mg, 48.2 μl, 0.156 mmol), LiCl (3.3 mg, 0.078 mmol) and Pd(PPh₃)₄ (9 mg, 0.0078 mmol) in DMF (1 mL) was evacuated and back filled with nitrogen. This was repeated four times then the reaction mixture was heated under nitrogen at 90° C. for 18 h. Solvent was removed under reduced pressure and the resulting residue was purified by preparatory TLC two times (hexane:CH₂Cl₂:EtOAC:MeOH—NH₃ (7N), 2:2:1:0.5 and CH₂Cl₂:MeOH:AcOH, 20:1:0.5) to give 10.2 mg (56%) of DZ4-24. ¹H NMR (500 MHz, CDCl₃/MeOH-d₄) δ 7.77 (d, J=3.3 Hz, 1H), 7.36 (d, J=3.3 Hz, 1H), 7.17 (s, 1H), 6.80 (s, 1H), 6.05 (s, 2H), 4.58 (s, 2H), 4.15 (t, J=6.6 Hz, 2H), 2.85 (t, J=6.6 Hz, 2H), 2.35 (d, J=6.8 Hz, 2H), 1.64 (m, 1H), 0.86 (d, J=6.8 Hz, 6H); HRMS (ESI) m/z [M+H]⁺ calcd. for $C_{22}H_{25}FN_7O_2S$, 470.1774; found. 470.1770; HPLC: method A $R_t$=6.68, method B $R_t$=7.79.

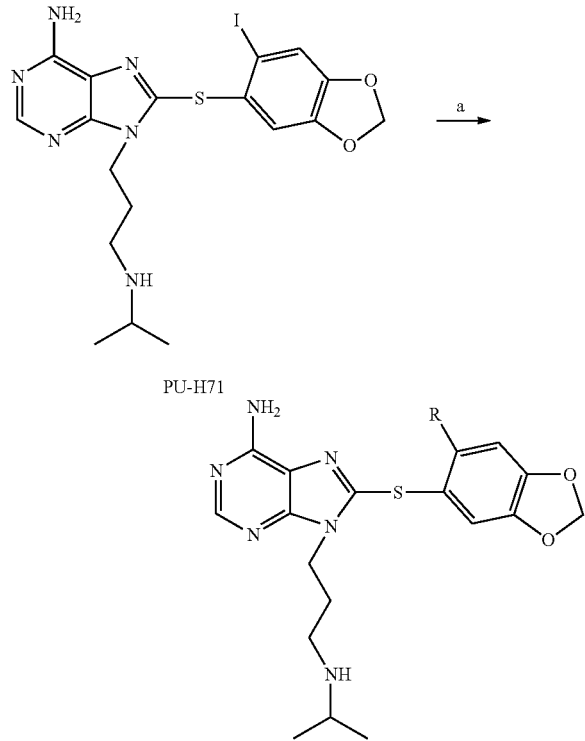

Scheme 22. Heck coupling of PU-H71.

Reagents and conditions: (a) alkene (R), Pd(PPh₃)₄, i-Pr₂NEt, NMP, 55-100° C.

8-(6-(cyclopent-2-enyl)benzo[d][1,3]dioxol-5-ylthio)-9-(3-(isopropylamino)propyl)-9H-purin-6-amine [TT-VI-116]. A solution of PU-H71 (30 mg, 0.0585 mmol) in NMP (1 mL) was evacuated and back filled with nitrogen. This was repeated four times, then DIEA (15.1 mg, 21 μL, 0.117 mmol), cyclopentene (80 mg, 103 μL, 1.171 mmol) and Pd(PPh₃)₄ (6.8 mg, 0.00586 mmol) were added and the reaction mixture was heated under nitrogen at 100° C. for 20 h. Solvent was removed under reduced pressure and the resulting residue was purified by preparatory TLC two times (CH₂Cl₂:MeOH—NH₃ (7N), 15:1 then CH₂Cl₂:MeOH, 7:3) to give 9.2 mg (35%) of TT-VI-116. ¹H NMR (500 MHz, CDCl₃/MeOH-d₄) δ 8.16 (s, 1H), 6.99 (s, 1H), 6.82 (s, 1H), 6.01 (s, 2H), 5.98 (m, 1H), 5.63 (m, 1H), 4.41 (t, J=6.4 Hz, 2H), 3.39 (m, 1H), 3.34 (septet, J=6.6 Hz, 1H), 2.95 (t, J=6.4 Hz, 2H), 2.22-2.52 (m, 5H), 1.50-1.59 (m, 1H), 1.44 (d, J=6.6 Hz, 6H); HRMS (ESI) m/z [M+H]⁺ calcd. for $C_{23}H_{29}N_6O_2S$, 453.2073; found. 453.2064; HPLC: method A $R_t$=6.51, method B $R_t$=7.79.

8-(6-(2,5-dihydro-1H-pyrrol-2-yl)benzo[d][1,3]dioxol-5-ylthio)-9-(3-(isopropylamino)propyl)-9H-purin-6-amine [DZ3-141]. A solution of PU-H71 (30 mg, 0.0585 mmol) and N-Boc-2,3-dihydro-1H-pyrrole (19.8 mg, 20.2 μL, 0.117 mmol) in NMP (1.5 mL) was evacuated and back filled with nitrogen. This was repeated four times, then DIEA (15.1 mg, 21 μL, 0.117 mmol) and Pd(PPh₃)₄ (13.5 mg, 0.0117 mmol) were added and the reaction mixture was heated under nitrogen at 100° C. for 20 h. Solvent was removed under reduced pressure and the resulting residue was purified by preparatory TLC (CH₂Cl₂:MeOH—NH₃ (7N), 15:1) and the resulting residue was dissolved into 2 mL of CH₂Cl₂:TFA (4:1) and stirred for 1 h. Solvent was removed under reduced pressure and the resulting residue was purified by preparatory TLC (CH₂Cl₂:MeOH—NH₃ (7N), 10:1) to give 6.0 mg (23%) of DZ3-141. ¹H NMR (500 MHz, CDCl₃/MeOH-d₄) δ 8.19 (s, 1H), 6.98 (s, 2H), 6.04 (m, 1H), 6.01 (s, 2H), 5.74 (m, 1H), 5.62 (d, J=2.0 Hz, 1H), 4.31 (t, J=6.9 Hz, 2H), 3.81-3.88 (m, 1H), 3.89-3.95 (m, 1H), 2.87 (septet, J=6.3 Hz, 1H), 2.68 (t, J=6.7 Hz, 2H), 2.14 (m, 2H), 1.15 (d, J=6.3 Hz, 6H); HRMS (ESI) m/z [M+H]⁺ calcd. for $C_{22}H_{28}N_7O_2S$, 454.2025; found. 454.2046; HPLC: method A $R_t$=5.27, method B $R_t$=2.72.

8-(6-(2,3-dihydrofuran-2-yl)benzo[d][1,3]dioxol-5-ylthio)-9-(3-(isopropylamino)propyl)-9H-purin-6-amine [DZ3-142]. A solution of PU-H71 (30 mg, 0.0585 mmol) in NMP (1.5 mL) was evacuated and back filled with nitrogen. This was repeated four times, then DIEA (15.1 mg, 21 μL, 0.117 mmol), 2,3-dihydrofuran (82 mg, 88 μL, 1.17 mmol) and Pd(PPh₃)₄ (13.5 mg, 0.0117 mmol) were added and the reaction mixture was heated under nitrogen at 55° C. for 20 h. Solvent was removed under reduced pressure and the resulting residue was purified by preparatory TLC two times (hexane:EtOAc:CH₂Cl₂:MeOH—NH₃ (7N), 2:1:2:0.5, then CH₂Cl₂:MeOH—NH₃ (7N), 15:1) to give 7.0 mg (26%) of DZ3-142. ¹H NMR (500 MHz, CDCl₃) δ 8.23 (s, 1H), 7.06 (s, 1H), 6.96 (s, 1H), 6.43 (m, 1H), 6.01 (s, 2H), 5.94 (dd, J=8.1, 10.8 Hz, 1H), 5.72 (br s, 2H), 4.93 (m, 1H), 4.35 (t, J=6.8 Hz, 2H), 2.95-3.55 (m, 2H), 2.70 (t, J=6.5 Hz, 2H), 2.39-2.47 (m, 1H), 2.22 (m, 2H), 1.25 (d, J=6.2 Hz, 6H); HRMS (ESI) m/z [M+H]⁺ calcd. for $C_{22}H_{27}H_6O_3S$, 455.1865; found. 455.1865; HPLC: method A $R_t$=6.07, method B $R_t$=6.49.

8-(6-(2,3-dihydrofuran-3-yl)benzo[d][1,3]dioxol-5-ylthio)-9-(3-(isopropylamino)propyl)-9H-purin-6-amine [DZ3-143]. A solution of PU-H71 (30 mg, 0.0585 mmol) in NMP (1.5 mL) was evacuated and back filled with nitrogen.

This was repeated four times, then DIEA (15.1 mg, 21 μL, 0.117 mmol), 2,5-dihydrofuran (82 mg, 88 μL, 1.17 mmol) and Pd(PPh$_3$)$_4$ (13.5 mg, 0.0117 mmol) were added and the reaction mixture was heated under nitrogen at 55° C. for 20 h. Solvent was removed under reduced pressure and the resulting residue was purified by preparatory TLC two times (CH$_2$Cl$_2$:MeOH—NH$_3$ (7N), 10:1, then hexane:EtOAc:CH$_2$Cl$_2$:MeOH—NH$_3$ (7N), 2:1:2:0.5) to give 5.0 mg (19%) of DZ3-143. $^1$H NMR (500 MHz, CDCl$_3$/MeOH-d4) δ 8.18 (s, 1H), 7.02 (s, 1H), 7.00 (s, 1H), 6.55 (m, 1H), 6.04 (s, 2H), 4.99 (m, 1H), 4.64-4.69 (m, 1H), 4.45 (m, 1H), 4.31 (t, J=6.8 Hz, 2H), 4.05 (dd, J=6.2, 9.2 Hz, 1H), 3.40 (m, 1H), 2.67 (t, J=6.4 Hz, 2H), 2.14 (m, 2H), 1.16 (d, J=6.1 Hz, 6H); HRMS (ESI) m/z [M+H]$^+$ calcd. for C$_{22}$H$_{27}$N$_6$O$_3$S, 455.1865; found. 455.1862; HPLC: method A R$_t$=6.04, method B R$_t$=6.32.

Scheme 23. Cross-coupling reactions of PU-WS21.

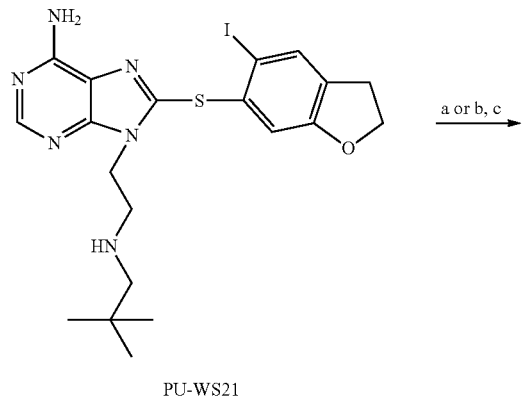

PU-WS21

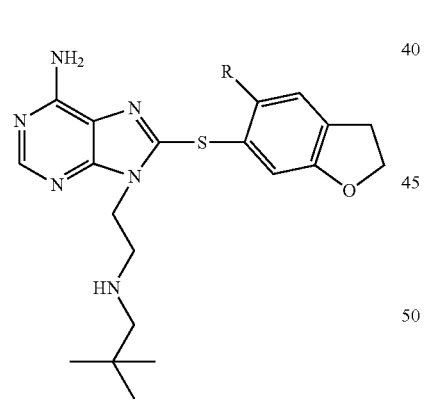

PU-WS23 R = 2-furanyl
PU-WS24 R = 2-thiophenyl
PU-WS28 R = CCH

Reagents and conditions: (a) RB(OH)$_2$, PdCl$_2$(PPh$_3$)$_2$, NaHCO$_3$, H$_2$O, DMF, 90° C.; (b) CuI, PdCl$_2$(PPh$_3$)$_2$, trimethylsilanylacetylene, Et$_3$N, DMF, 90° C.; (c) KOH, MeOH, rt.

8-(5-(furan-2-yl)-2,3-dihydrobenzofuran-6-ylthio)-9-(2-(neopentylamino)ethyl)-9H-purin-6-amine [PU-WS23]. Following the procedure to make PU-DZ3-4, compound PU-WS23 was obtained as a white solid. $^1$HNMR (500 MHz, CDCl$_3$) δ 8.31 (s, 1H), 7.49 (s, 2H), 6.68 (d, J=3.4 Hz, 1H), 6.58 (s, 1H), 6.49 (m, 1H), 5.60 (br s, 2H), 4.58 (t, J=8.7 Hz, 2H), 4.25 (m, 2H), 3.22 (t, J=8.7 Hz, 2H), 2.86 (m, 2H), 2.25 (s, 2H), 0.86 (s, 9H); HRMS (m/z): [M+H]$^+$ calcd for C$_{24}$H$_{29}$N$_6$O$_2$ 465.2073; found. 465.2077.

9-(2-(neopentylamino)ethyl)-8-(5-(thiophen-2-yl)-2,3-dihydrobenzofuran-6-ylthio)-9H-purin-6-amine [PU-WS24]. Following the procedure to make PU-DZ2-395, compound PU-WS24 was obtained as a white solid. $^1$HNMR (500 MHz, CDCl$_3$) δ 8.31 (s, 1H), 7.32 (m, 1H), 7.27 (s, 1H), 7.03-7.07 (m, 2H), 6.67 (s, 1H), 5.59 (br s, 2H), 4.58 (t, J=8.7 Hz, 2H), 4.15 (m, 2H), 3.21 (t, J=8.7 Hz, 2H), 2.86 (m, 2H), 2.25 (s, 2H), 0.83 (s, 9H); HRMS (m/z): [M+H]$^+$ calcd for C$_{24}$H$_{29}$N$_6$O$_2$ 481.1844; found. 481.1825.

8-(5-ethynyl-2,3-dihydrobenzofuran-6-ylthio)-9-(2-(neopentylamino)ethyl)-9H-purin-6-amine [PU-WS28]. Following the procedure to make PU-WS8, compound PU-WS28 was obtained as a white solid. $^1$HNMR (500 MHz, CDCl$_3$, δ): 8.33 (s, 1H), 7.36 (s, 1H), 6.59 (s, 1H), 5.70 (br, 2H), 4.58 (t, J=8.7 Hz, 2H), 4.41 (m, 2H), 3.33 (t, J=8.7 Hz, 2H), 3.49 (m, 2H), 3.02 (s, 2H), 2.44 (s, 2H), 0.91 (s, 9H); HRMS (m/z): [M+H]$^+$ calcd for C$_{22}$H$_{27}$N$_6$OS 423.1967; found. 423.1968.

Scheme 24.

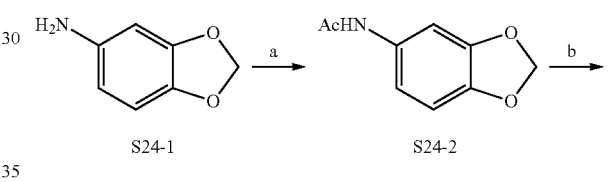

S24-1       S24-2

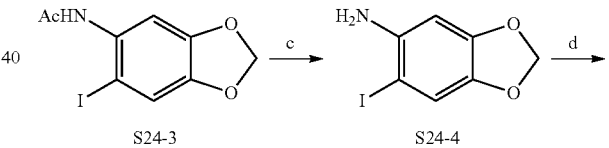

S24-3       S24-4

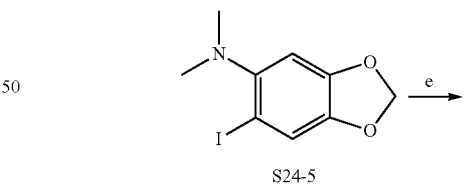

S24-5

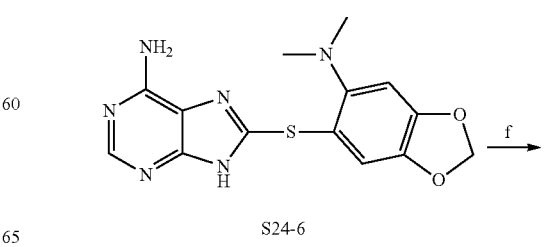

S24-6

-continued

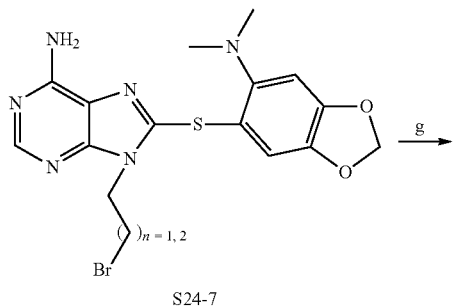

S24-7

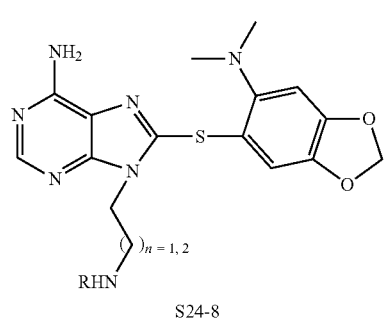

S24-8

Reagents and conditions: (a) Ac₂O, AcOH, rt; (b) ICl, CH₂Cl₂, AcOH, rt; (c) NaOH, EtOH, H₂O, reflux; (d) paraformaldehyde, NaBH₃CN, MeOH, 50° C.; (e) 8-mercaptoadenine, neocuproine, CuI, NaOtBu, DMF, 115° C.; (f) Cs₂CO₃, 1,3-dibromopropane or 1,2-dibromoethane, DMF, rt; (g) amine, DMF, rt.

Similarly,

Scheme 25. Synthesis of various bromides required for alkylation of the purine skeleton

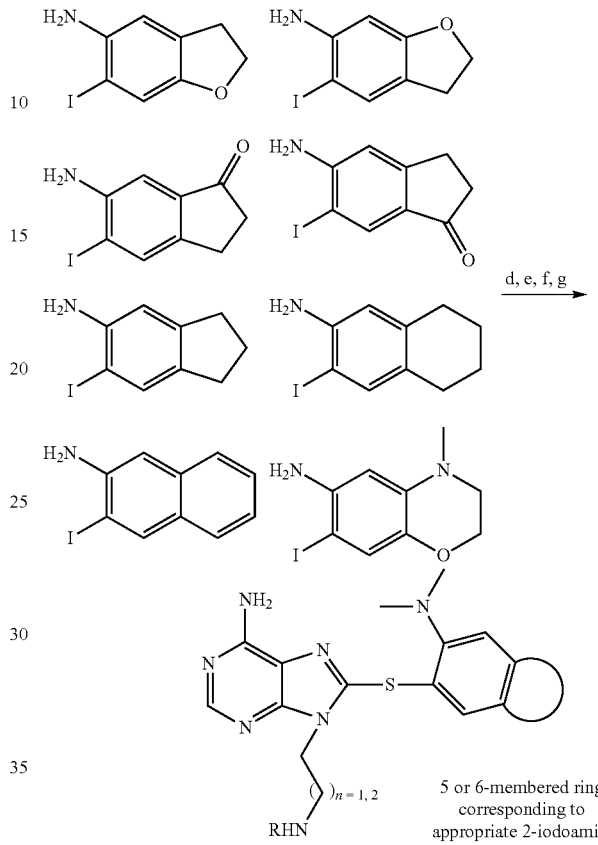

5 or 6-membered ring corresponding to appropriate 2-iodoamine

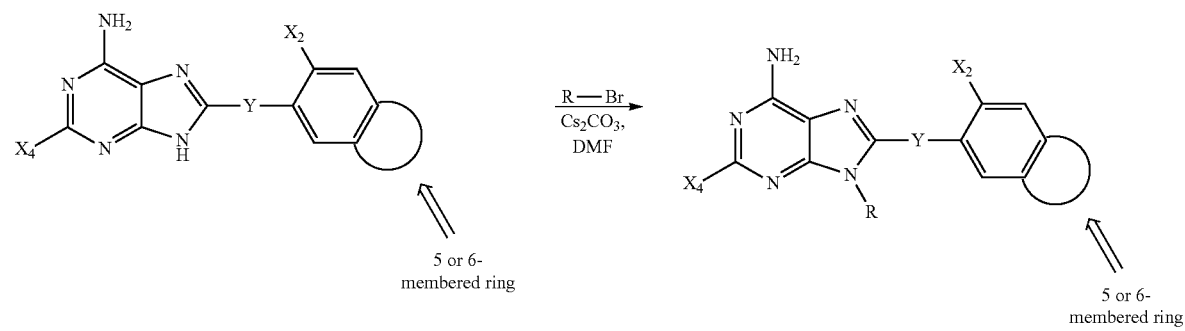

5 or 6-membered ring 5 or 6-membered ring

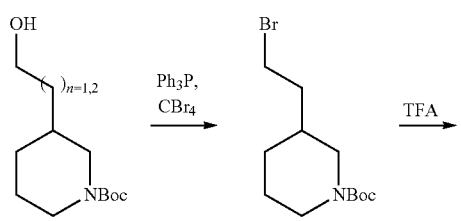

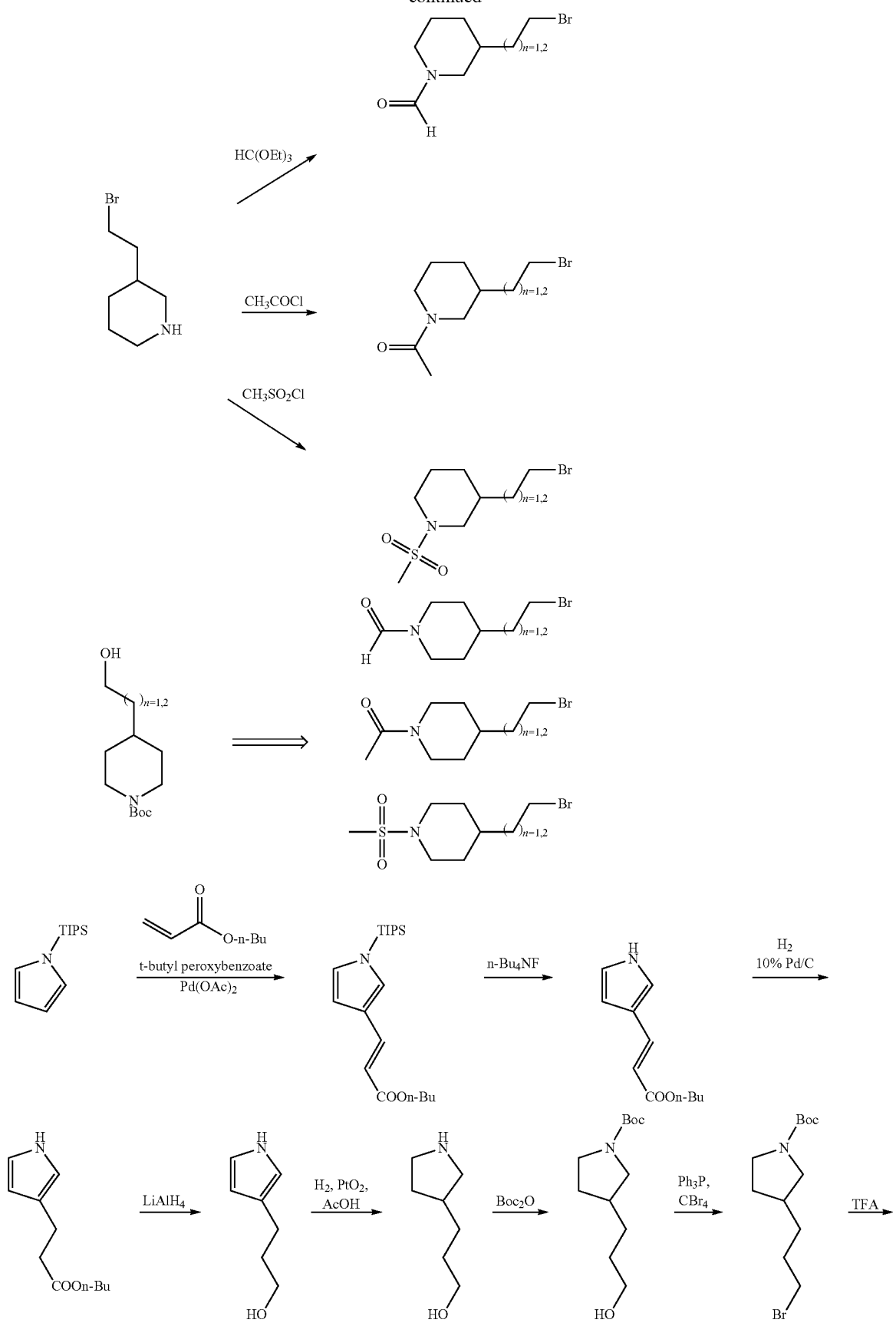

111 112
-continued
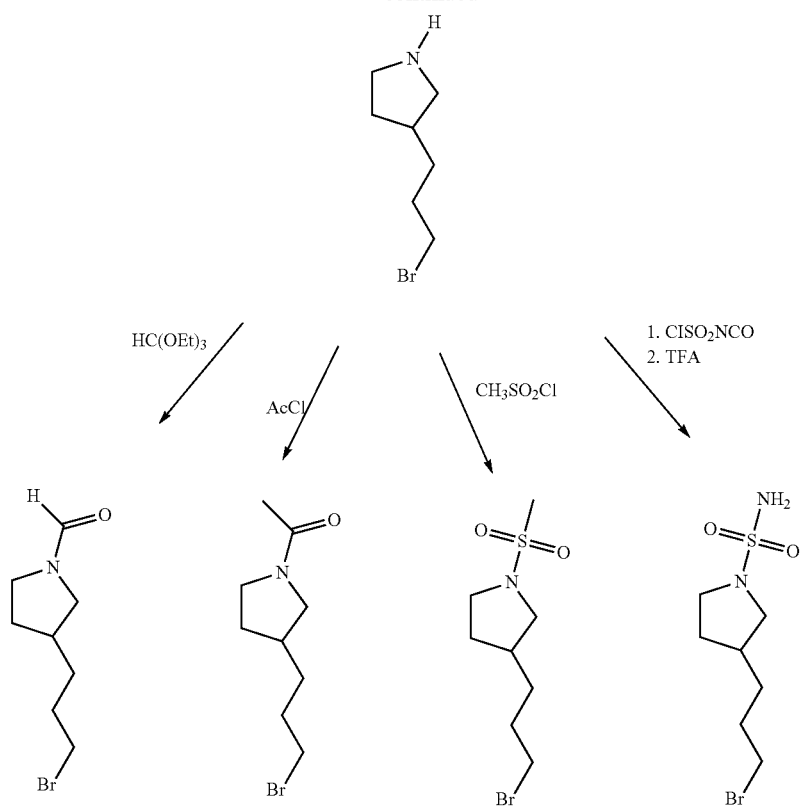
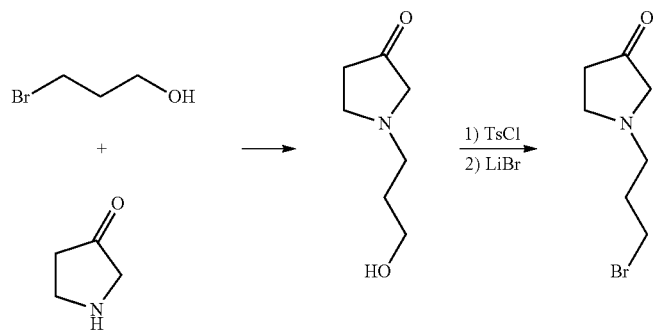
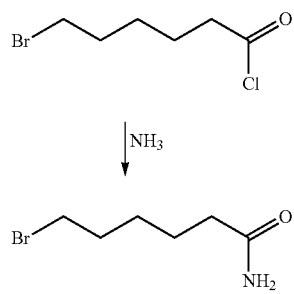
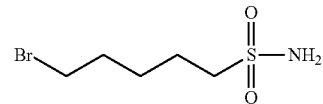

-continued

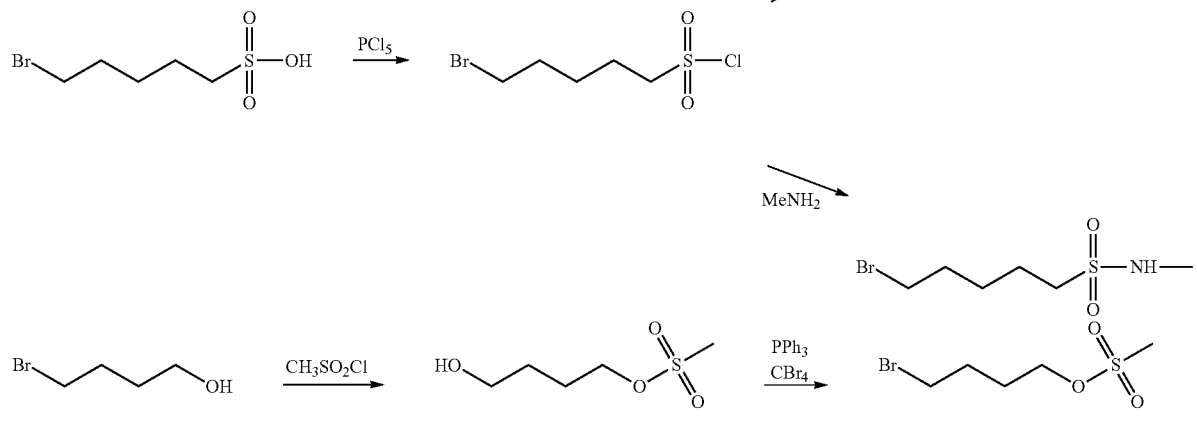

TABLE 1A

| No. | Name |
|---|---|
| 1A-1 | PU-WS10<br>8-((6-iodo-2,3-dihydrobenzofuran-5-yl)thio)-9-(3-(isopropylamino)propyl)-9H-purin-6-amine |
| 1A-2 | 8-((6-iodo-2,3-dihydrobenzofuran-5-yl)thio)-9-(2-(isobutylamino)ethyl)-9H-purin-6-amine |
| 1A-3 | 1-(6-amino-8-(6-iodo-2,3-dihydrobenzofuran-5-ylthio)-9H-purin-9-yl)-3-(tert-butylamino)propan-2-ol |
| 1A-4 | 2-fluoro-8-((6-iodo-2,3-dihydrobenzofuran-5-yl)methyl)-9-(2-(isobutylamino)ethyl)-9H-purin-6-amine |
| 1A-5 | 2-chloro-8-((6-(furan-2-yl)-2,3-dihydrobenzofuran-5-yl)methyl)-9-(3-(isopropylamino)propyl)-9H-purin-6-amine |
| 1A-6 | 2-fluoro-8-((6-iodo-2,3-dihydrobenzofuran-5-yl)methyl)-9-(3-(isopropylamino)propyl)-9H-purin-6-amine |
| 1A-7 | 8-((6-(furan-2-yl)-2,3-dihydrobenzofuran-5-yl)thio)-9-(3-(isopropylamino)propyl)-9H-purin-6-amine |
| 1A-8 | 8-((6-ethynyl-2,3-dihydrobenzofuran-5-yl)thio)-9-(3-(isopropylamino)propyl)-9H-purin-6-amine |
| 1A-9 | 5-((6-amino-9-(3-(isopropylamino)propyl)-9H-purin-8-yl)thio)-2,3-dihydrobenzofuran-6-carbonitrile |
| 1A-10 | 8-((6-(aziridin-1-yl)-2,3-dihydrobenzofuran-5-yl)methyl)-2-fluoro-9-(2-(neopentylamino)ethyl)-9H-purin-6-amine |
| 1A-11 | 8-((6-iodo-2,3-dihydrobenzofuran-5-yl)thio)-9-(2-(isobutylamino)ethyl)-9H-purin-6-amine |
| 1A-12 | 3-(2-(6-amino-8-(6-(5-methylfuran-2-yl)-2,3-dihydrobenzofuran-5-ylthio)-9H-purin-9-yl)ethyl)piperidine-1-sulfonamide |
| 1A-13 | 1-(3-(2-(8-(6-(1H-pyrazol-3-yl)-2,3-dihydrobenzofuran-5-ylthio)-6-amino-9H-purin-9-yl)ethyl)piperidin-1-yl)ethanone |
| 1A-14 | 4-(3-(6-amino-8-(6-ethynyl-2,3-dihydrobenzofuran-5-ylthio)-9H-purin-9-yl)propyl)piperidine-1-carbaldehyde |
| 1A-15 | 1-(3-(2-(6-amino-2-fluoro-8-((6-(furan-2-yl)-2,3-dihydrobenzofuran-5-yl)methyl)-9H-purin-9-yl)ethyl)piperidin-1-yl)ethanone |
| 1A-16 | N-(2-((2-(6-amino-8-((6-(furan-2-yl)-2,3-dihydrobenzofuran-5-yl)thio)-9H-purin-9-yl)ethyl)amino)ethyl sulfamide |
| 1A-17 | 3-((2-(6-amino-8-((6-(furan-2-yl)-2,3-dihydrobenzofuran-5-yl)thio)-9H-purin-9-yl)ethyl)amino)-N-hydroxypropanamide |
| 1A-18 | 2-fluoro-8-((6-iodo-2,3-dihydrobenzofuran-5-yl)thio)-9-(3-(isopropylamino)propyl)-9H-purin-6-amine |
| 1A-19 | 2-chloro-8-((6-iodo-2,3-dihydrobenzofuran-5-yl)methyl)-9-(2-(isobutylamino)ethyl)-9H-purin-6-amine |
| 1A-20 | 9-(2-aminoethyl)-2-fluoro-8-((6-iodo-2,3-dihydrobenzofuran-5-yl)methyl)-9H-purin-6-amine |
| 1A-21 | 9-(3-aminopropyl)-8-((6-iodo-2,3-dihydrobenzofuran-5-yl)thio)-9H-purin-6-amine |
| 1A-22 | 9-(2-aminoethyl)-8-((6-iodo-2,3-dihydrobenzofuran-5-yl)thio)-9H-purin-6-amine |

TABLE 1A-continued

| No. | Name |
|---|---|
| 1A-23 | 9-(3-(tert-butylamino)propyl)-8-((6-iodo-2,3-dihydrobenzofuran-5-yl)thio)-9H-purin-6-amine |
| 1A-24 | 1-(6-amino-8-((6-iodo-2,3-dihydrobenzofuran-5-yl)thio)-9H-purin-9-yl)-3-(isopropylamino)propan-2-ol |
| 1A-25 | 1-(3-(6-amino-2-fluoro-8-((6-iodo-2,3-dihydrobenzofuran-5-yl)methyl)-9H-purin-9-yl)propyl)pyrrolidin-3-one |
| 1A-26 | 1-(3-(6-amino-8-(6-iodo-2,3-dihydrobenzofuran-5-ylthio)-9H-purin-9-yl)propyl)pyrrolidin-3-one |
| 1A-27 | 5-(6-amino-8-(6-iodo-2,3-dihydrobenzofuran-5-ylthio)-9H-purin-9-yl)pentane-1-sulfonamide |
| 1A-28 | 1-(6-amino-2-fluoro-8-((6-iodo-2,3-dihydrobenzofuran-5-yl)methyl)-9H-purin-9-yl)-3-(isopropylamino)propan-2-ol |
| 1A-29 | 8-((6-ethynyl-2,3-dihydrobenzofuran-5-yl)methyl)-2-fluoro-9-(5-(methylsulfonyl)pentyl)-9H-purin-6-amine |
| 1A-30 | 2-fluoro-8-((6-iodo-2,3-dihydrobenzofuran-5-yl)methyl)-9-(2-(1-(methylsulfonyl)pyrrolidin-3-yl)ethyl)-9H-purin-6-amine |
| 1A-31 | N-(4-(6-amino-2-fluoro-8-((6-iodo-2,3-dihydrobenzofuran-5-yl)methyl)-9H-purin-9-yl)butyl)methanesulfonamide |
| 1A-32 | 1-(6-amino-8-((6-ethynyl-2,3-dihydrobenzofuran-5-yl)methyl)-2-fluoro-9H-purin-9-yl)-3-(isopropylamino)propan-2-ol |
| 1A-33 | 6-(6-amino-8-((6-ethynyl-2,3-dihydrobenzofuran-5-yl)methyl)-2-fluoro-9H-purin-9-yl)hexanamide |
| 1A-34 | 1-(4-(2-(6-amino-8-((6-ethynyl-2,3-dihydrobenzofuran-5-yl)methyl)-2-fluoro-9H-purin-9-yl)ethyl)piperidin-1-yl)ethanone |
| 1A-35 | 8-((6-ethynyl-2,3-dihydrobenzofuran-5-yl)methyl)-2-fluoro-9-(2-(1-(methylsulfonyl)piperidin-3-yl)ethyl)-9H-purin-6-amine |
| | 9-(3-(isopropylamino)propyl)-8-((6-(5-methylfuran-2-yl)-2,3-dihydrobenzofuran-5-yl)thio)-9H-purin-6-amine |
| | 9-(3-(tert-butylamino)propyl)-8-((6-(5-methylfuran-2-yl)-2,3-dihydrobenzofuran-5-yl)thio)-9H-purin-6-amine |
| | 9-(3-(tert-butylamino)propyl)-8-((6-(dimethylamino)-2,3-dihydrobenzofuran-5-yl)thio)-9H-purin-6-amine |
| | 1-(4-(2-(6-amino-8-((6-(dimethylamino)-2,3-dihydrobenzofuran-5-yl)thio)-9H-purin-9-yl)ethyl)piperidin-1-yl)ethanone |
| 1A-40 | 8-((6-(dimethylamino)-2,3-dihydrobenzofuran-5-yl)thio)-9-(2-(1-(methylsulfonyl)piperidin-3-yl)ethyl)-9H-purin-6-amine |
| 1A-41 | 4-(3-(6-amino-8-(6-(aziridin-1-yl)-2,3-dihydrobenzofuran-5-ylthio)-9H-purin-9-yl)propyl)piperidine-1-carbaldehyde |
| 1A-42 | 8-((6-(furan-2-yl)-2,3-dihydrobenzofuran-5-yl)thio)-9-(2-(1-(methylsulfonyl)piperidin-3-yl)ethyl)-9H-purin-6-amine |

TABLE 1A-continued

| No. | Name |
|---|---|
| 1A-43 | 8-((6-(dimethylamino)-2,3-dihydrobenzofuran-5-yl)methyl)-2-fluoro-9-(2-(isobutylamino)ethyl)-9H-purin-6-amine |
| 1A-44 | 8-((6-(dimethylamino)-2,3-dihydrobenzofuran-5-yl)thio)-9-(2-(neopentylamino)ethyl)-9H-purin-6-amine |
| 1A-45 | 9-(3-(tert-butylamino)propyl)-8-((6-(oxazol-2-yl)-2,3-dihydrobenzofuran-5-yl)thio)-9H-purin-6-amine |
| 1A-46 | 1-(3-(2-(6-amino-8-(6-(oxazol-2-yl)-2,3-dihydrobenzofuran-5-ylthio)-9H-purin-9-yl)ethyl)piperidin-1-yl)ethanone |
| 1A-47 | 4-(3-(6-amino-8-(6-(oxazol-2-yl)-2,3-dihydrobenzofuran-5-ylthio)-9H-purin-9-yl)propyl)piperidine-1-carbaldehyde |
| 1A-48 | 9-(2-(1-(methylsulfonyl)piperidin-3-yl)ethyl)-8-((6-(oxazol-2-yl)-2,3-dihydrobenzofuran-5-yl)thio)-9H-purin-6-amine |
| 1A-49 | 1-(2-(3-(6-amino-8-(6-iodo-2,3-dihydrobenzofuran-5-ylthio)-9H-purin-9-yl)propyl)pyrrolidin-1-yl)ethanone |
| 1A-50 | 9-(3-(tert-butylamino)propyl)-8-((6-(5-methyloxazol-2-yl)-2,3-dihydrobenzofuran-5-yl)thio)-9H-purin-6-amine |
| 1A-51 | 9-(3-(tert-butylamino)propyl)-8-((6-(thiazol-2-yl)-2,3-dihydrobenzofuran-5-yl)thio)-9H-purin-6-amine |
| 1A-52 | 9-(3-(tert-butylamino)propyl)-8-((6-(5-methylthiazol-2-yl)-2,3-dihydrobenzofuran-5-yl)thio)-9H-purin-6-amine |

TABLE 1B

| No. | Name |
|---|---|
| 1B-1 | PU-WS9<br>8-((5-iodo-2,3-dihydrobenzofuran-6-yl)thio)-9-(2-(isobutylamino)ethyl)-9H-purin-6-amine |
| 1B-2 | PU-WS4<br>8-((5-iodo-2,3-dihydrobenzofuran-6-yl)thio)-9-(3-(isopropylamino)propyl)-9H-purin-6-amine |
| 1B-3 | PU-WS17<br>2-fluoro-8-((5-iodo-2,3-dihydrobenzofuran-6-yl)methyl)-9-(2-(isobutylamino)ethyl)-9H-purin-6-amine |
| 1B-4 | PU-WS18<br>2-fluoro-8-((5-iodo-2,3-dihydrobenzofuran-6-yl)methyl)-9-(3-(isopropylamino)propyl)-9H-purin-6-amine |
| 1B-5 | 2-chloro-8-((5-iodo-2,3-dihydrobenzofuran-6-yl)methyl)-9-(3-(isopropylamino)propyl)-9H-purin-6-amine |
| 1B-6 | 8-((5-(furan-2-yl)-2,3-dihydrobenzofuran-6-yl)thio)-9-(3-(isopropylamino)propyl)-9H-purin-6-amine |
| 1B-7 | 8-((5-(dimethylamino)-2,3-dihydrobenzofuran-6-yl)methyl)-2-fluoro-9-(2-(neopentylamino)ethyl)-9H-purin-6-amine |
| 1B-8 | 8-((5-(1H-pyrazol-3-yl)-2,3-dihydrobenzofuran-6-yl)thio)-9-(2-(isobutylamino)ethyl)-9H-purin-6-amine |
| 1B-9 | 8-((5-cyclopentyl-2,3-dihydrobenzofuran-6-yl)thio)-9-(3-(isopropylamino)propyl)-9H-purin-6-amine |
| 1B-10 | 8-((5-ethynyl-2,3-dihydrobenzofuran-6-yl)methyl)-2-fluoro-9-(2-(isobutylamino)ethyl)-9H-purin-6-amine |
| 1B-11 | 6-((6-amino-2-fluoro-9-(3-(isopropylamino)propyl)-9H-purin-8-yl)methyl)-2,3-dihydrobenzofuran-5-carbonitrile |
| 1B-12 | 2-chloro-9-(3-(isopropylamino)propyl)-8-((5-(5-methylfuran-2-yl)-2,3-dihydrobenzofuran-6-yl)methyl)-9H-purin-6-amine |
| 1B-13 | 4-(2-(6-amino-8-((5-ethynyl-2,3-dihydrobenzofuran-6-yl)thio)-9H-purin-9-yl)ethyl)piperidine-1-carbaldehyde |
| 1B-14 | 1-(4-(2-(6-amino-2-fluoro-8-((5-(furan-2-yl)-2,3-dihydrobenzofuran-6-yl)methyl)-9H-purin-9-yl)ethyl)piperidin-1-yl)ethanone |
| 1B-15 | N-(2-((2-(6-amino-8-((5-(furan-2-yl)-2,3-dihydrobenzofuran-6-yl)thio)-9H-purin-9-yl)ethyl)amino)ethyl)sulfamide |
| 1B-16 | 3-((2-(6-amino-8-((5-ethynyl-2,3-dihydrobenzofuran-6-yl)thio)-9H-purin-9-yl)ethyl)amino)-N-hydroxypropanamide |
| 1B-17 | 9-(2-(isobutylamino)ethyl)-8-((5-(thiophen-2-yl)-2,3-dihydrobenzofuran-6-yl)thio)-9H-purin-6-amine |
| 1B-18 | 3-(3-(6-amino-8-(5-iodo-2,3-dihydrobenzofuran-6-ylthio)-9H-purin-9-yl)propyl)-2-oxoimidazolidine-1-carbaldehyde |
| 1B-19 | 2-chloro-8-((5-ethynyl-2,3-dihydrobenzofuran-6-yl)methyl)-9-(2-(isobutylamino)ethyl)-9H-purin-6-amine |
| 1B-20 | 6-((6-amino-2-chloro-9-(3-(isopropylamino)propyl)-9H-purin-8-yl)methyl)-2,3-dihydrobenzofuran-5-carbonitrile |
| 1B-21 | 2-chloro-8-((5-(dimethylamino)-2,3-dihydrobenzofuran-6-yl)methyl)-9-(2-(neopentylamino)ethyl)-9H-purin-6-amine |
| 1B-22 | 8-((5-cyclopentyl-2,3-dihydrobenzofuran-6-yl)thio)-2-fluoro-9-(3-(isopropylamino)propyl)-9H-purin-6-amine |
| 1B-23 | 1-(3-(6-amino-8-(5-iodo-2,3-dihydrobenzofuran-6-ylthio)-9H-purin-9-yl)propyl)pyrrolidin-3-one |
| 1B-24 | PU-WS21<br>8-((5-iodo-2,3-dihydrobenzofuran-6-yl)thio)-9-(2-(neopentylamino)ethyl)-9H-purin-6-amine |
| 1B-25 | PU-WS22<br>2-fluoro-8-((5-iodo-2,3-dihydrobenzofuran-6-yl)methyl)-9-(2-(neopentylamino)ethyl)-9H-purin-6-amine |
| 1B-26 | PU-WS23<br>8-((5-(furan-2-yl)-2,3-dihydrobenzofuran-6-yl)thio)-9-(2-(neopentylamino)ethyl)-9H-purin-6-amine |

TABLE 1B-continued

| No. | Name |
|---|---|
| 1B-27 | PU-WS24<br>9-(2-(neopentylamino)ethyl)-8-((5-(thiophen-2-yl)-2,3-dihydrobenzofuran-6-yl)thio)-9H-purin-6-amine |
| 1B-28 | PU-WS28<br>8-((5-ethynyl-2,3-dihydrobenzofuran-6-yl)thio)-9-(2-(neopentylamino)ethyl)-9H-purin-6-amine |
| 1B-29 | 9-(3-aminopropyl)-8-((5-iodo-2,3-dihydrobenzofuran-6-yl)thio)-9H-purin-6-amine |
| 1B-30 | 9-(2-aminoethyl)-2-fluoro-8-((5-iodo-2,3-dihydrobenzofuran-6-yl)methyl)-9H-purin-6-amine |
| 1B-31 | 9-(2-aminoethyl)-8-((5-iodo-2,3-dihydrobenzofuran-6-yl)thio)-9H-purin-6-amine |
| 1B-32 | 9-(3-(tert-butylamino)propyl)-8-((5-iodo-2,3-dihydrobenzofuran-6-yl)thio)-9H-purin-6-amine |
| 1B-33 | 2-fluoro-8-((5-(5-methylfuran-2-yl)-2,3-dihydrobenzofuran-6-yl)methyl)-9-(2-(1-(methylsulfonyl)piperidin-3-yl)ethyl)-9H-purin-6-amine |
| 1B-34 | 1-(3-(6-amino-8-((5-iodo-2,3-dihydrobenzofuran-6-ylthio)-9H-purin-9-yl)propyl)-4-hydroxypyrrolidin-2-one |
| 1B-35 | N-(3-(6-amino-8-((5-iodo-2,3-dihydrobenzofuran-6-yl)thio)-9H-purin-9-yl)propyl)methanesulfonamide |
| 1B-36 | 1-(3-(6-amino-8-(5-ethynyl-2,3-dihydrobenzofuran-6-ylthio)-9H-purin-9-yl)propyl)pyrrolidin-3-one |
| 1B-37 | 8-(5-iodo-2,3-dihydrobenzofuran-6-ylthio)-9-(2-(1-(methylsulfonyl)pyrrolidin-3-yl)ethyl)-9H-purin-6-amine |
| 1B-38 | N-(3-(6-amino-8-((5-ethynyl-2,3-dihydrobenzofuran-6-yl)thio)-9H-purin-9-yl)propyl)methanesulfonamide |
| 1B-39 | 1-(4-(2-(6-amino-8-((5-ethynyl-2,3-dihydrobenzofuran-6-yl)thio)-9H-purin-9-yl)ethyl)piperidin-1-yl)ethanone |
| 1B-40 | 8-((5-ethynyl-2,3-dihydrobenzofuran-6-yl)thio)-9-(2-(1-(methylsulfonyl)piperidin-3-yl)ethyl)-9H-purin-6-amine |
| 1B-41 | 5-(6-amino-8-(5-ethynyl-2,3-dihydrobenzofuran-6-ylthio)-9H-purin-9-yl)pentane-1-sulfonamide |
| 1B-42 | 1-(4-(2-(6-amino-8-((5-(furan-2-yl)-2,3-dihydrobenzofuran-6-yl)thio)-9H-purin-9-yl)ethyl)piperidin-1-yl)ethanone |
| 1B-43 | 8-(5-(5-methylfuran-2-yl)-2,3-dihydrobenzofuran-6-ylthio)-9-(2-(1-(methylsulfonyl)piperidin-3-yl)ethyl)-9H-purin-6-amine |
| 1B-44 | 2-(3-(6-amino-8-(5-(5-methylfuran-2-yl)-2,3-dihydrobenzofuran-6-ylthio)-9H-purin-9-yl)propyl)pyrrolidine-1-carbaldehyde |
| 1B-45 | N-(2-(6-amino-8-((5-ethynyl-2,3-dihydrobenzofuran-6-yl)thio)-9H-purin-9-yl)ethyl) N'-methyl-sulfuric diamide |
| 1B-46 | 9-(3-(tert-butylamino)propyl)-8-((5-(oxazol-2-yl)-2,3-dihydrobenzofuran-6-yl)thio)-9H-purin-6-amine |
| 1B-47 | 9-(3-(tert-butylamino)propyl)-8-((5-ethynyl-2,3-dihydrobenzofuran-6-yl)thio)-9H-purin-6-amine |
| 1B-48 | 9-(3-(tert-butylamino)propyl)-8-((5-(dimethylamino)-2,3-dihydrobenzofuran-6-yl)thio)-9H-purin-6-amine |
| 1B-49 | 1-(6-amino-8-((5-iodo-2,3-dihydrobenzofuran-6-yl)thio)-9H-purin-9-yl)-3-(isopropylamino)propan-2-ol |
| 1B-50 | 1-(4-(2-(6-amino-8-((5-(oxazol-2-yl)-2,3-dihydrobenzofuran-6-yl)thio)-9H-purin-9-yl)ethyl)piperidin-1-yl)ethanone |
| 1B-51 | 9-(2-(1-(methylsulfonyl)piperidin-3-yl)ethyl)-8-((5-(oxazol-2-yl)-2,3-dihydrobenzofuran-6-yl)thio)-9H-purin-6-amine |
| 1B-52 | 3-(3-(6-amino-8-(5-iodo-2,3-dihydrobenzofuran-6-ylthio)-9H-purin-9-yl)propyl)pyrrolidine-1-sulfonamide |
| 1B-53 | 9-(3-(tert-butylamino)propyl)-8-((5-(5-methyloxazol-2-yl)-2,3-dihydrobenzofuran-6-yl)thio)-9H-purin-6-amine |
| 1B-54 | 9-(3-(tert-butylamino)propyl)-8-((5-(thiazol-2-yl)-2,3-dihydrobenzofuran-6-yl)thio)-9H-purin-6-amine |
| 1B-55 | 9-(3-(tert-butylamino)propyl)-8-((5-(5-methylthiazol-2-yl)-2,3-dihydrobenzofuran-6-yl)thio)-9H-purin-6-amine |
| 1B-56 | 6-(6-amino-8-(5-iodo-2,3-dihydrobenzofuran-6-ylthio)-9H-purin-9-yl)hexanamide |
| 1B-57 | 5-(6-amino-8-(5-iodo-2,3-dihydrobenzofuran-6-ylthio)-9H-purin-9-yl)pentane-1-sulfonamide |
| 1B-58 | 3-(6-amino-8-(5-ethynyl-2,3-dihydrobenzofuran-6-ylthio)-9H-purin-9-yl)propyl sulfamate |

TABLE 1C

| No. | Name |
|---|---|
| 1C-1 | 8-((6-iodo-2,3-dihydrobenzo[b]thiophen-5-yl)thio)-9-(3-(isopropylamino)propyl)-9H-purin-6-amine |
| 1C-2 | 8-((6-iodo-2,3-dihydrobenzo[b]thiophen-5-yl)thio)-9-(2-(isobutylamino)ethyl)-9H-purin-6-amine |
| 1C-3 | 8-((6-iodo-2,3-dihydrobenzo[b]thiophen-5-yl)thio)-9-(3-(isopropylamino)propyl)-9H-purin-6-amine |

TABLE 1C-continued

| No. | Name |
| --- | --- |
| 1C-4 | 2-fluoro-8-((6-iodo-2,3-dihydrobenzo[b]thiophen-5-yl)methyl)-9-(2-(isobutylamino)ethyl)-9H-purin-6-amine |
| 1C-5 | 2-chloro-8-((6-(furan-2-yl)-2,3-dihydrobenzo[b]thiophen-5-yl)methyl)-9-(3-(isopropylamino)propyl)-9H-purin-6-amine |
| 1C-6 | 8-((6-(1H-imidazol-4-yl)-2,3-dihydrobenzo[b]thiophen-5-yl)methyl)-2-fluoro-9-(3-(isopropylamino)propyl)-9H-purin-6-amine |
| 1C-7 | 8-((6-(furan-2-yl)-2,3-dihydrobenzo[b]thiophen-5-yl)thio)-9-(3-(isopropylamino)propyl)-9H-purin-6-amine |
| 1C-8 | 8-((6-ethynyl-2,3-dihydrobenzo[b]thiophen-5-yl)thio)-9-(3-(isopropylamino)propyl)-9H-purin-6-amine |
| 1C-9 | 5-((6-amino-9-(3-(isopropylamino)propyl)-9H-purin-8-yl)thio)-2,3-dihydrobenzo[b]thiophene-6-carbonitrile |
| 1C-10 | 8-((6-(aziridin-1-yl)-2,3-dihydrobenzo[b]thiophen-5-yl)methyl)-2-fluoro-9-(2-(neopentylamino)ethyl)-9H-purin-6-amine |
| 1C-11 | 8-((6-iodo-2,3-dihydrobenzo[b]thiophen-5-yl)thio)-9-(2-(isobutylamino)ethyl)-9H-purin-6-amine |
| 1C-12 | 1-(4-(2-(6-amino-8-((6-(furan-2-yl)-2,3-dihydrobenzo[b]thiophen-5-yl)thio)-9H-purin-9-yl)ethyl)piperidin-1-yl)ethanone |
| 1C-13 | 4-(2-(8-((6-(1H-pyrazol-3-yl)-2,3-dihydrobenzo[b]thiophen-5-yl)thio)-6-amino-9H-purin-9-yl)ethyl)piperidine-1-carbaldehyde |
| 1C-14 | 4-(2-(6-amino-8-((6-ethynyl-2,3-dihydrobenzo[b]thiophen-5-yl)thio)-9H-purin-9-yl)ethyl)piperidine-1-carbaldehyde |
| 1C-15 | 1-(4-(2-(6-amino-2-fluoro-8-((6-(furan-2-yl)-2,3-dihydrobenzo[b]thiophen-5-yl)methyl)-9H-purin-9-yl)ethyl)piperidin-1-yl)ethanone |
| 1C-16 | N-(2-((2-(6-amino-8-((6-(furan-2-yl)-2,3-dihydrobenzo[b]thiophen-5-yl)thio)-9H-purin-9-yl)ethyl)amino)ethyl)sulfamide |
| 1C-17 | 3-((2-(6-amino-8-((6-(furan-2-yl)-2,3-dihydrobenzo[b]thiophen-5-yl)thio)-9H-purin-9-yl)ethyl)amino)-N-hydroxypropanamide |
| 1C-18 | 9-(3-aminopropyl)-8-((6-iodo-2,3-dihydrobenzo[b]thiophen-5-yl)thio)-9H-purin-6-amine |
| 1C-19 | 9-(2-aminoethyl)-2-fluoro-8-((6-iodo-2,3-dihydrobenzo[b]thiophen-5-yl)methyl)-9H-purin-6-amine |
| 1C-20 | 9-(2-aminoethyl)-8-((6-iodo-2,3-dihydrobenzo[b]thiophen-5-yl)thio)-9H-purin-6-amine |
| 1C-21 | 9-(3-(tert-butylamino)propyl)-8-((6-iodo-2,3-dihydrobenzo[b]thiophen-5-yl)thio)-9H-purin-6-amine |

TABLE 1D

| No. | Name |
| --- | --- |
| 1D-1 | 8-((5-iodo-2,3-dihydrobenzo[b]thiophen-6-yl)thio)-9-(2-(isobutylamino)ethyl)-9H-purin-6-amine |
| 1D-2 | 8-((5-iodo-2,3-dihydrobenzo[b]thiophen-6-yl)thio)-9-(3-(isopropylamino)propyl)-9H-purin-6-amine |
| 1D-3 | 2-fluoro-8-((5-iodo-2,3-dihydrobenzo[b]thiophen-6-yl)methyl)-9-(2-(isobutylamino)ethyl)-9H-purin-6-amine |
| 1D-4 | 2-fluoro-8-((5-iodo-2,3-dihydrobenzo[b]thiophen-6-yl)methyl)-9-(3-(isopropylamino)propyl)-9H-purin-6-amine |
| 1D-5 | 8-((5-iodo-2,3-dihydrobenzo[b]thiophen-6-yl)thio)-9-(2-(isobutylamino)ethyl)-9H-purin-6-amine |
| 1D-6 | 8-((5-(furan-2-yl)-2,3-dihydrobenzo[b]thiophen-6-yl)thio)-9-(3-(isopropylamino)propyl)-9H-purin-6-amine |
| 1D-7 | 8-((5-(dimethylamino)-2,3-dihydrobenzo[b]thiophen-6-yl)methyl)-2-fluoro-9-(2-(neopentylamino)ethyl)-9H-purin-6-amine |
| 1D-8 | 8-((5-(1H-pyrazol-3-yl)-2,3-dihydrobenzo[b]thiophen-6-yl)thio)-9-(2-(isobutylamino)ethyl)-9H-purin-6-amine |
| 1D-9 | 8-((5-cyclopentyl-2,3-dihydrobenzo[b]thiophen-6-yl)thio)-9-(3-(isopropylamino)propyl)-9H-purin-6-amine |
| 1D-10 | 8-((5-ethynyl-2,3-dihydrobenzo[b]thiophen-6-yl)methyl)-2-fluoro-9-(2-(isobutylamino)ethyl)-9H-purin-6-amine |
| 1D-11 | 6-((6-amino-2-fluoro-9-(3-(isopropylamino)propyl)-9H-purin-8-yl)methyl)-2,3-dihydrobenzo[b]thiophene-5-carbonitrile |
| 1D-12 | 2-chloro-8-((5-(furan-2-yl)-2,3-dihydrobenzo[b]thiophen-6-yl)methyl)-9-(3-(isopropylamino)propyl)-9H-purin-6-amine |
| 1D-13 | 4-(2-(6-amino-8-((5-ethynyl-2,3-dihydrobenzo[b]thiophen-6-yl)thio)-9H-purin-9-yl)ethyl)piperidine-1-carbaldehyde |
| 1D-14 | 1-(4-(2-(6-amino-2-fluoro-8-((5-(furan-2-yl)-2,3-dihydrobenzo[b]thiophen-6-yl)methyl)-9H-purin-9-yl)ethyl)piperidin-1-yl)ethanone |
| 1D-15 | N-(2-((2-(6-amino-8-((5-(furan-2-yl)-2,3-dihydrobenzo[b]thiophen-6-yl)thio)-9H-purin-9-yl)ethyl)amino)ethyl)sulfamide |
| 1D-16 | 3-((2-(6-amino-8-((5-ethynyl-2,3-dihydrobenzo[b]thiophen-6-yl)thio)-9H-purin-9-yl)ethyl)amino)-N-hydroxypropanamide |
| 1D-17 | 2-chloro-8-((5-iodo-2,3-dihydrobenzo[b]thiophen-6-yl)methyl)-9-(3-(isopropylamino)propyl)-9H-purin-6-amine |

TABLE 1D-continued

| No. | Name |
| --- | --- |
| 1D-18 | 9-(3-aminopropyl)-8-((5-iodo-2,3-dihydrobenzo[b]thiophen-6-yl)thio)-9H-purin-6-amine |
| 1D-19 | 9-(2-aminoethyl)-2-fluoro-8-((5-iodo-2,3-dihydrobenzo[b]thiophen-6-yl)methyl)-9H-purin-6-amine |
| 1D-20 | 9-(2-aminoethyl)-8-((5-iodo-2,3-dihydrobenzo[b]thiophen-6-yl)thio)-9H-purin-6-amine |
| 1D-21 | 9-(3-(tert-butylamino)propyl)-8-((5-iodo-2,3-dihydrobenzo[b]thiophen-6-yl)thio)-9H-purin-6-amine |

TABLE 1E

| No. | Name |
| --- | --- |
| 1E-1 | 1-(6-amino-8-(6-iodo-2,3-dihydro-1H-inden-5-ylthio)-9H-purin-9-yl)-3-(tert-butylamino)propan-2-ol |
| 1E-2 | PU-WS26 8-((6-iodo-2,3-dihydro-1H-inden-5-yl)thio)-9-(2-(isobutylamino)ethyl)-9H-purin-6-amine |
| 1E-3 | 1-(3-(6-amino-8-(6-iodo-2,3-dihydro-1H-inden-5-ylthio)-9H-purin-9-yl)propyl)pyrrolidin-3-one |
| 1E-4 | 2-fluoro-8-((6-iodo-2,3-dihydro-1H-inden-5-yl)methyl)-9-(2-(isobutylamino)ethyl)-9H-purin-6-amine |
| 1E-5 | 2-chloro-8-((6-(furan-2-yl)-2,3-dihydro-1H-inden-5-yl)methyl)-9-(3-(isopropylamino)propyl)-9H-purin-6-amine |
| 1E-6 | 2-fluoro-8-((6-iodo-2,3-dihydro-1H-inden-5-yl)methyl)-9-(3-(isopropylamino)propyl)-9H-purin-6-amine |
| 1E-7 | 8-((6-(furan-2-yl)-2,3-dihydro-1H-inden-5-yl)thio)-9-(3-(isopropylamino)propyl)-9H-purin-6-amine |
| 1E-8 | 8-((6-ethynyl-2,3-dihydro-1H-inden-5-yl)thio)-9-(3-(isopropylamino)propyl)-9H-purin-6-amine |
| 1E-9 | 6-((6-amino-9-(3-(isopropylamino)propyl)-9H-purin-8-yl)thio)-2,3-dihydro-1H-indene-5-carbonitrile |
| 1E-10 | 8-((6-(azetidin-1-yl)-2,3-dihydro-1H-inden-5-yl)methyl)-2-fluoro-9-(2-(neopentylamino)ethyl)-9H-purin-6-amine |
| 1E-11 | 9-(3-(isopropylamino)propyl)-8-((6-(oxazol-2-yl)-2,3-dihydro-1H-inden-5-yl)thio)-9H-purin-6-amine |
| 1E-12 | 1-(3-(2-(6-amino-8-(6-(oxazol-2-yl)-2,3-dihydro-1H-inden-5-ylthio)-9H-purin-9-yl)ethyl)piperidin-1-yl)ethanone |
| 1E-13 | 3-(2-(8-(6-(1H-pyrazol-3-yl)-2,3-dihydro-1H-inden-5-ylthio)-6-amino-9H-purin-9-yl)ethyl)piperidine-1-carbaldehyde |
| 1E-14 | 1-(3-(2-(6-amino-8-(6-ethynyl-2,3-dihydro-1H-inden-5-ylthio)-9H-purin-9-yl)ethyl)piperidin-1-yl)ethanone |
| 1E-15 | 2-fluoro-9-(3-(1-(methylsulfonyl)pyrrolidin-3-yl)propyl)-8-((6-(oxazol-2-yl)-2,3-dihydro-1H-inden-5-yl)methyl)-9H-purin-6-amine |
| 1E-16 | N-(2-((2-(6-amino-8-((6-(oxazol-2-yl)-2,3-dihydro-1H-inden-5-yl)thio)-9H-purin-9-yl)ethyl)amino)ethyl)sulfamide |
| 1E-17 | 3-(2-(6-amino-8-(6-(oxazol-2-yl)-2,3-dihydro-1H-inden-5-ylthio)-9H-purin-9-yl)ethylamino)-N-hydroxypropanamide |
| 1E-18 | 1-(3-(3-(6-amino-8-(6-iodo-2,3-dihydro-1H-inden-5-ylthio)-9H-purin-9-yl)propyl)pyrrolidin-1-yl)ethanone |
| 1E-19 | 1-(3-(3-(6-amino-8-(6-ethynyl-2,3-dihydro-1H-inden-5-ylthio)-9H-purin-9-yl)propyl)pyrrolidin-1-yl)ethanone |
| 1E-20 | 2-chloro-8-((6-ethynyl-2,3-dihydro-1H-inden-5-yl)methyl)-9-(3-(isopropylamino)propyl)-9H-purin-6-amine |
| 1E-21 | PU-WS25 8-((6-iodo-2,3-dihydro-1H-inden-5-yl)thio)-9-(2-(neopentylamino)ethyl)-9H-purin-6-amine |
| 1E-22 | PU-WS27 8-((6-ethynyl-2,3-dihydro-1H-inden-5-yl)thio)-9-(2-(neopentylamino)ethyl)-9H-purin-6-amine |
| 1E-23 | PU-WS29 8-((6-iodo-2,3-dihydro-1H-inden-5-yl)thio)-9-(3-(isopropylamino)propyl)-9H-purin-6-amine |
| 1E-24 | 9-(3-aminopropyl)-8-((6-iodo-2,3-dihydro-1H-inden-5-yl)thio)-9H-purin-6-amine |
| 1E-25 | 9-(2-aminoethyl)-8-((6-iodo-2,3-dihydro-1H-inden-5-yl)thio)-9H-purin-6-amine |
| 1E-26 | 9-(3-(tert-butylamino)propyl)-8-((6-iodo-2,3-dihydro-1H-inden-5-yl)thio)-9H-purin-6-amine |
| 1E-27 | 9-(3-(isopropylamino)propyl)-8-((6-(5-methyloxazol-2-yl)-2,3-dihydro-1H-inden-5-yl)thio)-9H-purin-6-amine |
| 1E-28 | 1-(4-(3-(6-amino-8-(6-(dimethylamino)-2,3-dihydro-1H-inden-5-ylthio)-9H-purin-9-yl)propyl)piperidin-1-yl)ethanone |
| 1E-29 | 1-(3-(2-(6-amino-2-fluoro-8-((6-(4-methylthiazol-2-yl)-2,3-dihydro-1H-inden-5-yl)methyl)-9H-purin-9-yl)ethyl)piperidin-1-yl)ethanone |
| 1E-30 | 8-((6-(5-methyloxazol-2-yl)-2,3-dihydro-1H-inden-5-yl)thio)-9-(2-(1-(methylsulfonyl)piperidin-3-yl)ethyl)-9H-purin-6-amine |

TABLE 1E-continued

| No. | Name |
|---|---|
| 1E-31 | 9-(3-aminopropyl)-8-((6-(5-methyloxazol-2-yl)-2,3-dihydro-1H-inden-5-yl)thio)-9H-purin-6-amine |
| 1E-32 | 9-(3-(tert-butylamino)propyl)-2-fluoro-8-((6-(4-methylthiazol-2-yl)-2,3-dihydro-1H-inden-5-yl)methyl)-9H-purin-6-amine |
| 1E-33 | 8-((6-(1H-pyrazol-3-yl)-2,3-dihydro-1H-inden-5-yl)methyl)-9-(3-(tert-butylamino)propyl)-2-fluoro-9H-purin-6-amine |
| 1E-34 | 8-(6-(aziridin-1-yl)-2,3-dihydro-1H-inden-5-ylthio)-9-(3-(1-(methylsulfonyl)pyrrolidin-3-yl)propyl)-9H-purin-6-amine |
| 1E-35 | 1-(3-(6-amino-2-fluoro-8-((6-iodo-2,3-dihydro-1H-inden-5-yl)methyl)-9H-purin-9-yl)propyl)pyrrolidin-3-one |
| 1E-36 | 8-((6-(5-methyloxazol-2-yl)-2,3-dihydro-1H-inden-5-yl)thio)-9-(2-(neopentylamino)ethyl)-9H-purin-6-amine |
| 1E-37 | 1-(6-amino-8-((6-(5-methyloxazol-2-yl)-2,3-dihydro-1H-inden-5-yl)thio)-9H-purin-9-yl)-3-(isopropylamino)propan-2-ol |
| 1E-38 | 5-(6-amino-8-(6-iodo-2,3-dihydro-1H-inden-5-ylthio)-9H-purin-9-yl)-N-methylpentane-1-sulfonamide |
| 1E-39 | 5-(6-amino-8-(6-iodo-2,3-dihydro-1H-inden-5-ylthio)-9H-purin-9-yl)pentane-1-sulfonamide |
| 1E-40 | 5-(6-amino-8-(6-ethynyl-2,3-dihydro-1H-inden-5-ylthio)-9H-purin-9-yl)pentane-1-sulfonamide |
| 1E-41 | 1-(2-(4-(6-amino-8-(6-(5-methylfuran-2-yl)-2,3-dihydro-1H-inden-5-ylthio)-9H-purin-9-yl)butyl)pyrrolidin-1-yl)ethanone |
| 1E-42 | 1-(3-(6-amino-8-(6-iodo-2,3-dihydro-1H-inden-5-ylthio)-9H-purin-9-yl)propyl)pyrrolidin-3-ol |
| 1E-43 | 6-(6-amino-8-(6-iodo-2,3-dihydro-1H-inden-5-ylthio)-9H-purin-9-yl)hexanamide |
| 1E-44 | 1-(3-(3-(6-amino-2-fluoro-8-((6-iodo-2,3-dihydro-1H-inden-5-yl)methyl)-9H-purin-9-yl)propyl)pyrrolidin-1-yl)ethanone |
| 1E-45 | 5-(6-amino-2-fluoro-8-((6-iodo-2,3-dihydro-1H-inden-5-yl)methyl)-9H-purin-9-yl)-N-methylpentane-1-sulfonamide |
| 1E-46 | 5-(6-amino-2-fluoro-8-((6-iodo-2,3-dihydro-1H-inden-5-yl)methyl)-9H-purin-9-yl)pentane-1-sulfonamide |
| 1E-47 | 9-(3-(tert-butylamino)propyl)-2-fluoro-8-((6-iodo-2,3-dihydro-1H-inden-5-yl)methyl)-9H-purin-6-amine |
| 1E-48 | 2-fluoro-8-((6-iodo-2,3-dihydro-1H-inden-5-yl)methyl)-9-(2-(neopentylamino)ethyl)-9H-purin-6-amine |
| 1E-49 | 1-(4-(3-(6-amino-8-(6-ethynyl-2,3-dihydro-1H-inden-5-ylthio)-9H-purin-9-yl)propyl)piperidin-1-yl)ethanone |
| 1E-50 | 1-(3-(2-(6-amino-8-((6-ethynyl-2,3-dihydro-1H-inden-5-yl)methyl)-2-fluoro-9H-purin-9-yl)ethyl)piperidin-1-yl)ethanone |
| 1E-51 | 9-(3-(tert-butylamino)propyl)-8-(6-ethynyl-2,3-dihydro-1H-inden-5-ylthio)-9H-purin-6-amine |
| 1E-52 | 9-(3-(tert-butylamino)propyl)-8-((6-ethynyl-2,3-dihydro-1H-inden-5-yl)methyl)-2-fluoro-9H-purin-6-amine |
| 1E-53 | 6-(6-amino-8-((6-ethynyl-2,3-dihydro-1H-inden-5-yl)methyl)-2-fluoro-9H-purin-9-yl)hexanamide |
| 1E-54 | 1-(3-(6-amino-8-((6-ethynyl-2,3-dihydro-1H-inden-5-yl)methyl)-2-fluoro-9H-purin-9-yl)propyl)pyrrolidin-3-one |
| 1E-55 | 4-(6-amino-8-((6-ethynyl-2,3-dihydro-1H-inden-5-yl)methyl)-2-fluoro-9H-purin-9-yl)butane-1-sulfonamide |
| 1E-56 | 8-((6-ethynyl-2,3-dihydro-1H-inden-5-yl)methyl)-2-fluoro-9-(3-(isopropylamino)propyl)-9H-purin-6-amine |
| 1E-57 | 8-((6-ethynyl-2,3-dihydro-1H-inden-5-yl)methyl)-2-fluoro-9-(2-(neopentylamino)ethyl)-9H-purin-6-amine |
| 1E-58 | 1-acetyl-3-(3-(6-amino-8-(6-ethynyl-2,3-dihydro-1H-inden-5-ylthio)-9H-purin-9-yl)propyl)imidazolidin-2-one |
| 1E-59 | 9-(3-(tert-butylamino)propyl)-8-(6-(oxazol-2-yl)-2,3-dihydro-1H-inden-5-ylthio)-9H-purin-6-amine |
| 1E-60 | 9-(3-(tert-butylamino)propyl)-8-(6-(5-methyloxazol-2-yl)-2,3-dihydro-1H-inden-5-ylthio)-9H-purin-6-amine |
| 1E-61 | 8-(6-(1H-pyrazol-3-yl)-2,3-dihydro-1H-inden-5-ylthio)-9-(3-(tert-butylamino)propyl)-9H-purin-6-amine |
| 1E-62 | 1-(3-(2-(6-amino-8-(6-(5-methyloxazol-2-yl)-2,3-dihydro-1H-inden-5-ylthio)-9H-purin-9-yl)ethyl)piperidin-1-yl)ethanone |
| 1E-63 | 6-(6-amino-8-(6-(oxazol-2-yl)-2,3-dihydro-1H-inden-5-ylthio)-9H-purin-9-yl)hexanamide |
| 1E-64 | 1-(3-(6-amino-8-(6-(4-methyloxazol-2-yl)-2,3-dihydro-1H-inden-5-ylthio)-9H-purin-9-yl)propyl)pyrrolidin-3-one |
| 1E-65 | 6-(6-amino-2-fluoro-8-((6-(oxazol-2-yl)-2,3-dihydro-1H-inden-5-yl)methyl)-9H-purin-9-yl)hexanamide |
| 1E-66 | 1-(3-(6-amino-2-fluoro-8-((6-(oxazol-2-yl)-2,3-dihydro-1H-inden-5-yl)methyl)-9H-purin-9-yl)propyl)pyrrolidin-3-one |
| 1E-67 | 5-(6-amino-2-fluoro-8-((6-(oxazol-2-yl)-2,3-dihydro-1H-inden-5-yl)methyl)-9H-purin-9-yl)pentane-1-sulfonamide |
| 1E-68 | 8-((6-iodo-2,3-dihydro-1H-inden-5-yl)thio)-9-(2-(1-methylpiperidin-2-yl)ethyl)-9H-purin-6-amine |

TABLE 1E-continued

| No. | Name |
|---|---|
| 1E-69 | 8-((6-iodo-2,3-dihydro-1H-inden-5-yl)thio)-9-(2-(1-methylpiperidin-3-yl)ethyl)-9H-purin-6-amine |
| 1E-70 | 8-((6-iodo-2,3-dihydro-1H-inden-5-yl)thio)-9-(2-(1-(methylsulfonyl)piperidin-3-yl)ethyl)-9H-purin-6-amine |
| 1E-71 | 3-(2-(6-amino-8-((6-iodo-2,3-dihydro-1H-inden-5-yl)thio)-9H-purin-9-yl)ethyl)piperidine-1-sulfonamide |
| 1E-72 | 2-fluoro-8-((6-iodo-2,3-dihydro-1H-inden-5-yl)methyl)-9-(2-(1-methylpiperidin-2-yl)ethyl)-9H-purin-6-amine |
| 1E-73 | 2-fluoro-8-((6-iodo-2,3-dihydro-1H-inden-5-yl)methyl)-9-(2-(1-methylpiperidin-3-yl)ethyl)-9H-purin-6-amine |
| 1E-74 | 2-fluoro-8-((6-iodo-2,3-dihydro-1H-inden-5-yl)methyl)-9-(2-(1-(methylsulfonyl)piperidin-3-yl)ethyl)-9H-purin-6-amine |
| 1E-75 | 3-(2-(6-amino-2-fluoro-8-((6-iodo-2,3-dihydro-1H-inden-5-yl)methyl)-9H-purin-9-yl)ethyl)piperidine-1-sulfonamide |
| 1E-76 | 9-(3-(tert-butylamino)propyl)-2-fluoro-8-((6-iodo-2,3-dihydro-1H-inden-5-yl)methyl)-9H-purin-6-amine |
| 1E-77 | 8-((6-ethynyl-2,3-dihydro-1H-inden-5-yl)thio)-9-(2-(1-methylpiperidin-2-yl)ethyl)-9H-purin-6-amine |
| 1E-78 | 8-((6-ethynyl-2,3-dihydro-1H-inden-5-yl)thio)-9-(2-(1-methylpiperidin-3-yl)ethyl)-9H-purin-6-amine |
| 1E-79 | 3-(2-(6-amino-8-((6-ethynyl-2,3-dihydro-1H-inden-5-yl)methyl)-2-fluoro-9H-purin-9-yl)ethyl)piperidine-1-sulfonamide |
| 1E-80 | 8-((6-ethynyl-2,3-dihydro-1H-inden-5-yl)thio)-9-(2-(1-(methylsulfonyl)piperidin-3-yl)ethyl)-9H-purin-6-amine |
| 1E-81 | 8-((6-ethynyl-2,3-dihydro-1H-inden-5-yl)methyl)-2-fluoro-9-(2-(1-methylpiperidin-2-yl)ethyl)-9H-purin-6-amine |
| 1E-82 | 8-((6-ethynyl-2,3-dihydro-1H-inden-5-yl)methyl)-2-fluoro-9-(2-(1-methylpiperidin-3-yl)ethyl)-9H-purin-6-amine |
| 1E-83 | 9-(3-(tert-butylamino)propyl)-8-(6-(4-methylthiazol-2-yl)-2,3-dihydro-1H-inden-5-ylthio)-9H-purin-6-amine |
| 1E-84 | 2-fluoro-9-(2-(1-methylpiperidin-2-yl)ethyl)-8-((6-(oxazol-2-yl)-2,3-dihydro-1H-inden-5-yl)methyl)-9H-purin-6-amine |
| 1E-85 | 2-fluoro-9-(2-(1-methylpiperidin-3-yl)ethyl)-8-((6-(oxazol-2-yl)-2,3-dihydro-1H-inden-5-yl)methyl)-9H-purin-6-amine |

TABLE 1F

| No. | Name |
|---|---|
| 1F-1 | 8-((6-iodoindolin-5-yl)thio)-9-(2-(isobutylamino)ethyl)-9H-purin-6-amine |
| 1F-2 | 2-fluoro-8-((6-iodoindolin-5-yl)methyl)-9-(2-(isobutylamino)ethyl)-9H-purin-6-amine |
| 1F-3 | 8-((6-(1H-pyrazol-3-yl)indolin-5-yl)thio)-9-(2-(isobutylamino)ethyl)-9H-purin-6-amine |
| 1F-4 | 8-((6-ethynylindolin-5-yl)thio)-9-(2-(isobutylamino)ethyl)-9H-purin-6-amine |
| 1F-5 | 8-((6-(1H-pyrrol-3-yl)indolin-5-yl)methyl)-2-fluoro-9-(2-(isobutylamino)ethyl)-9H-purin-6-amine |
| 1F-6 | 5-((6-amino-9-(3-(isopropylamino)propyl)-9H-purin-8-yl)thio)indoline-6-carbonitrile |
| 1F-7 | 8-((6-(furan-2-yl)-1-methylindolin-5-yl)thio)-9-(3-(isopropylamino)propyl)-9H-purin-6-amine |
| 1F-8 | 8-((6-cyclobutyl-1-methylindolin-5-yl)methyl)-2-fluoro-9-(2-(isobutylamino)ethyl)-9H-purin-6-amine |
| 1F-9 | 1-(5-((6-amino-2-fluoro-9-(2-(neopentylamino)ethyl)-9H-purin-8-yl)methyl)-6-(aziridin-1-yl)indolin-1-yl)ethanone |
| 1F-10 | 1-(4-(2-(6-amino-8-((6-(furan-2-yl)indolin-5-yl)thio)-9H-purin-9-yl)ethyl)piperidin-1-yl)ethanone |
| 1F-11 | 4-(2-(8-((6-(1H-pyrazol-3-yl)indolin-5-yl)thio)-6-amino-9H-purin-9-yl)ethyl)piperidine-1-carbaldehyde |
| 1F-12 | 4-(2-(6-amino-8-((6-ethynyl-1-methylindolin-5-yl)thio)-9H-purin-9-yl)ethyl)piperidine-1-carbaldehyde |
| 1F-13 | 1-(4-(2-(6-amino-2-fluoro-8-((6-(furan-2-yl)indolin-5-yl)methyl)-9H-purin-9-yl)ethyl)piperidin-1-yl)ethanone |
| 1F-14 | N-(2-((2-(6-amino-8-((6-(furan-2-yl)indolin-5-yl)thio)-9H-purin-9-yl)ethyl)amino)ethyl)sulfamide |
| 1F-15 | 3-((2-(6-amino-8-((6-(furan-2-yl)indolin-5-yl)thio)-9H-purin-9-yl)ethyl)amino)-N-hydroxypropanamide |
| 1F-16 | 2-chloro-8-((6-iodoindolin-5-yl)methyl)-9-(2-(isobutylamino)ethyl)-9H-purin-6-amine |
| 1F-17 | 9-(3-aminopropyl)-8-((6-iodoindolin-5-yl)thio)-9H-purin-6-amine |
| 1F-18 | 9-(2-aminoethyl)-8-((6-iodoindolin-5-yl)thio)-9H-purin-6-amine |
| 1F-19 | 9-(3-(tert-butylamino)propyl)-8-((6-iodoindolin-5-yl)thio)-9H-purin-6-amine |
| 1F-20 | 8-((6-iodoindolin-5-yl)thio)-9-(3-(isopropylamino)propyl)-9H-purin-6-amine |

TABLE 1G

| No. | Name |
|---|---|
| 1G-1 | 1-(6-(6-amino-9-(3-(isopropylamino)propyl)-9H-purin-8-ylthio)-5-iodoindolin-1-yl)ethanone |
| 1G-2 | 2-fluoro-8-((5-iodoindolin-6-yl)methyl)-9-(2-(isobutylamino)ethyl)-9H-purin-6-amine |
| 1G-3 | 8-((5-(1H-pyrazol-3-yl)indolin-6-yl)thio)-9-(2-(isobutylamino)ethyl)-9H-purin-6-amine |
| 1G-4 | 8-((5-ethynylindolin-6-yl)thio)-9-(2-(isobutylamino)ethyl)-9H-purin-6-amine |
| 1G-5 | 8-((5-(1H-pyrrol-3-yl)indolin-6-yl)methyl)-2-fluoro-9-(2-(isobutylamino)ethyl)-9H-purin-6-amine |
| 1G-6 | 6-((6-amino-9-(3-(isopropylamino)propyl)-9H-purin-8-yl)thio)indoline-5-carbonitrile |
| 1G-7 | 8-((5-(furan-2-yl)-1-methylindolin-6-yl)thio)-9-(3-(isopropylamino)propyl)-9H-purin-6-amine |
| 1G-8 | 8-((5-cyclobutyl-1-methylindolin-6-yl)methyl)-2-fluoro-9-(2-(isobutylamino)ethyl)-9H-purin-6-amine |
| 1G-9 | 1-(6-(((6-amino-2-fluoro-9-(2-(neopentylamino)ethyl)-9H-purin-8-yl)methyl)-5-(aziridin-1-yl)indolin-1-yl)ethanone |
| 1G-10 | 1-(4-(2-(6-amino-8-((5-(furan-2-yl)indolin-6-yl)thio)-9H-purin-9-yl)ethyl)piperidin-1-yl)ethanone |
| 1G-11 | 8-(5-(1H-pyrazol-3-yl)indolin-6-ylthio)-9-(2-(1-(methylsulfonyl)piperidin-3-yl)ethyl)-9H-purin-6-amine |
| 1G-12 | 3-(2-(6-amino-8-(1-ethyl-5-ethynylindolin-6-ylthio)-9H-purin-9-yl)ethyl)piperidine-1-carbaldehyde |
| 1G-13 | 1-(3-(2-(6-amino-2-fluoro-8-((1-methyl-5-(5-methylfuran-2-yl)indolin-6-yl)methyl)-9H-purin-9-yl)ethyl)piperidin-1-yl)ethanone |
| 1G-14 | N-(2-((2-(6-amino-8-((5-(furan-2-yl)indolin-6-yl)thio)-9H-purin-9-yl)ethyl)amino)ethyl)sulfamide |
| 1G-15 | 3-(2-(6-amino-8-(5-(5-methylfuran-2-yl)indolin-6-ylthio)-9H-purin-9-yl)ethylamino)-N-hydroxypropanamide |
| 1G-16 | 1-(3-(4-(6-amino-8-(5-iodo-1-methylindolin-6-ylthio)-9H-purin-9-yl)butyl)pyrrolidin-1-yl)ethanone |
| 1G-17 | 9-(3-aminopropyl)-8-((5-iodoindolin-6-yl)thio)-9H-purin-6-amine |
| 1G-18 | 9-(2-aminoethyl)-8-((5-iodoindolin-6-yl)thio)-9H-purin-6-amine |
| 1G-19 | 9-(3-(tert-butylamino)propyl)-8-(1-ethyl-5-iodoindolin-6-ylthio)-9H-purin-6-amine |
| 1G-20 | 8-(5-iodo-1-methylindolin-6-ylthio)-9-(3-(isopropylamino)propyl)-9H-purin-6-amine |
| 1G-21 | 1-(3-(6-amino-8-(5-iodo-1-methylindolin-6-ylthio)-9H-purin-9-yl)propyl)pyrrolidin-3-one |

TABLE 1H

| No. | Name |
|---|---|
| 1H-1 | 6-((6-amino-9-(2-(isobutylamino)ethyl)-9H-purin-8-yl)thio)-5-iodo-2,3-dihydro-1H-inden-1-one |
| 1H-2 | 6-((6-amino-9-(3-(isopropylamino)propyl)-9H-purin-8-yl)thio)-5-iodo-2,3-dihydro-1H-inden-1-one |
| 1H-3 | 6-((6-amino-2-fluoro-9-(2-(isobutylamino)ethyl)-9H-purin-8-yl)methyl)-5-iodo-2,3-dihydro-1H-inden-1-one |
| 1H-4 | 6-((6-amino-2-fluoro-9-(3-(isopropylamino)propyl)-9H-purin-8-yl)methyl)-5-iodo-2,3-dihydro-1H-inden-1-one |
| 1H-5 | 6-(6-amino-9-(2-hydroxy-3-(isopropylamino)propyl)-9H-purin-8-ylthio)-5-iodo-2,3-dihydro-1H-inden-1-one |
| 1H-6 | 6-((6-amino-9-(3-(isopropylamino)propyl)-9H-purin-8-yl)thio)-5-(furan-2-yl)-2,3-dihydro-1H-inden-1-one |
| 1H-7 | 6-((6-amino-2-fluoro-9-(2-(neopentylamino)ethyl)-9H-purin-8-yl)methyl)-5-(dimethylamino)-2,3-dihydro-1H-inden-1-one |
| 1H-8 | 6-((6-amino-9-(2-(isobutylamino)ethyl)-9H-purin-8-yl)thio)-5-(1H-pyrazol-3-yl)-2,3-dihydro-1H-inden-1-one |
| 1H-9 | 6-((6-amino-9-(3-(isopropylamino)propyl)-9H-purin-8-yl)thio)-5-cyclopropyl-2,3-dihydro-1H-inden-1-one |
| 1H-10 | 6-((6-amino-2-fluoro-9-(2-(isobutylamino)ethyl)-9H-purin-8-yl)methyl)-5-ethynyl-2,3-dihydro-1H-inden-1-one |
| 1H-11 | 6-((6-amino-2-fluoro-9-(3-(isopropylamino)propyl)-9H-purin-8-yl)methyl)-1-oxo-2,3-dihydro-1H-indene-5-carbonitrile |
| 1H-12 | 6-((6-amino-2-chloro-9-(3-(isopropylamino)propyl)-9H-purin-8-yl)methyl)-5-(furan-2-yl)-2,3-dihydro-1H-inden-1-one |
| 1H-13 | 4-(2-(6-amino-8-((6-ethynyl-3-oxo-2,3-dihydro-1H-inden-5-yl)thio)-9H-purin-9-yl)ethyl)piperidine-1-carbaldehyde |
| 1H-14 | 6-((9-(2-(1-acetylpiperidin-3-yl)ethyl)-6-amino-2-fluoro-9H-purin-8-yl)methyl)-5-(5-methylfuran-2-yl)-2,3-dihydro-1H-inden-1-one |
| 1H-15 | N-(2-((2-(6-amino-8-((6-(furan-2-yl)-3-oxo-2,3-dihydro-1H-inden-5-yl)thio)-9H-purin-9-yl)ethyl)amino)ethyl)sulfamide |
| 1H-16 | 3-((2-(6-amino-8-((6-ethynyl-3-oxo-2,3-dihydro-1H-inden-5-yl)thio)-9H-purin-9-yl)ethyl)amino)-N-hydroxypropanamide |
| 1H-17 | 6-((6-amino-9-(2-(isobutylamino)ethyl)-9H-purin-8-yl)thio)-5-iodo-2,3-dihydro-1H-indene-1-thione |
| 1H-18 | 6-((6-amino-2-fluoro-9-(3-(isopropylamino)propyl)-9H-purin-8-yl)methyl)-5-iodo-2,3-dihydro-1H-indene-1-thione |

TABLE 1H-continued

| No. | Name |
|---|---|
| 1H-19 | 6-((6-amino-9-(3-aminopropyl)-9H-purin-8-yl)thio)-5-iodo-2,3-dihydro-1H-inden-1-one |
| 1H-20 | 6-((6-amino-9-(2-aminoethyl)-2-fluoro-9H-purin-8-yl)methyl)-5-iodo-2,3-dihydro-1H-inden-1-one |
| 1H-21 | 6-((6-amino-9-(2-aminoethyl)-9H-purin-8-yl)thio)-5-iodo-2,3-dihydro-1H-inden-1-one |
| 1H-22 | 6-((6-amino-9-(3-(tert-butylamino)propyl)-9H-purin-8-yl)thio)-5-iodo-2,3-dihydro-1H-inden-1-one |
| 1H-23 | 3-(2-(6-amino-8-(6-iodo-3-oxo-2,3-dihydro-1H-inden-5-ylthio)-9H-purin-9-yl)ethyl)pyrrolidine-1-carbaldehyde |
| 1H-24 | 6-(6-amino-9-(2-(1-(methylsulfonyl)pyrrolidin-3-yl)ethyl)-9H-purin-8-ylthio)-5-iodo-2,3-dihydro-1H-inden-1-one |
| 1H-25 | N-(3-(6-amino-2-fluoro-8-((6-iodo-3-oxo-2,3-dihydro-1H-inden-5-yl)methyl)-9H-purin-9-yl)propyl)methanesulfonamide |
| 1H-26 | 6-((6-amino-9-(2-(1-(methylsulfonyl)piperidin-3-yl)ethyl)-9H-purin-8-yl)thio)-5-(1H-pyrazol-3-yl)-2,3-dihydro-1H-inden-1-one |
| 1H-27 | 6-((6-amino-9-(3-(tert-butylamino)propyl)-9H-purin-8-yl)thio)-5-(5-methylfuran-2-yl)-2,3-dihydro-1H-inden-1-one |
| 1H-28 | 6-((6-amino-9-(3-(tert-butylamino)propyl)-9H-purin-8-yl)thio)-5-(5-methylthiazol-2-yl)-2,3-dihydro-1H-inden-1-one |
| 1H-29 | 6-((6-amino-9-(3-(tert-butylamino)propyl)-9H-purin-8-yl)thio)-5-(thiophen-2-yl)-2,3-dihydro-1H-inden-1-one |
| 1H-30 | 2-(3-(6-amino-8-(6-iodo-3-oxo-2,3-dihydro-1H-inden-5-ylthio)-9H-purin-9-yl)propyl)azetidine-1-carbaldehyde |
| 1H-31 | 6-((6-amino-9-(3-(tert-butylamino)propyl)-2-fluoro-9H-purin-8-yl)methyl)-5-ethynyl-2,3-dihydro-1H-inden-1-one |
| 1H-32 | 6-((6-amino-9-(2-(1-(methylsulfonyl)piperidin-3-yl)ethyl)-9H-purin-8-yl)thio)-5-(dimethylamino)-2,3-dihydro-1H-inden-1-one |
| 1H-33 | 6-((6-amino-9-(3-(tert-butylamino)propyl)-2-fluoro-9H-purin-8-yl)methyl)-5-(5-methyloxazol-2-yl)-2,3-dihydro-1H-inden-1-one |
| 1H-34 | 6-((9-(2-(1-acetylpiperidin-4-yl)ethyl)-6-amino-2-fluoro-9H-purin-8-yl)methyl)-5-(5-methylthiazol-2-yl)-2,3-dihydro-1H-inden-1-one |
| 1H-35 | N-(3-(6-amino-2-fluoro-8-((6-(5-methyloxazol-2-yl)-3-oxo-2,3-dihydro-1H-inden-5-yl)methyl)-9H-purin-9-yl)propyl)methanesulfonamide |
| 1H-36 | 1-(3-(6-amino-8-(6-iodo-3-oxo-2,3-dihydro-1H-inden-5-ylthio)-9H-purin-9-yl)propyl)pyrrolidin-3-one |
| 1H-37 | 1-(3-(6-amino-8-(6-iodo-3-oxo-2,3-dihydro-1H-inden-5-ylthio)-9H-purin-9-yl)propyl)pyrrolidin-2-one |

TABLE 2A

| Compound # | Name | $EC_{50}$; binding to JNPL3 brain Hsp90 (nM) | $EC_{50}$; binding to SKBr3 cell Hsp90 (nM) |
|---|---|---|---|
| 1B-1 | PU-WS9 | 5.5 | ND |
| 1B-2 | PU-WS4 | 8.0-14 | ND |
| 1A-1 | PU-WS10 | 132.9-346 | ND |

TABLE 2B

| Compound # | Name | $EC_{50}$; binding to JNPL3 brain Hsp90 (nM) | $EC_{50}$; binding to SKBr3 cell Hsp90 (nM) |
|---|---|---|---|
| 1B-3 | PU-WS17 | 17.3 | ND |
| 1B-4 | PU-WS18 | 33.3 | ND |
| 1B-24 | PU-WS21 | 10.8 | ND |
| 1B-25 | PU-WS22 | 8.0 | ND |

TABLE 2C

| Compound # | Name | $EC_{50}$; binding to JNPL3 brain Hsp90 (nM) | $EC_{50}$; binding to SKBr3 cell Hsp90 (nM) |
|---|---|---|---|
| 1B-26 | PU-WS23 | 12.2 | ND |
| 1B-27 | PU-WS24 | 25.4 | ND |

TABLE 2D

| Compound # | Name | $EC_{50}$; binding to JNPL3 brain Hsp90 (nM) | $EC_{50}$; binding to SKBr3 cell Hsp90 (nM) |
|---|---|---|---|
| 1B-28 | PU-WS28 | 8.1 | ND |

TABLE 2E

| Compound # | Name | $EC_{50}$; binding to JNPL3 brain Hsp90 (nM) | $EC_{50}$; binding to SKBr3 cell Hsp90 (nM) |
|---|---|---|---|
| 1E-2 | PU-WS26 | 3.6 | ND |
| 1E-21 | PU-WS25 | 7.2 | ND |
| 1E-23 | PU-WS29 | 4.5 | ND |

TABLE 2F

| Compound # | Name | $EC_{50}$; binding to JNPL3 brain Hsp90 (nM) | $EC_{50}$; binding to SKBr3 cell Hsp90 (nM) |
|---|---|---|---|
| 1E-22 | PU-WS27 | 15 | ND |

TABLE 2G

| Compound # | Name | EC$_{50}$; binding to JNPL3 brain Hsp90 (nM) | EC$_{50}$; binding to SKBr3 cell Hsp90 (nM) |
| --- | --- | --- | --- |
| 4A-1 | DZ2-388 | 270 | 645 |
| 4A-2 | DZ2-390 | 2,666 | 6,240 |
| 4A-3 | DZ2-391 | >100,000 | >100,000 |
| 4A-4 | TT-V-47B | 8,287 | 15,010 |
| 4A-5 | DZ2-392 | 1,388 | 2,520 |
| 4A-6 | DZ3-3 | 438 | 1,030 |
| 4A-7 | DZ3-6 | 732 | 1,385 |
| 4A-8 | DZ3-50 | 2,333 | >3000 |
| 4C-1 | DZ3-4 | 11 | 22 |
| 4C-2 | DZ3-27 | 48 | 86 |
| 4C-3 | DZ3-25 | 3.9 | 5.2 |
| 4C-4 | DZ3-26 | 14 | 26 |
| 4C-5 | TT5-53A | 5.3 | 6.5 |
| 4C-6 | DZ3-33 | 56 | 141 |
| 4C-7 | DZ3-34 | 82 | 142 |
| 4C-8 | DZ3-35 | 23 | 37 |
| 4C-9 | DZ3-36 | 6.0 | 12 |
| 4C-10 | DZ3-49 | >300 | >300 |
| 4C-11 | DZ3-51 | 153 | 185 |
| 4C-14 | DZ3-60 | ND | 10.1 |
| 4C-16 | DZ3-56 | ND | 10.2 |
| 4C-38 | DZ4-20 | ND | 7.9 |
| 4C-39 | DZ4-23 | ND | 11.4 |
| 4C-40 | DZ3-142 | ND | 509 |
| 4C-41 | DZ3-143 | ND | 2,081 |
| 4D-1 | DZ2-395 | 43 | 80 |
| 4D-2 | DZ3-48 | 24 | 59 |
| 4D-3 | DZ3-58 | ND | 18.5 |
| 4D-16 | DZ4-21 | ND | 47 |
| 4D-17 | DZ4-24 | ND | 19.7 |
| 4F-1 | DZ3-5 | 4,120 | 9,620 |

TABLE 2H

| Compound # | Name | EC$_{50}$; binding to JNPL3 brain Hsp90 (nM) | EC$_{50}$; binding to SKBr3 cell Hsp90 (nM) |
| --- | --- | --- | --- |
| 4B-1 | PU-WS8 | 19.1 | ND |
| 4B-2 | PU-WS6 | 403 | ND |
| 4B-3 | PU-WS7 | 731 | ND |
| 4B-4 | PU-WS16 | 13.7 | ND |
| 4B-13 | PU-WS19 | 8.6 | ND |
| 4B-14 | PU-WS20 | <200 | ND |

TABLE 2I

| Compound # | Name | EC$_{50}$; binding to JNPL3 brain Hsp90 (nM) | EC$_{50}$; binding to SKBr3 cell Hsp90 (nM) |
| --- | --- | --- | --- |
| 4E-1 | PU-WS3 | 218.8 | ND |
| 4E-2 | PU-WS5 | 285 | ND |
| 4E-3 | DZ3-39 | 542 | 1126 |
| 4E-4 | DZ3-40 | 46 | 93 |

TABLE 2J

| Compound # | Name | EC$_{50}$; binding to JNPL3 brain Hsp90 (nM) | EC$_{50}$; binding to SKBr3 cell Hsp90 (nM) |
| --- | --- | --- | --- |
| 4I-12 | TT-VI-116 | ND | 394 |

TABLE 2K

| Compound # | Name | EC$_{50}$; binding to JNPL3 brain Hsp90 (nM) | EC$_{50}$; binding to SKBr3 cell Hsp90 (nM) |
| --- | --- | --- | --- |
| 4G-1 | DZ3-30 | 374 | 1024 |
| 4G-2 | DZ3-32 | 107 | 128 |
| 4G-3 | DZ3-43 | 2.6 | 7.2 |
| 4G-4 | DZ3-44 | >300 | >300 |
| 4G-5 | DZ3-45 | >300 | >300 |
| 4G-6 | DZ3-46 | 4.0 | 5.5 |
| 4G-9 | DZ3-61 | ND | 5.5 |

TABLE 2L

| Compound # | Name | EC$_{50}$; binding to JNPL3 brain Hsp90 (nM) | EC$_{50}$; binding to SKBr3 cell Hsp90 (nM) |
| --- | --- | --- | --- |
| 4H-1 | DZ3-29 | 309 | 740 |
| 4H-2 | DZ3-31 | 89 | 121 |
| 4H-3 | DZ3-41 | 57 | 161 |
| 4H-4 | DZ3-59 | ND | 24.6 |
| 4H-6 | DZ3-38 | 23 | 47 |
| 4H-7 | DZ3-141 | ND | 26,653 |

TABLE 2M

| Compound # | Name | EC$_{50}$; binding to JNPL3 brain Hsp90 (nM) | EC$_{50}$; binding to SKBr3 cell Hsp90 (nM) |
| --- | --- | --- | --- |
| 5A-1 | PU-RK11 | ND | 34.5 |
| 5A-2 | PU-HT165 | ND | 34.6 |
| 5A-3 | PU-HT175 | ND | 34.8 |
| 5A-4 | PU-RK12 | ND | 62.8 |
| 5A-5 | DZ3-73 | ND | 9.4 |
| 5A-6 | DZ4-84 | 45.1 | ND |

TABLE 2N

| Compound # | Name | EC$_{50}$; binding to JNPL3 brain Hsp90 (nM) | EC$_{50}$; binding to SKBr3 cell Hsp90 (nM) |
| --- | --- | --- | --- |
| 5B-1 | HJP18 | ND | 6.9 |
| 5B-7 | TT-VI-53A | ND | 5.3 |
| 5B-33 | HJP23 | 46.3 | ND |
| 5B-34 | HJP20 | ND | 3.5 |

TABLE 2O

| Compound # | Name | EC$_{50}$; binding to JNPL3 brain Hsp90 (nM) | EC$_{50}$; binding to SKBr3 cell Hsp90 (nM) |
| --- | --- | --- | --- |
| 5D-2 | HJP19 | ND | 11.2 |
| 5D-4 | TT-VI-54A | ND | 7.7 |

TABLE 2P

| Compound # | Name | EC$_{50}$; binding to JNPL3 brain Hsp90 (nM) | EC$_{50}$; binding to SKBr3 cell Hsp90 (nM) |
| --- | --- | --- | --- |
| 6B-25 | DZ4-52-N9 | ND | 97.0 |

TABLE 2Q

| Compound # | Name | EC$_{50}$; binding to JNPL3 brain Hsp90 (nM) | EC$_{50}$; binding to SKBr3 cell Hsp90 (nM) |
|---|---|---|---|
| 7A-20 | PU-WS31 | <200 | ND |
| 7C-13 | TT-V-138 | ND | 84 |
| 7D-3 | TT-V-139 | ND | 240 |
| 7E-6 | TT-V-140 | ND | 32 |

TABLE 3A

| No. | Name |
|---|---|
| 3A-1 | 2-fluoro-8-((5-(furan-2-yl)benzofuran-6-yl)methyl)-9-(2-(neopentylamino)ethyl)-9H-purin-6-amine |
| 3A-2 | 2-fluoro-8-((5-iodo-1H-indol-6-yl)methyl)-9-(2-(neopentylamino)ethyl)-9H-purin-6-amine |
| 3A-3 | N-(2-((2-(6-amino-8-((5-(furan-2-yl)benzo[b]thiophen-6-yl)thio)-9H-purin-9-yl)ethyl)amino)ethyl)sulfamide |
| 3A-4 | 3-((2-(8-((1-acetyl-5-(furan-2-yl)-1H-indol-6-yl)thio)-6-amino-9H-purin-9-yl)ethyl)amino)-N-hydroxypropanamide |
| 3A-5 | 8-((5-(azetidin-1-yl)benzofuran-6-yl)thio)-9-(2-(isobutylamino)ethyl)-9H-purin-6-amine |
| 3A-6 | 8-((5-iodobenzo[b]thiophen-6-yl)thio)-9-(2-(isobutylamino)ethyl)-9H-purin-6-amine |
| 3A-7 | 8-((5-(1H-pyrazol-3-yl)-1H-indol-6-yl)thio)-9-(3-(isopropylamino)propyl)-9H-purin-6-amine |
| 3A-8 | 8-((5-ethynyl-1H-indol-6-yl)thio)-9-(2-(isobutylamino)ethyl)-9H-purin-6-amine |
| 3A-9 | 6-((6-amino-9-(2-(isobutylamino)ethyl)-9H-purin-8-yl)thio)-1-methyl-1H-indole-5-carbonitrile |
| 3A-10 | 9-(3-aminopropyl)-8-((5-iodobenzofuran-6-yl)thio)-9H-purin-6-amine |
| 3A-11 | 9-(2-aminoethyl)-8-((5-iodobenzofuran-6-yl)thio)-9H-purin-6-amine |
| 3A-12 | 9-(3-(tert-butylamino)propyl)-8-((5-iodobenzofuran-6-yl)thio)-9H-purin-6-amine |
| 3A-13 | 2-fluoro-8-((5-iodobenzofuran-6-yl)methyl)-9-(2-(neopentylamino)ethyl)-9H-purin-6-amine |
| 3A-14 | 1-(4-(2-(6-amino-2-fluoro-8-((5-(5-methylfuran-2-yl)benzofuran-6-yl)methyl)-9H-purin-9-yl)ethyl)piperidin-1-yl)ethanone |
| 3A-15 | 9-(3-(tert-butylamino)propyl)-8-((5-ethynylbenzofuran-6-yl)thio)-9H-purin-6-amine |
| 3A-16 | 2-fluoro-8-((5-(5-methyloxazol-2-yl)benzofuran-6-yl)methyl)-9-(2-(neopentylamino)ethyl)-9H-purin-6-amine |
| 3A-17 | 9-(3-(tert-butylamino)propyl)-8-((5-(dimethylamino)benzofuran-6-yl)thio)-9H-purin-6-amine |
| 3A-18 | 8-((5-iodobenzofuran-6-yl)thio)-9-(2-(1-(methylsulfonyl)piperidin-3-yl)ethyl)-9H-purin-6-amine |
| 3A-19 | 8-((5-(1H-pyrazol-3-yl)benzofuran-6-yl)thio)-9-(2-(neopentylamino)ethyl)-9H-purin-6-amine |
| 3A-20 | N-(3-(6-amino-8-((5-(aziridin-1-yl)benzofuran-6-yl)thio)-9H-purin-9-yl)propyl)methanesulfonamide |
| 3A-21 | 3-(6-amino-8-((5-iodobenzofuran-6-yl)thio)-9H-purin-9-yl)propyl sulfamate |
| 3A-22 | 9-(3-(tert-butylamino)propyl)-8-((5-(oxazol-2-yl)benzofuran-6-yl)thio)-9H-purin-6-amine |
| 3A-23 | 8-((5-ethynylbenzofuran-6-yl)thio)-9-(2-(neopentylamino)ethyl)-9H-purin-6-amine |
| 3A-24 | 1-(6-amino-8-((5-iodobenzofuran-6-yl)thio)-9H-purin-9-yl)-3-(tert-butylamino)propan-2-ol |
| 3A-25 | 8-((5-iodobenzofuran-6-yl)thio)-9-(3-(isopropylamino)propyl)-9H-purin-6-amine |
| 3A-26 | 9-(3-(tert-butylamino)propyl)-8-((5-(5-methylthiazol-2-yl)benzofuran-6-yl)thio)-9H-purin-6-amine |

TABLE 3B

| No. | Name |
|---|---|
| 3B-1 | 5-((6-amino-9-(2-(isobutylamino)ethyl)-9H-purin-8-yl)thio)benzofuran-6-carbonitrile |
| 3B-2 | 8-((6-iodobenzofuran-5-yl)thio)-9-(2-(isobutylamino)ethyl)-9H-purin-6-amine |
| 3B-3 | 8-((6-(furan-2-yl)benzofuran-5-yl)thio)-9-(2-(isobutylamino)ethyl)-9H-purin-6-amine |
| 3B-4 | N-(2-((2-(6-amino-8-((6-(furan-2-yl)benzofuran-5-yl)thio)-9H-purin-9-yl)ethyl)amino)teeth)sulfamide |

TABLE 3B-continued

| No. | Name |
|---|---|
| 3B-5 | 3-((2-(6-amino-8-((6-(furan-2-yl)benzofuran-5-yl)thio)-9H-purin-9-yl)ethyl)amino)-N-hydroxypropanamide |
| 3B-6 | 2-fluoro-8-((6-(furan-2-yl)-1H-indol-5-yl)methyl)-9-(2-(neopentylamino)ethyl)-9H-purin-6-amine |
| 3B-7 | 8-((6-(azetidin-1-yl)-1H-indol-5-yl)thio)-9-(2-(isobutylamino)ethyl)-9H-purin-6-amine |
| 3B-8 | 9-(2-(isobutylamino)ethyl)-8-((6-(pyrrolidin-1-yl)-1H-indol-5-yl)thio)-9H-purin-6-amine |
| 3B-9 | 8-((6-(furan-2-yl)-1-methyl-1H-indol-5-yl)thio)-9-(3-(isopropylamino)propyl)-9H-purin-6-amine |
| 3B-10 | 2-fluoro-8-((6-iodo-1-isopropyl-1H-indol-5-yl)methyl)-9-(2-(isobutylamino)ethyl)-9H-purin-6-amine |
| 3B-11 | 2-fluoro-8-((6-(furan-2-yl)benzo[b]thiophen-5-yl)methyl)-9-(3-(isopropylamino)propyl)-9H-purin-6-amine |
| 3B-12 | 2-fluoro-8-((6-iodobenzo[b]thiophen-5-yl)methyl)-9-(2-(neopentylamino)ethyl)-9H-purin-6-amine |
| 3B-13 | 8-((6-(1H-pyrrol-3-yl)benzo[b]thiophen-5-yl)methyl)-2-fluoro-9-(2-(isobutylamino)ethyl)-9H-purin-6-amine |
| 3B-14 | 8-((6-ethynylbenzo[b]thiophen-5-yl)methyl)-2-fluoro-9-(2-(isobutylamino)ethyl)-9H-purin-6-amine |
| 3B-15 | 2-chloro-8-((6-ethynylbenzo[b]thiophen-5-yl)methyl)-9-(2-(isobutylamino)ethyl)-9H-purin-6-amine |
| 3B-16 | 8-((6-(azetidin-1-yl)-1H-indol-5-yl)thio)-9-(2-(isobutylamino)ethyl)-9H-purin-6-amine |
| 3B-17 | 8-((6-(aziridin-1-yl)-1H-indol-5-yl)thio)-9-(2-(isobutylamino)ethyl)-9H-purin-6-amine |
| 3B-18 | 9-(3-aminopropyl)-8-((6-iodobenzofuran-5-yl)thio)-9H-purin-6-amine |
| 3B-19 | 9-(2-aminoethyl)-8-((6-iodobenzofuran-5-yl)thio)-9H-purin-6-amine |
| 3B-20 | 9-(3-(tert-butylamino)propyl)-8-((6-iodobenzofuran-5-yl)thio)-9H-purin-6-amine |
| 3B-21 | 1-(4-(2-(6-amino-2-fluoro-8-((6-(5-methylfuran-2-yl)benzofuran-5-yl)methyl)-9H-purin-9-yl)ethyl)piperidin-1-yl)ethanone |
| 3B-22 | 9-(3-(tert-butylamino)propyl)-8-((6-ethynylbenzofuran-5-yl)thio)-9H-purin-6-amine |
| 3B-23 | 2-fluoro-8-((6-(5-methyloxazol-2-yl)benzofuran-5-yl)methyl)-9-(2-(neopentylamino)ethyl)-9H-purin-6-amine |
| 3B-24 | 9-(3-(tert-butylamino)propyl)-8-((6-(dimethylamino)benzofuran-5-yl)thio)-9H-purin-6-amine |
| 3B-25 | 8-((6-iodobenzofuran-5-yl)thio)-9-(2-(1-(methylsulfonyl)piperidin-3-yl)ethyl)-9H-purin-6-amine |
| 3B-26 | 8-((6-(1H-pyrazol-3-yl)benzofuran-5-yl)thio)-9-(2-(neopentylamino)ethyl)-9H-purin-6-amine |
| 3B-27 | N-(3-(6-amino-8-((6-(aziridin-1-yl)benzofuran-5-yl)thio)-9H-purin-9-yl)propyl)methanesulfonamide |
| 3B-28 | 3-(6-amino-8-((6-iodobenzofuran-5-yl)thio)-9H-purin-9-yl)propyl sulfamate |
| 3B-29 | 9-(3-(tert-butylamino)propyl)-8-((6-(oxazol-2-yl)benzofuran-5-yl)thio)-9H-purin-6-amine |
| 3B-30 | 8-((6-ethynylbenzofuran-5-yl)thio)-9-(2-(neopentylamino)ethyl)-9H-purin-6-amine |
| 3B-31 | 1-(6-amino-8-((6-iodobenzofuran-5-yl)thio)-9H-purin-9-yl)-3-(tert-butylamino)propan-2-ol |
| 3B-32 | 8-((6-iodobenzofuran-5-yl)thio)-9-(3-(isopropylamino)propyl)-9H-purin-6-amine |
| 3B-33 | 9-(3-(tert-butylamino)propyl)-8-((6-(5-methylthiazol-2-yl)benzofuran-5-yl)thio)-9H-purin-6-amine |
| 3B-34 | 1-(3-(6-amino-8-(6-iodobenzofuran-5-ylthio)-9H-purin-9-yl)propyl)pyrrolidin-3-ol |
| 3B-35 | 1-(3-(6-amino-8-(6-iodobenzofuran-5-ylthio)-9H-purin-9-yl)propyl)pyrrolidin-3-one |

TABLE 3C

| No. | Name |
|---|---|
| 3C-1 | 6-((6-amino-9-(2-(isobutylamino)ethyl)-9H-purin-8-yl)thio)benzo[d]oxazole-5-carbonitrile |
| 3C-2 | 8-((5-(furan-2-yl)benzo[d]thiazol-6-yl)thio)-9-(2-(neopentylamino)ethyl)-9H-purin-6-amine |
| 3C-3 | 2-fluoro-8-((5-(furan-2-yl)benzo[d]oxazol-6-yl)methyl)-9-(2-(neopentylamino)ethyl)-9H-purin-6-amine |
| 3C-4 | 8-((5-(azetidin-1-yl)benzo[d]oxazol-6-yl)thio)-9-(2-(isobutylamino)ethyl)-9H-purin-6-amine |
| 3C-5 | 9-(2-(isobutylamino)ethyl)-8-((5-(pyrrolidin-1-yl)benzo[d]thiazol-6-yl)thio)-9H-purin-6-amine |
| 3C-6 | 8-((5-ethynylbenzo[d]thiazol-6-yl)methyl)-2-fluoro-9-(2-(isobutylamino)ethyl)-9H-purin-6-amine |
| 3C-7 | N-(2-((2-(6-amino-8-((5-iodobenzo[d]oxazol-6-yl)thio)-9H-purin-9-yl)ethyl)amino)ethyl) sulfamide |
| 3C-8 | 3-((2-(6-amino-8-((5-(furan-2-yl)benzo[d]oxazol-6-yl)thio)-9H-purin-9-yl)ethyl)amino)-N-hydroxypropanamide |

TABLE 3D

| No. | Name |
|---|---|
| 3D-1 | 5-((6-amino-9-(2-(isobutylamino)ethyl)-9H-purin-8-yl)thio)-1H-benzo[d]imidazole-6-carbonitrile |
| 3D-2 | 8-((6-(furan-2-yl)-1H-benzo[d]imidazol-5-yl)thio)-9-(2-(neopentylamino)ethyl)-9H-purin-6-amine |
| 3D-3 | 2-fluoro-8-((6-(furan-2-yl)-1H-benzo[d]imidazol-5-yl)methyl)-9-(2-(neopentylamino)ethyl)-9H-purin-6-amine |
| 3D-4 | 8-((6-(azetidin-1-yl)-1H-benzo[d]imidazol-5-yl)thio)-9-(2-(isobutylamino)ethyl)-9H-purin-6-amine |
| 3D-5 | 9-(2-(isobutylamino)ethyl)-8-((6-(pyrrolidin-1-yl)-1H-benzo[d]imidazol-5-yl)thio)-9H-purin-6-amine |
| 3D-6 | 8-((6-ethynyl-1-methyl-1H-benzo[d]imidazol-5-yl)methyl)-2-fluoro-9-(2-(isobutylamino)ethyl)-9H-purin-6-amine |
| 3D-7 | N-(2-((2-(8-((1-acetyl-6-iodo-1H-benzo[d]imidazol-5-yl)thio)-6-amino-9H-purin-9-yl)ethyl)amino)ethyl)methanesulfonamide |
| 3D-8 | 3-((2-(6-amino-8-((6-(furan-2-yl)-1H-benzo[d]imidazol-5-yl)thio)-9H-purin-9-yl)ethyl)amino)-N-hydroxypropanamide |
| 3D-9 | 5-(6-amino-9-(2-(isobutylamine)ethyl)-9H-purin-8-yl)thio)benzo[d]oxazole-6-carbonitrile |
| 3D-10 | 8-((6-iodobenzo[d]oxazol-5-yl)thio)-9-(2-(neopentylamino)ethyl)-9H-purin-6-amine |
| 3D-11 | 5-((6-amino-9-(2-(isobutylamino)ethyl)-9H-purin-8-yl)thio)benzo[d]thiazole-6-carbonitrile |
| 3D-12 | 8-((6-(furan-2-yl)benzo[d]thiazol-5-yl)thio)-9-(2-(neopentylamino)ethyl)-9H-purin-6-amine |
| 3D-13 | 2-fluoro-8-((6-(furan-2-yl)benzo[d]oxazol-5-yl)methyl)-9-(2-(neopentylamino)ethyl)-9H-purin-6-amine |
| 3D-14 | 8-((6-(azetidin-1-yl)benzo[d]oxazol-5-yl)thio)-9-(2-(isobutylamino)ethyl)-9H-purin-6-amine |
| 3D-15 | 9-(2-(isobutylamino)ethyl)-8-((6-(pyrrolidin-1-yl)benzo[d]thiazol-5-yl)thio)-9H-purin-6-amine |
| 3D-16 | 8-((6-ethynylbenzo[d]thiazol-5-yl)methyl)-2-fluoro-9-(2-(isobutylamino)ethyl)-9H-purin-6-amine |

TABLE 3E

| No. | Name |
|---|---|
| 3E-1 | 6-((6-amino-9-(2-(isobutylamino)ethyl)-9H-purin-8-yl)thio)benzo[d][1,2,3]oxadiazole-5-carbonitrile |
| 3E-2 | 8-((5-(furan-2-yl)benzo[d][1,2,3]thiadiazol-6-yl)thio)-9-(2-(neopentylamino)ethyl)-9H-purin-6-amine |
| 3E-3 | 2-fluoro-8-((5-(furan-2-yl)benzo[d][1,2,3]oxadiazol-6-yl)methyl)-9-(2-neopentylamino)ethyl)-9H-purin-6-amine |
| 3E-4 | 8-((5-(azetidin-1-yl)benzo[d][1,2,3]oxadiazol-6-yl)thio)-9-(2-(isobutylamino)ethyl)-9H-purin-6-amine |
| 3E-5 | 9-(2-(isobutylamino)ethyl)-8-((5-(pyrrolidin-1-yl)benzo[d][1,2,3]thiadiazol-6-yl)thio)-9H-purin-6-amine |
| 3E-6 | 8-((5-ethynylbenzo[d][1,2,3]thiadiazol-6-yl)methyl)-2-fluoro-9-(2-(isobutylamino)ethyl)-9H-purin-6-amine |
| 3E-7 | N-(2-((2-(6-amino-8-((5-iodobenzo[d][1,2,3]oxadiazol-6-yl)thio)-9H-purin-9-yl)ethyl)amino)ethyl)sulfamide |
| 3E-8 | 3-((2-(6-amino-8-((5-(furan-2-yl)benzo[d][1,2,3]oxadiazol-6-yl)thio)-9H-purin-9-yl)ethyl)amino)-N-hydroxypropanamide |
| 3E-9 | 5-((6-amino-9-(2-(isobutylamino)ethyl)-9H-purin-8-yl)thio)-3H-indazole-6-carbonitrile |
| 3E-10 | 8-((6-(furan-2-yl)-3H-indazol-5-yl)thio)-9-(2-(neopentylamino)ethyl)-9H-purin-6-amine |
| 3E-11 | 2-fluoro-8-((6-(furan-2-yl)-3H-indazol-5-yl)methyl)-9-(2-(neopentylamino)ethyl)-9H-purin-6-amine |
| 3E-12 | 8-(6-(azetidin-1-yl)-3H-indazol-5-ylthio)-9-(2-(isobutylamino)ethyl)-9H-purin-6-amine |

TABLE 3F

| No. | Name |
|---|---|
| 3F-1 | 5-((6-amino-9-(2-(isobutylamino)ethyl)-9H-purin-8-yl)thio)benzo[d][1,2,3]oxadiazole-6-carbonitrile |
| 3F-2 | 8-((6-(1H-pyrazol-3-yl)benzo[d][1,2,3]oxadiazol-5-yl)thio)-9-(2-(neopentylamino)ethyl)-9H-purin-6-amine |
| 3F-3 | 2-fluoro-8-((6-(furan-2-yl)-1H-benzo[d][1,2,3]triazol-5-yl)methyl)-9-(2-(neopentylamino)ethyl)-9H-purin-6-amine |
| 3F-4 | 8-((6-(azetidin-1-yl)benzo[d][1,2,3]thiadiazol-5-yl)thio)-9-(2-(isobutylamino)ethyl)-9H-purin-6-amine |
| 3F-5 | 9-(2-(isobutylamino)ethyl)-8-((5-(pyrrolidin-1-yl)-3H-indazol-6-yl)thio)-9H-purin-6-amine |
| 3F-6 | 8-((6-ethynyl-1-methyl-1H-benzo[d][1,2,3]triazol-5-yl)methyl)-2-fluoro-9-(2-(isobutylamino)ethyl)-9H-purin-6-amine |
| 3F-7 | N-(2-((2-(6-amino-8-((6-iodobenzo[d][1,2,3]oxadiazol-5-yl)thio)-9H-purin-9-yl)ethyl)amino)ethyl)sulfamide |
| 3F-8 | 3-((2-(6-amino-8-((5-(furan-2-yl)-3H-indazol-6-yl)thio)-9H-purin-9-yl)ethyl)amino)-N-hydroxypropanamide |
| 3F-9 | 6-((6-amino-9-(2-(isobutylamino)ethyl)-9H-purin-8-yl)thio)-3H-indazole-5-carbonitrile |
| 3F-10 | 8-((6-iodobenzo[d][1,2,3]oxadiazol-5-yl)thio)-9-(2-(neopentylamino)ethyl)-9H-purin-6-amine |
| 3F-11 | 5-((6-amino-9-(2-(isobutylamino)ethyl)-9H-purin-8-yl)thio)benzo[d][1,2,3]thiadiazole-6-carbonitrile |
| 3F-12 | 8-((6-(furan-2-yl)benzo[d][1,2,3]thiadiazol-5-yl)thio)-9-(2-(neopentylamino)ethyl)-9H-purin-6-amine |
| 3F-13 | 2-fluoro-8-((6-(furan-2-yl)benzo[d][1,2,3]oxadiazol-5-yl)methyl)-9-(2-(neopentylamino)ethyl)-9H-purin-6-amine |
| 3F-14 | 8-((6-(azetidin-1-yl)benzo[d][1,2,3]oxadiazol-5-yl)thio)-9-(2-isobutylamino)ethyl)-9H-purin-6-amine |
| 3F-15 | 9-(2-(isobutylamino)ethyl)-8-((6-(pyrrolidin-1-yl)benzo[d][1,2,3]thiadiazol-5-yl)thio)-9H-purin-6-amine |
| 3F-16 | 8-((5-ethynyl-3H-indazol-6-yl)methyl)-2-fluoro-9-(2-(isobutylamino)ethyl)-9H-purin-6-amine |

TABLE 4A

| No. | Name |
|---|---|
| 4A-1 | DZ2-388<br>9-(2-(isopropylamino)propyl)-8-(6-phenylbenzo[d][1,3]dioxol-5-ylthio)-9H-purin-6-amine |
| 4A-2 | DZ2-390<br>8-(6-(4-tert-butylphenyl)benzo[d][1,3]dioxol-5-ylthio)-9-(3-(isopropylamino)propyl)-9H-purin-6-amine |
| 4A-3 | DZ2-391<br>8-(6-(3,5-bis(trifluoromethyl)phenyl)benzo[d][1,3]dioxol-5-ylthio)-9-(3-(isopropylamino)propyl)-9H-purin-6-amine |
| 4A-4 | TT-V-47B<br>N1-(3-(6-amino-8-(6-(3,5-bis(trifluoromethyl)phenyl)benzo[d]-[1,3]dioxol-5-ylthio)-9H-purin-9-yl)propyl)hexane-1,6-diamine |
| 4A-5 | DZ2-392<br>8-(6-(4-(dimethylamino)phenyl)benzo[d][1,3]dioxol-5-ylthio)-9-(3-(isopropylamino)propyl)-9H-purin-6-amine |
| 4A-6 | DZ3-3<br>9-(3-(isopropylamino)propyl)-8-(6-(4-methoxyphenyl)benzo[d]-[1,3]dioxol-5-ylthio)-9H-purin-6-amine |
| 4A-7 | DZ3-6<br>8-(6-(4-bromophenyl)benzo[d][1,3]dioxol-5-ylthio)-9-(3-(isopropylamino)propyl)-9H-purin-6-amine |
| 4A-8 | DZ3-50<br>4-(6-(6-amino-9-(3-(isopropylamino)propyl)-9H-purin-8-ylthio)benze[d][1,3]dioxol-5-yl)benzaldehyde |
| 4A-9 | 4-(2-(6-amino-8-(6-phenylbenzo[d][1,3]dioxol-5-ylthio)-9H-purin-9-yl)ethyl)piperidine-1-carbaldehyde |
| 4A-10 | 1-(4-(2-(6-amino-2-fluoro-8-((6-phenylbenzo[d]-[1,3]dioxol-5-yl)methyl)-9H-purin-9-yl)ethyl)piperidin-1-yl)ethanone |
| 4A-11 | N-(2-((2-(6-amino-8-((6-phenylbenzo[d][1,3]dioxol-5-yl)thio)-9H-purin-9-yl)ethyl)amino)ethyl)sulfamide |
| 4A-12 | 3-(2-(6-amino-8-(6-phenylbenzo[d][1,3]dioxol-5-ylthio)-9H-purin-9-yl)ethylamino)-N-hydroxypropanamide |
| 4A-13 | 9-(3-aminopropyl)-8-(6-phenylbenzo[d][1,3]dioxol-5-ylthio)-9H-purin-6-amine |

TABLE 4B

| No. | Name |
|---|---|
| 4B-1 | PU-WS8<br>8-(6-ethynylbenzo[d][1,3]dioxol-5-ylthio)-9-(3-(isopropylamino)propyl)-9H-purin-6-amine |
| 4B-2 | PU-WS6<br>8-(6-(3,3-dimethylbut-1-ynyl)benzo[d][1,3]dioxol-5-ylthio)-9-(3-(isopropylamino)propyl)-9H-purin-6-amine |
| 4B-3 | PU-WS7<br>9-(3-(isopropylamino)propyl)-8-(6-(phenylethynyl)benzo[d][1,3]dioxol-5-ylthio)-9H-purin-6-amine |
| 4B-4 | PU-WS16<br>8-(6-ethynylbenzo[d][1,3]dioxol-5-ylthio)-9-(2-(isobutylamino)ethyl)-9H-purin-6-amine |
| 4B-5 | 1-(3-(2-(6-amino-8-(6-ethynylbenzo[d][1,3]dioxol-5-ylthio)-9H-purin-9-yl)ethyl)piperidin-1-yl)ethanone |
| 4B-6 | 8-(6-ethynylbenzo[d][1,3]dioxol-5-ylthio)-9-(2-(1-(methylsulfonyl)piperidin-3-yl)ethyl)-9H-purin-6-amine |
| 6B-7 | 1-(3-(4-(6-amino-8-((6-ethynylbenzo[d][1,3]dioxol-5-yl)methyl)-2-fluoro-9H-purin-9-yl)butyl)pyrrolidin-1-yl)ethanone |
| 4B-8 | 5-(6-amino-8-((6-ethynylbenzo[d][1,3]dioxol-5-yl)methyl)-2-fluoro-9H-purin-9-yl)pentane-1-sulfonamide |
| 4B-9 | 3-(2-(6-amino-2-chloro-8-((6-ethynylbenzo[d][1,3]dioxol-5-yl)methyl)-9H-purin-9-yl)ethyl)piperidine-1-carbaldehyde |
| 4B-10 | 3-(2-(6-amino-8-((6-ethynylbenzo[d][1,3]dioxol-5-yl)methyl)-2-fluoro-9H-purin-9-yl)ethyl)piperidine-1-sulfonamide |
| 4B-11 | N-(2-((2-(6-amino-8-((6-ethynylbenzo[d][1,3]dioxol-5-yl)thio)-9H-purin-9-yl)-ethyl)amino)ethyl)sulfamide |
| 4B-12 | 3-(2-(6-amino-8-(6-ethynylbenzo[d][1,3]dioxol-5-ylthio)-9H-purin-9-yl)ethylamino)-N-hydroxypropanamide |
| 4B-13 | PU-WS19<br>8-(6-ethynylbenzo[d][1,3]dioxol-5-ylthio)-9-(2-(neopentylamino)ethyl)-9H-purin-6-amine |
| 4B-14 | PU-WS20<br>8-((6-ethynylbenzo[d][1,3]dioxol-5-yl)methyl)-2-fluoro-9-(2-(isobutylamino)ethyl)-9H-purin-6-amine |
| 4B-15 | 9-(3-aminopropyl)-8-(6-ethynylbenzo[d][1,3]dioxol-5-ylthio)-9H-purin-6-amine |
| 4B-16 | 9-(2-aminoethyl)-8-(6-ethynylbenzo[d][1,3]dioxol-5-ylthio)-9H-purin-6-amine |
| 4B-17 | 9-(3-(tert-butylamino)propyl)-8-(6-ethynylbenzo[d][1,3]dioxol-5-ylthio)-9H-purin-6-amine |
| 4B-18 | 1-(3-(6-amtno-8-(6-ethynylbenzo[d][1,3]dioxol-5-ylthio)-9H-purin-9-yl)propyl)pyrrolidin-3-one |
| 4B-19 | 3-(2-(6-amino-8-((6-ethynylbenzo[d][1,3]dioxol-5-yl)thio)-9H-purin-9-yl)ethyl)piperidine-1-sulfonamide |
| 4B-20 | 6-(6-amino-8-(6-ethynylbenzo[d][1,3]dioxol-5-ylthio)-9H-purin-9-yl)hexanamide |
| 4B-21 | 1-(6-amino-8-(6-ethynylbenzo[d][1,3]dioxol-5-ylthio)-9H-purin-9-yl)-3-(tert-butylamino)propan-2-ol |
| 4B-22 | 6-(6-amino-8-((6-ethynylbenzo[d][1,3]dioxol-5-yl)methyl)-2-fluoro-9H-purin-9-yl)hexanamide |
| 4B-23 | 1-(2-((2-(6-amino-8-(6-ethynylbenzo[d][1,3]dioxol-5-ylthio)-9H-purin-9-yl)ethylamino)methyl)pyrrolidin-1-yl)ethanone |
| 4B-24 | 5-(6-amino-8-(6-ethynylbenzo[d][1,3]dioxol-5-ylthio)-9H-purin-9-yl)pentane-1-sulfonamide |
| 4B-25 | 1-(3-(2-(6-amino-8-((6-ethynylbenzo[d][1,3]dioxol-5-yl)methyl)-2-fluoro-9H-purin-9-yl)ethyl)piperidin-1-yl)ethanone |
| 4B-26 | 8-((6-ethynylbenzo[d][1,3]dioxol-5-yl)methyl)-2-fluoro-9-(2-(neopentylamino)ethyl)-9H-purin-6-amine |
| 4B-27 | 8-((6-ethynylbenzo[d][1,3]dioxol-5-yl)methyl)-2-fluoro-9-(3-(isopropylamino)propyl)-9H-purin-6-amine |
| 4B-28 | 9-(3-(tert-butylamino)propyl)-8-((6-ethynylbenzo[d][1,3]dioxol-5-yl)methyl)-2-fluoro-9H-purin-6-amine |
| 4B-29 | 8-((6-ethynylbenzo[d][1,3]dioxol-5-yl)methyl)-2-fluoro-9-(2-(1-(methylsulfonyl)piperidin-3-yl)ethyl)-9H-purin-6-amine |
| 4B-30 | 1-(3-(6-amino-8-((6-ethynylbenzo[d][1,3]dioxol-5-yl)methyl)-2-fluoro-9H-purin-9-yl)propyl)pyrrolidin-3-one |
| 4B-31 | 8-((6-ethynylbenzo[d][1,3]dioxol-5-yl)methyl)-2-fluoro-9-(2-(1-methylpiperidin-3-yl)ethyl)-9H-purin-6-amine |
| 4B-32 | 8-(6-ethynylbenzo[d][1,3]dioxol-5-ylthio)-9-(2-(1-methylpiperidin-2-yl)ethyl)-9H-purin-6-amine |
| 4B-33 | 1-(2-((2-(6-amino-8-((6-ethynylbenzo[d][1,3]dioxol-5-yl)methyl)-2-fluoro-9H-purin-9-yl)ethylamino)methyl)pyrrolidin-1-yl)ethanone |
| 4B-34 | 8-(6-ethynylbenzo[d][1,3]dioxol-5-ylthio)-9-(2-(1-methylpiperidin-3-yl)ethyl)-9H-purin-6-amine |
| 4B-35 | 8-((6-ethynylbenzo[d][1,3]dioxol-5-yl)methyl)-2-fluoro-9-(2-(1-methylpiperidin-2-yl)ethyl)-9H-purin-6-amine |

TABLE 4C

| No. | Name |
|---|---|
| 4C-1 | DZ3-4<br>8-((6-(furan-2-yl)benzo[d][1,3]dioxol-5-yl)thio)-9-(3-(isopropylamino)propyl)-9H-purin-6-amine |
| 4C-2 | DZ3-27<br>8-((6-(furan-3-yl)benzo[d][1,3]dioxol-5-yl)thio)-9-(3-(isopropylamino)propyl)-9H-purin-6-amine |
| 4C-3 | DZ3-25<br>2-fluoro-8-((6-(furan-2-yl)benzo[d][1,3]dioxol-5-yl)methyl)-9-(2-(isobutylamino)ethyl)-9H-purin-6-amine |
| 4C-4 | DZ3-26<br>2-fluoro-8-((6-(furan-3-yl)benzo[d][1,3]dioxol-5-yl)methyl)-9-(2-(isobutylamino)ethyl)-9H-purin-6-amine |
| 4C-5 | TT5-53A<br>8-((6-(furan-2-yl)benzo[d][1,3]dioxol-5-yl)thio)-9-(2-(neopentylamino)ethyl)-9H-purin-6-amine |
| 4C-6 | DZ3-33<br>5-(6-(((6-amino-9-(3-(isopropylamino)propyl)-9H-purin-8-yl)thio)benzo[d][1,3]dioxol-5-yl)furan-2-carbaldehyde |
| 4C-7 | DZ3-34<br>5-(6-(((6-amino-2-fluoro-9-(2-(isobutylamino)ethyl)-9H-purin-8-yl)methyl)benzo[d][1,3]dioxol-5-yl)furan-2-carbaldehyde |
| 4C-8 | DZ3-35<br>9-(3-(isopropylamino)propyl)8-((6-(5-methylfuran-2-yl)benzo[d][1,3]dioxol-5-yl)thio)-9H-purin-6-amine |
| 4C-9 | DZ3-36<br>2-fluoro-9-(2-(isobutylamino)ethyl)-8-((6-(5-methylfuran-2-yl)benzo[d][1,3]dioxol-5-yl)methyl)-9H-purin-6-amine |
| 4C-10 | DZ3-49<br>9-(3-(isopropylamino)propyl)-8-((6-(isoxazol-4-yl)benzo[d][1,3]dioxol-5-yl)thio)-9H-purin-6-amine |
| 4C-11 | DZ3-51<br>2-fluoro-9-(2-(isobutylamino)ethyl)-8-((6-(isoxazol-4-yl)benzo[d][1,3]dioxol-5-yl)methyl)-9H-purin-6-amine |
| 4C-12 | 8-((6-(5-(aminomethyl)furan-2-yl)benzo[d][1,3]dioxol-5-yl)thio)-9-(3-(isopropylamino)propyl)-9H-purin-6-amine |
| 4C-13 | 8-((6-(5-(aminomethyl)furan-2-yl)benzo[d][1,3]dioxol-5-yl)methyl)-2-fluoro-9-(2-(isobutylamino)ethyl)-9H-purin-6-amine |
| 4C-14 | DZ3-60<br>8-((6-(furan-3-yl)benzo[d][1,3]dioxol-5-yl)thio)-9-(2-(neopentylamino)ethyl)-9H-purin-6-amine |
| 4C-15 | 8-(6-(5-methyloxazol-2-yl)benzo[d][1,3]dioxol-5-ylthio)-9-(2-(neopentylamino)ethyl)-9H-purin-6-amine |
| 4C-16 | DZ3-56<br>8-((6-(5-methylfuran-2-yl)benzo[d][1,3]dioxol-5-yl)thio)-9-(2-(neopentylamino)ethyl)-9H-purin-6-amine |
| 4C-17 | 1-(3-(6-amino-2-fluoro-8-((6-(5-methyloxazol-2-yl)benzo[d][1,3]dioxol-5-yl)methyl)-9H-purin-9-yl)propyl)pyrrolidin-3-one |
| 4C-18 | 8-((6-(5-(aminomethyl)furan-2-yl)benzo[d][1,3]dioxol-5-yl)thio)-9-(2-(neopentylamino)ethyl)-9H-purin-6-amine |
| 4C-19 | 1-(3-(2-(6-amino-8-(6-(5-methylfuran-2-yl)benzo[d][1,3]dioxol-5-ylthio)-9H-purin-9-yl)ethyl)piperidin-1-yl)ethanone |
| 4C-20 | 8-(6-(5-methylfuran-2-yl)benzo[d][1,3]dioxol-5-ylthio)-9-(2-(1-(methylsulfonyl)piperidin-3-yl)ethyl)-9H-purin-6-amine |
| 4C-21 | 1-(3-(2-(6-amino-2-fluoro-8-((6-(5-methylfuran-2-yl)benzo[d][1,3]dioxol-5-yl)methyl)-9H-purin-9-yl)ethyl)piperidin-1-yl)ethanone |
| 4C-22 | 4-(2-(6-amino-2-fluoro-8-((6-(furan-2-yl)benzo[d][1,3]dioxol-5-yl)methyl)-9H-purin-9-yl)ethyl)piperidine-1-carbaldehyde |
| 4C-23 | 1-(3-(6-amino-8-(6-(oxazol-2-yl)benzo[d][1,3]dioxol-5-ylthio)-9H-purin-9-yl)propyl)pyrrolidin-3-one |
| 4C-24 | 6-(6-amino-8-(6-(5-methyloxazol-2-yl)benzo[d][1,3]dioxol-5-ylthio)-9H-purin-9-yl)hexanamide |
| 4C-25 | 6-(6-amino-2-fluoro-8-((6-(5-methyloxazol-2-yl)benzo[d][1,3]dioxol-5-yl)methyl)-9H-purin-9-yl)hexanamide |
| 4C-26 | 1-(4-(2-(6-amino-2-fluoro-8-((6-(5-methylfuran-2-yl)benzo[d][1,3]dioxol-5-yl)methyl)-9H-purin-9-yl)ethyl)piperidin-1-yl)ethanone |
| 4C-27 | 1-(4-(2-(6-amino-2-chloro-8-((6-(5-methylfuran-2-yl)benzo[d][1,3]dioxol-5-yl)methyl)-9H-purin-9-yl)ethyl)piperidin-1-yl)ethanone |
| 4C-28 | 1-(3-(2-(6-amino-8-(6-(5-methyloxazol-2-yl)benzo[d][1,3]dioxol-5-ylthio)-9H-purin-9-yl)ethyl)piperidin-1-yl)ethanone |
| 4C-29 | 1-(3-(2-(6-amino-2-fluoro-8-((6-(5-methyloxazol-2-yl)benzo[d][1,3]dioxol-5-yl)methyl)-9H-purin-9-yl)ethyl)piperidin-1-yl)ethanone |
| 4C-30 | 3-(2-(6-amino-2-chloro-8-((6-(5-methyloxazol-2-yl)benzo[d][1,3]dioxol-5-yl)methyl)-9H-purin-9-yl)ethyl)piperidine-1-sulfonamide |
| 4C-31 | 1-(4-(2-(6-amino-8-((6-(5-(aminomethyl)furan-2-yl)benzo[d][1,3]dioxol-5-yl)thio)-9H-purin-9-yl)ethyl)piperidin-1-yl)ethanone |
| 4C-32 | 1-(3-(2-(6-amino-8-((6-(5-(aminomethyl)oxazol-2-yl)benzo[d][1,3]dioxol-5-yl)methyl)-2-fluoro-9H-purin-9-yl)ethyl)piperidin-1-yl)ethanone |

TABLE 4C-continued

| No. | Name |
|---|---|
| 4C-33 | 5-(6-amino-2-fluoro-8-((6-(5-methyloxazol-2-yl)benzo[d][1,3]dioxol-5-yl)methyl)-9H-purin-9-yl)pentane-1-sulfonamide |
| | 2-fluoro-9-(3-(isopropylamino)propyl)-8-((6-(5-methyloxazol-2-yl)benzo[d][1,3]dioxol-5-yl)methyl)-9H-purin-6-amine |
| | 9-(3-(tert-butylamino)propyl)-2-fluoro-8-((6-(5-methyloxazol-2-yl)benzo[d][1,3]dioxol-5-yl)methyl)-9H-purin-6-amine |
| | N-(2-((2-(6-amino-8-((6-(5-methylfuran-2-yl)benzo[d][1,3]dioxol-5-yl)thio)-9H-purin-9-yl)ethyl)amino)ethyl) sulfamide |
| | 3-(2-(6-amino-8-(6-(5-methylfuran-2-yl)benzo[d][1,3]dioxol-5-ylthio)-9H-purin-9-yl)ethylamino)-N-hydroxypropanamide |
| | DZ4-20 |
| | 9-(3-(isopropylamino)propyl)-8-((6-(oxazol-2-yl)benzo[d][1,3]dioxol-5-yl)thio)-9H-purin-6-amine |
| | DZ4-23 |
| | 2-fluoro-9-(2-(isobutylamino)ethyl)-8-((6-(oxazol-2-yl)benzo[d][1,3]dioxol-5-yl)methyl)-9H-purin-6-amine |
| | DZ3-142 |
| | 8-((6-(2,3-dihydrofuran-2-yl)benzo[d][1,3]dioxol-5-yl)thio)-9-(3-(isopropylamino)propyl)-9H-purin-6-amine |
| | DZ3-143 |
| | 8-((6-(2,3-dihydrofuran-3-yl)benzo[d][1,3]dioxol-5-yl)thio)-9-(3-(isopropylamino)propyl)-9H-purin-6-amine |
| | 9-(3-aminopropyl)-8-(6-(5-methyloxazol-2-yl)benzo[d][1,3]dioxol-5-ylthio)-9H-purin-6-amine |
| | 9-(2-aminoethyl)-2-fluoro-8-((6-(5-methylfuran-2-yl)benzo[d][1,3]dioxol-5-yl)methyl)-9H-purin-6-amine |
| | 9-(3-(tert-butylamino)propyl)-8-(6-(5-methylfuran-2-yl)benzo[d][1,3]dioxol-5-ylthio)-9H-purin-6-amine |
| | 9-(3-(tert-butylamino)propyl)-8-((6-(oxazol-2-yl)benzo[d][1,3]dioxol-5-yl)thio)-9H-purin-6-amine |
| | 1-(4-(2-(6-amino-8-((6-(oxazol-2-yl)benzo[d][1,3]dioxol-5-yl)thio)-9H-purin-9-yl)ethyl)piperidin-1-yl)ethanone |
| | 8-((6-(5-methyloxazol-2-yl)benzo[d][1,3]dioxol-5-yl)thio)-9-(2-(1-(methylsulfonyl)piperidin-3-yl)ethyl)-9H-purin-6-amine |
| | 9-(3-(tert-butylamino)propyl)-8-((6-(5-methyloxazol-2-yl)benzo[d][1,3]dioxol-5-yl)thio)-9H-purin-6-amine |
| | 1-(6-amino-8-(6-(5-methylfuran-2-yl)benzo[d][1,3]dioxol-5-ylthio)-9H-purin-9-yl)-3-(tert-butylamino)propan-2-ol |
| | 1-(6-amino-8-((6-(5-methyloxazol-2-yl)benzo[d][1,3]dioxol-5-yl)thio)-9H-purin-9-yl)-3-(isopropylamino)propan-2-ol |
| | 2-(3-(6-amino-8-(6-(5-methylfuran-2-yl)benzo[d][1,3]dioxol-5-ylthio)-9H-purin-9-yl)propyl)aziridine-1-carbaldehyde |
| | 5-(6-amino-8-(6-(5-methylfuran-2-yl)benzo[d][1,3]dioxol-5-ylthio)-9H-purin-9-yl)pentane-1-sulfonamide |
| | 5-(6-amino-8-(6-(5-methyloxazol-2-yl)benzo[d][1,3]dioxol-5-ylthio)-9H-purin-9-yl)pentane-1-sulfonamide |
| | 8-(6-(5-methyloxazol-2-yl)benzo[d][1,3]dioxol-5-ylthio)-9-(3-(1-(methylsulfonyl)pyrrolidin-3-yl)propyl)-9H-purin-6-amine |
| | 1-(3-(6-amino-8-(6-(5-methyloxazol-2-yl)benzo[d][1,3]dioxol-5-ylthio)-9H-purin-9-yl)propyl)pyrrolidin-3-one |
| | 9-(3-(tert-butylamino)propyl)-2-fluoro-8-((6-(oxazol-2-yl)benzo[d][1,3]dioxol-5-yl)methyl)-9H-purin-6-amine |
| | 5-(6-amino-2-fluoro-8-((6-(5-methylfuran-2-yl)benzo[d][1,3]dioxol-5-yl)methyl)-9H-purin-9-yl)pentane-1-sulfonamide |
| | 6-(6-amino-2-fluoro-8-((6-(5-methylfuran-2-yl)benzo[d][1,3]dioxol-5-yl)methyl)-9H-purin-9-yl)hexanamide |
| | 2-fluoro-9-(3-(isopropylamino)propyl)-8-((6-(5-methylfuran-2-yl)benzo[d][1,3]dioxol-5-yl)methyl)-9H-purin-6-amine |
| | 9-(3-(tert-butylamino)propyl)-2-fluoro-8-((6-(5-methylfuran-2-yl)benzo[d][1,3]dioxol-5-yl)methyl)-9H-purin-6-amine |
| | 9-(3-aminopropyl)-2-fluoro-8-((6-(5-methylfuran-2-yl)benzo[d][1,3]dioxol-5-yl)methyl)-9H-purin-6-amine |
| | 9-(3-aminopropyl)-2-fluoro-8-((6-(5-methyloxazol-2-yl)benzo[d][1,3]dioxol-5-yl)methyl)-9H-purin-6-amine |

TABLE 4D

| No. | Name |
| --- | --- |
| 4D-1 | DZ2-395<br>9-(3-(isopropylamino)propyl)-8-((6-(thiophen-2-yl)benzo[d][1,3]dioxol-5-yl)thio)-9H-purin-6-amine |
| 4D-2 | DZ3-48<br>2-fluoro-9-(2-(isobutylamino)ethyl)-8-((6-(thiophen-2-yl)benzo[d][1,3]dioxol-5-yl)methyl)-9H-purin-6-amine |
| 4D-3 | DZ3-58<br>9-(2-(neopentylamino)ethyl)-8-((6-(thiophen-2-yl)benzo[d][1,3]dioxol-5-yl)thio)-9H-purin-6-amine |
| 4D-4 | 9-(3-(isopropylamino)propyl)-8-((6-(thiophen-3-yl)benzo[d][1,3]dioxol-5-yl)thio)-9H-purin-6-amine |
| 4D-5 | 2-fluoro-9-(2-(isobutylamino)ethyl)-8-((6-(thiophen-3-yl)benzo[d][1,3]dioxol-5-yl)methyl)-9H-purin-6-amine |
| 4D-6 | 9-(2-(neopentylamino)ethyl)-8-((6-(thiophen-3-yl)benzo[d][1,3]dioxol-5-yl)thio)-9H-purin-6-amine |
| 4D-7 | 1-(4-(2-(6-amino-8-((6-(thiophen-2-yl)benzo[d][1,3]dioxol-5-yl)thio)-9H-purin-9-yl)ethyl)piperidin-1-yl)ethanone |
| 4D-8 | 4-(2-(6-amino-8-((6-(thiophen-2-yl)benzo[d][1,3]dioxol-5-yl)thio)-9H-purin-9-yl)ethyl)piperidine-1-carbaldehyde |
| 4D-9 | 1-(4-(2-(6-amino-2-fluoro-8-((6-(thiophen-2-yl)benzo[d][1,3]dioxol-5-yl)methyl)-9H-purin-9-yl)ethyl)piperidin-1-yl)ethanone |
| 4D-10 | 4-(2-(6-amino-2-fluoro-8-((6-(thiophen-2-yl)benzo[d][1,3]dioxol-5-yl)methyl)-9H-purin-9-yl)ethyl)piperidine-1-carbaldehyde |
| 4D-11 | 4-(2-(6-amino-8-((6-(thiophen-3-yl)benzo[d][1,3]dioxol-5-yl)thio)-9H-purin-9-yl)ethyl)piperidine-1-carbaldehyde |
| 4D-12 | 4-(2-(6-amino-2-fluoro-8-((6-(thiophen-3-yl)benzo[d][1,3]dioxol-5-yl)methyl)-9H-purin-9-yl)ethyl)piperidine-1-carbaldehyde |
| 6D-13 | 4-(2-(6-amino-2-chloro-8-((6-(thiophen-3-yl)benzo[d][1,3]dioxol-5-yl)methyl)-9H-purin-9-yl)ethyl)piperidine-1-carbaldehyde |
| 4D-14 | N-(2-((2-(6-amino-8-((6-(thiophen-2-yl)benzo[d][1,3]dioxol-5-yl)thio)-9H-purin-9-yl)ethyl)amino)ethyl) sulfamide |
| 4D-15 | 3-((2-(6-amino-8-((6-(thiophen-2-yl)benzo[d][1,3]dioxol-5-yl)thio)-9H-purin-9-yl)ethyl)amino)-N-hydroxypropanamide |
| 4D-16 | DZ4-21<br>9-(3-(isopropylamino)propyl)-8-((6-(thiazol-2-yl)benzo[d][1,3]dioxol-5-yl)thio)-9H-purin-6-amine |
| 4D-17 | DZ4-24<br>2-fluoro-9-(2-(isobutylamino)ethyl)-8-((6-(thiazol-2-yl)benzo[d][1,3]dioxol-5-yl)methyl)-9H-purin-6-amine |
| 4D-18 | 9-(3-aminopropyl)-8-((6-(thiophen-2-yl)benzo[d][1,3]dioxol-5-yl)thio)-9H-purin-6-amine |
| 4D-19 | 9-(3-(tert-butylamino)propyl)-8-((6-(thiophen-2-yl)benzo[d][1,3]dioxol-5-yl)thio)-9H-purin-6-amine |
| 4D-20 | 9-(3-(tert-butylamino)propyl)-8-((6-(thiazol-2-yl)benzo[d][1,3]dioxol-5-yl)thio)-9H-purin-6-amine |
| 4D-21 | 9-(3-(tert-butylamino)propyl)-8-((6-(5-methylthiophen-2-yl)benzo[d][1,3]dioxol-5-yl)thio)-9H-purin-6-amine |
| 4D-22 | 9-(3-(tert-butylamino)propyl)-8-((6-(5-methylthiazol-2-yl)benzo[d][1,3]dioxol-5-yl)thio)-9H-purin-6-amine |
| 4D-23 | 1-(3-(2-(6-amino-8-(6-(5-methylthiazol-2-yl)benzo[d][1,3]dioxol-5-ylthio)-9H-purin-9-yl)ethyl)piperidin-1-yl)ethanone |
| 4D-24 | 1-(6-amino-8-((6-(5-methylthiophen-2-yl)benzo[d][1,3]dioxol-5-yl)thio)-9H-purin-9-yl)-3-(isopropylamino)propan-2-ol |
| 4D-25 | 1-(6-amino-8-((6-(5-methylthiazol-2-yl)benzo[d][1,3]dioxol-5-yl)thio)-9H-purin-9-yl)-3-(isopropylamino)propan-2-ol |
| 4D-26 | 6-(6-amino-8-(6-(5-methylthiophen-2-yl)benzo[d][1,3]dioxol-5-ylthio)-9H-purin-9-yl)hexanamide |
| 4D-27 | 5-(6-amino-8-(6-(5-methylthiazol-2-yl)benzo[d][1,3]dioxol-5-ylthio)-9H-purin-9-yl)pentane-1-sulfonamide |
| 4D-28 | 9-(3-(1-(methylsulfonyl)pyrrolidin-3-yl)propyl)-8-(6-(5-methylthiophen-2-yl)benzo[d][1,3]dioxol-5-ylthio)-9H-purin-6-amine |
| 4D-29 | 2-(2-(6-amino-8-(6-(5-methylthiazol-2-yl)benzo[d][1,3]dioxol-5-ylthio)-9H-purin-9-yl)ethyl)pyrrolidine-1-carbaldehyde |
| 4D-30 | 2-fluoro-9-(2-(isobutylamino)ethyl)-8-((6-(5-methylthiophen-2-yl)benzo[d][1,3]dioxol-5-yl)methyl)-9H-purin-6-amine |
| 4D-31 | 8-((6-(5-methylthiophen-2-yl)benzo[d][1,3]dioxol-5-yl)thio)-9-(2-(neopentylamino)ethyl)-9H-purin-6-amine |
| 4D-32 | 2-fluoro-9-(2-(isobutylamino)ethyl)-8-((6-(5-methylthiazol-2-yl)benzo[d][1,3]dioxol-5-yl)methyl)-9H-purin-6-amine |
| 4D-33 | 8-((6-(5-methylthiazol-2-yl)benzo[d][1,3]dioxol-5-yl)thio)-9-(2-(neopentylamino)ethyl)-9H-purin-6-amine |

TABLE 4E

| No. | Name |
|---|---|
| 4E-1 | PU-WS3<br>6-((6-amino-2-fluoro-9-(3-(isopropylamino)propyl)-9H-purin-8-yl)methyl)benzo[d][1,3]dioxole-5-carbonitrile |
| 4E-2 | PU-WS5<br>6-((6-amino-9-(3-(isopropylamino)propyl)-9H-purin-8-yl)thio)benzo[d][1,3]dioxole-5-carbonitrile |
| 4E-3 | DZ3-39<br>2-(6-(((6-amino-9-(3-(isopropylamino)propyl)-9H-purin-8-yl)thio)benzo[d][1,3]dioxol-5-yl)acetonitrile |
| 4E-4 | DZ3-40<br>2-(6-(((6-amino-2-fluoro-9-(2-(isobutylamino)ethyl)-9H-purin-8-yl)methyl)benzo[d][1,3]dioxol-5-yl)acetonitrile |
| 6E-5 | N-(2-((2-(6-amino-8-((6-(cyanomethyl)benzo[d][1,3]-dioxol-5-yl)thio)-9H-purin-9-yl)ethyl)amino)ethyl)sulfamide |
| 4E-6 | 3-((2-(6-amino-8-((6-cyanobenzo[d][1,3]dioxol-5-yl)thio)-9H-purin-9-yl)ethyl)amino)-N-hydroxypropanamide |
| 4E-7 | 6-((6-amino-2-chloro-9-(3-(isopropylamino)propyl)-9H-purin-8-yl)methyl)benzo[d][1,3]dioxole-5-carbonitrile |

TABLE 4F

| No. | Name |
|---|---|
| 4F-1 | DZ3-5<br>9-(3-(isopropylamino)propyl)-8-(6-(pyridin-4-yl)benzo[d]-[1,3]dioxol-5-ylthio)-9H-purin-6-amine |

TABLE 5A

| No. | Name |
|---|---|
| 5A-1 | PU-RK11<br>8-((7-iodo-2,3-dihydrobenzo[b][1,4]dioxin-6-yl)thio)-9-(3-(isopropylamino)propyl)-9H-purin-6-amine |
| 5A-2 | PU-HT165<br>8-((7-iodo-2,3-dihydrobenzo[b][1,4]dioxin-6-yl)thio)-9-(2-(isobutylamino)ethyl)-9H-purin-6-amine |
| | PU-HT175<br>8-((7-iodo-2,3-dihydrobenzo[b][1,4]dioxin-6-yl)thio)-9-(2-(neopentylamino)ethyl)-9H-purin-6-amine |
| | PU-RK12<br>9-(3-(1H-imidazol-1-yl)propyl)-8-((7-iodo-2,3-dihydrobenzo[b][1,4]dioxin-6-yl)thio)-9H-purin-6-amine |
| | PU-DZ3-73<br>2-fluoro-8-((7-iodo-2,3-dihydrobenzo[b][1,4]dioxin-6-yl)methyl)-9-(2-(isobutylamino)ethyl)-9H-purin-6-amine |
| | PU-DZ4-84<br>9-(2-(tert-butylamino)ethyl)-2-fluoro-8-((7-iodo-2,3-dihydrobenzo[b][1,4]dioxin-6-yl)methyl)-9H-purin-6-amine |
| | 9-(3-aminopropyl)-8-((7-iodo-2,3-dihydrobenzo[b][1,4]dioxin-6-yl)thio)-9H-purin-6-amine |
| | 9-(2-aminoethyl)-8-((7-iodo-2,3-dihydrobenzo[b][1,4]dioxin-6-yl)thio)-9H-purin-6-amine |
| | 9-(3-(tert-butylamino)propyl)-8-((7-iodo-2,3-dihydrobenzo[b][1,4]dioxin-6-yl)thio)-9H-purin-6-amine |
| | 1-(6-amino-8-((7-iodo-2,3-dihydrobenzo[b][1,4]dioxin-6-yl)thio)-9H-purin-9-yl)-3-(isopropylamino)propan-2-ol |
| | 5-(6-amino-8-(7-iodo-2,3-dihydrobenzo[b][1,4]dioxin-6-ylthio)-9H-purin-9-yl)pentane-1-sulfonamide |
| | 1-(3-(6-amino-8-(7-iodo-2,3-dihydrobenzo[b][1,4]dioxin-6-ylthio)-9H-purin-9-yl)propyl)pyrrolidin-3-one |
| | 6-(6-amino-8-(7-iodo-2,3-dihydrobenzo[b][1,4]dioxin-6-ylthio)-9H-purin-9-yl)hexanamide |
| | 9-(3-(tert-butylamino)propyl)-2-fluoro-8-((7-iodo-2,3-dihydrobenzo[b][1,4]dioxin-6-yl)methyl)-9H-purin-6-amine |
| | 1-(3-(4-(6-amino-8-(7-iodo-2,3-dihydrobenzo[b][1,4]dioxin-6-ylthio)-9H-purin-9-yl)butyl)pyrrolidin-1-yl)ethanone |
| | 2-fluoro-8-((7-iodo-2,3-dihydrobenzo[b][1,4]dioxin-6-yl)methyl)-9-(3-(isopropylamino)propyl)-9H-purin-6-amine |
| | 1-(3-(6-amino-2-fluoro-8-((7-iodo-2,3-dihydrobenzo[b][1,4]dioxin-6-yl)methyl)-9H-purin-9-yl)propyl)pyrrolidin-3-one |
| | 6-(6-amino-2-fluoro-8-((7-iodo-2,3-dihydrobenzo[b][1,4]dioxin-6-yl)methyl)-9H-purin-9-yl)hexanamide |
| | 5-(6-amino-2-fluoro-8-((7-iodo-2,3-dihydrobenzo[b][1,4]dioxin-6-yl)methyl)-9H-purin-9-yl)pentane-1-sulfonamide |

TABLE 5B

| No. | Name |
|---|---|
| 5B-1 | HJP18<br>8-((7-(furan-2-yl)-2,3-dihydrobenzo[b][1,4]dioxin-6-yl)thio)-9-(3-(isopropylamino)propyl)-9H-purin-6-amine |
| 5B-2 | 1-(3-(6-amino-8-(7-(oxazol-2-yl)-2,3-dihydrobenzo[b][1,4]dioxin-6-ylthio)-9H-purin-9-yl)propyl)pyrrolidin-3-one |
| 5B-3 | 9-(3-(isopropylamino)propyl)-8-((7-(5-methylfuran-2-yl)-2,3-dihydrobenzo[b][1,4]dioxin-6-yl)thio)-9H-purin-6-amine |
| 5B-4 | 6-(6-amino-2-fluoro-8-((7-(5-methyloxazol-2-yl)-2,3-dihydrobenzo[b][1,4]dioxin-6-yl)methyl)-9H-purin-9-yl)hexanamide |
| 5B-5 | 6-(6-amino-8-(7-(5-methyloxazol-2-yl)-2,3-dihydrobenzo[b][1,4]dioxin-6-ylthio)-9H-purin-9-yl)hexanamide |
| 5B-6 | 2-fluoro-8-((7-(5-methylfuran-2-yl)-2,3-dihydrobenzo[b][1,4]dioxin-6-yl)methyl)-9-(2-(1-(methylsulfonyl)piperidin-3-yl)ethyl)-9H-purin-6-amine |
| 5B-7 | TT-VI-53A<br>2-fluoro-8-((7-(furan-2-yl)-2,3-dihydrobenzo[b][1,4]dioxin-6-yl)methyl)-9-(2-(isobutylamino)ethyl)-9H-purin-6-amine |
| 5B-8 | 1-(3-(2-(6-amino-2-fluoro-8-((7-(5-methylfuran-2-yl)-2,3-dihydrobenzo[b][1,4]dioxin-6-yl)methyl)-9H-purin-9-yl)ethyl)piperidin-1-yl)ethanone |
| 5B-9 | 8-(7-(5-methylfuran-2-yl)-2,3-dihydrobenzo[b][1,4]dioxin-6-ylthio)-9-(2-(1-(methylsulfonyl)piperidin-3-yl)ethyl)-9H-purin-6-amine |
| 5B-10 | 2-fluoro-9-(2-(isobutylamino)ethyl)-8-((7-(5-methylfuran-2-yl)-2,3-dihydrobenzo[b][1,4]dioxin-6-yl)methyl)-9H-purin-6-amine |
| 5B-11 | 1-(3-(6-amino-2-fluoro-8-((7-(5-methyloxazol-2-yl)-2,3-dihydrobenzo[b][1,4]dioxin-6-yl)methyl)-9H-purin-9-yl)propyl)pyrrolidin-3-one |
| 5B-12 | 8-((7-(5-(aminomethyl)furan-2-yl)-2,3-dihydrobenzo[b][1,4]dioxin-6-yl)methyl)-2-fluoro-9-(2-(isobutylamino)ethyl)-9H-purin-6-amine |

TABLE 5B-continued

| No. | Name |
|---|---|
| 5B-13 | 8-(7-(5-methyloxazol-2-yl)-2,3-dihydrobenzo[b][1,4]dioxin-6-ylthio)-9-(2-(neopentylamino)ethyl)-9H-purin-6-amine |
| 5B-14 | 1-(3-(2-(6-amino-8-(7-(5-methylfuran-2-yl)-2,3-dihydrobenzo[b][1,4]dioxin-6-ylthio)-9H-purin-9-yl)ethyl)piperidin-1-yl)ethanone |
| 5B-15 | 8-((7-(5-methylfuran-2-yl)-2,3-dihydrobenzo[b][1,4]dioxin-6-yl)thio)-9-(2-(neopentylamino)ethyl)-9H-purin-6-amine |
| 5B-16 | 8-((7-(isoxazol-4-yl)-2,3-dihydrobenzo[b][1,4]dioxin-6-yl)thio)-9-(2-(neopentylamino)ethyl)-9H-purin-6-amine |
| 5B-17 | 1-(3-(2-(6-amino-8-(7-(5-methyloxazol-2-yl)-2,3-dihydrobenzo[b][1,4]dioxin-6-ylthio)-9H-purin-9-yl)ethyl)piperidin-1-yl)ethanone |
| 5B-18 | 8-((7-(5-(aminomethyl)furan-2-yl)-2,3-dihydrobenzo[b][1,4]dioxin-6-yl)thio)-9-(2-(neopentylamino)ethyl)-9H-purin-6-amine |
| 5B-19 | 5-(6-amino-8-(7-(5-methylfuran-2-yl)-2,3-dihydrobenzo[b][1,4]dioxin-6-ylthio)-9H-purin-9-yl)pentane-1-sulfonamide |
| 5B-20 | 5-(6-amino-8-(7-(5-methyloxazol-2-yl)-2,3-dihydrobenzo[b][1,4]dioxin-6-ylthio)-9H-purin-9-yl)pentane-1-sulfonamide |
| 5B-21 | 1-(4-(2-(6-amino-2-chloro-8-((7-(furan-2-yl)-2,3-dihydrobenzo[b][1,4]dioxin-6-yl)methyl)-9H-purin-9-yl)ethyl)piperidin-1-yl)ethanone |
| 5B-22 | 1-(4-(2-(6-amino-8-((7-(5-methylfuran-2-yl)-2,3-dihydrobenzo[b][1,4]dioxin-6-yl)thio)-9H-purin-9-yl)ethyl)piperidin-1-yl)ethanone |
| 5B-23 | 1-(4-(2-(6-amino-2-fluoro-8-((7-(5-methylfuran-2-yl)-2,3-dihydrobenzo[b][1,4]dioxin-6-yl)methyl)-9H-purin-9-yl)ethyl)piperidin-1-yl)ethanone |
| 5B-24 | 1-(3-(6-amino-8-(7-(5-methylfuran-2-yl)-2,3-dihydrobenzo[b][1,4]dioxin-6-ylthio)-9H-purin-9-yl)propyl)pyrrolidin-3-one |
| 5B-25 | 9-(3-(tert-butylamino)propyl)-8-(7-(5-methylfuran-2-yl)-2,3-dihydrobenzo[b][1,4]dioxin-6-ylthio)-9H-purin-6-amine |
| 5B-26 | 2-chloro-8-((7-(5-methylfuran-2-yl)-2,3-dihydrobenzo[b][1,4]dioxin-6-yl)methyl)-9-(2-(1-(methylsulfonyl)pyrrolidin-3-yl)ethyl)-9H-purin-6-amine |
| 5B-27 | 1-(3-(2-(6-amino-8-(7-(5-(aminomethyl)furan-2-yl)-2,3-dihydrobenzo[b][1,4]dioxin-6-ylthio)-9H-purin-9-yl)ethyl)piperidin-1-yl)ethanone |
| 5B-28 | 1-(3-(2-(6-amino-8-((7-(5-(aminomethyl)furan-2-yl)-2,3-dihydrobenzo[b][1,4]dioxin-6-yl)methyl)-2-fluoro-9H-purin-9-yl)ethyl)piperidin-1-yl)ethanone |
| 5B-29 | 5-(6-amino-2-fluoro-8-((7-(5-methylfuran-2-yl)-2,3-dihydrobenzo[b][1,4]dioxin-6-yl)methyl)-9H-purin-9-yl)pentane-1-sulfonamide |
| 5B-30 | 4-(2-(6-amino-2-chloro-8-((7-(isoxazol-4-yl)-2,3-dihydrobenzo[b][1,4]dioxin-6-yl)methyl)-9H-purin-9-yl)ethyl)piperidine-1-carbaldehyde |
| 5B-31 | N-(2-((2-(6-amino-8-((7-(furan-2-yl)-2,3-dihydrobenzo[b][1,4]dioxin-6-yl)thio)-9H-purin-9-yl)ethyl)amino)ethyl)sulfamide |
| 5B-32 | 3-((2-(6-amino-8-((7-(furan-2-yl)-2,3-dihydrobenzo[b][1,4]dioxin-6-yl)thio)-9H-purin-9-yl)ethyl)amino)-N-hydroxypropanamide |
| 5B-33 | HJP23 8-((7-(furan-2-yl)-2,3-dihydrobenzo[b][1,4]dioxin-6-yl)thio)-9-(2-(isobutylamino)ethyl)-9H-purin-6-amine |
| 5B-34 | HJP20 9-(3-(isopropylamino)propyl)-8-((7-(oxazol-2-yl)-2,3-dihydrobenzo[b][1,4]dioxin-6-yl)thio)-9H-purin-6-amine |
| 5B-35 | 9-(3-aminopropyl)-2-fluoro-8-((7-(5-methylfuran-2-yl)-2,3-dihydrobenzo[b][1,4]dioxin-6-yl)methyl)-9H-purin-6-amine |
| 5B-36 | 9-(3-aminopropyl)-8-(7-(5-methylfuran-2-yl)-2,3-dihydrobenzo[b][1,4]dioxin-6-ylthio)-9H-purin-6-amine |
| 5B-37 | 9-(3-(tert-butylamino)propyl)-8-(7-(5-methylfuran-2-yl)-2,3-dihydrobenzo[b][1,4]dioxin-6-ylthio)-9H-purin-6-amine |
| 5B-38 | 9-(3-aminopropyl)-8-((7-(oxazol-2-yl)-2,3-dihydrobenzo[b][1,4]dioxin-6-yl)thio)-9H-purin-6-amine |
| 5B-39 | 9-(3-(tert-butylamino)propyl)-8-((7-(oxazol-2-yl)-2,3-dihydrobenzo[b][1,4]dioxin-6-yl)thio)-9H-purin-6-amine |
| 5B-40 | 9-(3-(tert-butylamino)propyl)-8-((7-(5-methyloxazol-2-yl)-2,3-dihydrobenzo[b][1,4]dioxin-6-yl)thio)-9H-purin-6-amine |
| 5B-41 | 1-(4-(2-(6-amino-8-((7-(5-methyloxazol-2-yl)-2,3-dihydrobenzo[b][1,4]dioxin-6-yl)thio)-9H-purin-9-yl)ethyl)piperidin-1-yl)ethanone |
| 5B-42 | 8-((7-(5-methyloxazol-2-yl)-2,3-dihydrobenzo[b][1,4]dioxin-6-yl)thio)-9-(2-(1-(methylsulfonyl)piperidin-3-yl)ethyl)-9H-purin-6-amine |
| 5B-43 | 1-(6-amino-8-((7-(5-methylfuran-2-yl)-2,3-dihydrobenzo[b][1,4]dioxin-6-yl)thio)-9H-purin-9-yl)-3-(isopropylamino)propan-2-ol |
| 5B-44 | 1-(6-amino-8-((7-(5-methyloxazol-2-yl)-2,3-dihydrobenzo[b][1,4]dioxin-6-yl)thio)-9H-purin-9-yl)-3-(isopropylamino)propan-2-ol |
| 5B-45 | 6-(6-amino-2-fluoro-8-((7-(5-methylfuran-2-yl)-2,3-dihydrobenzo[b][1,4]dioxin-6-yl)methyl)-9H-purin-9-yl)hexanamide |
| 5B-46 | N-(3-(6-amino-8-((7-(5-methyloxazol-2-yl)-2,3-dihydrobenzo[b][1,4]dioxin-6-yl)thio)-9H-purin-9-yl)propyl)methanesulfonamide |
| 5B-47 | 1-(2-(4-(6-amino-8-(7-(5-methyloxazol-2-yl)-2,3-dihydrobenzo[b][1,4]dioxin-6-ylthio)-9H-purin-9-yl)butyl)pyrrolidin-1-yl)ethanone |
| 5B-48 | 9-(3-aminopropyl)-2-fluoro-8-((7-(5-methyloxazol-2-yl)-2,3-dihydrobenzo[b][1,4]dioxin-6-yl)methyl)-9H-purin-6-amine |
| 5B-49 | 2-fluoro-9-(3-(isopropylamino)propyl)-8-((7-(oxazol-2-yl)-2,3-dihydrobenzo[b][1,4]dioxin-6-yl)methyl)-9H-purin-6-amine |
| 5B-50 | 2-fluoro-9-(3-(isopropylamino)propyl)-8-((7-(5-methyloxazol-2-yl)-2,3-dihydrobenzo[b][1,4]dioxin-6-yl)methyl)-9H-purin-6-amine |

TABLE 5B-continued

| No. | Name |
|---|---|
| 5B-51 | 9-(3-(tert-butylamino)propyl)-2-fluoro-8-((7-(oxazol-2-yl)-2,3-dihydrobenzo[b][1,4]dioxin-6-yl)methyl)-9H-purin-6-amine |
| 5B-52 | 9-(3-(tert-butylamino)propyl)-2-fluoro-8-((7-(5-methyloxazol-2-yl)-2,3-dihydrobenzo[b][1,4]dioxin-6-yl)methyl)-9H-purin-6-amine |
| 5B-53 | 6-(6-amino-2-fluoro-8-((7-(5-methyloxazol-2-yl)-2,3-dihydrobenzo[b][1,4]dioxin-6-yl)methyl)-9H-purin-9-yl)hexanamide |
| 5B-54 | 5-(6-amino-2-fluoro-8-((7-(5-methyloxazol-2-yl)-2,3-dihydrobenzo[b][1,4]dioxin-6-yl)methyl)-9H-purin-9-yl)pentane-1-sulfonamide |
| 5B-55 | 1-(3-(6-amino-2-fluoro-8-((7-(5-methyloxazol-2-yl)-2,3-dihydrobenzo[b][1,4]dioxin-6-yl)methyl)-9H-purin-9-yl)propyl)pyrrolidin-3-one |
| 5B-56 | 1-(3-(6-amino-2-fluoro-8-((7-(oxazol-2-yl)-2,3-dihydrobenzo[b][1,4]dioxin-6-yl)methyl)-9H-purin-9-yl)propyl)pyrrolidin-3-one |

TABLE 5C

| No. | Name |
|---|---|
| 5C-1 | 9-(3-(isopropylamino)propyl)-8-((7-(thiophen-2-yl)-2,3-dihydrobenzo[b][1,4]dioxin-6-yl)thio)-9H-purin-6-amine |
| 5C-2 | 2-fluoro-9-(2-(isobutylamino)ethyl)-8-((7-(thiophen-2-yl)-2,3-dihydrobenzo[b][1,4]dioxin-6-yl)methyl)-9H-purin-6-amine |
| 5C-3 | 9-(2-(neopentylamino)ethyl)-8-((7-(thiophen-2-yl)-2,3-dihydrobenzo[b][1,4]dioxin-6-yl)thio)-9H-purin-6-amine |
| 5C-4 | 9-(3-(isopropylamino)propyl)-8-((7-(thiophen-3-yl)-2,3-dihydrobenzo[b][1,4]dioxin-6-yl)thio)-9H-purin-6-amine |
| 5C-5 | 2-fluoro-9-(2-(isobutylamino)ethyl)-8-((7-(thiophen-3-yl)-2,3-dihydrobenzo[b][1,4]dioxin-6-yl)methyl)-9H-purin-6-amine |
| 5C-6 | 9-(2-(neopentylamino)ethyl)-8-((7-(thiophen-3-yl)-2,3-dihydrobenzo[b][1,4]dioxin-6-yl)thio)-9H-purin-6-amine |
| 5C-7 | 1-(4-(2-(6-amino-8-((7-(thiophen-2-yl)-2,3-dihydrobenzo[b][1,4]dioxin-6-yl)thio)-9H-purin-9-yl)ethyl)piperidin-1-yl)ethanone |
| 5C-8 | 4-(2-(6-amino-8-((7-(thiophen-2-yl)-2,3-dihydrobenzo[b][1,4]dioxin-6-yl)thio)-9H-purin-9-yl)ethyl)piperidine-1-carbaldehyde |
| 5C-9 | 1-(4-(2-(6-amino-2-fluoro-8-((7-(thiophen-2-yl)-2,3-dihydrobenzo[b][1,4]dioxin-6-yl)methyl)-9H-purin-9-yl)ethyl)piperidin-1-yl)ethanone |
| 5C-11 | 4-(2-(6-amino-8-((7-(thiophen-3-yl)-2,3-dihydrobenzo[b][1,4]dioxin-6-yl)thio)-9H-purin-9-yl)ethyl)piperidine-1-carbaldehyde |
| 5C-13 | 4-(2-(6-amino-2-chloro-8-((7-(thiophen-3-yl)-2,3-dihydrobenzo[b][1,4]dioxin-6-yl)methyl)-9H-purin-9-yl)ethyl)piperidine-1-carbaldehyde |
| 5C-14 | N-(2-((2-(6-amino-8-((7-(thiophen-2-yl)-2,3-dihydrobenzo[b][1,4]dioxin-6-yl)thio)-9H-purin-9-yl)ethyl)amino)ethyl)sulfamide |
| 5C-15 | 3-((2-(6-amino-8-((7-(thiophen-2-yl)-2,3-dihydrobenzo[b][1,4]dioxin-6-yl)thio)-9H-purin-9-yl)ethyl)amino)-N-hydroxypropanamide |
| 5C-16 | 9-(3-aminopropyl)-8-((7-(thiophen-2-yl)-2,3-dihydrobenzo[b][1,4]dioxin-6-yl)thio)-9H-purin-6-amine |
| 5C-17 | 9-(3-(isopropylamino)propyl)-8-((7-5-methylthiophen-2-yl)-2,3-dihydrobenzo[b][1,4]dioxin-6-yl)thio-9H-purin-6-amine |
| 5C-18 | 1-(6-amino-8-((7-(5-methylthiophen-2-yl)-2,3-dihydrobenzo[b][1,4]dioxin-6-yl)thio)-9H-purin-9-yl)-3-(isoproylamino)propan-2-ol |
| 5C-19 | 1-(2-(3-(6-amino-8-(7-(5-methylthiazol-2-yl)-2,3-dihydrobenzo[b][1,4]dioxin-6-ylthio)-9H-purin-9-yl)propyl)pyrrolidin-1-yl)ethanone |
| 5C-20 | 9-(2-(1-(methylsulfonyl)piperidin-3-yl)ethyl)-8-((7-(5-methylthiazol-2-yl)-2,3-dihydrobenzo[b][1,4]dioxin-6-yl)thio)-9H-purin-6-amine |
| 5C-21 | 1-(6-amino-8-((7-(5-methylthiazol-2-yl)-2,3-dihydrobenzo[b][1,4]dioxin-6-yl)thio)-9H-purin-9-yl)-3-(isopropylamino)propan-2-ol |
| 5C-22 | 9-(3-(tert-butylamino)propyl)-8-((7-(thiazol-2-yl)-2,3-dihydrobenzo[b][1,4]dioxin-6-yl)thio)-9H-purin-6-amine |
| 5C-23 | 9-(3-(tert-butylamino)propyl)-8-((7-(5-methylthiophen-2-yl)-2,3-dihydrobenzo[b][1,4]dioxin-6-yl)thio)-9H-purin-6-amine |

TABLE 5D

| No. | Name |
|---|---|
| 5D-1 | 8-((7-(1H-pyrazol-4-yl)-2,3-dihydrobenzo[b][1,4]dioxin-6-yl)thio-9-(3-(isopropylamino)propyl)-9H-purin-6-amine |
| 5D-2 | HJP19 8-((7-(1H-pyrazol-3-yl)-2,3-dihydrobenzo[b][1,4]dioxin-6-yl)thio)-9-(3-(isopropylamino)propyl)-9H-purin-6-amine |
| 5D-3 | 8-((7-(1H-pyrazol-4-yl)-2,3-dihydrobenzo[b][1,4]dioxin-6-yl)methyl)-2-fluoro-9-(2-(isobutylamino)ethyl)-9H-purin-6-amine |

TABLE 5D-continued

| No. | Name |
|---|---|
| 5D-4 | TT-VI-54A<br>8-((7-(1H-pyrazol-3-yl)-2,3-dihydrobenzo[b][1,4]dioxin-6-yl)methyl)-2-fluoro-9-(2-isobutylamino)ethyl)-9H-purin-6-amine |
| 5D-5 | 1-(3-(8-(7-(1H-pyrazol-3-yl)-2,3-dihydrobenzo[b][1,4]dioxin-6-ylthio)-6-amino-9H-purin-9-yl)propyl)pyrrolidin-3-one |
| 5D-6 | 8-((7-(1H-pyrazol-3-yl)-2,3-dihydrobenzo[b][1,4]dioxin-6-yl)thio)-9-(2-(neopentylamino)ethyl)-9H-purin-6-amine |
| 5D-7 | 1-(4-(2-(8-((7-(1H-pyrazol-3-yl)-2,3-dihydrobenzo[b][1,4]dioxin-6-yl)thio)-6-amino-9H-purin-9-yl)ethyl)piperidin-1-yl)ethanone |
| 5D-8 | 8-((7-(1H-pyrazol-3-yl)-2,3-dihydrobenzo[b][1,4]dioxin-6-yl)methyl)-9-(2-aminoethyl)-2-fluoro-9H-purin-6-amine |
| 5D-9 | 1-(4-(2-(8-((7-(1H-pyrazol-3-yl)-2,3-dihydrobenzo[b][1,4]dioxin-6-yl)methyl)-6-amino-2-fluoro-9H-purin-9-yl)ethyl)piperidin-1-yl)ethanone |
| 5D-10 | 1-(3-(2-(8-((7-(1H-pyrazol-3-yl)-2,3-dihydrobenzo[b][1,4]dioxin-6-yl)methyl)-6-amino-2-fluoro-9H-purin-9-yl)ethyl)piperidin-1-yl)ethanone |
| 5D-11 | 8-((7-(1H-pyrazol-3-yl)-2,3-dihydrobenzo[b][1,4]dioxin-6-yl)methyl)-2-fluoro-9-(2-(1-(methylsulfonyl)piperidin-3-yl)ethyl)-9H-purin-6-amine |
| 5D-12 | 1-(3-(8-((7-(1H-pyrazol-3-yl)-2,3-dihydrobenzo[b][1,4]dioxin-6-yl)methyl)-6-amino-2-fluoro-9H-purin-9-yl)propyl)pyrrolidin-3-one |
| 5D-13 | 8-(7-(1H-pyrazol-3-yl)-2,3-dihydrobenzo[b][1,4]dioxin-6-ylthio)-9-(2-(1-(methylsulfonyl)piperidin-3-yl)ethyl)-9H-purin-6-amine |
| 5D-14 | N-(2-((2-(8-((7-(1H-pyrazol-3-yl)-2,3-dihydrobenzo[b][1,4]dioxin-6-yl)thio)-6-amino-9H-purin-9-yl)ethyl)amino)ethyl)sulfamide |
| 5D-15 | 3-((2-(8-((7-(1H-pyrazol-3-yl)-2,3-dihydrobenzo[b][1,4]dioxin-6-yl)thio)-6-amino-9H-purin-9-yl)ethyl)amino)-N-hydroxypropanamide |
| 5D-16 | 8-((7-(1H-imidazol-4-yl)-2,3-dihydrobenzo[b][1,4]dioxin-6-yl)thio)-9-(3-(isopropylamino)propyl)-9H-purin-6-amine |
| 5D-17 | 8-((7-(1H-pyrazol-3-yl)-2,3-dihydrobenzo[b][1,4]dioxin-6-yl)thio)-9-(3-aminopropyl)-9H-purin-6-amine |
| 5D-18 | 8-((7-(1H-pyrazol-3-yl)-2,3-dihydrobenzo[b][1,4]dioxin-6-yl)thio)-9-(3-(tert-butylamino)propyl)-9H-purin-6-amine |
| 5D-19 | 8-((7-(1H-pyrazol-3-yl)-2,3-dihydrobenzo[b][1,4]dioxin-6-yl)methyl)-9-(3-(tert-butylamino)propyl)-2-fluoro-9H-purin-6-amine |
| 5D-20 | 9-(3-(isopropylamino)propyl)-8-((7-(5-methyl-1H-pyrazol-3-yl)-2,3-dihydrobenzo[b][1,4]dioxin-6-yl)thio)-9H-purin-6-amine |
| 5D-21 | 8-((7-(5-methyl-1H-pyrazol-3-yl)-2,3-dihydrobenzo[b][1,4]dioxin-6-yl)thio-9-(2-(neopentylamino)ethyl)-9H-purin-6-amine |
| 5D-22 | 9-(3-(tert-butylamino)propyl)-2-fluoro-8-((7-(5-methyl-1H-pyrazol-3-yl)-2,3-dihydrobenzo[b][1,4]dioxin-6-yl)methyl)-9H-purin-6-amine |
| 5D-23 | 1-(8-((7-(1H-pyrazol-3-yl)-2,3-dihydrobenzo[b][1,4]dioxin-6-yl)thio)-6-amino-9H-purin-9-yl)-3-(isopropylamino)propan-2-ol |
| 5D-24 | 1-(8-((7-(1H-pyrazol-3-yl)-2,3-dihydrobenzo[b][1,4]dioxin-6-yl)methyl)-6-amino-2-fluoro-9H-purin-9-yl)-3-(tert-butylamino)propan-2-ol |
| 5D-25 | 5-(8-((7-(1H-pyrazol-3-yl)-2,3-dihydrobenzo[b][1,4]dioxin-6-yl)methyl)-6-amino-2-fluoro-9H-purin-9-yl)pentane-1-sulfonamide |
| 5D-26 | 6-(8-((7-(1H-pyrazol-3-yl)-2,3-dihydrobenzo[b][1,4]dioxin-6-yl)methyl)-6-amino-2-fluoro-9H-purin-9-yl)hexanamide |
| 5D-27 | 5-(8-(7-(1H-pyrazol-3-yl)-2,3-dihydrobenzo[b][1,4]dioxin-6-ylthio)-6-amino-9H-purin-9-yl)pentane-1-sulfonamide |
| 5D-28 | 6-(8-(7-(1H-pyrazol-3-yl)-2,3-dihydrobenzo[b][1,4]dioxin-6-ylthio)-6-amino-9H-purin-9-yl)hexanamide |

TABLE 5E

| No. | Name |
|---|---|
| 5E-1 | 8-((7-ethynyl-2,3-dihydrobenzo[b][1,4]dioxin-6-yl)thio)-9-(3-(isopropylamino)propyl)-9H-purin-6-amine |
| 5E-2 | 3-(3-(6-amino-8-(7-ethynyl-2,3-dihydrobenzo[b][1,4]dioxin-6-ylthio)-9H-purin-9-yl)propyl)pyrrolidine-1-carbaldehyde |
| 5E-3 | 8-((7-ethynyl-2,3-dihydrobenzo[b][1,4]dioxin-6-yl)methyl)-2-fluoro-9-(2-(isobutylamino)ethyl)-9H-purin-6-amine |
| 5E-4 | 9-(2-aminoethyl)-8-(7-ethynyl-2,3-dihydrobenzo[b][1,4]dioxin-6-ylthio)-9H-purin-6-amine |
| 5E-5 | 8-((7-ethynyl-2,3-dihydrobenzo[b][1,4]dioxin-6-yl)thio)-9-(2-(neopentylamino)ethyl)-9H-purin-6-amine |
| 5E-6 | 9-(2-aminoethyl)-8-((7-ethynyl-2,3-dihydrobenzo[b][1,4]dioxin-6-yl)thio)-9H-purin-6-amine |
| 5E-7 | 1-(3-(2-(6-amino-8-(7-ethynyl-2,3-dihydrobenzo[b][1,4]dioxin-6-ylthio)-9H-purin-9-yl)ethyl)piperidin-1-yl)ethanone |
| 5E-8 | 8-(7-ethynyl-2,3-dihydrobenzo[b][1,4]dioxin-6-ylthio)-9-(2-(1-methylsulfonyl)piperidin-3-yl)ethyl)-9H-purin-6-amine |
| 5E-9 | 8-((7-ethynyl-2,3-dihydrobenzo[b][1,4]dioxin-6-yl)methyl)-2-fluoro-9-(2-(1-(methylsulfonyl)piperidin-3-yl)ethyl)-9H-purin-6-amine |

TABLE 5E-continued

| No. | Name |
|---|---|
| 5E-10 | 1-(3-(2-(6-amino-8-((7-ethynyl-2,3-dihydrobenzo[b][1,4]dioxin-6-yl)methyl)-2-fluoro-9H-purin-9-yl)ethyl)piperidin-1-yl)ethanone |
| 5E-11 | 3-(2-(6-amino-8-((7-ethynyl-2,3-dihydrobenzo[b][1,4]dioxin-6-yl)methyl)-2-fluoro-9H-purin-9-yl)ethyl)piperidine-1-carbaldehyde |
| 5E-12 | 1-(3-(6-amino-8-((7-ethynyl-2,3-dihydrobenzo[b][1,4]dioxin-6-yl)methyl)-2-fluoro-9H-purin-9-yl)propyl)pyrrolidin-3-one |
| 5E-13 | 6-(6-amino-8-((7-ethynyl-2,3-dihydrobenzo[b][1,4]dioxin-6-yl)methyl)-2-fluoro-9H-purin-9-yl)hexanamide |
| 5E-14 | N-(2-((2-(6-amino-8-((7-ethynyl-2,3-dihydrobenzo[b][1,4]dioxin-6-yl)thio)-9H-purin-9-yl)ethyl)amino)ethyl)sulfamide |
| 5E-15 | 3-((2-(6-amino-8-((7-ethynyl-2,3-dihydrobenzo[b][1,4]dioxin-6-yl)thio)-9H-purin-9-yl)ethyl)amino)-N-hydroxypropanamide |
| 5E-16 | 9-(3-aminopropyl)-8-((7-ethynyl-2,3-dihydrobenzo[b][1,4]dioxin-6-yl)thio)-9H-purin-6-amine |
| 5E-17 | 6-(6-amino-8-(7-ethynyl-2,3-dihydrobenzo[b][1,4]dioxin-6-ylthio)-9H-purin-9-yl)hexanamide |
| 5E-18 | 5-(6-amino-8-(7-ethynyl-2,3-dihydrobenzo[b][1,4]dioxin-6-ylthio)-9H-purin-9-yl)pentane-1-sulfonamide |
| 5E-19 | 1-(6-amino-8-((7-ethynyl-2,3-dihydrobenzo[b][1,4]dioxin-6-yl)methyl)-2-fluoro-9H-purin-9-yl)-3-(tert-butylamino)propan-2-ol |
| 5E-20 | 1-(6-amino-8-((7-ethynyl-2,3-dihydrobenzo[b][1,4]dioxin-6-yl)thio)-9H-purin-9-yl)-3-(isopropylamino)propan-2-ol |
| 5E-21 | 5-(6-amino-8-((7-ethynyl-2,3-dihydrobenzo[b][1,4]dioxin-6-yl)methyl)-2-fluoro-9H-purin-9-yl)pentane-1-sulfonamide |
| 5E-22 | 8-((7-ethynyl-2,3-dihydrobenzo[b][1,4]dioxin-6-yl)methyl)-2-fluoro-9-(3-(isopropylamino)propyl)-9H-purin-6-amine |
| 5E-23 | 9-(3-(tert-butylamino)propyl)-8-((7-ethynyl-2,3-dihydrobenzo[b][1,4]dioxin-6-yl)methyl)-2-fluoro-9H-purin-6-amine |
| 5E-24 | 9-(3-aminopropyl)-8-((7-ethynyl-2,3-dihydrobenzo[b][1,4]dioxin-6-yl)methyl)-2-fluoro-9H-purin-6-amine |
| 5E-25 | 9-(3-(tert-butylamino)propyl)-8-(7-ethynyl-2,3-dihydrobenzo[b][1,4]dioxin-6-ylthio)-9H-purin-6-amine |
| 5E-26 | 8-(7-ethynyl-2,3-dihydrobenzo[b][1,4]dioxin-6-ylthio)-9-(2-(1-methylpiperidin-2-yl)ethyl)-9H-purin-6-amine |
| 5E-27 | 8-(7-ethynyl-2,3-dihydrobenzo[b][1,4]dioxin-6-ylthio)-9-(2-(1-methylpiperidin-3-yl)ethyl)-9H-purin-6-amine |
| 5E-28 | 8-((7-ethynyl-2,3-dihydrobenzo[b][1,4]dioxin-6-yl)methyl)-2-fluoro-9-(2-(1-methylpiperidin-2-yl)ethyl)-9H-purin-6-amine |
| 5E-29 | 8-((7-ethynyl-2,3-dihydrobenzo[b][1,4]dioxin-6-yl)methyl)-2-fluoro-9-(2-(1-methylpiperidin-3-yl)ethyl)-9H-purin-6-amine |

TABLE 5F

| No. | Name |
|---|---|
| 5F-1 | 7-((6-amino-9-(3-(isopropylamino)propyl)-9H-purin-8-yl)thio)-2,3-dihydrobenzo[b][1,4]dioxine-6-carbonitrile |
| 5F-2 | 7-((6-amino-9-(3-(isopropylamino)propyl)-9H-purin-8-yl)thio)-2,3-dihydrobenzo[b][1,4]dioxine-6-carbonitrile |
| 5F-3 | 7-((6-amino-2-fluoro-9-(2-(isobutylamino)ethyl)-9H-purin-8-yl)methyl)-2,3-dihydrobenzo[b][1,4]dioxine-6-carbonitrile |
| 5F-4 | 7-((6-amino-2-fluoro-9-(2-(isobutylamino)ethyl)-9H-purin-8-yl)methyl)-2,3-dihydrobenzo[b][1,4]dioxine-6-carbonitrile |
| 5F-5 | 7-((6-amino-9-(2-(neopentylamino)ethyl)-9H-purin-8-yl)thio)-2,3-dihydrobenzo[b][1,4]dioxine-6-carbonitrile |
| 5F-6 | 7-((6-amino-9-(2-(neopentylamino)ethyl)-9H-purin-8-yl)thio)-2,3-dihydrobenzo[b][1,4]dioxine-6-carbonitrile |

TABLE 5F-continued

| No. | Name |
|---|---|
| 5F-7 | 2-(7-((6-amino-2-fluoro-9-(2-(isobutylamino)ethyl)-9H-purin-8-yl)methyl)-2,3-dihydrobenzo[b][1,4]dioxin-6-yl)acetonitrile |
| 5F-8 | N-(2-((2-(6-amino-8-((7-(cyanomethyl)-2,3-dihydrobenzo[b][1,4]dioxin-6-yl)thio)-9H-purin-9-yl)ethyl)amino)ethyl)sulfamide |
| 5F-9 | 3-((2-(6-amino-8-((7-(cyanomethyl)-2,3-dihydrobenzo[b][1,4]dioxin-6-yl)thio)-9H-purin-9-yl)ethyl)amino)-N-hydroxypropanamide |
| 5F-10 | 7-((6-amino-2-chloro-9-(2-(isobutylamino)ethyl)-9H-purin-8-yl)methyl)-2,3-dihydrobenzo[b][1,4]dioxine-6-carbonitrile |

TABLE 5G

| No. | Name |
|---|---|
| 5G-1 | 8-((7-(aziridin-1-yl)-2,3-dihydrobenzo[b][1,4]dioxin-6-yl)thio)-9-(2-(neopentylamino)ethyl)-9H-purin-6-amine |
| 5G-2 | 8-((7-(azetidin-1-yl)-2,3-dihydrobenzo[b][1,4]dioxin-6-yl)thio)-9-(2-(isobutylamino)ethyl)-9H-purin-6-amine |
| 5G-3 | 9-(2-(isobutylamino)ethyl)-8-((7-(pyrrolidin-1-yl)-2,3-dihydrobenzo[b][1,4]dioxin-6-yl)thio)-9H-purin-6-amine |
| 5G-4 | 8-((7-(aziridin-1-yl)-2,3-dihydrobenzo[b][1,4]dioxin-6-yl)methyl)-2-fluoro-9-(2-(neopentylamino)ethyl)-9H-purin-6-amine |
| 5G-5 | 8-((7-(azetidin-1-yl)-2,3-dihydrobenzo[b][1,4]dioxin-6-yl)methyl)-2-fluoro-9-(2-(isobutylamino)ethyl)-9H-purin-6-amine |
| 5G-6 | 2-fluoro-9-(2-(isobutylamino)ethyl)-8-((7-(pyrrolidin-1-yl)-2,3-dihydrobenzo[b][1,4]dioxin-6-yl)methyl)-9H-purin-6-amine |

TABLE 5G-continued

| No. | Name |
|---|---|
| 5G-7 | 2-chloro-9-(2-(isobutylamino)ethyl)-8-((7-(pyrrolidin-1-yl)-2,3-dihydrobenzo[b][1,4]dioxin-6-yl)methyl)-9H-purin-6-amine |
| 5G-8 | 1-(4-(2-(6-amino-8-((7-(aziridin-1-yl)-2,3-dihydrobenzo[b][1,4]dioxin-6-yl)thio)-9H-purin-9-yl)ethyl)piperidin-1-yl)ethanone |
| 5G-9 | 1-(3-(2-(6-amino-8-(7-(azetidin-1-yl)-2,3-dihydrobenzo[b][1,4]dioxin-6-ylthio)-9H-purin-9-yl)ethyl)piperidin-1-yl)ethanone |
| 5G-10 | 4-(2-(6-amino-2-chloro-8-((7-(pyrrolidin-1-yl)-2,3-dihydrobenzo[b][1,4]dioxin-6-yl)methyl)-9H-purin-9-yl)ethyl)piperidine-1-carbaldehyde |
| 5G-11 | 8-((7-(dimethylamino)-2,3-dihydrobenzo[b][1,4]dioxin-6-yl)thio)-9-(2-(isobutylamino)ethyl)-9H-purin-6-amine |
| 5G-12 | 8-((7-(dimethylamino)-2,3-dihydrobenzo[b][1,4]dioxin-6-yl)methy)-2-fluoro-9-(2-(isobutylamino)ethyl)-9H-purin-6-amine |
| 5G-13 | 1-(3-(2-(6-amino-8-(7-(dimethylamino)-2,3-dihydrobenzo[b][1,4]dioxin-6-ylthio)-9H-purin-9-yl)ethyl)piperidin-1-yl)ethanone |
| 5G-14 | 1-(3-(2-(6-amino-8-((7-(dimethylamino)-2,3-dihydrobenzo[b][1,4]dioxin-6-yl)methyl)-2-fluoro-9H-purin-9-yl)ethyl)piperidin-1-yl)ethanone |
| 5G-15 | 8-(7-(dimethylamino)-2,3-dihydrobenzo[b][1,4]dioxin-6-ylthio)-9-(2-(1-(methylsulfonyl)piperidin-3-yl)ethyl)-9H-purin-6-amine |
| 5G-16 | 8-((7-(dimethylamino)-2,3-dihydrobenzo[b][1,4]dioxin-6-yl)methyl)-2-fluoro-9-(2-(1-(methylsulfonyl)piperidin-3-yl)ethyl)-9H-purin-6-amine |
| 5G-17 | 8-((7-(ethylamino)-2,3-dihydrobenzo[b][1,4]dioxin-6-yl)thio)-9-(2-(isobutylamino)ethyl)-9H-purin-6-amine |
| 5G-18 | 1-(3-(2-(6-amino-8-(7-(ethylamino)-2,3-dihydrobenzo[b][1,4]dioxin-6-ylthio)-9H-purin-9-yl)ethyl)piperidin-1-yl)ethanone |
| 5G-19 | 8-(7-(ethylamino)-2,3-dihydrobenzo[b][1,4]dioxin-6-ylthio)-9-(2-(1-(methylsulfonyl)piperidin-3-yl)ethyl)-9H-purin-6-amine |
| 5G-20 | 2-fluoro-9-(2-(isobutylamino)ethyl)-8-((7-(isopropylamino)-2,3-dihydrobenzo[b][1,4]dioxin-6-yl)methyl)-9H-purin-6-amine |
| 5G-21 | 8-(7-(isopropylamino)-2,3-dihydrobenzo[b][1,4]dioxin-6-ylthio)-9-(2-(1-(methylsulfonyl)piperidin-3-yl)ethyl)-9H-purin-6-amine |
| 5G-22 | 1-(3-(2-(6-amino-2-fluoro-8-((7-(isopropylamino)-2,3-dihydrobenzo[b][1,4]dioxin-6-yl)methyl)-9H-purin-9-yl)ethyl)piperidin-1-yl)ethanone |
| 5G-23 | 8-((7-(dimethylamino)-2,3-dihydrobenzo[b][1,4]dioxin-6-yl)thio)-9-(3-(isopropylamino)propyl)-9H-purin-6-amine |
| 5G-24 | 8-((7-(dimethylamino)-2,3-dihydrobenzo[b][1,4]dioxin-6-yl)thio)-9-(2-(1-(methylsulfonyl)piperidin-3-yl)ethyl-9H-purin-6-amine |
| 5G-25 | 5-(6-amino-8-(7-(dimethylamino)-2,3-dihydrobenzo[b][1,4]dioxin-6-ylthio)-9H-purin-9-yl)pentane-1-sulfonamide |
| 5G-26 | 6-(6-amino-8-(7-(dimethylamino)-2,3-dihydrobenzo[b][1,4]dioxin-6-ylthio)-9H-purin-9-yl)hexanamide |
| 5G-27 | 9-(3-(tert-butylamino)propyl)-8-((7-(dimethylamino)-2,3-dihydrobenzo[b][1,4]dioxin-6-yl)thio)-9H-purin-6-amine |
| 5G-28 | 1-(3-(6-amino-8-(7-(dimethylamino)-2,3-dihydrobenzo[b][1,4]dioxin-6-ylthio)-9H-purin-9-yl)propyl)pyrrolidin-3-one |

TABLE 5H

| No. | Name |
|---|---|
| 5H-1 | 8-((7-cyclopropyl-2,3-dihydrobenzo[b][1,4]dioxin-6-yl)thio)-9-(2-(neopentylamino)ethyl)-9H-purin-6-amine |
| 5H-2 | 8-((7-cyclobutyl-2,3-dihydrobenzo[b][1,4]dioxin-6-yl)thio)-9-(2-(isobutylamino)ethyl)-9H-purin-6-amine |
| 5H-3 | 8-((7-cyclopentyl-2,3-dihydrobenzo[b][1,4]dioxin-6-yl)thio)-9-(2-(isobutylamino)ethyl)-9H-purin-6-amine |
| 5H-4 | 8-((7-cyclopropyl-2,3-dihydrobenzo[b][1,4]dioxin-6-yl)methyl)-2-fluoro-9-(2-(neopentylamino)ethyl)-9H-purin-6-amine |
| 5H-5 | 8-((7-cyclobutyl-2,3-dihydrobenzo[b][1,4]dioxin-6-yl)methyl)-2-fluoro-9-(2-(isobutylamino)ethyl)-9H-purin-6-amine |
| 5H-6 | 8-((7-cyclopentyl-2,3-dihydrobenzo[b][1,4]dioxin-6-yl)methyl)-2-fluoro-9-(2-(isobutylamino)ethyl)-9H-purin-6-amine |
| 5H-7 | 1-(4-(2-(6-amino-8-((7-cyclopropyl-2,3-dihydrobenzo[b][1,4]dioxin-6-yl)thio)-9H-purin-9-yl)ethyl)piperidin-1-yl)ethanone |
| 5H-8 | 1-(4-(2-(6-amino-8-((7-cyclopropyl-2,3-dihydrobenzo[b][1,4]dioxin-6-yl)methyl)-2-fluoro-9H-purin-9-yl)ethyl)piperidin-1-yl)ethanone |
| 5H-9 | 1-(4-(2-(6-amino-2-chloro-8-((7-cyclobutyl-2,3-dihydrobenzo[b][1,4]dioxin-6-yl)methyl)-9H-purin-9-yl)ethyl)piperidin-1-yl)ethanone |
| 5H-10 | 4-(2-(6-amino-8-((7-cyclobutyl-2,3-dihydrobenzo[b][1,4]dioxin-6-yl)thio)-9H-purin-9-yl)ethyl)piperidine-1-carbaldehyde |
| 5H-11 | 4-(2-(6-amino-8-((7-cyclopentyl-2,3-dihydrobenzo[b][1,4]dioxin-6-yl)methyl)-2-fluoro-9H-purin-9-yl)ethyl)piperidine-1-carbaldehyde |
| 5H-12 | 3-(6-amino-8-((7-cyclopropyl-2,3-dihydrobenzo[b][1,4]dioxin-6-yl)thio)-9H-purin-9-yl)propyl sulfamate |
| 5H-13 | 8-((7-cyclopropyl-2,3-dihydrobenzo[b][1,4]dioxin-6-yl)thio)-9-(2-(1-(methylsulfonyl)piperidin-3-yl)ethyl)-9H-purin-6-amine |

TABLE 5H-continued

| No. | Name |
|---|---|
| 5H-14 | 9-(3-(tert-butylamino)propyl)-8-((7-cyclopropyl-2,3-dihydrobenzo[b][1,4]dioxin-6-yl)thio)-9H-purin-6-amine |
| 5H-15 | 2-(3-(6-amino-8-(7-cyclobutyl-2,3-dihydrobenzo[b][1,4]dioxin-6-ylthio)-9H-purin-9-yl)propyl)pyrrolidine-1-sulfonamide |
| 5H-16 | 3-(2-(6-amino-8-(7-cyclopentyl-2,3-dihydrobenzo[b][1,4]dioxin-6-ylthio)-9H-purin-9-yl)ethyl)pyrrolidine-1-sulfonamide |
| 5H-17 | 8-(7-cyclopentyl-2,3-dihydrobenzo[b][1,4]dioxin-6-ylthio)-9-(2-(1-(methylsulfonyl)piperidin-3-yl)ethyl)-9H-purin-6-amine |
| 5H-18 | 9-(3-(tert-butylamino)propyl)-8-(7-cyclopentyl-2,3-dihydrobenzo[b][1,4]dioxin-6-ylthio)-9H-purin-6-amine |
| 5H-19 | 1-(6-amino-8-(7-cyclopentyl-2,3-dihydrobenzo[b][1,4]dioxin-6-ylthio)-9H-purin-9-yl)-3-(isopropylamino)propan-2-ol |

TABLE 6A

| No. | Name |
|---|---|
| 6A-1 | 8-((7-iodo-2,3-dihydrobenzo[b][1,4]oxathiin-6-yl)thio)-9-(3-(isopropylamino)propyl)-9H-purin-6-amine |
| 6A-2 | 8-((7-(furan-2-yl)-2,3-dihydrobenzo[b][1,4]oxathiin-6-yl)thio)-9-(3-(isopropylamino)propyl)-9H-purin-6-amine |
| 6A-3 | 8-((7-ethynyl-2,3-dihydrobenzo[b][1,4]oxathiin-6-yl)thio)-9-(3-(isopropylamino)propyl)-9H-purin-6-amine |
| 6A-4 | 4-(2-(6-amino-8-((7-(furan-2-yl)-2,3-dihydrobenzo[b][1,4]oxathiin-6-yl)thio)-9H-purin-9-yl)ethyl)piperidine-1-carbaldehyde |
| 6A-5 | 2-fluoro-9-(2-(isobutylamino)ethyl)-8-((7-(pyrrolidin-1-yl)-2,3 dihydrobenzo[b][1,4]oxathiin-6-yl)methyl)-9H-purin-6-amine |
| 6A-6 | 8-((7-(aziridin-1-yl)-2,3-dihydrobenzo[b][1,4]oxathiin-6-yl)thio)-9-(2-(neopentylamino)ethyl)-9H-purin-6-amine |
| 6A-7 | 8-((6-(furan-2-yl)-2,3-dihydrobenzo[b][1,4]oxathiin-7-yl)thio)-9-(3-(isopropylamino)propyl)-9H-purin-6-amine |
| 6A-8 | 8-((6-ethynyl-2,3-dihydrobenzo[b][1,4]oxathiin-7-yl)thio)-9-(3-(isopropylamino)propyl)-9H-purin-6-amine |
| 6A-9 | 4-(2-(6-amino-8-((6-(furan-2-yl)-2,3-dihydrobenzo[b][1,4]oxathiin-7-yl)thio)-9H-purin-9-yl)ethyl)piperidine-1-carbaldehyde |
| 6A-10 | 2-fluoro-9-(2-(isobutylamino)ethyl)-8-((6-(pyrrolidin-1-yl)-2,3-dihydrobenzo[b][1,4]oxathiin-7-yl)methyl)-9H-purin-6-amine |
| 6A-11 | 8-((6-(aziridin-1-yl)-2,3-dihydrobenzo[b][1,4]oxathiin-7-yl)thio)-9-(2-(neopentylamino)ethyl)-9H-purin-6-amine |
| 6A-12 | 8-((7-(furan-2-yl)-4-methyl-3,4-dihydro-2H-benzo[b][1,4]oxazin-6-yl)thio)-9-(2-(neopentylamino)ethyl)-9H-purin-6-amine |
| 6A-13 | 8-((4-methyl-7-(1H-pyrazol-3-yl)-3,4-dihydro-2H-benzo[b][1,4]oxazin-6-yl)thio)-9-(2-(neopentylamino)ethyl)-9H-purin-6-amine |
| 6A-14 | 8-((7-ethynyl-4-methyl-3,4-dihydro-2H-benzo[b][1,4]oxazin-6-yl)thio)-9-(2-(isobutylamino)ethyl)-9H-purin-6-amine |
| 6A-15 | 2-fluoro-8-((7-(furan-2-yl)-4-methyl-3,4-dihydro-2H-benzo[b][1,4]oxazin-6-yl)methyl)-9-(2-(neopentylamino)ethyl)-9H-purin-6-amine |
| 6A-16 | 4-(2-(6-amino-8-((7-(furan-2-yl)-4-methyl-3,4-dihydro-2H-benzo[b][1,4]thiazin-6-yl)thio)-9H-purin-9-yl)ethyl)piperidine-1-carbaldehyde |
| 6A-17 | 8-((6-(furan-2-yl)-4-methyl-3,4-dihydro-2H-benzo[b][1,4]oxazin-7-yl)thio)-9-(3-(isopropylamino)propyl)-9H-purin-6-amine |
| 6A-18 | 9-(3-(isopropylamino)propyl)-8-((4-methyl-6-(thiophen-2-yl)-3,4-dihydro-2H-benzo[b][1,4]oxazin-7-yl)thio)-9H-purin-6-amine |
| 6A-19 | 4-(2-(6-amino-8-((6-(furan-2-yl)-4-methyl-3,4-dihydro-2H-benzo[b][1,4]oxazin-7-yl)thio)-9H-purin-9-yl)ethyl)piperidine-1-carbaldehyde |
| 6A-20 | 4-(2-(6-amino-8-((6-ethynyl-4-methyl-3,4-dihydro-2H-benzo[b][1,4]oxazin-7-yl)thio)-9H-purin-9-yl)ethyl)piperidine-1-carbaldehyde |
| 6A-21 | 8-((6-(azetidin-1-yl)-4-methyl-3,4-dihydro-2H-benzo[b][1,4]oxazin-7-yl)thio)-9-(2-(isobutylamino)ethyl)-9H-purin-6-amine |
| 6A-22 | 8-((6-(furan-2-yl)-4-methyl-3,4-dihydro-2H-benzo[b][1,4]thiazin-7-yl)thio)-9-(3-(isopropylamino)propyl)-9H-purin-6-amine |
| 6A-23 | 8-((6-iodochroman-7-yl)thio)-9-(3-(isopropylamino)propyl)-9H-purin-6-amine |
| 6A-24 | 8-((6-(furan-2-yl)chroman-7-yl)thio)-9-(3-(isopropylamino)propyl)-9H-purin-6-amine |
| 6A-25 | 8-((6-ethynylthiochroman-7-yl)thio)-9-(3-(isopropylamino)propyl)-9H-purin-6-amine |
| 6A-26 | 4-(2-(6-amino-8-((6-(furan-2-yl)thiochroman-7-yl)thio)-9H-purin-9-yl)ethyl)piperidine-1-carbaldehyde |
| 6A-27 | 2-fluoro-9-(2-(isobutylamino)ethyl)-8-((1-methyl-6-(pyrrolidin-1-yl)-1,2,3,4-tetrahydroquinolin-7-yl)methyl)-9H-purin-6-amine |
| 6A-28 | 4-(2-(6-amino-8-((6-(furan-2-yl)-1,2,3,4-tetrahydroquinolin-7-yl)thio)-9H-purin-9-yl)ethyl)piperidine-1-carbaldehyde |
| 6A-29 | 8-((7-iodochroman-6-yl)thio)-9-(3-(isopropylamino)propyl)-9H-purin-6-amine |
| 6A-30 | 8-((7-(furan-2-yl)chroman-6-yl)thio)-9-(3-(isopropylamino)propyl)-9H-purin-6-amine |
| 6A-31 | 8-((7-ethynylthiochroman-6-yl)thio)-9-(3-(isopropylamino)propyl)-9H-purin-6-amine |
| 6A-32 | 4-(2-(6-amino-8-((7-(furan-2-yl)thiochroman-6-yl)thio)-9H-purin-9-yl)ethyl)piperidine-1-carbaldehyde |

TABLE 6A-continued

| No. | Name |
|---|---|
| 6A-33 | 2-fluoro-9-(2-(isobutylamino)ethyl)-8-((7-(pyrrolidin-1-yl)-1,2,3,4-tetrahydroquinolin-6-yl)methyl)-9H-purin-6-amine |
| 6A-34 | 4-(2-(6-amino-8-((7-(furan-2-yl)-1-methyl-1,2,3,4-tetrahydroquinolin-6-yl)thio)-9H-purin-9-yl)ethyl)piperidine-1-carbaldehyde |
| 6A-35 | 2-chloro-8-((7-iodo-2,3-dihydrobenzo[b][1,4]oxathiin-6-yl)methyl)-9-(2-(isobutylamino)ethyl)-9H-purin-6-amine |
| 6A-36 | 2-chloro-8-((6-iodo-2,3-dihydrobenzo[b][1,4]oxathiin-7-yl)methyl)-9-(2-(isobutylamino)ethyl)-9H-purin-6-amine |
| 6A-37 | 2-chloro-8-((6-iodochroman-7-yl)methyl)-9-(2-(isobutylamino)ethyl)-9H-purin-6-amine |
| 6A-38 | 9-(3-(tert-butylamino)propyl)-8-((6-iodochroman-7-yl)thio)-9H-purin-6-amine |
| 6A-39 | N-(3-(6-amino-8-((6-iodochroman-7-yl)thio)-9H-purin-9-yl)propyl)methanesulfonamide |
| 6A-40 | 3-(6-amino-8-((6-iodochroman-7-yl)thio)-9H-purin-9-yl)propyl sulfamate |
| 6A-41 | 1-(6-amino-8-((6-iodochroman-7-yl)thio)-9H-purin-9-yl)-3-(isopropylamino)propan-2-ol |
| 6A-42 | 9-(3-(tert-butylamino)propyl)-8-((6-ethynylchroman-7-yl)thio)-9H-purin-6-amine |
| 6A-43 | N-(3-(6-amino-8-((6-ethynylchroman-7-yl)thio)-9H-purin-9-yl)propyl)methanesulfonamide |
| 6A-44 | 3-(6-amino-8-((6-(furan-2-yl)chroman-7-yl)thio)-9H-purin-9-yl)propyl sulfamate |
| 6A-45 | 1-(6-amino-8-((6-(5-methyloxazol-2-yl)chroman-7-yl)thio)-9H-purin-9-yl)-3-(isopropylamino)propan-2-ol |
| 6A-46 | 9-(3-(tert-butylamino)propyl)-8-((6-iodo-4-methyl-3,4-dihydro-2H-benzo[b][1,4]oxazin-7-yl)thio)-9H-purin-6-amine |
| 6A-47 | N-(3-(6-amino-8-((6-iodo-4-methyl-3,4-dihydro-2H-benzo[b][1,4]oxazin-7-yl)thio)-9H-purin-9-yl)propyl)methanesulfonamide |
| 6A-48 | 3-(6-amino-8-((6-iodo-4-methyl-3,4-dihydro-2H-benzo[b][1,4]oxazin-7-yl)thio)-9H-purin-9-yl)propyl sulfamate |
| 6A-49 | 1-(6-amino-8-((6-iodo-4-methyl-3,4-dihydro-2H-benzo[b][1,4]oxazin-7-yl)thio)-9H-purin-9-yl)-3-(isopropylamino)propan-2-ol |
| 6A-50 | 9-(3-(tert-butylamino)propyl)-8-((6-ethynyl-4-methyl-3,4-dihydro-2H-benzo[b][1,4]oxazin-7-yl)thio)-9H-purin-6-amine |
| 6A-51 | N-(3-(6-amino-8-((6-ethynyl-4-methyl-3,4-dihydro-2H-benzo[b][1,4]oxazin-7-yl)thio)-9H-purin-9-yl)propyl)methanesulfonamide |
| 6A-52 | 3-(6-amino-8-((6-(furan-2-yl)-4-methyl-3,4-dihydro-2H-benzo[b][1,4]oxazin-7-yl)thio)-9H-purin-9-yl)propyl sulfamate |
| 6A-53 | 1-(6-amino-8-((4-methyl-6-(5-methyloxazol-2-yl)-3,4-dihydro-2H-benzo[b][1,4]oxazin-7-yl)thio)-9H-purin-9-yl)-3-(isopropylamino)propan-2-ol |
| 6A-54 | 9-(3-(tert-butylamino)propyl)-8-((4-methyl-6-(5-methyloxazol-2-yl)-3,4-dihydro-2H-benzo[b][1,4]oxazin-7-yl)thio)-9H-purin-6-amine |

TABLE 6B

| No. | Name |
|---|---|
| 6B-1 | 8-((3-iodo-5,6,7,8-tetrahydronaphthalen-2-yl)thio)-9-(3-(isopropylamino)propyl)-9H-purin-6-amine |
| 6B-2 | 8-((3-iodo-5,6,7,8-tetrahydronaphthalen-2-yl)thio)-9-(2-(isobutylamino)ethyl)-9H-purin-6-amine |
| 6B-3 | 8-((3-iodo-5,6,7,8-tetrahydronaphthalen-2-yl)thio)-9-(2-(neopentylamino)ethyl)-9H-purin-6-amine |
| 6B-4 | 2-fluoro-8-((3-iodo-5,6,7,8-tetrahydronaphthalen-2-yl)methyl)-9-(2-isobutylamino)ethyl)-9H-purin-6-amine |
| 6B-5 | 2-chloro-8-((3-(furan-2-yl)-5,6,7,8-tetrahydronaphthalen-2-yl)methyl)-9-(3-(isopropylamino)propyl)-9H-purin-6-amine |
| 6B-6 | 2-fluoro-8-((3-iodo-5,6,7,8-tetrahydronaphthalen-2-yl)methyl)-9-(3-isopropylamino)propyl)-9H-purin-6-amine |
| 6B-7 | 8-((3-(furan-2-yl)-5,6,7,8-tetrahydronaphthalen-2-yl)thio)-9-(3-(isopropylamino)propyl)-9H-purin-6-amine |
| 6B-8 | 8-((3-ethynyl-5,6,7,8-tetrahydronaphthalen-2-yl)thio)-9-(3-(isopropylamino)propyl)-9H-purin-6-amine |
| 6B-9 | 3-((6-amino-9-(3-(isopropylamino)propyl)-9H-purin-8-yl)thio-5,6,7,8-tetrahydronaphthalene-2-carbonitrile |
| 6B-10 | 8-((3-(azetidin-1-yl)-5,6,7,8-tetrahydronaphthalen-2-yl)methyl)-2-fluoro-9-(2-(neopentylamino)ethyl)-9H-purin-6-amine |
| 6B-11 | 8-((3-iodo-5,6,7,8-tetrahydronaphthalen-2-yl)thio)-9-(2-(isobutylamino)ethyl)-9H-purin-6-amine |
| 6B-12 | 6-(6-amino-8-(3-(oxazol-2-yl)-5,6,7,8-tetrahydronaphthalen-2-ylthio)-9H-purin-9-yl)hexanamide |
| 6B-13 | 1-(3-(2-(8-(3-(1H-pyrazol-3-yl)-5,6,7,8-tetrahydronaphthalen-2-ylthio)-6-amino-9H-purin-9-yl)ethyl)piperidin-1-yl)ethanone |
| 6B-14 | 1-(3-(2-(6-amino-8-(3-ethynyl-5,6,7,8-tetrahydronaphthalen-2-ylthio)-9H-purin-9-yl)ethyl)piperidin-1-yl)ethanone |
| 6B-15 | 1-(3-(2-(6-amino-2-fluoro-8-((3-(5-methylfuran-2-yl)-5,6,7,8-tetrahydronaphthalen-2-yl)methyl)-9H-purin-9-yl)ethyl)piperidin-1-yl)ethanone |
| 6B-16 | N-(2-((2-(6-amino-8-((3-(furan-2-yl)-5,6,7,8-tetrahydronaphthalen-2-yl)thio)-9H-purin-9-yl)ethyl)amino)ethyl)methanesulfonamide |

TABLE 6B-continued

| No. | Name |
|---|---|
| 6B-17 | 3-((2-(6-amino-8-((3-(furan-2-yl)-5,6,7,8-tetrahydronaphthalen-2-yl)thio)-9H-purin-9-yl)ethyl)amino)-N-hydroxypropanamide |
| 6B-18 | 9-(3-aminopropyl)-8-((3-iodo-5,6,7,8-tetrahydronaphthalen-2-yl)thio)-9H-purin-6-amine |
| 6B-19 | 9-(3-(isopropylamino)propyl)-8-((3-(oxazol-2-yl)-5,6,7,8-tetrahydronaphthalen-2-yl)thio)-9H-purin-6-amine |
| 6B-20 | 9-(3-(tert-butylamino)propyl)-8-((3-iodo-5,6,7,8-tetrahydronaphthalen-2-yl)thio)-9H-purin-6-amine |
| 6B-21 | 1-(3-(2-(6-amino-8-(3-(5-methylfuran-2-yl)-5,6,7,8-tetrahydronaphthalen-2-ylthio)-9H-purin-9-yl)ethyl)piperidin-1-yl)ethanone |
| 6B-22 | 1-(3-(2-(6-amino-8-(3-(oxazol-2-yl)-5,6,7,8-tetrahydronaphthalen-2-ylthio)-9H-purin-9-yl)ethyl)piperidin-1-yl)ethanone |
| 6B-23 | 8-((3-(dimethylamino)-5,6,7,8-tetrahydronaphthalen-2-yl)thio)-9-(2-(neopentylamino)ethyl)-9H-purin-6-amine |
| 6B-24 | 9-(2-(1-(methylsulfonyl)piperidin-3-yl)ethyl)-8-((3-(5-methylthiazol-2-yl)-5,6,7,8-tetrahydronaphthalen-2-yl)thio)-9H-purin-6-amine |
| 6B-25 | DZ4-52-N9 8-((3-iodonaphthalen-2-yl)thio)-9-(3-(isopropylamino)propyl)-9H-purin-6-amine |
| 6B-26 | 8-((3-(dimethylamino)naphthalen-2-yl)thio)-9-(2-(neopentylamino)ethyl)-9H-purin-6-amine |
| 6B-27 | 1-(3-(2-(6-amino-8-(3-(5-methylfuran-2-yl)naphthalen-2-ylthio)-9H-purin-9-yl)ethyl)piperidin-1-yl)ethanone |
| 6B-28 | 9-(2-(1-(methylsulfonyl)piperidin-3-yl)ethyl)-8-((3-(5-methylthiazol-2-yl)naphthalen-2-yl)thio)-9H-purin-6-amine |
| 6B-29 | 8-((3-ethynylnaphthalen-2-yl)thio)-9-(3-(isopropylamino)propyl)-9H-purin-6-amine |
| 6B-30 | 8-((3-(1H-pyrazol-3-yl)naphthalen-2-yl)thio)-9-(3-(isopropylamino)propyl)-9H-purin-6-amine |
| 6B-31 | 1-(6-amino-8-((3-iodonaphthalen-2-yl)thio)-9H-purin-9-yl)-3-(isopropylamino)propan-2-ol |
| 6B-32 | 5-(6-amino-8-(3-ethynylnaphthalen-2-ylthio)-9H-purin-9-yl)pentane-1-sulfonamide |
| 6B-33 | 9-(3-(tert-butylamino)propyl)-8-((3-iodonaphthalen-2-yl)thio)-9H-purin-6-amine |
| 6B-34 | 8-((3-(5-methyloxazol-2-yl)naphthalen-2-yl)thio)-9-(2-(1-(methylsulfonyl)piperidin-3-yl)ethyl)-9H-purin-6-amine |
| 6B-35 | 2-fluoro-8-((3-iodonaphthalen-2-yl)methyl)-9-(2-(isobutylamino)ethyl)-9H-purin-6-amine |
| 6B-36 | 1-(3-(2-(6-amino-8-(3-(aziridin-1-yl)naphthalen-2-ylthio)-9H-purin-9-yl)ethyl)piperidine-1-yl)ethanone |
| 6B-37 | 6-(6-amino-8-(3-(5-methyloxazol-2-yl)-5,6,7,8-tetrahydronaphthalen-2-ylthio)-9H-purin-9-yl)hexanamide |
| 6B-38 | 6-(6-amino-8-(3-iodo-5,6,7,8-tetrahydronaphthalen-2-ylthio)-9H-purin-9-yl)hexanamide |
| 6B-39 | 5-(6-amino-8-(3-iodo-5,6,7,8-tetrahydronaphthalen-2-ylthio)-9H-purin-9-yl)pentane-1-sulfonamide |
| 6B-40 | 1-(3-(6-amino-8-(3-iodo-5,6,7,8-tetrahydronaphthalen-2-ylthio)-9H-purin-9-yl)propyl)pyrrolidin-3-one |

TABLE 7A

| No. | Name |
|---|---|
| 7A-1 | 8-(2-ethynyl-5-methoxyphenylthio)-9-(3-(isopropylamino)propyl)-9H-purin-6-amine |
| 7A-2 | 9-(3-(isopropylamino)propyl)-8-(5-methoxy-2-(prop-1-ynyl)phenylthio)-9H-purin-6-amine |
| 7A-3 | 9-(3-(isopropylamino)propyl)-8-(5-methoxy-2-(phenylethynyl)phenylthio)-9H-purin-6-amine |
| 7A-4 | 8-(2-ethynyl-5-methoxyphenylthio)-9-(2-(isobutylamino)ethyl)-9H-purin-6-amine |
| 7A-5 | 1-(4-(2-(6-amino-8-(2-ethynyl-5-methoxyphenylthio)-9H-purin-9-yl)ethyl)piperidin-1-yl)ethanone |
| 7A-6 | 4-(2-(6-amino-8-(2-ethynyl-5-methoxyphenylthio)-9H-purin-9-yl)ethyl)piperidine-1-carbaldehyde |
| 7A-7 | 1-(4-(2-(6-amino-8-(2-ethynyl-5-methoxybenzyl)-2-fluoro-9H-purin-9-yl)ethyl)piperidin-1-yl)ethanone |
| 7A-8 | 4-(2-(6-amino-8-(2-ethynyl-5-methoxybenzyl)-2-fluoro-9H-purin-9-yl)ethyl)piperidine-1-carbaldehyde |
| 7A-9 | 1-(4-(2-(6-amino-2-chloro-8-(2-ethynyl-5-methoxybenzyl)-9H-purin-9-yl)ethyl)piperidin-1-yl)ethanone |
| 7A-10 | 4-(2-(6-amino-2-chloro-8-(2-ethynyl-5-methoxybenzyl)-9H-purin-9-yl)ethyl)piperidine-1-carbaldehyde |
| 7A-11 | N-(2-(2-(6-amino-8-(2-ethynyl-5-methoxyphenylthio)-9H-purin-9-yl)ethylamino)ethyl)sulfamide |
| 7A-12 | 3-(2-(6-amino-8-(2-ethynyl-5-methoxyphenylthio)-9H-purin-9-yl)ethylamino)-N-hydroxypropanamide |
| 7A-13 | 8-(5-ethoxy-2-ethynylphenylthio)-9-(3-(isopropylamino)propyl)-9H-purin-6-amine |
| 7A-14 | 1-(6-amino-8-(2-ethynyl-5-methoxyphenylthio)-9H-purin-9-yl)-3-(isopropylamino)propan-2-ol |
| 7A-15 | 8-(2-ethynyl-5-methoxyphenylthio)-9-(2-(1-(methylsulfonyl)piperidin-3-yl)ethyl)-9H-purin-6-amine |
| 7A-16 | N-(3-(6-amino-8-(2-ethynyl-5-methoxyphenylthio)-9H-purin-9-yl)propyl)methanesulfonamide |

TABLE 7A-continued

| No. | Name |
| --- | --- |
| 7A-17 | 2-(3-(6-amino-8-(2-ethynyl-5-methoxyphenylthio)-9H-purin-9-yl)propyl)pyrrolidine-1-carbaldehyde |
| 7A-18 | 8-(2-ethynyl-5-methoxybenzyl)-2-fluoro-9-(3-(isopropylamino)propyl)-9H-purin-6-amine |
| 7A-19 | 1-(3-(6-amino-8-(2-ethynyl-5-methoxyphenylthio)-9H-purin-9-yl)propyl)pyrrolidin-3-one |
| 7A-20 | PU-WS31<br>8-((2-ethynyl-5-methoxyphenyl)thio)-9-(2-(neopentylamino)ethyl)-9H-purin-6-amine |

TABLE 7B

| No. | Name |
| --- | --- |
| 7B-1 | 2-((6-amino-2-fluoro-9-(3-(isopropylamino)propyl)-9H-purin-8-yl)methyl)-4-methoxybenzonitrile |
| 7B-2 | 2-(6-amino-9-(3-(isopropylamino)propyl)-9H-purin-8-ylthio)-4-methoxybenzonitrile |
| 7B-3 | 2-(2-(6-amino-9-(3-(isopropylamino)propyl)-9H-purin-8-ylthio)-4-methoxyphenyl)acetonitrile |
| 7B-4 | 2-(2-((6-amino-2-fluoro-9-(2-(isobutylamino)ethyl)-9H-purin-8-yl)methyl)-4-methoxyphenyl)acetonitrile |
| 7B-5 | 2-(9-(2-(1-acetylpiperidin-4-yl)ethyl)-6-amino-9H-purin-8-ylthio)-4-methoxybenzonitrile |
| 7B-6 | 2-((6-amino-2-fluoro-9-(2-(1-formylpiperidin-4-yl)ethyl)-9H-purin-8-yl)methyl)-4-methoxybenzonitrile |
| 7B-7 | 2-((9-(2-(1-acetylpiperidin-4-yl)ethyl)-6-amino-2-chloro-9H-purin-8-yl)methyl)-4-methoxybenzonitrile |
| 7B-8 | 2-(2-(6-amino-9-(2-(1-formylpiperidin-4-yl)ethyl)-9H-purin-8-ylthio)-4-methoxyphenyl)acetonitrile |
| 7B-9 | 2-((9-(2-(1-acetylpiperidin-4-yl)ethyl)-6-amino-2-fluoro-9H-purin-8-yl)methyl)-4-methoxyphenyl)acetonitrile |
| 7B-10 | 2-((6-amino-2-fluoro-9-(3-(isopropylamino)propyl)-9H-purin-8-yl)methyl)-4-ethoxybenzonitrile |
| 7B-11 | N-(2-(2-(6-amino-8-(2-cyano-5-methoxyphenylthio)-9H-purin-9-yl)ethylamino)ethyl)methanesulfonamide |
| 7B-12 | 3-(2-(6-amino-8-(2-cyano-5-methoxyphenylthio)-9H-purin-9-yl)ethylamino)-N-hydroxypropanamide |

TABLE 7C

| No. | Name |
| --- | --- |
| 7C-1 | 8-(2-(furan-2-yl)-5-methoxyphenylthio)-9-(3-(isopropylamino)propyl)-9H-purin-6-amine |
| 7C-2 | 9-(3-(isopropylamino)propyl)-8-(5-methoxy-2-(5-methylfuran-2-yl)phenylthio)-9H-purin-6-amine |
| 7C-3 | 9-(3-(isopropylamino)propyl)-8-(2-(isoxazol-4-yl)-5-methoxyphenylthio)-9H-purin-6-amine |
| 7C-4 | 8-(2-(5-(aminomethyl)furan-2-yl)-5-methoxyphenylthio)-9-(3-(isopropylamino)propyl)-9H-purin-6-amine |
| 7C-5 | 2-fluoro-8-(2-(furan-2-yl)-5-methoxybenzyl)-9-(2-(isobutylamino)ethyl)-9H-purin-6-amine |
| 7C-6 | 2-fluoro-8-(2-(furan-3-yl)-5-methoxybenzyl)-9-(2-(isobutylamino)ethyl)-9H-purin-6-amine |
| 7C-7 | 2-fluoro-9-(2-(isobutylamino)ethyl)-8-(5-methoxy-2-(5-methylfuran-2-yl)benzyl)-9H-purin-6-amine |
| 7C-8 | 2-fluoro-9-(2-(isobutylamino)ethyl)-8-(2-(isoxazol-4-yl)-5-methoxybenzyl)-9H-purin-6-amine |
| 7C-9 | 8-(2-(5-(aminomethyl)furan-2-yl)-5-methoxybenzyl)-2-fluoro-9-(2-(isobutylamino)ethyl)-9H-purin-6-amine |
| 7C-10 | 1-(3-(6-amino-8-(5-methoxy-2-(5-methylfuran-2-yl)phenylthio)-9H-purin-9-yl)propyl)pyrrolidin-3-one |
| 7C-11 | 8-(5-methoxy-2-(5-methylfuran-2-yl)phenylthio)-9-(2-(1-(methylsulfonyl)piperidin-3-yl)ethyl)-9H-purin-6-amine |
| 7C-12 | 5-(6-amino-8-(5-methoxy-2-(oxazol-2-yl)phenylthio)-9H-purin-9-yl)pentane-1-sulfonamide |
| 7C-13 | TT-V-138<br>8-(2-(furan-2-yl)-5-methoxyphenylthio)-9-(2-(neopentylamino)ethyl)-9H-purin-6-amine |
| 7C-14 | 8-(2-(furan-3-yl)-5-methoxyphenylthio)-9-(2-(neopentylamino)ethyl)-9H-purin-6-amine |
| 7C-15 | 8-(5-methoxy-2-(5-methylfuran-2-yl)phenylthio)-9-(2-(neopentylamino)ethyl)-9H-purin-6-amine |
| 7C-16 | 8-(2-(isoxazol-4-yl)-5-methoxyphenylthio)-9-(2-(neopentylamino)ethyl)-9H-purin-6-amine |
| 7C-17 | 6-(6-amino-8-(5-methoxy-2-(5-methylfuran-2-yl)phenylthio)-9H-purin-9-yl)hexanamide |
| 7C-18 | 8-(2-(5-(aminomethyl)furan-2-yl)-5-methoxyphenylthio)-9-(2-(neopentylamino)ethyl)-9H-purin-6-amine |
| 7C-19 | 1-(3-(2-(6-amino-8-(5-methoxy-2-(oxazol-2-yl)phenylthio)-9H-purin-9-yl)ethyl)piperidin-1-yl)ethanone |
| 7C-20 | 1-(3-(2-(6-amino-2-fluoro-8-(5-methoxy-2-(oxazol-2-yl)benzyl)-9H-purin-9-yl)ethyl)piperidin-1-yl)ethanone |
| 7C-21 | 3-(2-(6-amino-2-chloro-8-(5-methoxy-2-(5-methylfuran-2-yl)benzyl)-9H-purin-9-yl)ethyl)piperidine-1-carbaldehyde |
| 7C-22 | 1-(3-(2-(6-amino-8-(5-methoxy-2-(5-methylfuran-2-yl)phenylthio)-9H-purin-9-yl)ethyl)piperidin-1-yl)ethanone |
| 7C-23 | 1-(4-(2-(6-amino-2-fluoro-8-(5-methoxy-2-(5-methylfuran-2-yl)benzyl)-9H-purin-9-yl)ethyl)piperidin-1-yl)ethanone |
| 7C-24 | 1-(3-(6-amino-8-(5-methoxy-2-(thiazol-2-yl)phenylthio)-9H-purin-9-yl)propyl)pyrrolidin-3-one |

TABLE 7C-continued

| No. | Name |
|---|---|
| 7C-25 | 9-(3-aminopropyl)-8-(5-methoxy-2-(5-methylfuran-2-yl)phenylthio)-9H-purin-6-amine |
| 7C-26 | 9-(3-(isopropylamino)propyl)-8-(5-methoxy-2-(oxazol-2-yl)phenylthio)-9H-purin-6-amine |
| 7C-27 | 1-(4-(2-(6-amino-8-(2-(5-(aminomethyl)furan-2-yl)-5-methoxyphenylthio)-9H-purin-9-yl)ethyl)piperidin-1-yl)ethanone |
| 7C-28 | 1-(4-(2-(6-amino-8-(2-(5-(aminomethyl)furan-2-yl)-5-methoxybenzyl)-2-fluoro-9H-purin-9-yl)ethyl)-piperidin-1-yl)ethanone |
| 7C-29 | 4-(2-(6-amino-8-(2-(isoxazol-4-yl)-5-methoxyphenylthio)-9H-purin-9-yl)ethyl)piperidine-1-carbaldehyde |
| 7C-30 | 4-(2-(6-amino-2-chloro-8-(2-(isoxazol-4-yl)-5-methoxybenzyl)-9H-purin-9-yl)ethyl)piperidine-1-carbaldehyde |
| 7C-31 | N-(2-(2-(6-amino-8-(2-(furan-2-yl)-5-methoxyphenylthio)-9H-purin-9-yl)ethylamino)ethyl)sulfamide |
| 7C-32 | 3-(2-(6-amino-8-(2-(furan-2-yl)-5-methoxyphenylthio)-9H-purin-9-yl)ethylamino)-N-hydroxypropanamide |
| 7C-33 | 8-(5-ethoxy-2-(furan-2-yl)phenylthio)-9-(3-(isopropylamino)propyl)-9H-purin-6-amine |
| 7C-34 | 9-(3-(isopropylamino)propyl)-8-(5-methoxy-2-(oxazol-2-yl)phenylthio)-9H-purin-6-amine |
| 7C-35 | 9-(3-(tert-butylamino)propyl)-8-(2-(furan-2-yl)-5-methoxyphenylthio)-9H-purin-6-amine |

TABLE 7D

| No. | Name |
|---|---|
| 7D-1 | 9-(3-(isopropylamino)propyl)-8-(5-methoxy-2-(thiophen-2-yl)phenylthio)-9H-purin-6-amine |
| 7D-2 | 2-fluoro-9-(2-(isobutylamino)ethyl)-8-(5-methoxy-2-(thiophen-2-yl)benzyl)-9H-purin-6-amine |
| 7D-3 | TT-V-139<br>8-(5-methoxy-2-(thiophen-2-yl)phenylthio)-9-(2-(neopentylamino)ethyl)-9H-purin-6-amine |
| 7D-4 | 9-(3-(isopropylamino)propyl)-8-(5-methoxy-2-(thiophen-3-yl)phenylthio)-9H-purin-6-amine |
| 7D-5 | N-(3-(6-amino-8-(5-methoxy-2-(thiazol-2-yl)phenylthio)-9H-purin-9-yl)propyl)methanesulfonamide |
| 7D-6 | 8-(5-methoxy-2-(thiophen-3-yl)phenylthio)-9-(2-(neopentylamino)ethyl)-9H-purin-6-amine |
| 7D-7 | 1-(4-(2-(6-amino-8-(5-methoxy-2-(thiophen-2-yl)phenylthio)-9H-purin-9-yl)ethyl)piperidin-1-yl)ethanone |
| 7D-8 | 4-(2-(6-amino-8-(5-methoxy-2-(thiophen-2-yl)phenylthio)-9H-purin-9-yl)ethyl)piperidine-1-carbaldehyde |
| 7D-9 | 1-(4-(2-(6-amino-2-fluoro-8-(5-methoxy-2-(thiophen-2-yl)benzyl)-9H-purin-9-yl)ethyl)piperidin-1-yl)ethanone |
| 7D-10 | 1-(6-amino-8-(5-methoxy-2-(thiophen-2-yl)phenylthio)-9H-purin-9-yl)-3-(isopropylamino)propan-2-ol |
| 7D-11 | 8-(5-methoxy-2-(5-methylthiophen-2-yl)phenylthio)-9-(2-(1-(methylsulfonyl)piperidin-3-yl)ethyl)-9H-purin-6-amine |
| 7D-12 | N-(2-(2-(6-amino-8-(5-methoxy-2-(thiophen-2-yl)phenylthio)-9H-purin-9-yl)ethylamino)ethyl)sulfamide |
| 7D-13 | 3-(2-(6-amino-8-(5-methoxy-2-(thiophen-2-yl)phenylthio)-9H-purin-9-yl)ethylamino)-N-hydroxypropanamide |
| 7D-14 | 8-(5-ethoxy-2-(thiophen-2-yl)benzyl)-2-fluoro-9-(2-(isobutylamino)ethyl)-9H-purin-6-amine |
| 7D-15 | 9-(3-aminopropyl)-8-(5-methoxy-2-(thiophen-2-yl)phenylthio)-9H-purin-6-amine |
| 7D-16 | 9-(3-(isopropylamino)propyl)-8-(5-methoxy-2-(thiazol-2-yl)phenylthio)-9H-purin-6-amine |

TABLE 7E

| No. | Name |
|---|---|
| 7E-1 | 9-(3-(isopropylamino)propyl)-8-(5-methoxy-2-(1H-pyrazol-4-yl)phenylthio)-9H-purin-6-amine |
| 7E-2 | 9-(3-(isopropylamino)propyl)-8-(5-methoxy-2-(1H-pyrazol-3-yl)phenylthio)-9H-purin-6-amine |
| 7E-3 | 2-fluoro-9-(2-(isobutylamino)ethyl)-8-(5-methoxy-2-(1H-pyrazol-4-yl)benzyl)-9H-purin-6-amine |
| 7E-4 | 2-fluoro-9-(2-(isobutylamino)ethyl)-8-(5-methoxy-2-(1H-pyrazol-3-yl)benzyl)-9H-purin-6-amine |
| 7E-5 | 1-(3-(2-(6-amino-8-(5-methoxy-2-(1H-pyrazol-3-yl)phenylthio)-9H-purin-9-yl)ethyl)pyrrolidin-1-yl)ethanone |
| 7E-6 | TT-V-140<br>8-(5-methoxy-2-(1H-pyrazol-3-yl)phenylthio)-9-(2-(neopentylamino)ethyl)-9H-purin-6-amine |
| 7E-7 | 1-(4-(2-(6-amino-8-(5-methoxy-2-(1H-pyrazol-3-yl)phenylthio)-9H-purin-9-yl)ethyl)piperidin-1-yl)ethanone |
| 7E-8 | 4-(2-(6-amino-8-(5-methoxy-2-(1H-pyrazol-3-yl)phenylthio)-9H-purin-9-yl)ethyl)piperidine-1-carbaldehyde |
| 7E-9 | 1-(4-(2-(6-amino-2-fluoro-8-(5-methoxy-2-(1H-pyrazol-3-yl)benzyl)-9H-purin-9-yl)ethyl)piperidin-1-yl)ethanone |
| 7E-10 | 4-(2-(6-amino-2-fluoro-8-(5-methoxy-2-(1H-pyrazol-3-yl)benzyl)-9H-purin-9-yl)ethyl)piperidine-1-carbaldehyde |
| 7E-11 | 1-(4-(2-(6-amino-2-chloro-8-(5-methoxy-2-(1H-pyrazol-3-yl)benzyl)-9H-purin-9-yl)ethyl)piperidin-1-yl)ethanone |
| 7E-12 | 4-(2-(6-amino-8-(5-methoxy-2-(1H-pyrazol-4-yl)phenylthio)-9H-purin-9-yl)ethyl)piperidine-1-carbaldehyde |
| 7E-13 | 1-(6-amino-8-(5-methoxy-2-(1H-pyrazol-3-yl)phenylthio)-9H-purin-9-yl)-3-(isopropylamino)propan-2-ol |

TABLE 7E-continued

| No. | Name |
| --- | --- |
| 7E-14 | N-(2-(2-(6-amino-8-(5-methoxy-2-(1H-pyrazol-3-yl)phenylthio)-9H-purin-9-yl)ethylamino)ethyl)sulfamide |
| 7E-15 | 3-(2-(6-amino-8-(5-methoxy-2-(1H-pyrazol-3-yl)phenylthio)-9H-purin-9-yl)ethylamino)-N-hydroxypropanamide |
| 7E-16 | 8-(5-ethoxy-2-(1H-pyrazol-3-yl)phenylthio)-9-(3-(isopropylamino)propyl)-9H-purin-6-amine |
| 7E-17 | 8-(5-ethoxy-2-(1H-pyrazol-3-yl)benzyl)-2-fluoro-9-(2-(isobutylamino)ethyl)-9H-purin-6-amine |
| 7E-18 | 9-(3-(tert-butylamino)propyl)-8-(5-methoxy-2-(1H-pyrazol-3-yl)phenylthio)-9H-purin-6-amine |
| 7E-19 | 9-(3-aminopropyl)-8-(5-methoxy-2-(1H-pyrazol-3-yl)phenylthio)-9H-purin-6-amine |
| 7E-20 | 8-(5-methoxy-2-(1H-pyrazol-3-yl)phenylthio)-9-(2-(1-(methylsulfonyl)piperidin-3-yl)ethyl)-9H-purin-6-amine |
| 7E-21 | N-(3-(6-amino-8-(5-methoxy-2-(1H-pyrazol-3-yl)phenylthio)-9H-purin-9-yl)propyl)methanesulfonamide |
| 7E-22 | 9-(3-(isopropylamino)propyl)-8-(5-methoxy-2-(5-methyl-1H-pyrazol-3-yl)phenylthio)-9H-purin-6-amine |

TABLE 7F

| No. | Name |
| --- | --- |
| 7F-1 | 9-(3-(isopropylamino)propyl)-8-(5-methoxy-2-(1H-pyrrol-3-yl)phenylthio)-9H-purin-6-amine |
| 7F-2 | 9-(3-(isopropylamino)propyl)-8-(5-methoxy-2-(1H-pyrrol-2-yl)phenylthio)-9H-purin-6-amine |
| 7F-3 | 2-fluoro-9-(2-(isobutylamino)ethyl)-8-(5-methoxy-2-(1H-pyrrol-3-yl)benzyl)-9H-purin-6-amine |
| 7F-4 | 8-(5-methoxy-2-(1H-pyrrol-3-yl)phenylthio)-9-(2-(1-(methylsulfonyl)pyrrolidin-2-yl)ethyl)-9H-purin-6-amine |
| 7F-5 | 8-(5-methoxy-2-(1H-pyrrol-3-yl)phenylthio)-9-(2-(neopentylamino)ethyl)-9H-purin-6-amine |
| 7F-6 | 9-(3-(isopropylamino)propyl)-8-(5-methoxy-2-(5-methyl-1H-pyrrol-3-yl)phenylthio)-9H-purin-6-amine |
| 7F-7 | 4-(3-(6-amino-8-(5-methoxy-2-(1H-pyrrol-3-yl)phenylthio)-9H-purin-9-yl)propyl)piperidine-1-carbaldehyde |
| 7F-8 | 4-(2-(6-amino-8-(5-methoxy-2-(1H-pyrrol-3-yl)phenylthio)-9H-purin-9-yl)ethyl)piperidine-1-carbaldehyde |
| 7F-9 | 1-(4-(2-(6-amino-2-fluoro-8-(5-methoxy-2-(1H-pyrrol-3-yl)benzyl)-9H-purin-9-yl)ethyl)piperidin-1-yl)ethanone |
| 7F-10 | 1-(4-(3-(6-amino-2-fluoro-8-(5-methoxy-2-(1H-pyrrol-3-yl)benzyl)-9H-purin-9-yl)propyl)piperidin-1-yl)ethanone |
| 7F-11 | 1-(4-(2-(6-amino-2-chloro-8-(5-methoxy-2-(1H-pyrrol-3-yl)benzyl)-9H-purin-9-yl)ethyl)piperidin-1-yl)ethanone |
| 7F-12 | N-(3-(6-amino-8-(5-methoxy-2-(1H-pyrrol-3-yl)phenylthio)-9H-purin-9-yl)propyl)methanesulfonamide |
| 7F-13 | 8-(5-methoxy-2-(1H-pyrrol-3-yl)phenylthio)-9-(2-(1-(methylsulfonyl)piperidin-3-yl)ethyl)-9H-purin-6-amine |
| 7F-14 | N-(2-(2-(6-amino-8-(5-methoxy-2-(1H-pyrrol-3-yl)phenylthio)-9H-purin-9-yl)ethylamino)ethyl)sulfamide |
| 7F-15 | 3-(2-(6-amino-8-(5-methoxy-2-(1H-pyrrol-3-yl)phenylthio)-9H-purin-9-yl)ethylamino)-N-hydroxypropanamide |
| 7F-16 | 8-(5-ethoxy-2-(1H-pyrrol-3-yl)phenylthio)-9-(3-(isopropylamino)propyl)-9H-purin-6-amine |
| 7F-17 | 8-(5-ethoxy-2-(1H-pyrrol-3-yl)benzyl)-2-fluoro-9-(2-(isobutylamino)ethyl)-9H-purin-6-amine |
| 7F-18 | 9-(3-(tert-butylamino)propyl)-8-(5-methoxy-2-(1H-pyrrol-3-yl)phenylthio)-9H-purin-6-amine |
| 7F-19 | 9-(3-aminopropyl)-8-(5-methoxy-2-(1H-pyrrol-3-yl)phenylthio)-9H-purin-6-amine |
| 7F-20 | 1-(6-amino-8-(5-methoxy-2-(1H-pyrrol-3-yl)phenylthio)-9H-purin-9-yl)-3-(isopropylamino)propan-2-ol |

TABLE 8

Options for R.
1. R is hydrogen, a $C_1$ to $C_{10}$ alkyl, alkenyl, alkynyl, or an alkoxyalkyl group, optionally including heteroatoms such as N or O, or a targeting moiety connected to N9 via a linker,
2. R is hydrogen, straight- or branched-, substituted or unsubstituted alkyl, substituted or unsubstituted alkenyl, substituted or unsubstituted alkynyl, in which one or more methylenes can be interrupted or terminated by O, S, S(O), $SO_2$, $N(R_{218})$, C(O), substituted or unsubstituted aryl, substituted or unsubstituted heteroaryl, substituted or unsubstituted heterocyclic; substituted or unsubstituted cycloalkyl; or

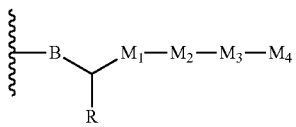

B is a linker; $R_{210}$ is selected from the group consisting of hydrogen, $N(R_2)COR_4$, $N(R_2)CON(R_3)R_4$, $N(R_2)COOR_4$, $N(R_2)S(O)_nR_3$, $N(R_2)S(O)_nN(R_3)R_4$; where $R_2$ and $R_3$ are independently selected from hydrogen, aliphatic or substituted aliphatic; $R_4$ is selected from the group consisting of: aryl, substituted aryl, heteroaryl, substituted heteroaryl, heterocyclic, substituted heterocyclic, cyloalkyl, substituted cycloalkyl, cycloalkenyl, substituted cycloalkenyl, and substituted or unsubstituted —$C_i$—$C_6$ alkyl,—$C_2$-$C_6$ alkenyl, or —$C_2$-$C_6$ alkynyl each containing O, 1, 2, or 3 heteroatoms selected from O, S or N; n is 1 or 2;
Mi is absent or selected from substituted or unsubstituted —$C_i$—$C_6$ alkyl, —$C_2$-$C_6$ alkenyl, or —$C_2$-$C_6$ alkynyl, aryl, substituted aryl, heteroaryl, substituted heteroaryl;
$M_2$ is absent, O, S, SO, $SO_2$, $N(R_2)$ or CO;
$M_3$ is absent, O, S, SO, $SO_2$, $N(R_2)$, CO, $C_i$—$C_6$ alkyl, $C_2$-$C_6$ alkenyl, $C_2$-$C_6$ alkynyl, cycloalkyl, heterocyclic, aryl, or heteroaryl;
$M_4$ is hydrogen, $NR_5R_6$, $CF_3$, $OR_4$, halogen, substituted or unsubstituted —$C_i$—$C_6$ alkyl, —$C_2$-$C_6$ alkenyl, or —$C_2$-$C_6$ alkynyl, cycloalkyl, substituted cycloalkyl, heterocyclic, substituted heterocyclic, aryl, substituted aryl, heteroaryl or substituted heteroaryl; where $R_5$ and $R_6$ are independently selected from the group consisting of hydrogen, aliphatic, substituted aliphatic, aryl, substituted aryl, heteroaryl, substituted heteroaryl, heterocyclic, substituted heterocyclic, cycloalkyl or substituted cycloalkyl; provided that —R and —Mi—$M_2$—$M_3$—$M_4$ cannot be both hydrogen.
3. R is

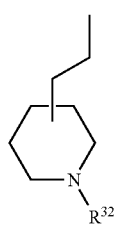

wherein $R^{32}$ is
(a) hydro;
(b) $C_1$-$C_6$ alkyl optionally substituted with 1, 2, 3, 4, or 5 substituents each independently chosen from the group of halo, hydroxyl, amino, cyano, and —C(=O)$R^{31}$ wherein $R^{31}$ is amino;
(c) —C(=O)$R^{33}$, wherein $R^{33}$ is selected from the group consisting of:
(1) hydro,
(2) $C_1$-$C_{10}$ (e.g., $C_1$-$C_6$,) alkyl optionally substituted with 1, 2, 3, 4, or 5 substituents each independently chosen from the group of (A) halo, (B) hydroxyl, (C) thiol, (D) cyano, (E) $C_1$-$C_6$ haloalkyl (e.g., trifluoromethyl), (F) $C_1$-$C_6$ alkoxy (e.g., methoxy) optionally substituted with $C_1$-$C_6$ alkoxy (e.g., methoxy), (G) C-amido, (H) N-amido, (I) sulfonyl (J) —N($R^{22}$)($R^{23}$) wherein $R^{22}$ and $R^{23}$ are independently hydro, $C_1$-$C_6$ alkyl, sulfonyl, and C-carboxy,
(3) $C_1$-$C_6$ cycloalkyl optionally substituted with 1, 2, 3, 4, or 5 substituents each independently chosen from the group of halo, hydroxyl, amino, cyano, and $C_1$-$C_6$ haloalkyl (e.g., trifluoromethyl), and
(4) $C_1$-$C_6$ alkoxy optionally substituted with 1, 2, 3, 4, or 5 substituents each independently chosen from halo, hydroxyl, amino, cyano, and $C_1$-$C_6$ haloalkyl (e.g., trifluoromethyl),
(f) heterocycle or heterocyclylalkyl, optionally substituted with 1, 2, 3, 4, or 5 substituents independently chosen from halo, hydroxyl, amino, cyano, trihalomethyl, and $C_1$-$C_4$ alkyl optionally substituted with 1, 2, 3, or 4 substituents independently chosen from halo, hydroxyl, amino, cyano,

TABLE 8-continued $C_1$-$C_6$, haloalkyl (e.g., trifluoromethyl) (e.g., tetrazole-5-yl optionally substituted with 1, 2, 3, or 4 $C_1$-$C_4$, alkyl);
(g) sulfonyl; and
(h) optionally substituted heteroaryl
4. R is —$R^{54}$-$R^{55}$, wherein
$R^{54}$ is —$(CH_2)_n$— wherein n = 0-3, —C(O), —C(S), —$SO_2$—, or —$SO_2N$—; and
$R^{55}$ is alkyl, aromatic, heteroaromatic, alicyclic, or heterocyclic, each of which is optionally bi-or tri-cyclic, and optionally substituted with H, halogen, lower alkyl, lower alkenyl, lower alkynyl, lower aryl, lower alicyclic, aralkyl, aryloxyalkyl, alkoxyalkyl, perhaloalkyl, perhaloalkyloxy, perhaloacyl, —$N_3$, —$SR^{58}$, —O $R^{58}$, —CN, —$CO_2R^{59}$, —$NO_2$, or ---N $R^{58}R^{510}$,
$R^{58}$ is hydrogen, lower alkyl, lower aryl, or —C(O) $R^{59}$;
$R^{59}$ is lower alkyl, lower aryl, lower heteroaryl, —N $R^{510}$ $R^{510}$ or —$OR^{511}$;
$R^{510}$ is independently hydrogen or lower alkyl; and
$R^{511}$ is _____
5. R is selected from the group consisting of H, optionally substituted alkyl, optionally substituted alkenyl, optionally substituted alkynyl, optionally substituted aryl, optionally substituted alicyclic, optionally substituted araalkyl, optionally substituted aryloxyalkyl, optionally substituted alkoxyalkyl, alkylaminoalkyl, alkylcarbonylaminoalkyl, alkylcarbonyoxylalkyl, optionally substituted heterocyclic, hydroxyalkyl, haloalkyl, perhaloalkyl, C(O)$R^{62}$, S(O)$_2R^{62}$, C(O)NHR$^{62}$, and C(O)OR$^{62}$; where $R^{62}$ is _____
6. R is H, $SR_{71}$, $SOR_{71}$, $SO_2R_{71}$, $OR_{71}$, $COOR_{71}$, $CONR_{71}R_{72}$, ---CN, $C_{1-6}$ alkyl, $C_{2-6}$ alkenyl, $C_{2-6}$ alkynyl, ---$R_{7A}OR_{7B}$---, ---$R_{7A}NR_{7B}$, ---$R_{7A}NR_{71}R_{7B}$, ---$R_{7A}SR_{7B}$, ---$R_{7A}SOR_{7B}$ or ---$R_{7A}SO_2R_{7B}$, cycloalkyl, heteroalkyl, heterocycloalkyl, aryl, heteroaryl, alkylaryl, arylalkyl, alkylheteroaryl, heteroarylalkyl, $NR_{71}R_{72}$, ---$OSO_2N(R_{7C})_2$, ---$N(R_{7C})SO_2OH$, ---$N(R_{7C})SO_2R_{7C}$, ---$R_{7A}OSO_2N(R_{7C})2$, or ---$R_{7A}N(R_{7C})OSO_2R_{7C}$;
$R_{71}$, $R_{72}$ are independently selected from the group consisting of H, $COOR_{7B}$, $CON(R_{7C})_2$ $C_{1-6}$ alkyl, $C_{2-6}$ alkenyl, $C_{2-6}$ alkynyl, --$R_{7A}OR_{7B}$---, ---$R_{7A}NR_{7B}$, ---$R_{7A}NR_{71}R_{7B}$, ---$R_{7A}SR_{7B}$, ---$R_{7A}SOR_{7B}$ or ---$R_{7A}SO_2R_{7B}$ cycloalkyl, heteroalkyl, heterocycloalkyl, aryl, heteroaryl, alkylaryl, arylalkyl, alkylheteroaryl, and heteroarylalkyl;
each $R_{7A}$ is independently $C_{1-6}$ alkyl, $C_{2-6}$ alkenyl, $C_{2-6}$ alkynyl, cycloalkyl, heteroalkyl, heterocycloalkyl, aryl, heteroaryl, alkylaryl, arylalkyl, alkylheteroaryl, alkylheteroarylalkyl, or heteroarylalkyl; and
each $R_{7B}$ is independently H, $C_{1-6}$ alkyl, $C_{2-6}$ alkenyl, $C_{2-6}$ alkynyl, cycloalkyl, heteroalkyl, heterocycloalkyl, aryl, heteroaryl, alkylaryl, arylalkyl, alkylheteroaryl, heteroarylalkyl, ---$SO_2OH$, ---$SO_2N(R_{7A})_2$, ---$SO_2NHR_{7A}$ or ---$SO_2NH_2$; and
each R.sub.C is independently H, $C_{1-6}$ alkyl, $C_{2-6}$ alkenyl, $C_{2-6}$ alkynyl, cycloalkyl, heteroalkyl, heterocycloalkyl, aryl, heteroaryl, alkylaryl, arylalkyl, alkylheteroaryl, or heteroarylalkyl;
7A. R is hydrogen, straight- or branched-, substituted or unsubstituted alkyl, substituted or unsubstituted alkenyl, substituted or unsubstituted alkynyl, which one or more methylenes can be interrupted or terminated by O, S, S(O), $SO_2$, $N(R_{88})$, C(O), substituted or unsubstituted aryl, substituted or unsubstituted heteroaryl, substituted or unsubstituted heterocyclic; substituted or unsubstituted cycloalkyl; where $R_{88}$ is hydrogen, acyl, aliphatic or substituted aliphatic.
7B. R is —M1—M2—M3—M4, wherein
$M_1$ is absent, $C_1$-$C_6$ alkyl, $C_2$-$C_6$ alkenyl, $C_2$-$C_6$ alkynyl, aryl or heteroaryl;
$M_2$ is absent, O, S, SO, $SO_2$, $N(R_{88})$, or C=O;
$M_3$ is absent, C=O, O, S, SO, $SO_2$ or $N(R_{88})$; and
$M_4$ is hydrogen, halogen, CN, $N_3$, hydroxy, substituted hydroxy, amino, substituted amino, $CF_3$, $C_1$-$C_6$ alkyl, $C_2$-$C_6$ alkenyl, $C_2$-$C_6$ alkynyl, cycloalkyl, heterocyclic, aryl or heteroaryl.

The invention claimed is:

1. A compound of the formula:

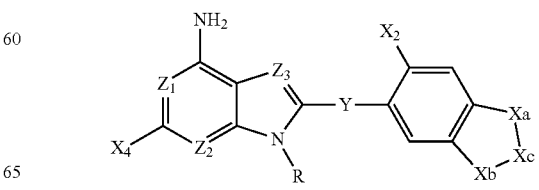

wherein
- (a) each of $Z_1$, $Z_2$ and $Z_3$ is independently N;
- (b) Xa and Xb are O and Xc is $CH_2$;
- (c) Y is —$CH_2$— or —S—;
- (d) $X_4$ is hydrogen or halogen; and
- (e) $X_2$ is an aryl, an alkynyl, a cycloalkyl, or a cycloalkenyl group, each of which is optionally substituted, and R is:
  - (a) hydrogen; or
  - (b) a straight-chain- or branched-$C_1$ to $C_{10}$ alkyl, $C_2$ to $C_6$ alkenyl, or $C_2$ to $C_6$ alkynyl, which is unsubstituted or substituted; or
  - (c) aryl, heteroaryl, heterocyclic, cycloalkyl, alkylaryl, or arylalkyl, which is unsubstituted or substituted; or
  - (d) —$SR_{71}$, —$S(O)R_{71}$, —$SO_2R_{71}$, —$OR_{71}$, —$COOR_{71}$, —$CONR_{71}R_{72}$, —CN, —$R_{7A}OR_{7B}$, —$R_{7A}NR_{7B}$, —$R_{7A}NR_{71}R_{7B}$, —$R_{7A}SR_{7B}$, —$R_{7A}S(O)R_{7B}$, —$R_{7A}SO_2R_{7B}$, —$NR_{71}R_{72}$, —$OSO_2N(R_{7C})_2$, —$N(R_{7C})SO_2OH$, —$N(R_{7C})SO_2R_{7C}$, —$R_{7A}OSO_2N(R_{7C})_2$, or —$R_{7A}N(R_{7C})OSO_2R_{7C}$,
    wherein each $R_{71}$ and $R_{72}$ is independently selected from the group consisting of hydrogen, $COOR_{7B}$, $CON(R_{7C})_2$, $C_1$ to $C_6$ alkyl, $C_2$ to $C_6$ alkenyl, $C_2$ to $C_6$ alkynyl, —$R_{7A}OR_{7B}$, —$R_{7A}NR_{7B}$, —$R_{7A}SR_{7B}$, —$R_{7A}S(O)R_{7B}$, —$R_{7A}SO_2R_{7B}$, cycloalkyl, heterocycloalkyl, aryl, heteroaryl, alkylaryl, arylalkyl, alkylheteroaryl, and heteroarylalkyl,
    each $R_{7A}$ is independently $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, or arylalkyl, and
    each $R_{7B}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, heteroarylalkyl, —$SO_2OH$, —$SO_2N(R_{7A})_2$, —$SO_2NHR_{7A}$, or —$SO_2NH_2$; and
    each $R_{7C}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, or heteroarylalkyl.

2. The compound of claim 1 wherein Y is S, $X_4$ is H, and $X_2$ is acetylenyl, 2-furanyl, 3-furanyl, 5-methyl-2-furanyl, 2-thiophene, 3-thiophene, 2-pyrazolyl, 3-pyrazolyl, 2-thiazolyl, 5-methyl-2-thiazolyl, 2-oxazolyl, 5-methyl-2-oxazolyl, or optionally substituted imidazole.

3. The compound of claim 1 wherein Y is S, $X_4$ is H, and $X_2$ is acetylenyl, 2-furanyl, 3-furanyl, 5-methyl-2-furanyl, 2-pyrazolyl, 3-pyrazolyl, 2-thiazolyl, 5-methyl-2-thiazolyl, 2-oxazolyl, or 5-methyl-2-oxazolyl.

4. The compound of claim 1 wherein $X_2$ is optionally substituted alkynyl.

5. The compound of claim 4 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-isopropyl-amino)ethyl, 2-(hydroxyethyl(isopropyl)amino)ethyl, 3-(cyclopentylamino)propyl, 3-(cyclopentyl(methyl)amino)propyl, 3-(ethylamino)propyl, 3-(ethyl(methyl)amino)propyl, 2-(neopentyl-amino)ethyl, 3-(methyl(isopropyl)amino)propyl, 3-(ethyl(isopropyl)amino)propyl, 3-(hydroxyethyl(isopropyl)amino)propyl, 3-(methyl(propargyl)amino)propyl, 2-(methyl(propargyl)amino)ethyl, 3-(allyl(methyl)amino)propyl, 3-(propyl(cyclopropyl)methyl-amino)propyl, 3-(hydroxyethyl(cyclohexyl)amino)propyl, 2-(cyclopropylmethyl-amino)ethyl, and 2-(methyl(isobutyl)amino)ethyl.

6. The compound of claim 5 wherein R is 3-(isopropyl-amino)propyl.

7. The compound of claim 4 wherein the compound is selected from the group consisting of: 8-[6(3,3dimethyl-but-1-ynyl)-benzo[1,3]dioxol-5-ylsulfanyl]9-(3-(isopropylaminopropyl)-9H-purin-6-ylamine, 9-(3-isopropylamino-propyl)-8-(6-phenylethynyl-benzo[1,3]dioxol-5-ylsulfanyl)-9H-purin-6-ylamine; 8-(6-ethynylbenzo[d][1,3]dioxol-5-ylthio)-9-(3-(isopropylamino)propyl)-9H-purin-6-amine, 8-(6-ethynylbenzo[d][1,3]dioxol-5-ylthio)-9-(2-(isobutylamino)ethyl)-9H-purin-6-amine, 1-(3-(2-(6-amino-8-(6-ethynylbenzo[d][1,3]dioxol-5-ylthio)-9H-purin-9-yl)ethyl)piperidin-1-yl)ethanone, 8-(6-ethynylbenzo[d][1,3]dioxol-5-ylyhio)-9-(2-(1-(methylsulfonyl)piperidin-3-yl)ethyl)-9H-purin-6-amine, N-(2-((2-(6-amino-8-((6-ethynylbenzo[d][1,3]dioxol-5-yl)thio)-9H-purin-9-yl)ethyl)amino)ethyl)sulfamide, 3-(2-(6-amino-8-(6-ethynylbenzo[d][1,3]dioxol-5-ylthio)-9H-purin-9-yl)ethylamino)-N-hydroxypropanamide, 8-(6-ethynylbenzo[d][1,3]dioxol-5-ylthio)-9-(2-(neopentylamino)ethyl)-9H-purin-6-amine, 8-((6-ethynylbenzo[d][1,3]dioxol-5-yl)methyl)-2-fluoro-9-(2-(isobutylamino)ethyl)-9H-purin-6-amine, 9-(3-aminopropyl)-8-(6-ethynylbenzo[d][1,3]dioxol-5-ylthio)-9H-purin-6-amine, 9-(2-aminoethyl)-8-(6-ethynylbenzo[d][1,3]dioxol-5-ylthio)-9H-purin-6-amine, 9-(3-(tert-butylamino)propyl)-8-(6-ethynylbenzo[d][1,3]dioxol-5-ylthio)-9H-purin-6-amine, 1-(3-(6-amino-8-(6-ethynylbenzo[d][1,3]dioxol-5-ylthio)-9H-purin-9-yl)propyl)pyrrolidin-3-one, 3-(2-(6-amino-8-((6-ethynylbenzo[d][1,3]dioxol-5-ylthio)-9H-purin-9-yl)ethyl)piperidine-1-sulfonamide, 6-(6-amino-8-(6-ethynylbenzo[d][1,3]dioxol-5-ylthio)-9H-purin-9-yl)hexanamide, 1-(6-amino-8-(6-ethynylbenzo[d][1,3]dioxol-5-ylthio)-9H-purin-9-yl)-3-(tert-butylamino)propan-2-ol, 1-(2-((2-(6-amino-8-(6-ethynylbenzo[d][1,3]dioxol-5-ylthio)-9H-purin-9-yl)ethylamino)methyl)pyrrolidin-1-yl)ethanone, 5-(6-amino-8-(6-ethynylbenzo[d][1,3]dioxol-5-ylthio)-9H-purin-9-yl)pentane-1-sulfonamide, 8-(6-ethynylbenzo[d][1,3]dioxol-5-ylthio)-9-(2-(1-methylpiperidin-2-yl)ethyl)-9H-purin-6-amine, 8-(6-ethynylbenzo[d][1,3]dioxol-5-ylthio)-9-(2-(1-methylpiperidin-3-yl)ethyl)-9H-purin-6-amine, 1-(3-(4-(6-amino-8-((6-ethynylbenzo[d][1,3]dioxol-5-yl)methyl)-2-fluoro-9H-purin-9-yl)butyl)pyrrolidin-1-yl)ethanone; 5-(6-amino-8-((6-ethynylbenzo[d][1,3]dioxol-5-yl)methyl)-2-fluoro-9H-purin-9-yl)pentane-1-sulfonamide, 3-(2-(6-amino-2-chloro-8-((6-ethynylbenzo[d][1,3]dioxol-5-yl)methyl)-9H-purin-9-yl)ethyl)piperidine-1-carbaldehyde, 3-(2(6-amino-8-((6-ethynylbenzo[d][1,3]dioxol-5-yl)methyl)-2-fluoro-9H-purin-9-yl)ethyl)piperidine-1-sulfonamide, 8-((6-ethynylbenzo[d][1,3]dioxol-5-yl)methyl)-2-fluoro-9-(2-(isobutylamino)ethyl)-9H-purin-6-amine, 6-(6-amino-8-((6-ethynylbenzo[d][1,3]dioxol-5-yl)methyl)-2-fluoro-9H-purin-9-yl)hexanamide, 1-(3-(2-(6-amino-8-((6-ethynylbenzo[d][1,3]dioxol-5-yl)methyl)-2-fluoro-9H-purin-9-yl)ethyl)piperidin-1-yl)ethanone, 8-((6-ethynylbenzo[d][1,3]dioxol-5-yl)methyl)-2-fluoro-9-(2-(neopentylamino)ethyl)-9H-purin-6-amine, 8-((6-ethynylbenzo[d][1,3]dioxol-5-yl)methyl)-2-fluoro-9-(3-(isopropylamino)propyl)-9H-purin-6-amine, 9-(3-(tert-butylamino)propyl)-8-((6-ethynylbenzo[d][1,3]dioxol-5-yl)methyl)-2-fluoro-9H-purin-6-amine, 8-((6-ethynylbenzo[d][1,3]dioxol-5-yl)methyl)-2-fluoro-9-(2-(1-(methylsulfonyl)piperidin-3-yl)ethyl)-9H-purin-6-amine, 1-(3-(6-amino-8-((6-ethynylbenzo[d][1,3]dioxol-5-yl)methyl)-2-fluoro-9H-purin-9-yl)propyl)pyrrolidin-3-one, 8-((6-ethynylbenzo[d][1,3]dioxol-5-yl)methyl)-2-fluoro-9-(2-(1-methylpiperidin-3-yl)ethyl)-9H-purin-6-amine, 1-(2-((2-(6-amino-8-((6-ethynylbenzo[d][1,3]dioxol-5-yl)methyl)-2-fluoro-9H-purin-9-yl)ethylamino)methyl)pyrrolidin-1-yl)ethanone, and 8-((6-ethynylbenzo[d][1,3]dioxol-5-yl)methyl)-2-fluoro-9-(2-(1-methylpiperidin-2-yl)ethyl)-9H-purin-6-amine.

8. The compound of claim 1 wherein $X_2$ is an optionally substituted heteroaryl group.

9. The compound of claim 8 wherein $X_2$ is optionally substituted furanyl.

10. The compound of claim 9 wherein the compound is selected from the group consisting of: 8-(6-(furan-3-yl)benzo[d][1,3]dioxol-5-ylthio)-9-(3-(isopropylamino)propyl)-9H-purin-6-amine, 2-fluoro-8-((6-(furan-3-yl)benzo[d][1,3]dioxol-5-yl)methyl)-9-(2-(isobutylamino)ethyl)-9H-purin-6-amine, 8-((6-(furan-2-yl)benzo[d][1,3]dioxol-5-yl)thio)-9-(3-(isopropylamino)propyl)-9H-purin-6-amine, 8-((6-(furan-2-yl)benzo[d][1,3]dioxol-5-yl)thio)-9-(2-(neopentylamino)ethyl)-9H-purin-6-amine, 5-(6-((6-amino-9-(3-(isopropylamino)propyl)-9H-purin-8-yl)thio)benzo[d][1,3]dioxol-5-yl)furan-2-carbaldehyde, 9-(3-(isopropylamino)propyl)-8-((6-(5-methylfuran-2-yl)benzo[d][1,3]dioxol-5-yl)thio(-9H-purin-6-amine, 8-((6-(5-(aminomethyl)furan-2-yl)benzo[d][1,3]dioxol-5-yl)thio)-9-(3-(isopropylamino)propyl)-9H-purin-6-amine, 8-((6-(5-methylfuran-2-yl)benzo[d][1,3]dioxol-5-yl)thio)-9-(2-(neopentylamino)ethyl)-9H-purin-6-amine, 8-((6-(5-(aminomethyl)furan-2-yl)benzo[d][1,3]dioxol-5-yl)thio)-9-(2-(neopentylamino)ethyl)-9H-purin-6-amine, 1-(3-(2-(6-amino-8-((6-(5-methylfuran-2-yl)benzo[d][1,3]dioxol-5-ylthio)-9H-purin-9-yl)ethyl)piperidin-1-yl)ethanone, 8-(6-(5-methylfuran-2-yl)benzo[d][1,3]dioxol-5-ylthio)-9-(2-(1-(methylsulfonyl)piperidin-3-yl)ethyl)-9H-purin-6-amine, 1-(4-(2-(6-amino-8-((6-(5-(aminomethyl)furan-2-yl)benzo[d][1,3]dioxol-5-yl)thio)-9H-purin-9-yl)ethyl)piperidin-1-yl)ethanone, N-(2-((2-(6-amino-8-((6-(5-methylfuran-2-yl)benzo[d][1,3]diozol-5-yl)thio)-9H-purin-9-yl)ethyl)amino)ethyl)sulfamide, 3-(2-(6-amino-8-(6-(5-methylfuran-2-yl)benzo[d][1,3]dioxol-5-ylthio)-9H-purin-9-yl)ethylamino)-N-hydroxypropanamide, 9-(3-(tert-buiylamino)propyl)-8-(6-(5-methylfuran-2-yl)benzo[d][1,3]dioxol-5-ylthio)-9H-purin-6-amine, 1-(6-amino-8-(6-(5-methylfuran-2-yl)benzo[d][1,3]dioxol-5-ylthio)-9H-purin-9-yl)-3-(tert-butylamino)propan-2-ol, 2-(3-(6-amino-8-(6-(5-methylfuran-2-yl)benzo[d][1,3]dioxol-5-ylthio)-9H-purin-9-yl(propyl)aziridine-1-carbaldehyde, 5-(6-amino-8-(6-(5-methylfuran-2-yl)benzo[d][1,3]dioxol-5-ylthio)-9H-purin-9-yl)pentane-1-sulfonamide, 1-(3-(2-(6-amino-2-fluoro-8-((6-(5-methylfuran-2-yl)benzo[d][1,3]dioxol-5-yl)methyl)-9H-purin-9-yl)ethyl)piperidin-1-yl)ethanone, 4-(2-(6-amino-2-fluoro-8-((6-(furan-2-yl)benzo[d][1,3]dioxol-5-yl)methyl)-9H-purin-9-yl)ethyl)piperidine-1-carbaldehyde, 1-(4-(2-(6-amino-2-fluoro-8-((6-(5-methylfuran-2-yl)benzo[d][1,3]dioxol-5-yl)methyl)-9H-purin-9-yl)ethyl)piperidin-1-yl)ethanone, 1-(4-(2-(6-amino-2-chloro-8-((6-(5-methylfuran-2-yl)benzo[d][1,3]dioxol-5-yl)methyl)-9H-purin-9-yl)ethyl)piperidin-1-yl)ethanone, 1-(4-(2-(6-amino-8-((6-(5-(aminomethyl)furan-2-yl)benzo[d][1,3]dioxol-5-yl)thio)-9H-purin-9-yl)ethyl)piperidin-1-yl)ethanone, 2-fluoro-8-((6-(furan-2-yl)benzo[d][1,3]dioxol-5-yl)methyl)-9-(2-(isobutylamino)ethyl)-9H-purin-6-amine, 5-(6-((6-amino-2-fluoro-9-(2-(isobutylamino)ethyl)-9H-purin-8-yl)methyl)benzo[d][1,3]dioxol-5-yl)furan-2-carbaldehyde, 2-fluoro-9-(2-(isobutylamino)ethyl)-8-((6-(5-methylfuran-2-yl)benzo[d][1,3]dioxol-5-yl)methyl)-9H-purin-6-amine, 8-((6-(5-(aminomethyl)furan-2-yl)benzo[d][1,3]dioxol-5-yl)methyl)-2-fluoro-9-(2-(isobutylamino)ethyl)-9H-purin-6-amine, 5-(6-amino-2-fluoro-8-((6-(5-methylfuran-2-yl)benzo[d][1,3]dioxol-5-yl)methyl)-9H-purin-9-yl)pentane-1-sulfonamide, 6-(6-amino-2-(fluoro-8-((6-(5-methylfuran-2-yl)benzo[d][1,3]dioxol-5-yl)methyl)-9H-purin-9-yl)hexanamide, 2-fluoro-9-(3-(isopropylamino)propyl)-8-((6-(5-methylfuran-2-yl)benzo[d][1,3]dioxol-5-yl)methyl)-9H-purin-6-amine, 9-(3-(tert-butylamino)propyl)-2-fluoro-8-((6-(5-methylfuran-2-yl)benzo[d][1,3]dioxol-5-yl)methyl)-9H-purin-6-amine, and 9-(3-aminopropyl)-2-fluoro-8-((6-(5-methylfuran-2-yl)benzo[d][1,3]dioxol-5-yl)methyl)-9H-purin-6-amine.

11. The compound of claim 8 wherein $X_2$ is optionally substituted oxazolyl.

12. The compound of claim 11 wherein the compound is selected from the group consisting of: 8-(6-(5-methyloxazol-2-yl)benzo[d][1,3]dioxol-5-ylthio)-9-(2-(neopentylamino)ethyl)-9H-purin-6-amine, 6-(6-amino-8-(6-(5-methyloxazol-2-yl)benzo[d][1,3]dioxol-5-ylthio)-9H-purin-9-yl)hexanamide, 1-(3-(2-(6-amino-8-(6-(5-methyloxazol-2-yl)benzo[d][1,3]dioxol-5-ylthio)-9H-purin-9-yl)ethyl)piperidin-1-yl)ethanone, 9-(3-(isopropylamino)propyl)-8-((6-oxazol-2-yl)benzo[d][1,3]dioxol-5-yl)thio)-9H-purin-6-amine, 9-(3-aminopropyl)-8-(6-(5-methyloxazol-2-yl)benzo[d][1,3]dioxol-5-ylthio)-9H-purin-6-amine, 9-(3-(tert-butylamino)propyl)-8-((6-(oxazol-2-yl)benzo[d][1,3]dioxol-5-yl)thio)-9H-purin-6-amine, 1-(4-(2-(6-amino-8-((6-(oxazol-2-yl)benzo[d][1,3]dioxol-5-yl)thio)-9H-purin-9-yl(ethyl)piperidin-1-yl)ethanone, 8-((6-(5-methyloxazol-2-yl)benzo[d][1,3]dioxol-5-yl)thio)-9-(2-(1-(methylsulfonyl)piperidin-3-yl)ethyl)-9H-purin-6-amine, 9-(3-(tert-butylamino)propyl)-8-((6-(5-methyloxazol-2-yl)benzo[d][1,3]dioxol-5-yl)thio)-9H-purin-6-amine, 1-(6-amino-8-((6-(5-methyloxazol-2-yl)benzo[d][1,3]dioxol-5-yl)thio)-9H-purin-9-yl)-3-(isopropylamino)propan-2-ol, 5-(6-amino-8-(6-(5-methyloxazol-2-yl)benzo[d][1,3]dioxol-5-ylthio)-9H-purin-9-yl)pentane-1-sulfonamide, 8-(6-(5-methyloxazol-2-yl)benzo[d][1,3]dioxol-5-ylthio)-9-(3-(1-(methylsulfonyl)pyrrolidin-3-yl)propyl)-9H-purin-6-amine, 1-(3-(6-amino-8-(6-(5-methyloxazol-2-yl)benzo[d][1,3]dioxol-5-ylthio)-9H-purin-9-yl)propyl)pyrrolidin-3-one, 1-(3-(2-(6-amino-2-fluoro-8-((6-(5-methyloxazol-2-yl)benzo[d][1,3]dioxol-5-yl)methyl)-9H-purin-9-yl)ethyl)piperidin-1-yl)ethanone, 3-(2-(6-amino-2-chloro-8-((6-(5-methyloxazol-2-yl)benzo[d][1,3]dioxol-5-yl)methyl)-9H-purin-9-yl)ethyl)piperidine-1-sulfonamide, 1-(3-(2-(6-amino-8-((6-(5-(aminomethyl)oxazol-2-yl)benzo[d][1,3]dioxol-5-yl)methyl)-2-fluoro-9H-purin-9-yl)ethyl)piperidin-1-yl)ethanone, 2-fluoro-9-(2-(isobutylamino)ethyl)-8-((6-(oxazol-2-yl)benzo[d][1,3]dioxol-5-yl)methyl)-9H-purin-6-amine, 1-(3-(6-amino-2-fluoro-8-((6-(5-methyloxazol-2-yl)benzo[d][1,3]dioxol-5-yl)methyl)-9H-purin-9-yl)propyl)pyrrolidin-3-one, 6-(6-amino-2-fluoro-8-((6-(5-methyloxazol-2-yl)benzo[d][1,3]dioxol-5-yl)methyl)-9H-purin-9-yl)hexanamide, 5-(6-amino-2-fluoro-8-((6-(5-methyloxazol-2-yl)benzo[d][1,3]dioxol-5-yl)methyl)-9H-purin-9-yl)pentane-1-sulfonamide, 2-fluoro-9-(3-(isopropylamino)propyl)-8-((6-(5-methyloxazol-2-yl)benzo[d][1,3]dioxol-5-yl)methyl)-9H-purin-6-amine, 9-(3-(tert-butylamino)propyl)-2-fluoro-8-((6-(5-methyloxazol-2-yl)benzo[d][1,3]dioxol-5-yl)methyl)-9H-purin-6-amine, 9-(3-(tert-butylamino)propyl)-2-fluoro-8-((6-(oxazol-2-yl)benzo[d][1,3]dioxol-5-yl)methyl)-9H-purin-6-amine, and 9-(3-aminopropyl)-2-fluoro-8-((6-(5-methyloxazol-2-yl)benzo[d][1,3]dioxol-5-yl)methyl)-9H-purin-6-amine.

13. The compound of claim 8 wherein $X_2$ is optionally substituted pyrazolyl.

14. The compound of claim 13 wherein the compound is selected from the group consisting of: 8-((6-(1H-pyrazol-3-yl)benzo[d][1,3]dioxol-5-yl)thio)-9-(3-(isopropylamino)propyl)-9H-purin-6-amine, 8-((6-(5-methyl-1H-pyrazol-3- yl)benzo[d][1,3]dioxol-5-yl)thio)-9-(2-(neopentylamino) ethyl)-9H-purin-6-amine, 1-(3-(2-(6-amino-8-(6-(5-methyl-1H-pyrazol-3-yl)benzo[d][1,3]dioxol-5-ylthio)-9H-purin-9-yl)ethyl)piperidin-1-yl)ethanone, 8-((6-(1H-pyrazol-3-yl)benzo[d][1,3]dioxol-5-yl)thio)-9-(2-(neopentylamino) ethyl)-9H-purin-6-amine, 8-(6-(1H-pyrazol-3-yl)benzo[d][1,3]dioxol-5-ylthio)-9-(2-(1-(methylsulfonyl)piperidin-3-yl)ethyl)-9H-purin-6-amine, 1-(3-(2-(8-(6-(1H-pyrazol-3-yl)benzo[d][1,3]dioxol-5-ylthio)-6-amino-9H-purin-9-yl) ethyl)piperidin-1-yl)ethanone, 1-(3-(2-(6-amino-8-(6-(5-methyl-1H-pyrazol-3-yl)benzo[d][1,3]dioxol-5-ylthio)-9H-purin-9-yl)ethyl)piperidin-1-yl)ethanone, 4-(2-(8-((6-(1H-pyrazol-3-yl)benzo[d][1,3]dioxol-5-yl)thio(-6-amino-9H-purin-9-yl)piperidine-1-carbaldehyde, N-(2-((2-(8-((6-(1H-pyrazol-3-yl)benzo[d][1,3]dioxol-5-yl)thio)-6-amino-9H-purin-9-yl)ethyl)amino)ethyl)sulfamide, N-(2-((2-(8-((6-(1H-pyrazol-3-yl)benzo[d][1,3]dioxol-5-yl)thio)-6-amino-9H-purin-9-yl)ethyl)amino)ethyl)sulfamide, 3-((2-(8-((6-(1H-pyrazol-3-yl)benzo[d][1,3]dioxol-5-yl)thio)-6-amino-9H-purin-9-yl)ethyl)amino)-N-hydroxypropanamide, 8-((6-(1H-pyrazol-3-yl)benzo[d][1,3]dioxol-5-yl)thio)-9-(3-aminopropyl)-9H-purin-6-amine, 8-((6-(1H-pyrazol-3-yl)benzo[d][1,3]dioxol-5-yl)thio)-9-(3-(tert-butylamino) propyl)-9H-purin-6-amine, 1-(8-((6-(1H-pyrazol-3-yl)benzo[d][1,3]dioxol-5-yl)thio)-6-amino-9H-purin-9-yl)-3-(isopropylamino)propan-2-ol, 5-(8-(6-(1H-pyrazol-3-yl)benzo[d][1,3]dioxol-5-ylthio)-6-amino-9H-purin-9-yl)pentane-1-sulfonamide, 6-(8-(6-(1H-pyrazol-3-yl) benzo[d][1,3]dioxol-5-ylthio)-6-amino-9H-purin-9-yl)hexanamide, 1-(3-(8-(6-(1H-pyrazol-3-yl)benzo[d][1,3]dioxol-5-ylthio)-6-amino-9H-purin-9-yl(propyl)pyrrolidin-3-one, 8-((6-(1H-pyrazol-3-yl)benzo[d][1,3]dioxol-5-yl)methyl)-2-fluoro-9-(2-(isobutylamino)ethyl)-9H-purin-6-amine, 2-fluoro-9-(2-(isobutylamino)ethyl)-8-((6-(5-methyl-1H-pyrazol-3-yl) benzo[d][1,3]dioxol-5-yl)methyl)-9H-purin-6-amine, 8-((6-(1H-pyrazol-3-yl)benzo[d][1,3]dioxol-5-yl)methyl)-2-fluoro-9-(2-(1-(methylsulfonyl)piperidin-3-yl)ethyl)-9H-purin-6-amine, 1-(3-(2-(8-((6-(1H-pyrazol-3-yl)benzo[d][1,3]dioxol-5-yl)methyl)-6-amino-2-fluoro-9H-purin-9-yl) ethyl)piperidin-1-yl)ethanone, 4-(2-(8-((6-(1H-pyrazol-3-yl)benzo[d][1,3]dioxol-5-yl)methyl-6-amino-2-chloro-9H-purin-9-yl)ethyl)piperidine-1-carbaldehyde, 8-((6-(1H-pyrazol-3-yl)benzo[d][1,3]dioxol-5-yl)methyl)-9-(2-aminoethyl)-2-fluoro-9H-purin-6-amine, 1-(3-(8-((6-(1H-pyrazol)-3-yl)benzo[d][1,3]dioxol-5-yl)methyl)-6-amino-2-fluoro-9H-purin-9-yl)propyl)pyrrolidin-3-one, 5-(8-((6-(1H-pyrazol-3-yl)benzo[d][1,3]dioxol-5-yl)methyl)-6-amino-2-fluoro-9H-purin-9-yl)pentane-1-sulfonamide, 6-(8-((6-(1H-pyrazol-3-yl)benzo[d][1,3]dioxol-5-yl)methyl)-6-amino-2-fluoro-9H-purin-9-yl)hexanamide, and 8-((6-(1H-pyrazol-3-yl)benzo[d][1,3]dioxol-5-yl)methyl)-9-(3-(tert-butylamino) propyl)-2-fluoro-9H-purin-6-amine.

15. The compound of claim 8 wherein $X_2$ is optionally substituted thiazolyl.

16. The compound of claim 15 wherein the compound is selected from the group consisting of: 9-(3-(isopropylamino)propyl)-8-((6-(thiazol-2-yl)benzo[d][1,3]dioxol-5-yl)thio)-9H-purin-6-amine, 2-fluoro-9-(2-(isobutylamino)ethyl)-8-((6-(thiazol-2-yl)benzo[d][1,3]dioxol-5-yl)methyl)-9H-purin-6-amine, 9-(3-(tert-butylamino)propyl)-8-((6-(thiazol-2-yl)benzo[d][1,3]dioxol-5-yl)thio)-9H-purin-6-amine, 9-(3-(tert-butylamino)propyl)-8-((6-(5-methylthiazol-2-yl) benzo[d][1,3]dioxol-5-yl)thio)-9H-purin-6-amine, 1-(3-(2-(6-amino-8-(6-(5-methylthiazol-2-yl)benzo[d][1,3]dioxol-5-ylthio)-9H-purin-9-yl)ethyl)piperidin-1-yl)ethanone, 1-(6-amine-8-((6-(5-methylthiazol-2-yl)benzo[d][1,3]dioxol-5-yl)thio)-9H-purin-9-yl)-3-(isopropylamino)propan-2-ol, 5-(6-amino-8-(6-(5-methylthiazol-2-yl)benzo[d][1,3]di-oxol-5-ylthio)-9H-purin-9-yl)pentane-1-sulfonamide, 2-(2-(6-amine-8-(6-(5-methylthiazol-2-yl)benzo[d][1,3]dioxol-5-ylthio)-9H-purin-9-yl)ethyl)pyrrolidine-1-carbaldehyde, 2-fluoro-9-(2-(isobutylamino)ethyl)-8-((6-(5-methylthiazol-2-yl)benzo[d][1,3]dioxol-5-yl)methyl)-9H-purin-6-amine, and 8-((6-(5-methylthiazol-2-yl)benzo[d][1,3]dioxol-5-yl) thio)-9-(2-(neopentylamino)ethyl)-9H-purin-6-amine.

17. A pharmaceutical composition for the inhibition of Hsp90 comprising a compound of claim 1 together with a pharmaceutically acceptable carrier.

18. A compound of the formula (1A), (1B), or (4):

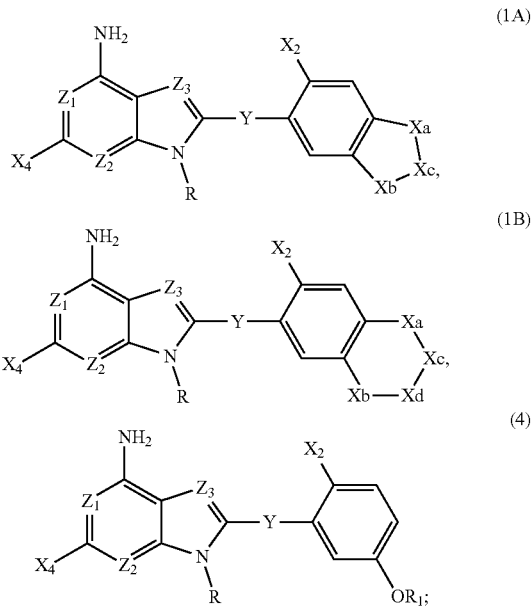

wherein the variable substituents of the formula (1A) are selected from one of the following groups (A)-(D), the variable substituents of the formula (1B) are selected from groups (E) and (F), and the variable substituents of the formula (4) are described in group (G):

(A) (a) each of $Z_1$, $Z_2$ and $Z_3$ is independently N;
(b) Xa-Xc-Xb is $CH_2—CH_2—CH_2$, $CH=CH—CH_2$, or $CH_2—CH=CH$;
(c) Y is $—CH_2—$ or $—S—$;
(d) $X_4$ is hydrogen or halogen; and
(e) $X_2$ is alkynyl, aryl, cycloalkyl, or cycloalkenyl, each of which is optionally substituted, and R is:
(a) hydrogen; or
(b) a straight-chain- or branched-$C_1$ to $C_{10}$ alkyl, $C_2$ to $C_6$ alkenyl, or $C_2$ to $C_6$ alkynyl, which is unsubstituted or substituted; or
(c) aryl, heteroaryl, heterocyclic, cycloalkyl, alkylaryl, or arylalkyl, which is unsubstituted or substituted; or
(d) $—SR_{71}$, $—S(O)R_{71}$, $—SO_2R_{71}$, $—OR_{71}$, $—COOR_{71}$, $—CONR_{71}R_{72}$, $—CN$, $—R_{7A}OR_{7B}$, $—R_{7A}NR_{7B}$, $—R^{7A}NR_{71}R_{7B}$, $—R_{7A}SR_{7B}$, $—R_{7A}S(O)R_{7B}$, $—R_{7A}SO_2R_{7B}$, $—NR_{71}R_{72}$, $—OSO_2N(R_{7C})_2$, $—N(R_{7C})SO_2OH$, $—N(R_{7C})SO_2R_{7C}$, $—R_{7A}OSO_2N(R_{7C})_2$, or $—R_{7A}N(R_{7C})OSO_2R_{7C}$,
wherein each $R_{71}$ and $R_{72}$ is independently selected from the group consisting of hydrogen, $COOR_{7B}$, $CON(R_{7C})_2$, $C_1$ to $C_6$ alkyl, $C_2$ to $C_6$ alkenyl, $C_2$ to $C_6$ alkynyl, $—R_{7A}OR_{7B}$, $—R_{7A}NR_{7B}$, $—R_{7A}SR_{7B}$, —$R_{7A}S(O)R_{7B}$, —$R_{7A}SO_2R_{7B}$, cycloalkyl, heterocycloalkyl, aryl, heteroaryl, alkylaryl, arylalkyl, alkylheteroaryl, and heteroarylalkyl, each $R_{7A}$ is independently $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, or arylalkyl, and each $R_{7B}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, heteroarylalkyl, —$SO_2OH$, —$SO_2N(R_{7A})_2$, —$SO_2NHR_{7A}$, or —$SO_2NH_2$; and each $R_{7C}$, is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, or heteroarylalkyl;

(B) (a) each of $Z_1$, $Z_2$ and $Z_3$ is independently N;
(b) one of Xa and Xb is O and Xc and the other of Xa and Xb are —$CH_2$—;
(c) Y is —$CH_2$— or —S—;
(d) $X_4$ is hydrogen or halogen; and
(e) $X_2$ is an aryl, an alkynyl, a cycloalkyl, or a cycloalkenyl, each of which is optionally substituted, and R is:
(a) hydrogen; or
(b) a straight-chain- or branched-$C_1$ to $C_{10}$ alkyl, $C_2$ to $C_6$ alkenyl, or $C_2$ to $C_6$ alkynyl, which is unsubstituted or substituted; or
(c) aryl, heteroaryl, heterocyclic, cycloalkyl, alkylaryl, or arylalkyl, which is unsubstituted or substituted; or
(d) —$SR_{71}$, —$S(O)R_{71}$, —$SO_2R_{71}$, —$OR_{71}$, —$COOR_{71}$, —$CONR_{71}R_{72}$, —CN, —$R_{7A}OR_{7B}$, —$R_{7A}NR_{7B}$, —$R_{7A}NR_{71}R_{7B}$, —$R_{7A}SR_{7B}$, —$R_{7A}S(O)R_{7B}$, —$R_{7A}SO_2R_{7B}$, —$NR_{71}R_{72}$, —$OSO_2N(R_{7C})_2$, —$N(R_{7C})SO_2OH$, —$N(R_{7C})SO_2R_{7C}$, —$R_{7A}OSO_2N(R_{7C})_2$, or —$R_{7A}N(R_{7C})OSO_2R_{7C}$, wherein each $R_{71}$ and $R_{72}$ is independently selected from the group consisting of hydrogen, $COOR_{7B}$, $CON(R_{7C})_2$, $C_1$ to $C_6$ alkyl, $C_2$ to $C_6$ alkenyl, $C_2$ to $C_6$ alkynyl, —$R_{7A}OR_{7B}$, —$R_{7A}NR_{7B}$, —$R_{7A}SR_{7B}$, —$R_{7A}S(O)R_{7B}$, —$R_{7A}SO_2R_{7B}$, cycloalkyl, heterocycloalkyl, aryl, heteroaryl, alkylaryl, arylalkyl, alkylheteroaryl, and heteroarylalkyl, each $R_{7A}$ is independently $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, or arylalkyl, and each $R_{7B}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, heteroarylalkyl, —$SO_2OH$, —$SO_2N(R_{7A})_2$, —$SO_2NHR_{7A}$, or —$SO_2NH_2$; and each $R_{7C}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, or heteroarylalkyl;

(C) (a) each of $Z_1$, $Z_2$ and $Z_3$ is independently N;
(b) one of Xa and Xb is S, C(=O), C(=S), NH or substituted N, and Xc and the other of Xa and Xb are —$CH_2$—;
(c) Y is —$CH_2$— or —S—;
(d) $X_4$ is hydrogen or halogen;
(e) $X_2$ is alkynyl, aryl, cycloalkyl, or cycloalkenyl, each of which is optionally substituted; and (f) R is:
(a) hydrogen; or
(b) a straight-chain- or branched-$C_1$ to $C_{10}$ alkyl, $C_2$ to $C_6$ alkenyl, or $C_2$ to $C_6$ alkynyl, which is unsubstituted or substituted; or
(c) aryl, heteroaryl, heterocyclic, cycloalkyl, alkylaryl, or arylalkyl, which is unsubstituted or substituted; or
(d) —$SR_{71}$, —$S(O)R_{71}$, —$SO_2R_{71}$, —$OR_{71}$, —$COOR_{71}$, —$CONR_{71}R_{72}$, —CN, —$R_{7A}OR_{7B}$, —$R_{7A}NR_{7B}$, —$R_{7A}NR_{71}R_{7B}$, —$R_{7A}SR_{7B}$, —$R_{7A}S(O)R_{7B}$, —$R_{7B}SO_2R_{7B}$, —$NR_{71}R_{72}$, —$OSO_2N(R_{7C})_2$, —$N(R_{7C})SO_2OH$, —$N(R_{7C})SO_2R_{7C}$, —$R_{7A}OSO_2N(R_{7C})_2$, or —$R_{7A}N(R_{7C})OSO_2R_{7C}$, wherein each $R_{71}$ and $R_{72}$ is independently selected from the group consisting of hydrogen, $COOR_{7B}$, $CON(R_{7C})_2$, $C_1$ to $C_6$ alkyl, $C_2$ to $C_6$ alkenyl, $C_2$ to $C_6$ alkynyl, —$R_{7A}OR_{7B}$, —$R_{7A}NR_{7B}$, —$R_{7A}SR_{7B}$, —$R_{7A}S(O)R_{7A}$, —$R_{7A}SO_2R_{7B}$, cycloalkyl, heterocycloalkyl, aryl, heteroaryl, alkylaryl, arylalkyl, alkylheteroaryl, and heteroarylalkyl, each $R_{7A}$ is independently $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, or arylalkyl, and each $R_{7B}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, heteroarylalkyl, —$SO_2OH$, —$SO_2N(R_{7A})_2$, —$SO_2NHR_{7A}$, or —$SO_2NH_2$; and each $R_{7C}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, or heteroarylalkyl;

(D) (a) each of $Z_1$, $Z_2$ and $Z_3$ is independently N;
(b) Xa-Xc-Xb is CH=CH—O, CH=CH—NH, CH=CH—S, O—CH=CH, NH—CH=CH, S—CH=CH, N=CH—O, N=CH—S, NH—CH=N, O—CH=N, S—CH=N, N=N—O, N=N—S, N=N—$CH_2$, O—N=N, NH—N=N, S—N=N, or $CH_2$—N=N;
(c) Y is —$CH_2$— or —S—;
(d) $X_4$ is hydrogen or halogen;
(e) $X_2$ is alkynyl, aryl, cycloalkyl, or cycloalkenyl, each of which is optionally substituted; and
(f) R is:
(a) hydrogen; or
(b) a straight-chain- or branched-$C_1$ to $C_{10}$ alkyl, $C_2$ to $C_6$ alkenyl, or $C_2$ to $C_6$ alkynyl, which is unsubstituted or substituted; or
(c) aryl, heteroaryl, heterocyclic, cycloalkyl, alkylaryl, or arylalkyl, which is unsubstituted or substituted; or
(d) —$SR_{71}$, —$S(O)R_{71}$, —$SO_2R_{71}$, —$OR_{71}$, —$COOR_{71}$, —$CONR_{71}R_{72}$, —CN, —$R_{7A}OR_{7B}$, —$R_{7A}NR_{7B}$, —$R_{7A}NR_{71}R_{7B}$, —$R_{7A}SR_{7B}$, —$R_{7A}S(O)R_{7B}$, —$R_{7A}SO_2R_{7B}$, —$NR_{71}R_{72}$, —$OSO_2N(R_{7C})_2$, —$N(R_{7C})SO_2OH$, —$N(R_{7C})SO_2R_{7C}$, —$R_{7A}OSO_2N(R_{7C})_2$, or —$R_{7A}N(R_{7C})OSO_2R_{7C}$, wherein each $R_{71}$ and $R_{72}$ is independently selected from the group consisting of hydrogen, $COOR_{7B}$, $CON(R_{7C})_2$, $C_1$ to $C_6$ alkyl, $C_2$ to $C_6$ alkenyl, $C_2$ to $C_6$ alkynyl, —$R_{7A}OR_{7B}$, —$R_{7A}NR_{7B}$, —$R_{7A}SR_{7B}$, —$R_{7A}S(O)R_{7B}$, —$R_{7A}SO_2R_{7B}$, cycloalkyl, heterocycloalkyl, aryl, heteroaryl, alkylaryl, arylalkyl, alkylheteroaryl, and heteroarylalkyl, each $R_{7A}$ is independently $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, or arylalkyl, and each $R_{7B}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, heteroarylalkyl, —SO$_2$OH, —SO$_2$N(R$_{7A}$)$_2$, —SO$_2$NHR$_{7A}$, or —SO$_2$NH$_2$; and each $R_{7C}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, or heteroarylalkyl;

(E) (a) each of $Z_1$, $Z_2$ and $Z_3$ is independently N;
(b) Xa and Xb are O, and Xc and Xd are CH$_2$;
(c) Y is —CH$_2$—, —O— or —S—;
(d) $X_4$ is hydrogen or halogen; and
(e) $X_2$ is aryl, alkynyl, cycloalkyl or cycloalkenyl, each of which is optionally substituted, and R is:
(a) hydrogen; or
(b) a straight-chain- or branched-$C_1$ to $C_{10}$ alkyl, $C_2$ to $C_6$ alkenyl, or $C_2$ to $C_6$ alkynyl, which is unsubstituted or substituted; or
(c) aryl, heteroaryl, heterocyclic, cycloalkyl, alkylaryl, or arylalkyl, which is unsubstituted or substituted; or
(d) —SR$_{71}$, —S(O)R$_{71}$, —SO$_2$R$_{71}$, —OR$_{71}$, —COOR$_{71}$, —CONR$_{71}$R$_{72}$, —CN, —R$_{7A}$OR$_{7B}$, —R$_{7A}$NR$_{7B}$, —R$_{7A}$NR$_{71}$R$_{7B}$, —R$_{7A}$SR$_{7B}$, —R$_{7A}$S(O)R$_{7B}$, —R$_{7A}$SO$_2$R$_{7B}$, —NR$_{71}$R$_{72}$, —OSO$_2$N(R$_{7C}$)$_2$, —N(R$_{7C}$)SO$_2$OH, —N(R$_{7C}$)SO$_2$R$_{7C}$, —R$_{7A}$OSO$_2$N(R$_{7C}$)$_2$, or —R$_{7A}$N(R$_{7C}$)OSO$_2$R$_{7C}$, wherein each $R_{71}$ and $R_{72}$ is independently selected from the group consisting of hydrogen, COOR$_{7B}$, CON(R$_{7C}$)$_2$, $C_1$ to $C_6$ alkyl, $C_2$ to $C_6$ alkenyl, $C_2$ to $C_6$ alkynyl, —R$_{7A}$OR$_{7B}$, —R$_{7A}$NR$_{7B}$, —R$_{7A}$SR$_{7B}$, —R$_{7A}$S(O)R$_{7B}$, —R$_{7A}$SO$_2$R$_{7B}$, cycloalkyl, heterocycloalkyl, aryl, heteroaryl, alkylaryl, arylalkyl, alkylheteroaryl, and heteroarylalkyl, each $R_{7A}$ is independently $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, or arylalkyl, and each $R_{7B}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, heteroarylalkyl, —SO$_2$OH, —SO$_2$N(R$_{7A}$)$_2$, —SO$_2$NHR$_{7A}$, or —SO$_2$NH$_2$; and each $R_{7C}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, or heteroarylalkyl;

(F) (a) each of $Z_1$, $Z_2$ and $Z_3$ is independently N;
(b) Xa, Xc, Xd and Xb are all carbon connected by single or double bonds;
(c) Y is —CH$_2$—, —O— or —S—;
(d) $X_4$ is hydrogen or halogen;
(e) $X_2$ is alkynyl, aryl, cycloalkyl, or cycloalkenyl, each of which is optionally substituted; and
(f) R is:
(a) hydrogen; or
(b) a straight-chain- or branched-$C_1$ to $C_{10}$ alkyl, $C_2$ to $C_6$ alkenyl, or $C_2$ to $C_6$ alkynyl, which is unsubstituted or substituted; or
(c) aryl, heteroaryl, heterocyclic, cycloalkyl, alkylaryl, or arylalkyl, which is unsubstituted or substituted; or
(d) —SR$_{71}$, —S(O)R$_{71}$, —SO$_2$R$_{71}$, —OR$_{71}$, —COOR$_{71}$, —CONR$_{71}$R$_{72}$, —CN, —R$_{7A}$OR$_{7B}$, —R$_{7A}$NR$_{7B}$, —R$_{7A}$NR$_{71}$R$_{7B}$, —R$_{7A}$SR$_{7B}$, —R$_{7A}$S(O)R$_{7B}$, —R$_{7A}$SO$_2$R$_{7B}$, —NR$_{71}$R$_{72}$, —OSO$_2$N(R$_{7C}$)$_2$, —N(R$_{7C}$)SO$_2$OH, —N(R$_{7C}$)SO$_2$R$_{7C}$, —R$_{7A}$OSO$_2$N(R$_{7C}$)$_2$, or —R$_{7A}$N(R$_{7C}$)OSO$_2$R$_{7C}$, wherein each $R_{71}$ and $R_{72}$ is independently selected from the group consisting of hydrogen, COOR$_{7B}$, CON(R$_{7C}$)$_2$, $C_1$ to $C_6$ alkyl, $C_2$ to $C_6$ alkenyl, $C_2$ to $C_6$ alkynyl, —R$_{7A}$OR$_{7B}$, —R$_{7A}$NR$_{7B}$, —R$_{7A}$SR$_{7B}$, —R$_{7A}$S(O)R$_{7B}$, —R$_{7A}$SO$_2$R$_{7B}$, cycloalkyl, heterocycloalkyl, aryl, heteroaryl, alkylaryl, arylalkyl, alkylheteroaryl, and heteroarylalkyl, each $R_{7A}$ is independently $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, or arylalkyl, and each $R_{7B}$ is independently hydrogen, $C_1$ to $C_6$ alkyl, $C_2$ to $C_6$ alkenyl, $C_2$ to $C_2$ alkynyl, cycloalkyl, heterocycloalkyl, aryl, heteroaryl, alkylaryl, arylalkyl, alkylheteroaryl, heteroarylalkyl, —SO$_2$OH, —SO$_2$N(R$_{7A}$)$_2$, —SO$_2$NHR$_{7A}$, or —SO$_2$NH$_2$; and each $R_{7C}$ is independently hydrogen, $C_1$ to $C_6$ alkyl, $C_2$ to $C_6$ alkenyl, $C_2$ to $C_6$ alkynyl, cycloalkyl, heterocycloalkyl, aryl, heteroaryl, alkylaryl, arylalkyl, alkylheteroaryl, or heteroarylalkyl;

(G) (a) $R_1$ is alkyl;
(b) Y is —CH$_2$— or —S—;
(c) $X_4$ is H or halogen;
(d) $X_2$ is cycloalkyl, cycloalkenyl, aryl, or alkynyl, each of which is optionally substituted; and
(e) R is hydrogen or linear, branched, or cyclic alkyl, alkenyl, or alkynyl, optionally including N, S, or O, and optionally part of an 8 to 10 member ring formed by joining the 2'-position $X_2$ and R.

19. The compound of claim 8 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 2-(hydroxyethyl(isopropyl)amino)ethyl, 3-(cyclopentylamino)propyl, 3-(cyclopentyl(methyl)amino)propyl, 3-(ethylamino)propyl, 3-(ethyl(methyl)amino)propyl, 2-(neopentyl-amino)ethyl, 3-(methyl(isopropyl)amino)propyl, 3-(ethyl(isopropyl)amino)propyl, 3-(hydroxyethyl(isopropyl)amino)propyl, 3-(methyl(propargyl)amino)propyl, 2-(methyl(propargyl)amino)ethyl, 3-(allyl(methyl)amino)propyl, 3-(propyl(cyclopropylmethyl)amino)propyl, 3-(hydroxyethyl(cyclohexyl)amino)propyl, 2-(cyclopropylmethyl-amino)ethyl, and 2-(methyl(isobutyl)amino)ethyl.

20. The compound of claim 19 wherein R is 3-(isopropyl-amino)propyl.

21. The compound of claim 8 wherein the compound is selected from the group consisting of: 9-(3-(isopropylamino)propyl)-8-(6-(thiophen-2-yl)benzo[d][1,3]dioxol-5-ylthio)-9H-purin-6-amine, 8-(6-(1H-pyrrol-3-yl)benzo[d][1,3]dioxol-5-ylthio)-9-(3-(isopropylamino)propyl)-9H-purin-6-amine, 9-(3-(isopropylamino)propyl(-8-(6-(pyridin-4-yl)benzo[d][1,3]dioxol-5-ylthio)-9H-purin-6-amine, 8-(6-(1H-pyrazol-4-yl)benzo[d][1,3]dioxol-5-ylthio)-9-(3-(isopropylamino)propyl)-9H-purin-6-amine, 9-(3-(isopropylamino)propyl)-8-(6-(1-methyl-1H-pyrazol-5-yl)benzo[d][1,3]dioxol-5-ylthio)-9H-purin-6-amine, 9-(3-(isopropylamino)propyl)-8-(6-(isoxazol-4-yl)benzo[d][1,3]dioxol-5-ylthio)-9H-purin-6-amine, 8-((6-(1H-pyrrol-2-yl)benzo[d][1,3]dioxol-5-yl)methyl)-2-fluoro-9-(2-(isobutylamino)ethyl)-9H-purin-6-amine, 8-((6-(1H-pyrazol-4-yl)benzo[d][1,3]dioxol-5-yl)methyl)-2-fluoro-9-(2-(isobutylamino)ethyl)-9H-purin-6-amine, 8-((6-(1H- pyrrol-3-yl)benzo[d][1,3]dioxol-5-yl)methyl)-2-fluoro-9-(2-(isobutylamino)ethyl)-9H-purin-6-amine, 2-fluoro-9-(2-(isobutylamino)ethyl)-8-((6-(1-methyl-1H-pyrazol-5-yl)benzo[d][1,3]dioxol-5-yl)methyl)9H-purin-6-amine, 2-fluoro-9-(2-(isobutylamino)ethyl)-8-((6-(thiophen-2-yl)benzo[d][1,3]dioxol-5-yl)methyl)-9H-purin-6-amine, 2-fluoro-9-(2-(isobutylamino)ethyl)-8-((6-(isoxazol-4-yl(benzo[d][1,3]dioxol-5-yl)methyl)-9H-purin-6-amine, 9-(2-(neopentylamino)ethyl)-8-(6-(thiophen-2-yl)benzo[d][1,3]dioxol-5-ylthio)-9H-purin-6-amine, 8-(6-(1H-pyrrol-3-yl)benzo[d][1,3]dioxol-5-ylthio)-9-(2-(neopentylamino)ethyl)-9H-purin-6-amine, and 8-(6-(furan-3-yl)benzo[d][1,3]dioxol-5-ylthio)-9-(2-(neopentylamino)ethyl)-9H-purin-6-amine.

22. The compound of claim 1 wherein $X_2$ is optionally substituted aryl.

23. The compound of claim 22 wherein the compound is selected from the group consisting of: 9-(3-(isopropylamino)propyl)-8-(6-phenylbenzo[d][1,3]dioxol-5-ylthio)-9H-purin-6-amine, 8-(6-(4-tert-butylphenyl)benzo[d][1,3]dioxol-5-ylthio)-9-(3-(isopropylamino)propyl)-9H-purin-6-amine, 8-(6-(3,5-bis(trifluoromethyl)phenyl)benzo[d][1,3]dioxol-5-ylthio)-9-(3-(isopropylamino)propyl)-9H-purin-6-amine, 8-(6-(4-(dimethylamino)phenyl)benzo[d][1,3]dioxol-5-ylthio)-9-(3-(isopropylamino)propyl)-9H-purin-6-amine, 9-(3-(isopropylamino)propyl)-8-(6-(4-methoxyphenyl)benzo[d][1,3]dioxol-5-ylthio)-9H-purin-6-amine, 8-(6-(4-bromophenyl)benzo[d][1,3]dioxol-5-ylthio)-9-(3-(isopropylamino)propyl)-9H-purin-6-amine, 4-(6-(6-amino-9-(3-(isopropylamino)propyl)-9H-purin-8-ylthio)benzo[d][1,3]dioxol-5-yl)benzaldehyde, tert-Butyl-6-(3-(6-amino-8-(6-(3,5-bis(trifluoromethyl)phenyl)benzo[d][1,3]dioxol-5-ylthio)-9H-purin-9-yl)propylamino)hexylcarbamate, and N-(3-(6-amino-8-(6-(3,5-bis(trifluoromethyl)phenyl)benzo[d][1,3]dioxol-5-ylthio)-9H-purin-9-yl)propylamino)hexylcarbamate, and N-(3-(6-amino-8-(6-(3,5-bis(trifluoromethyl)phenyl)benzo[d][1,3]dioxol-5-ylthio)-9H-purin-9-yl)propyl)hexane-1,6-diamine.

24. The compound of claim 1 wherein $X_2$ is optionally substituted cycloalkenyl.

25. The compound of claim 24 wherein the compound is 8-(6-(cyclopent-2-enyl)benzo[d][1,3]dioxol-5-ylthio)-9-(3-(isopropylamino)propyl)-9H-purin-6-amine.

26. The compound of claim 1 wherein the compound is 8-(6-(2,5-dihydro-1H-pyrrol-2-yl)benzo[d][1,3]dioxol-5-ylthio)-9-(3-(isopropylamino)propyl)-9H-purin-6-amine, 8-(6-(2,3-dihydrofuran-2-yl)benzo[d][1,3]dioxol-5-ylthio)-9-(3-(isopropylamino)propyl)-9H-purin-6-amine, or 8-(6-(2,3-dihydrofuran-3-yl)benzo[d][1,3]dioxol-5-ylthio)-9-(3-(isopropylamino)propyl)-9H-purin-6-amine.

27. The compound of claim 1 wherein R is a secondary or tertiary alkyl-amino-alkyl.

28. The compound of claim 27 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 2-(hydroxyethyl(isopropyl)amino)ethyl, 3-(cyclopentylamino)propyl, 3-(cyclopentyl(methyl)amino)propyl, 3-(ethylamino)propyl, 3-(ethyl(methyl)amino)propyl, 2-(neopentyl-amino)ethyl, 3-(methyl(isopropyl)amino)propyl, 3-(ethyl(isopropyl)amino)propyl, 3-(hydroxyethyl(isopropyl)amino)propyl, 3-(methyl(propargyl)amino)propyl, 2-(methyl(propargyl)amino)ethyl, 3-(allyl(methyl)amino)propyl, 3-(propyl(cyclopropylmethyl)amino)propyl, 3-(hydroxyethyl(cyclohexyl)amino)propyl, 2-(cyclopropylmethyl-amino)ethyl, and 2-(methyl(isobutyl)amino)ethyl.

29. The compound of claim 28 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 3-(cyclopentylamino)propyl, 3-(cyclopentyl(methyl)amino)propyl, 3-(ethylamino)propyl, 3-(ethyl(methyl)amino)propyl, 2-(neopentyl-amino)ethyl, 3-(methyl(isopropyl)amino)propyl, 3-(ethyl(isopropyl)amino)propyl, 3-(propyl(cyclopropylmethyl)amino)propyl, 2-(cyclopropylmethyl-amino)ethyl, and 2-(methyl(isobutyl)amino)ethyl.

30. The compound of claim 29 wherein $X_2$ is acetylene.

31. The compound of claim 29 wherein $X_2$ is optionally substituted furan, thiophene, oxazole, or pyrazole.

32. The compound of claim 18 wherein R is a secondary or tertiary alkyl-amino-alkyl.

33. The compound of claim 32 wherein the compound is of the formula (1A)

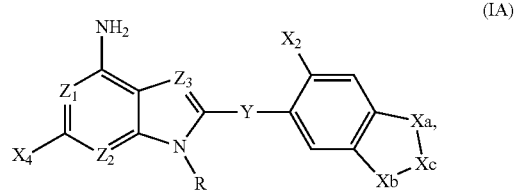

(a) each of $Z_1$, $Z_2$ and $Z_3$ is independently N;
(b) Xa-Xc-Xb is $CH_2$—$CH_2$—$CH_2$, CH=CH—$CH_2$, or $CH_2$—CH=CH; or one of Xa and Xb is O and Xc and the other of Xa and Xb are —$CH_2$—;
(c) Y is —$CH_2$— or —S—;
(d) $X_4$ is hydrogen or halogen; and
(e) $X_2$ is alkynyl, aryl, cycloalkyl, or cycloalkenyl, each of which is optionally substituted.

34. The compound of claim 33 wherein $X_2$ is alkynyl or hetcroaryl, each of which is optionally substituted.

35. The compound of claim 34 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 2-(hydroxyethyl(isopropyl)amino)ethyl, 3-(cyclopentylamino)propyl, 3-(cyclopentyl(methyl)amino)propyl, 3-(ethylamino)propyl, 3-(ethyl(methyl)amino)propyl, 2-(neopentyl-amino)ethyl, 3-(methyl(isopropyl)amino)propyl, 3-(elhyl(isopropyl)amino)propyl, 3-(hydroxyethyl(isopropyl)amino)propyl, 3-(methyl(propargyl)amino)propyl, 2-(methyl(propargyl)amino)ethyl, 3-(allyl(methyl)amino)propyl, 3-(propyl(cyclopropylmethyl)amino)propyl, 3-(hydroxyethyl(cyclohexyl)amino)propyl, 2-(cyclopropylmethyl-amino)ethyl, and 2-(methyl(isobutyl)amino)ethyl.

36. The compound of claim 35 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 3-(cyclopentylamino)propyl, 3-(cyclopentyl(methyl)amino)propyl, 3-(ethylamino)propyl, 3-(ethyl(methyl)amino)propyl, 2-(neopenlyl-amino)ethyl, 3-(methyl(isopropyl)amino)propyl, 3-(ethyl(isopropyl)amino)propyl, 3-(propyl(cyclopropylmethyl)amino)propyl, 2-(cyclopropylmethyl-amino)ethyl, and 2-(methyl(isobutyl)amino)ethyl.

37. The compound of claim 36 wherein $X_2$ Ls acetylene, furan, or thiophene.

38. The compound of claim 37 wherein the compound is

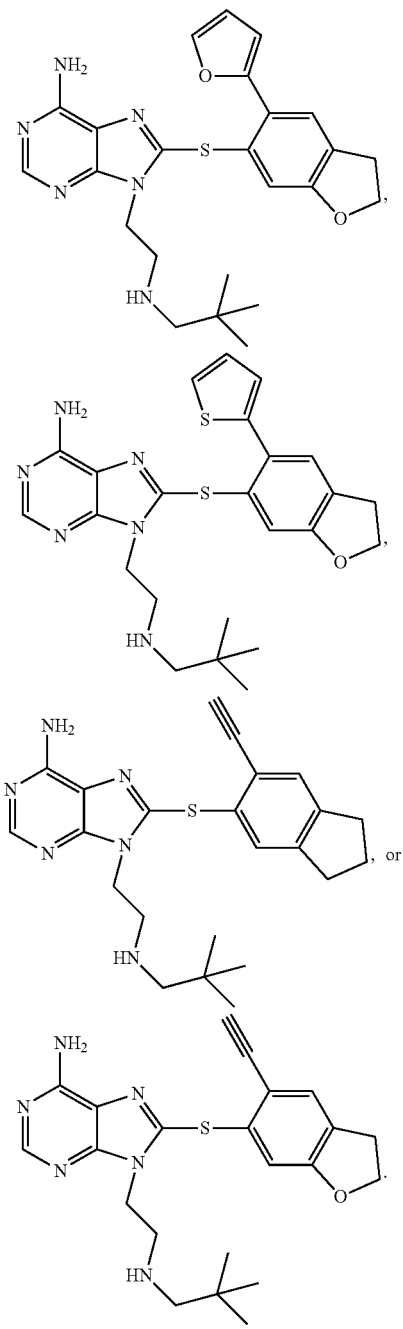

, or

39. The compound of claim 32 wherein the compound is of the formula (1B)

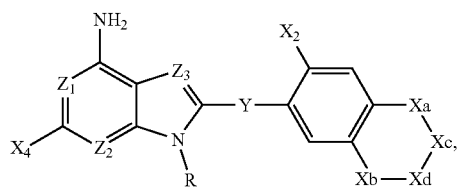

(1B)

(a) each of $Z_1$, $Z_2$ and $Z_3$ is independently N;
(b) Xa and Xb are O, and Xc and Xd are $CH_2$;
(c) Y is $—CH_2—$ or $—S—$;
(d) $X_4$ is hydrogen or halogen; and
(e) $X_2$ is alkynyl, aryl, cycloalkyl, or cycloalkenyl, each of which is optionally substituted.

40. The compound of claim 39 wherein $X_2$ is alkynyl or heteroaryl, each of which is optionally substituted.

41. The compound of claim 40 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 2-(hydroxyethyl(isopropyl)amino)ethyl, 3-(cyclopentylamino)propyl, 3-(cyclopentyl(methyl)amino)propyl, 3-(ethylamino)propyl, 3-(ethyl(methyl)amino)propyl, 2-(neopentyl-amino)ethyl, 3-(methyl(isopropyl)amino)propyl, 3-(ethyl(isopropyl)amino)propyl, 3-(hydroxyethyl(isopropyl)amino)propyl, 3-(methyl(propargyl)amino)propyl, 2-(methyl(propargyl)amino)ethyl, 3-(allyl(methyl)amino)propyl, 3-(propyl(cyclopropylmethyl)amino)propyl, 3-(hydroxyethyl(cyclohexyl)amino)propyl, 2-(cyclopropylmethyl-amino)ethyl, and 2-(methyl(isobutyl)amino)ethyl.

42. The compound of claim 41 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 3-(cyclopentylamino)propyl, 3-(cyclopentyl(methyl)amino)propyl, 3-(ethylamino)propyl, 3-(ethyl(methyl)amino)propyl, 2-(neopentyl-amino)ethyl, 3-(methyl(isopropyl)amino)propyl, 3-(ethyl(isopropyl)amino)propyl, 3-(propyl(cyclopropylmethyl)amino)propyl, 2-(cyclopropylmethyl-amino)ethyl, and 2-(methyl(isobutyl)amino)ethyl.

43. The compound of claim 42 wherein $X_2$ is acetylene, furan, oxazole, or pyrazole.

44. The compound of claim 43 wherein the compound is

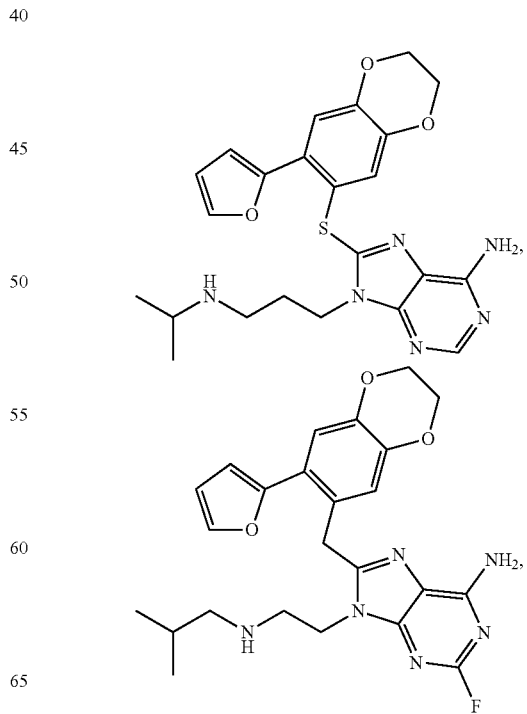

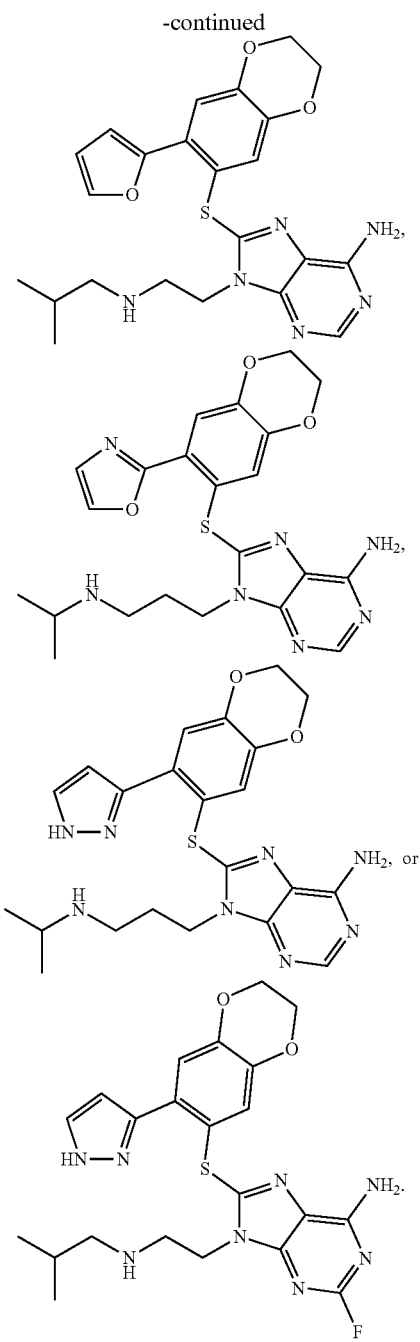

45. The compound of claim 32 wherein the compound is of the formula (4)

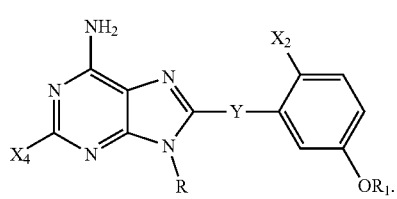

46. The compound of claim 45 wherein X₂ is alkynyl or heteroaryl, each of which is optionally substituted.

47. The compound of claim 46 wherein R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 2-(hydroxyethyl(isopropyl)amino)ethyl, 3-(cyclopentylamino)propyl, 3-(cyclopentyl(methyl)amino)propyl, 3-(ethylamino)propyl, 3-(ethyl(methyl)amino)propyl, 2-(neopentyl-amino)ethyl, 3-(methyl(isopropyl)amino)propyl, 3-(ethyl(isopropyl)amino)propyl, 3-(hydroxyethyl(isopropyl)amino)propyl, 3-(methyl(propargyl)amino(propyl, 2-(methyl(propargyl)amino)ethyl, 3-(allyl(methyl)amino)propyl, 3-(propyl(cyclopropylmethyl)amino)propyl, 3-(hydroxyethyl(cyclohexyl)amino)propyl, 2-(cyclopropylmethyl-amino)ethyl, and 2-(methyl(isobutyl)amino)ethyl.

48. The compound of claim 47 where in R is 2-(methyl(t-butyl)amino)ethyl, 2-(methyl(isopropyl)amino)ethyl, 3-(neopentyl-amino)propyl, 2-(isobutyl-amino)ethyl, 2-(ethyl(isopropyl)amino)ethyl, 3-(isopropyl-amino)propyl, 3-(t-butyl-amino)propyl, 2-(isopropyl-amino)ethyl, 3-(cyclopentylamino)propyl, 3-(cyclopentyl(methyl)amino)propyl, 3-(ethylamino)propyl, 3-(ethyl(methyl)amino)propyl, 2-(neopenlyl-amino)ethyl, 3-(methyl(isopropyl)amino)propyl, 3-(ethyl(isopropyl)amino)propyl, 3-(propyl(cyclopropylmethyl)amino)propyl, 2-(cyclopropylmethyl-amino)ethyl, and 2-(methyl(isobutyl)amino)ethyl.

49. The compound of claim 48 wherein X₂ is acetylene, furan, thiophene, or pyrazole.

50. The compound of claim 49 wherein the compound is

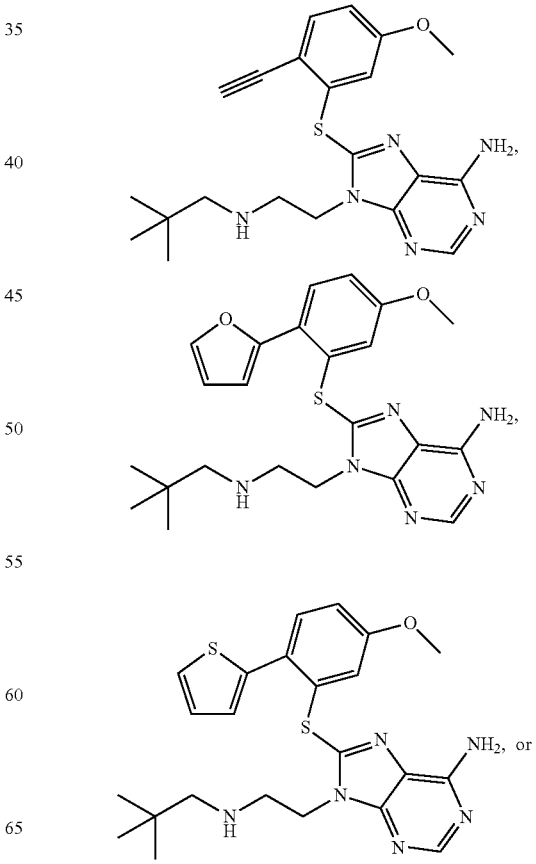

-continued
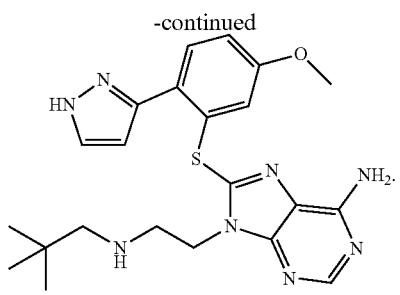
* * * * *